United States Patent
Narayanan et al.

(10) Patent No.: US 10,987,334 B2
(45) Date of Patent: Apr. 27, 2021

(54) METHOD OF TREATING ER MUTANT EXPRESSING BREAST CANCERS WITH SELECTIVE ANDROGEN RECEPTOR MODULATORS (SARMS)

(71) Applicant: GTx, Inc., Memphis, TN (US)

(72) Inventors: Ramesh Narayanan, Cordova, TN (US); Thamarai Ponnusamy, Memphis, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 16/051,042

(22) Filed: Jul. 31, 2018

(65) Prior Publication Data

US 2019/0111010 A1 Apr. 18, 2019

Related U.S. Application Data

(63) Continuation-in-part of application No. 15/371,104, filed on Dec. 6, 2016, now Pat. No. 10,314,807, which is a continuation-in-part of application No. 15/075,373, filed on Mar. 21, 2016, now Pat. No. 10,258,596, which is a continuation-in-part of application No. 14/798,208, filed on Jul. 13, 2015, now Pat. No. 9,744,149, which is a continuation-in-part of application No. 14/293,632, filed on Jun. 2, 2014, now Pat. No. 9,622,992, which is a continuation-in-part of application No. 13/953,492, filed on Jul. 29, 2013, now Pat. No. 9,969,683, which is a continuation-in-part of
(Continued)

(51) Int. Cl.
| | |
|---|---|
| *A61K 31/167* | (2006.01) |
| *A61K 31/277* | (2006.01) |
| *A61P 35/00* | (2006.01) |
| *A61K 31/404* | (2006.01) |
| *A61K 31/4704* | (2006.01) |
| A61K 9/00 | (2006.01) |
| A61K 9/06 | (2006.01) |
| A61K 9/48 | (2006.01) |
| A61K 9/10 | (2006.01) |
| A61K 9/02 | (2006.01) |
| A61K 9/16 | (2006.01) |
| A61K 9/107 | (2006.01) |
| A61K 9/08 | (2006.01) |

(52) U.S. Cl.
CPC .......... *A61K 31/277* (2013.01); *A61K 31/167* (2013.01); *A61K 31/404* (2013.01); *A61K 31/4704* (2013.01); *A61P 35/00* (2018.01); A61K 9/0014 (2013.01); A61K 9/0019 (2013.01); A61K 9/0024 (2013.01); A61K 9/0053 (2013.01); A61K 9/02 (2013.01); A61K 9/06 (2013.01); A61K 9/08 (2013.01); A61K 9/10 (2013.01); *A61K 9/107* (2013.01); *A61K 9/1605* (2013.01); *A61K 9/4866* (2013.01)

(58) Field of Classification Search
CPC ...... A61K 31/167; A61K 31/277; A61P 35/00
See application file for complete search history.

(56) References Cited

U.S. PATENT DOCUMENTS

| | | |
|---|---|---|
| 3,239,345 A | 3/1966 | Hodge et al. |
| 3,256,096 A | 6/1966 | Tucker et al. |
| 3,865,801 A | 2/1975 | Chiba et al. |

(Continued)

FOREIGN PATENT DOCUMENTS

| | | |
|---|---|---|
| AU | 2002364949 | 6/2003 |
| AU | 2003216174 | 9/2003 |

(Continued)

OTHER PUBLICATIONS

Fuqua et al. Breast Cancer Res. Treat., 2014, vol. 144, No. 1, pp. 1-17.*

(Continued)

*Primary Examiner* — Samira J Jean-Louis
(74) *Attorney, Agent, or Firm* — Mark S. Cohen; Pearl Cohen Zedek Latzer Baratz LLP

(57) ABSTRACT

This invention relates to the treatment of breast cancer in a subject, for example a female subject. Including methods of: treating metastatic breast cancer; refractory breast cancer; AR-positive breast cancer; AR-positive refractory breast cancer; AR-positive metastatic breast cancer; AR-positive and ER-positive breast cancer; triple negative breast cancer; advanced breast cancer; breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; metastasis in a subject suffering from breast cancer; HER2-positive; and/or treating a subject suffering from ER mutant expressing breast cancer, comprising administering to the subject a therapeutically effective amount of a selective androgen receptor modulator (SARM) compound.

5 Claims, 65 Drawing Sheets

Specification includes a Sequence Listing.

Related U.S. Application Data application No. 13/789,005, filed on Mar. 7, 2013, now Pat. No. 9,604,916.

(60) Provisional application No. 61/726,274, filed on Nov. 14, 2012, provisional application No. 61/671,366, filed on Jul. 13, 2012.

(56) References Cited

U.S. PATENT DOCUMENTS

| | | | |
|---|---|---|---|
| 3,875,229 A | 4/1975 | Gold | |
| 3,946,109 A | 3/1976 | Kolb et al. | |
| 3,949,085 A | 4/1976 | Feuer et al. | |
| 3,991,750 A | 11/1976 | Vickery et al. | |
| 4,036,979 A | 7/1977 | Asato et al. | |
| 4,139,638 A | 2/1979 | Neri et al. | |
| 4,191,775 A | 3/1980 | Glen | |
| 4,211,781 A | 7/1980 | Chapman et al. | |
| 4,239,776 A | 12/1980 | Glen et al. | |
| 4,282,218 A | 8/1981 | Glen et al. | |
| 4,386,080 A | 5/1983 | Crossley et al. | |
| 4,411,890 A | 10/1983 | Momany et al. | |
| 4,447,421 A | 5/1984 | Klothen et al. | |
| 4,465,507 A | 8/1984 | Konno et al. | |
| 4,636,505 A | 1/1987 | Tucker | |
| 4,670,249 A | 6/1987 | Ivy et al. | |
| 4,753,932 A | 6/1988 | Teutch et al. | |
| 4,837,004 A | 6/1989 | Wu et al. | |
| 4,849,447 A | 7/1989 | Jacobs et al. | |
| 4,880,839 A | 11/1989 | Tucker | |
| 4,904,473 A | 2/1990 | Schricker et al. | |
| 4,977,288 A | 12/1990 | Kassis et al. | |
| 5,030,657 A | 7/1991 | Burtle et al. | |
| 5,162,504 A | 11/1992 | Horoszewicz | |
| 5,179,080 A | 1/1993 | Rothkopf et al. | |
| 5,288,496 A | 2/1994 | Lewis et al. | |
| 5,441,868 A | 8/1995 | Lin et al. | |
| 5,547,933 A | 8/1996 | Lin et al. | |
| 5,609,849 A | 3/1997 | Kung | |
| 5,612,359 A | 3/1997 | Murugesan et al. | |
| 5,618,698 A | 4/1997 | Lin et al. | |
| 5,621,080 A | 4/1997 | Lin et al. | |
| 5,656,651 A | 8/1997 | Sovak et al. | |
| 6,019,957 A | 2/2000 | Miller et al. | |
| 6,022,137 A | 2/2000 | White et al. | |
| 6,043,265 A | 3/2000 | Murugesan et al. | |
| 6,071,957 A | 6/2000 | Miller et al. | |
| 6,160,011 A | 12/2000 | Miller et al. | |
| 6,482,861 B2 | 11/2002 | Miller et al. | |
| 6,492,554 B2 | 12/2002 | Dalton et al. | |
| 6,548,529 B1 | 4/2003 | Robl et al. | |
| 6,569,892 B2 | 5/2003 | Dalton et al. | |
| 6,569,896 B2 | 5/2003 | Dalton et al. | |
| 6,777,427 B2 | 8/2004 | Miyakawa et al. | |
| 6,777,446 B2 | 8/2004 | Houze et al. | |
| 6,780,625 B2 | 8/2004 | Eldar-Finkelman et al. | |
| 6,838,484 B2 | 1/2005 | Steiner et al. | |
| 6,899,888 B2 | 5/2005 | Steiner et al. | |
| 6,960,474 B2 | 11/2005 | Salvati et al. | |
| 6,995,284 B2 | 2/2006 | Dalton et al. | |
| 6,998,500 B2 | 2/2006 | Dalton et al. | |
| 7,022,870 B2 | 4/2006 | Dalton et al. | |
| 7,026,500 B2 | 4/2006 | Dalton et al. | |
| 7,041,844 B2 | 5/2006 | Miller et al. | |
| 7,157,422 B2 | 1/2007 | Eldar-Finkelman et al. | |
| 7,205,437 B2 | 4/2007 | Dalton et al. | |
| 7,214,693 B2 | 5/2007 | Dalton et al. | |
| 7,344,700 B2 | 3/2008 | Dalton et al. | |
| 7,518,013 B2 | 4/2009 | Dalton et al. | |
| 7,547,728 B2 | 6/2009 | Steiner et al. | |
| 7,622,503 B2 | 11/2009 | Dalton et al. | |
| 7,645,898 B2 | 1/2010 | Dalton et al. | |
| 7,705,182 B2 | 4/2010 | Dalton et al. | |
| 7,759,520 B2 | 7/2010 | Dalton et al. | |
| 7,772,433 B2 | 8/2010 | Dalton et al. | |
| 7,776,921 B2 | 8/2010 | Steiner et al. | |
| 7,803,970 B2 | 9/2010 | Dalton et al. | |
| 7,825,229 B2 | 11/2010 | Itzhak et al. | |
| 7,855,229 B2 | 12/2010 | Dalton et al. | |
| 8,008,348 B2 | 8/2011 | Steiner et al. | |
| 8,080,682 B2 | 12/2011 | Dalton et al. | |
| 8,426,465 B2 | 4/2013 | Dalton et al. | |
| 8,846,756 B2 | 9/2014 | Dalton et al. | |
| 8,853,266 B2 | 10/2014 | Dalton et al. | |
| 2001/0012839 A1 | 8/2001 | Miller et al. | |
| 2002/0099036 A1 | 7/2002 | Dalton et al. | |
| 2002/0099096 A1 | 7/2002 | Dalton et al. | |
| 2002/0173445 A1 | 11/2002 | Salvati et al. | |
| 2002/0173495 A1 | 11/2002 | Dalton et al. | |
| 2003/0162761 A1 | 8/2003 | Steiner et al. | |
| 2003/0225040 A1 | 12/2003 | Dalton et al. | |
| 2003/0229099 A1 | 12/2003 | Zhu et al. | |
| 2003/0232792 A1 | 12/2003 | Dalton et al. | |
| 2003/0232882 A1 | 12/2003 | Miller et al. | |
| 2004/0014975 A1 | 1/2004 | Dalton et al. | |
| 2004/0029913 A1 | 2/2004 | Dalton et al. | |
| 2004/0053897 A1 | 3/2004 | Dalton et al. | |
| 2004/0087557 A1 | 5/2004 | Steiner et al. | |
| 2004/0087810 A1 | 5/2004 | Dalton et al. | |
| 2004/0147489 A1 | 7/2004 | Dalton et al. | |
| 2004/0167103 A1 | 8/2004 | Dalton et al. | |
| 2004/0197928 A1 | 10/2004 | Dalton et al. | |
| 2004/0214790 A1 | 10/2004 | Borgens et al. | |
| 2004/0224979 A1 | 11/2004 | Dalton et al. | |
| 2004/0260092 A1 | 12/2004 | Miller et al. | |
| 2004/0260108 A1 | 12/2004 | Dalton et al. | |
| 2004/0265916 A1 | 12/2004 | Dalton et al. | |
| 2005/0033074 A1 | 2/2005 | Dalton et al. | |
| 2005/0038110 A1 | 2/2005 | Steiner et al. | |
| 2005/0137172 A1 | 6/2005 | Dalton et al. | |
| 2005/0154043 A1 | 7/2005 | Zhai et al. | |
| 2005/0209320 A1 | 9/2005 | Miller et al. | |
| 2005/0032750 A1 | 10/2005 | Steiner et al. | |
| 2006/0004042 A1 | 1/2006 | Dalton et al. | |
| 2006/0019931 A1 | 1/2006 | Dalton et al. | |
| 2006/0035965 A1 | 2/2006 | Dalton et al. | |
| 2006/0111441 A1 | 5/2006 | Dalton et al. | |
| 2006/0165744 A1 | 7/2006 | Jamil et al. | |
| 2006/0183931 A1 | 8/2006 | Dalton et al. | |
| 2006/0229362 A1 | 10/2006 | Dalton et al. | |
| 2006/0287349 A1 | 12/2006 | Meissner et al. | |
| 2007/0043029 A1 | 2/2007 | Sakaki et al. | |
| 2007/0066568 A1 | 3/2007 | Dalton et al. | |
| 2007/0078168 A1 | 4/2007 | Caulkett et al. | |
| 2007/0088017 A1 | 4/2007 | Gaillard et al. | |
| 2007/0012356 A1 | 5/2007 | Dalton et al. | |
| 2007/0099916 A1 | 5/2007 | Dehmlow et al. | |
| 2007/0099930 A1 | 5/2007 | Dudash et al. | |
| 2007/0099936 A1 | 5/2007 | Bian et al. | |
| 2007/0117805 A1 | 5/2007 | Dow et al. | |
| 2007/0123563 A1 | 5/2007 | Dalton et al. | |
| 2007/0161578 A1 | 7/2007 | Hwa et al. | |
| 2007/0161608 A1 | 7/2007 | Dalton et al. | |
| 2007/0173546 A1 | 7/2007 | Dalton et al. | |
| 2007/0265296 A1 | 11/2007 | Dalton et al. | |
| 2007/0281906 A1 | 12/2007 | Dalton et al. | |
| 2008/0076828 A1 | 3/2008 | Dalton et al. | |
| 2008/0076829 A1 | 3/2008 | Dalton et al. | |
| 2009/0030036 A1 | 1/2009 | Dalton et al. | |
| 2009/0062341 A1 | 3/2009 | Dalton et al. | |
| 2009/0088480 A1 | 4/2009 | Dalton et al. | |
| 2009/0264534 A1 | 10/2009 | Dalton et al. | |
| 2010/0022641 A1 | 1/2010 | Dalton et al. | |
| 2010/0137430 A1 | 6/2010 | Dalton et al. | |
| 2010/0144871 A1* | 6/2010 | Steiner | A61K 31/00 514/522 |
| 2010/0249228 A1 | 9/2010 | Dalton et al. | |
| 2010/0280107 A1 | 11/2010 | Dalton et al. | |
| 2011/0150979 A1 | 6/2011 | Ray et al. | |
| 2013/0034562 A1 | 2/2013 | Dalton et al. | |
| 2014/0011774 A1 | 1/2014 | Dalton et al. | |
| 2014/0018433 A1 | 1/2014 | Dalton et al. | |
| 2014/0080905 A1 | 3/2014 | Dalton et al. | |
| 2014/0350102 A1 | 11/2014 | Dalton et al. | |

(56) References Cited

U.S. PATENT DOCUMENTS

| | | |
|---|---|---|
| 2016/0089356 A1 | 3/2016 | Dalton et al. |
| 2016/0128968 A1 | 5/2016 | Dalton et al. |
| 2016/0128969 A1 | 5/2016 | Dalton et al. |
| 2016/0158185 A1 | 6/2016 | Dalton et al. |
| 2017/0014370 A1 | 1/2017 | Dalton et al. |
| 2017/0014371 A1 | 1/2017 | Dalton et al. |
| 2017/0050921 A1 | 2/2017 | Narayanan et al. |

FOREIGN PATENT DOCUMENTS

| | | |
|---|---|---|
| CA | 2420279 | 2/2002 |
| CA | 2458452 A1 | 2/2003 |
| CA | 2477737 | 9/2003 |
| CA | 2502209 | 4/2004 |
| CA | 2502355 | 4/2004 |
| CA | 2538095 | 4/2004 |
| CA | 2529464 | 1/2005 |
| CN | 1548442 A | 11/2004 |
| EP | 0040932 | 2/1981 |
| EP | 0100172 | 2/1984 |
| EP | 0002892 | 2/1985 |
| EP | 0253503 | 12/1991 |
| EP | 668351 | 8/1995 |
| EP | 0683172 | 11/1995 |
| EP | 0903146 | 3/1999 |
| EP | 1221439 | 7/2002 |
| EP | 1398029 | 3/2004 |
| EP | 1401801 | 11/2006 |
| EP | 1801140 | 6/2007 |
| GB | 1360001 | 3/1970 |
| JP | 52-128329 | 10/1977 |
| JP | 54-063047 | 12/1980 |
| JP | 59-033250 | 2/1984 |
| WO | WO 1989/007110 | 8/1989 |
| WO | WO 1989/007111 | 8/1989 |
| WO | WO 1991/005867 | 5/1991 |
| WO | WO 1993/004081 | 3/1993 |
| WO | WO 1995/019770 | 7/1995 |
| WO | WO 1998/005962 | 2/1998 |
| WO | WO 1998/027986 | 7/1998 |
| WO | WO 1998/053826 | 12/1998 |
| WO | WO 1998/055153 A1 | 12/1998 |
| WO | WO 2000/001389 | 1/2000 |
| WO | WO 2000/038721 | 7/2000 |
| WO | WO 2000/058293 | 10/2000 |
| WO | WO 2001/027086 | 4/2001 |
| WO | WO 2001/027622 | 4/2001 |
| WO | WO 2001/028990 | 4/2001 |
| WO | WO 2001/034563 | 5/2001 |
| WO | WO 2001/044216 | 6/2001 |
| WO | WO 2001/068603 | 9/2001 |
| WO | WO 2002/000617 | 1/2002 |
| WO | WO 2002/016310 | 2/2002 |
| WO | WO 2002/022585 | 3/2002 |
| WO | WO 2003/000262 | 1/2003 |
| WO | WO 2003/000267 | 1/2003 |
| WO | WO 2003/011302 | 2/2003 |
| WO | WO 2003/015774 | 2/2003 |
| WO | WO 2003/049675 | 6/2003 |
| WO | WO 2003/065983 | 8/2003 |
| WO | WO 2003/065992 | 8/2003 |
| WO | WO 2003/074449 | 9/2003 |
| WO | WO 2003/074471 | 9/2003 |
| WO | WO 2003/077919 | 9/2003 |
| WO | WO 2003/104207 | 12/2003 |
| WO | WO 2004/034978 | 4/2004 |
| WO | WO 2004/035736 | 4/2004 |
| WO | WO 2004/064747 | 8/2004 |
| WO | WO 2005/000794 | 1/2005 |
| WO | WO 2005/025579 | 3/2005 |
| WO | WO 2005/037201 | 4/2005 |
| WO | WO 2005/037205 | 4/2005 |
| WO | WO 2005/037206 | 4/2005 |
| WO | WO 2005/060647 | 7/2005 |
| WO | WO 2005/120483 | 12/2005 |
| WO | WO 2006/019741 | 2/2006 |
| WO | WO 2007/107305 A2 | 2/2007 |
| WO | WO 2007/027582 | 3/2007 |
| WO | WO 2008/008433 | 1/2008 |
| WO | WO 2008/024456 | 7/2008 |
| WO | WO 2008/127717 | 10/2008 |
| WO | WO 2008/130571 | 10/2008 |
| WO | WO 2009/155481 A1 | 12/2009 |
| WO | WO 2011/050353 A1 | 4/2011 |
| WO | WO 2011/085385 | 7/2011 |
| WO | WO 2011/119544 | 9/2011 |
| WO | WO 2011/140228 | 11/2011 |
| WO | WO 2012/068435 | 5/2012 |
| WO | WO 2012/139093 A2 | 10/2012 |
| WO | WO-2012139093 A2 * | 10/2012 ........... A61K 31/167 |

OTHER PUBLICATIONS

Abuchowski et al., "Immunosuppresive properties and circulating life of achromobacter glutaminase-asparaginase covalently attached to polyethylene glycol in man" Cancert Treat. Rep. 65:1077-1081, 1981.

Adair et al.; "The use of testosterone propionate in the treatment of advanced carcinoma of the breast", Ann Surg. 1946;123:1023-35.

American Cancer Society; Cancer Facts & Figures 2012, American Cancer Society, 2012.

Baird et al., "Hormonal Contraception—Drug Therapy", The New England Journal of Medicine , May 27, 1993, pp. 1543-1549.

Barbareschi et al. "p63, a p53 homologue, is a selective nuclear marker of myoepithelial cells of the human breast" The American journal of surgical pathology. Aug. 1, 2001;25(8):1054-60.

Barton et al. "Androgen receptor biology in triple negative breast cancer: a case for classification as AR+ or quadruple negative disease" Hormones and Cancer. Dec. 1, 2015;6(5-6):206-13.

Belani, C. P. et al, "Development of docetaxel inadvanced non-small-cell lung cancer." Lung Cancer, 46, pp. S3-S11, 2004.

Belikov "Pharmaceutical chemistry", high school, 1993, vol. 1, pp. 43-47.

Berger et al., "Concepts and limitations in the application of radiolabeled antiandrogens, estrogens, or androgens as isotropic scanning agents for the prostate", Invest. Urol, (1975), 1391, 10-16.

Bhasin et al. "Drug insight: Testosterone and selective androgen receptor modulators as anabolic therapies for chronic illness and aging" Nature, Clinical Practice in Endocrinology and Metabolism, 2(3):146-159, 2006.

Bisson et al. "Discovery of antiandrogen activity of nonsteroidal scaffolds of marketed drugs" Proceedings of the National Academy of Sciences, U S A. 104(29): 1927-11932, Jul. 17, 2007.

Bocchinfuso et al. "Induction of mammary gland development in estrogen receptor-α knockout mice" Endocrinology. Aug. 1, 2000;141(8):2982-94.

Bohl et al.; "Structural Basis for Accommodation of Nonsteroidal Ligands in the Androgen Receptor", Journal of Biological Chemistry, 280(45):37747-37754, 2005.

Bohl et al. "A Ligand-Based Approach to Identify Quantitative Structure-Activity Relationships for the Androgen Receptor" Journal of Medicinal Chemistry, 47(15):3765-3776, 2004.

Bohl et al. "Crystal structure of the TS77A human androgen receptor ligand-binding domain complexed to cyproterone acetate provides insight for ligand-induced conformational changes and structure-based drug design" Journal of Biological Chemistry, 282(18): 13648-13655, 2007.

Bohl et al. "Structural Basis for Antagonism and Resistance of Bicalutamide in Prostate Cancer" Proc Natl Acad Sci U S A. 102(17): 6201-6206, 2005.

Bohl et al. "The crystal structure of the androgen receptor W741L mutant ligand binding domain bound to R-bicalutamide" Proceedings of the American Association for Cancer Research, Abstract #2533, Apr. 2005.

Boyanov et al. "Testosterone supplementation in men with type 2 diabetes,visceral obesity and partial androgen deficiency" Aging Male., vol. 6 No. 1, pp. 1-7, Mar. 2003.

(56) References Cited

OTHER PUBLICATIONS

Buchwald et al., "Long-term, continuous intravenous heparin administration by an implantable infusion pump in ambulatory patients with recurrent venous thrombosis" Surgery 88:607 (1980).
Campfield et al., 1995, "Recombinant mouse OB protein: evidence for a peripheral signal linking adiposity and central neural networks" Science 269:546-549.
Caprio et al.; "Fat distribution and cardiovascular risk factors in obese adolescent girls: importance of the intraabodomina fat dept", Am J Clin Nutr 1996;64:12-7.
Cabrespine et al. "Randomized phase II study comparing paclitaxel and carboplatin versus mitoxantrone in patients with hormone-refractory prostate cancer", Urology, 2006; 67(2), 354-359.
Chen et al. "Preclinical Pharmacology, Pharmacokinetics, and Metabolism of a Novel Selective Androgen Receptor Modulator (SARM) in Male Rats" The AAPS Journal, vol. 6, No. 4, Abstract #W5299, Nov. 2004.
Chen et al. "A Selective Androgen Receptor Modulator for Hormonal Male Contraception" Journal of Pharmacology and Experimental Therapeutics, 312(2): 546-553, 2005.
Chen et al. "A Selective Androgen Receptor Modulator (SARM) for Male Contraception" The Endocrine Society, New Orleans, Abstract U P2-103, Jun. 2004.
Chen et al. "Discovery and Therapeutic Promise of Selective Androgen Receptor Modulators" Molecular Interventions, 5(3):173-188, 2005.
Chen et al. "In Vitro and In Vivo Characterization of a Selective Androgen Receptor Modulators (SARM)" The AAPS Journal, vol. 7(S2):T3259, 2005.
Chen et al. "In vitro and in vivo structure-activity relationships of novel androgen receptor ligands with multiple substituents in the B-ring" Endocrinology, 146(12):5444-54, 2005.
Chen et al. "Modulation of Hormonal Biomarkers and Target Organ Weights In Vivo by Selective Androgen Receptor Modulators (SARMs)" PharmSci 4(4): 2002.
Ciarloni et al. "Amphiregulin is an essential mediator of estrogen receptor α function in mammary gland development" Proceedings of the National Academy of Sciences. Mar. 27, 2007;104(13):5455-60.
Colvin et al. "Anatomy of female puberty: the clinical relevance of developmental changes in the reproductive system" Clinical Anatomy. Jan. 1, 2013;26(1):115-29.
Considine et al., 1995, "Evidence against either a premature stop codon or the absence of obese gene mRNA in human obesity." J. Clin. Invest. 95:2986-2988.
Corey (1987) "Asymmetric Bromolactonization Reaction: Synthesis of Optically Active 2-hydroxy-2-Methylalkanoic Acids from 2-Methylalkanoic Acids" Tetrahedron Letters vol. 28, No. 25 2801-2804.
Crawford et al.; "The association of time of day and serum testosterone concentration in a large screening population", Urological Oncology, BJU Interntional, 100, 509-513.
Cunha et al. "Elucidation of a role for stromal steroid hormone receptors in mammary gland growth and development using tissue recombinants" Journal of mammary gland biology and neoplasia. Oct. 1, 1997;2(4):393-402.
Dalton et al. "Preclinical Pharmacology and Pharmacokinetics of a Selective Androgen Receptor Modulator" International Society for Study of Xenobiotics. Drug Metabolism Reviews, 33(supplement 1): #222, 2001.
Dalton et al.; "The selective androgen receptor modulator GTx-024 (enobosarm) improves lean body mass and physical function in healthy elderly men and postmenopausal women: results of a double-blind, placebo-controlled phase II trial", J Cachexia Sarcopenia Muscle. 2011;2:153-61.
Dalton et al "Pharmacokinetics of Aminolevulinic Acid after Oral and Intravenous Dosing in Dogs." Drug Metabolism and Disposition, 27 (4):432-435, 1999.
Dalton et al.; "Discovery of Nonsteroidal Androgens", Biochem. Biophys. Res. Commun., 244(1):1-4, 1998.
Dalton, et al "Therapeutic Promise of Selective Androgen Receptor Modulators (SARSs): Preclinical and Clinical Proof-of-Concept Studies." The Endocrine Society—Programs and Abstracts—89th Annual Meeting—Paper S41-2.
De Amicis et al. "Androgen receptor overexpression induces tamoxifen resistance in human breast cancer cells", Breast Cancer Res Treat. May 2010;121(1):1-11.
Diebold et al.; "Innate antiviral responses by means of TLR7-mediated recognition of single-stranded RNA", Science. Mar. 5, 2004;303(5663):1529-31.
Djerassi et al., "A new look at male contraception", Nature, vol. 370, pp. 11-12.
Dobs et al.; "Effects of enobosarm on muscle wasting and physical function in patients with cancer: a double-blind, randomised controlled phase 2 trial", The lancet oncology. 2013;14:335-45.
Dodson et al.; "Muscle wasting in cancer cachexia: clinical implications, diagnosis, and emerging treatment strategies", Annu Rev Med. 2011;62:265-79.
Dunnwald et al. "Hormone receptor status, tumor characteristics, and prognosis: a prospective cohort of breast cancer patients", Breast Cancer Res. 2007;9(1):R6.
Edwards et al.; "New nonsteroidal androgen receptor modulators based on 4-(trifluoromethyl)-2-(1H)-Pyrololidino[3,2-g]quinolone", Bioorg. Med. Chem. Lett., 8: 745, 1998.
Edwards et al.; "Nonsteroidal androgen receptor agonists based on 4-(trifluoromethyl)-2H-pyrano[3,2-g]quinolin-2-one", Bioorg. Med. Chem. Lett., 9: 1003, 1999.
Eisenhauer et al.; "New response evaluation criteria in solid tumors: revised RECIST guideline (version 1.1)", European Journal of Cancer, 45:228-247, 2009.
Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.
Elsawa et al.; "Comprehensive analysis of tumor microenvironment cytokines in Waldenstrom macroglobulinemia identifies CCL5 as a novel modulator of IL-6 activity", Blood. 2011;118:5540-9.
Faulkner et al. (1991) "Noninvasive measurements of bone mass, structure, and strength: current methods and experimental techniques." Am J Rosentgenology 157:1229-1237.
Fearon et al.; "Understanding the mechanisms and treatment options in cancer cachexia", Nature reviews Clinical oncology. 2013;10:90-9.
Fearon; "Selective androgen receptor modulators in cancer cachexia?", The lancet oncology, 2013;14:271-2.
Fisher et al. "Preclinical Pharmacology and Pharmacokinetics of a Novel A-ring Substituted Selective Androgen Receptor Modulator (SARM) in Rats" The AAPS Journal, vol. 6, No. 4, Abstract #T2256, Nov. 2004.
Fisher et al. "Preclinical Pharmacology of A-Ring Substituted Selective Androgen Receptor Modulators (SARMs)" PhannSci 5 (4): W5248, 2003.
Francisco, et al., "Long-acting contraceptive agents: testosterone esters of unsaturated acids", Steroids, Jan. 1990, vol. 55, Butterworths.
Fukui M et al. "Role of endogenous androgen against insulin resistance and atherosclerosis in men with type 2 diabetes" Curr Diabetes Rev., vol. 3 No. 1, pp. 25-31, Feb. 2007.
Furuya et al.; "The novel non-steroidal selective androgen receptor modulator S-101479 has additive effects with bisphosphonate, selective estrogen receptor modulator, and parathyroid hormone on the bones of osteoporotic female rats", Biological & pharmaceutical bulletin, 2012;35:1096-104.
Gao et al.; "Expanding the therapeutic use of androgens via selective androgen receptor modulators (SARMs)" Drug Discovery Today, 12(5-6):241-248, 2007.
Gao et al.; "Ockham's razor and selective androgen receptor modulators (SARMs): are we overlooking the role of 5a-reductase?" Molecular Interventions, 7(1): 10-13, 2007.
Gao et al. "Selective Androgen Receptor Modulator Treatment Improves Muscle Strength and Body Composition, and Prevents Bone Loss in Orchidectomized Rats Endocrinology" 146(11):4887-4897, 2005.

(56) References Cited

OTHER PUBLICATIONS

Gao et al. "Characterization of the In vitro Metabolism of Selective Androgen Receptor Modulator (SARM) Using Human, Rat and Dog Liver Enzyme Preparations" Drug Metabolism and Disposition, 34(2):243-253, 2006.
Gao et al. "Comparison of the Pharmacological Effects of a Novel Selective Androgen Receptor Modulator, the 5{alpha}-Reductase Inhibitor Finasteride, and the Antiandrogen Hydroxyflutamide in Intact Rats: New Approach for Benign Prostate Hyperplasia" Endocrinology, 145(12): 5420-5428, 2004.
Gao et al. "Effects of a Novel Selective Androgen Receptor Modulator (SARM) on Skeletal Muscle Mass and Strength in Castrated Male Rats" The Endocrine Society, New Orleans, Abstract # P2-120, Jun. 16-19, 2004.
Gao et al. "InterSpecies Differences in Pharmacokinetics and Metabolism of S-3-(4-acetylamino-phenoxy)-2-hydroxy-2-methyl-N-(4-nitro-3-trifluoromethyl-phenyl)-propionamide: The Role of N-Acetyltransferase" Drug Metabolism and Disposition, 34(2):254-260, 2006.
Gao et al. "Pharmacokinetics and Pharmacodynamics of Nonsteroidal Androgen Receptor Ligands" Pharmaceutical Research, 23(8):1641-1658, Aug. 2006.
Gao et al. "Pharmacologic Effects of a Novel Selective Androgen Receptor Modulator (SARM), Flutamide and finasteride in Intact Male Rats" The Endocrine Society, Philadelphia, Jun. 2003, Abstract #P3-221.
Gao et al. "Pharmacologic Effects of Androxolutamide (GTx-007) on Male Rats of Varying Hormonal Status" The Endocrine Society, San Francisco, Jun. 2002.
Gao et al. "Phase I Metabolism Study of Selective Androgen Receptor Modulators (SARMs) with Human Liver Microsomes" PharmSci 5 (4): T3337, 2003.
Gao et al. "Regulation of Cytochrome P450s by Selective Androgen Receptor Modulators (SARMs) in Primary Culture of Human Hepatocytes.)" PharmSci 5 (4): T3338, 2003.
Gao et al. "Species Difference in the Metabolism of Selective Androgen Receptor Modulators (SARMs)" PhannSci 5 (4): T3336, 2003.
Gao et al. "Tissue-Specific Regulation of Transcription Repressor Slug Expression by Androgen Receptor Ligand (DHT)" The Endocrine Society, Boston, Abstract # P3-462, Jun. 2006.
Gao et al.; "Chemistry and structural biology of androgen receptor", Chemical Reviews, 1G5(9):3352-70,2005.
Gao et al.; "In Vitro Metabolism and In Vivo Tissue Selectivity of Andarine", PharmSci 4(4): 2002.
Garay et al.; "Androgen receptor as a targeted therapy for breast cancer", Am J Cancer Res., 2012;2:434-45.
Goldberger et al. "Using Mass Spectroscopy to Study Ligand-Specific Androgen Receptor (AR) Conformations and Complexes" The Endocrine Society, Boston, Abstract # P3-461, Jun. 2006.
Goldhirsch et al.; "Strategies for subtypes-dealing with the diversity of breast cancer: highlights of the St. Gallen International Expert Consensus on the Primary Therapy of Early Breast Cancer"; 2011, Ann Oncol. 2011;22:1736-47.
Goodson, "Dental Applications" in Medical Applications of Controlled Release, supra, vol. 2, pp. 116-138 (1984).
Goss et al. "Randomized trial of letrozole following tamoxifen as extended adjuvant therapy in receptor-positive breast cancer: updated findings from NCIC CTG MA.17", J Natl Cancer Inst. Sep. 7, 2005;97(17):1262-71.
Grattarola et al.; "Androgens in breast cancer. II. Endometrial adenocarcinoma and breast cancer in married postmenopausal women", American journal of obstetrics and gynecology, 1974;118:173-8.
Grattarola et al.; "Androgens in breast cancer. III. Breast cancer recurrences years after mastectomy and increased androgenic activity", American journal of obstetrics and gynecology, 1975;121:169-72.
Grundy; "Metabolic and health complications of obesity", 1990, Disease-a-Month 36:Dec; 36(12):641-731.

Haendler et al. "Recent developments in antiandrogens and selective androgen receptor modulators", Molecular and cellular endocrinology, 2012; 352(1), 79-91.
Halaas et al., 1995, "Weight-reducing effects of the plasma protein encoded by the obese gene." Science 269:543-546.
Hamann et al.; "Discovery of a potent, orally active nonsteroidal androgen receptor agonist: 4-ethyl-1,2,3,4-tetrahydro-6-(trifluoromethyl)-8-pyridono[5,6-g]-quinoline (LG121071)", J. Med. Chem., 42: 210, 1999.
Hamilton et al., 1995, « Increased obese mRNA expression in omental fat cells from massively obese humans. Nature Med. 1:953.
Hanada et al (2003) "Bone anabolic effects of S-40503, a novel nonsteroidal selective androgen receptor modulator (SARM), in rat models of osteoporosis." Biol. Pharm. Bull. 26:1563-1569.
Handelsman, "Bridging the gender gap in contraception: another hurdle cleared" The Medical Journal of Australia, vol. 154, Feb. 18, 1996, pp. 230-233.
He et al.; Novel Nonsteroidal Ligands with High Affinity and Potent Functional Activity for the Human Androgen Receptor. European Journal of Medicinal Chemistry, 37: 619-634, 2002.
Heil et al.; "Species-specific recognition of single-stranded RNA via toll-like receptor 7 and 8", Science. Mar. 5, 2004;303(5663):1526-9.
Heitzman et al., "The effectiveness of anabolic agents in increasing rate of growth in farm animals; report on experiments in cattle", Environ Qual Saf Suppl. 1976;(5):89-98.
Hickey et al. "Minireview: the androgen receptor in breast tissues: growth inhibitor, tumor suppressor, oncogene?" Molecular endocrinology. Jun. 28, 2012;26(8):1252-67.
Higgins et al.; "The androgen receptor in breast cancer: learning from the past", Breast Cancer Research and Treatment, 124.3 (Mar. 10, 2010, pp. 619-621.
Higuchi et al. 4-Alkyl- and 3,4-diaklyl-1,2,3,4-tetrahydro-8-pyridono[5,6-g]quinolines: potent, nonsteroidal androgen receptor agonists. Bioorg. Med. Chem. Lett., 9:1335, 1999.
Hild et al.; "Effects of synthetic androgens on liver function using the rabbit as a model", Journal of andrology, 2010;31:472-81.
Hoberman et al.; "The History of Synthetic Testosterone", Scientific American, Feb. 1995, pp. 76-81.
Hwang et al.;"Synthesis of isothiocyanate derivatives of irreversible selective androgen receptor modulators (SARMs) and biological testing in prostate cancer cell lines", Abstracts of Papers of the American Chemical Society, 229: U140-U140 177-MEDI Part 2, Mar. 13, 2005.
Hwang et al. "Synthesis and androgen receptor affinity of several linkages of 1 j3-disubstituted-2-hydroxy-2-metl1ylpropionamide selective androgen receptor modulators (SARMs)" Abstracts of Papers of the American Chemical Society, 229: U139-U139 173-MEDI Part 2, Mar. 13, 2005.
Hwang et al. "Synthesis and biological testing of (2S)-multi-halogenated B-ring 2-hydroxy-2-methylpropionamide selective androgen receptor modulators (SARMs): Probing the B-ring pocket" Abstracts of Papers of the American Chemical Society, 229:U140-U140 176-MEDI Part 2, Mar. 13, 2005.
Hwang et al. "Arylisothiocyanato selective androgen receptor modulators (SARMs) for prostate cancer" Bioorganic and Medicinal Chemistry, .14(19):6525-6538, 2006.
Hwang et al. "Synthesis and testing of both reversible and irreversible selective androgen receptor modulators (SARMs) for prostate cancer" Abstracts of Papers of the American Chemical Society, 231: 274-MEDI, Mar. 26, 2006.
Jones et al.; "Effects of (S)-N-(4-Cyano-3-Trifluoromethyl-Phenyl)-3-(3-Fluoro, 4-Chlorophenoxy)-2-Hydroxy-2-Methyl-Propanamide on Dexamethasone-Induced Muscle Atrophy", Endocrinology. 151, 3706-3719, 2010.
Jones et al.; "Preclinical Characterization of a (S)-N-(4-Cyano-3-Trifluoromethyl-Phenyl)-3-(3-Fluoro,4-Chlorophenoxy)-2-Hydroxy-2-Methyl-Propanamide: A Selective Androgen Receptor Modulator for Hormonal Male Contraception", Endocrinology, Jan. 2009, 150(1):385-395.
Kalu, (1991) "The ovariectomized rat model of postmenopausal bone loss. Bone Miner." 15: 175-91.
Karnoub et al.; "Mesenchymal stem cells within tumour stroma promote breast cancer metastasis", Nature. 2007;449:557-63.

(56) References Cited

OTHER PUBLICATIONS

Katre et al., "Chemical modification of recombinant interleukin 2 by polyethylene glycol increases its potency in the murine Meth A sarcoma model" 1987, Proc. Natl. Acad. Sci. vol. 84, pp. 1487-1491.

Katzenellenbogen et al. "Estrogen regulation of proliferation and hormonal modulation of estrogen and progesterone receptor biosynthesis and degradation in target cells" Progress in clinical and biological research. 1990;322:201.

Kearbey et al. "Effect of Androxolutamide (GTx-007) on Bone Mineralization in Rats: A Pilot Study" The Endocrine Society, San Francisco, Jun. 2002.

Kearbey et al. "Preclinical Pharmacology of a Novel Osteoanabolic Tissue Selective Androgen Receptor Modulator" The Endocrine Society, Boston, Abstract # P3-64, Jun. 2006.

Kearbey et al. "Selective Androgen Receptor Modulator (SARM) Treatment Prevents Bone Loss and Reduces Body Fat in Ovariectomized Rats" Pharmaceutical Research, 24(2):328-335, Feb. 2007.

Kearbey et al.; "Selective androgen receptor modulators inhibit bone resorption in rats" PharmSci 5 (4): R6167, 2003.

Kearbey et al. "Pharmacokinetics of S-3-(4-acetylamino-phenoxy)-2-hydroxy-2-methyl-N-(4-nitro-3-trifluoromethyl-phenyl)-propionamide in rats, a non-steroidal selective androgen receptor modulator"., Xenobiotica. Mar. 2004; 34(3): 273-280.

Kelly et al. "Dose escalation study of intravenous estramustine phosphate in combination with paclitaxel and carboplatin in patients with advanced prostate cancer", Clinical cancer research, 2003; 9(6), 2098-2107.

Kendrick et al. "Transcriptome analysis of mammary epithelial subpopulations identifies novel determinants of lineage commitment and cell fate" BMC genomics. Dec. 8, 2008;9(1):591.

Kennecke et al. "Metastatic behavior of breast cancer subtypes", J Clin Oncol. Jul. 10, 2010;28(20):3271-7.

Kennedy; "Fluoxymesterone therapy in advanced breast cancer", N Engl J Med. 1958;259:673-5.

Kim et al. "Effect of 4-cyano and 4-nitro Substitution on the Pharmacologic Activity and Pharmacokinetics of Selective Androgen Receptor Modulators" The AAPS Journal, vol. 6, No. 4, Abstract #W4118, Nov. 2004.

Kim et al. "In vitro and in vivo Pharmacologic Activity of 4-Halo Substituted SARMs" The Endocrine Society, Philadelphia, Jun. 2003, Abstract #P3-198, Jun. 19-22, 2003.

Kim et al. "Pharmacokinetics of Halogen Substituted SARMs in Rats" PharmSci 5 (4):W5259, 2003.

Kim et al. "Structure-Activity Relationships for Modification of the Linkage Group and B-Ring of Selective Androgen Receptor Modulators" The AAPS Journal, vol. 7(S2):T2117, 2005.

Kim et al.; "The Para Substituent of S-3-(Phenoxy)-2-hydroxy-2-methyl-N-(4-nitro-3-trifluoromethyl-phenyl)-propionamides Is a Major Structural Determinant of in Vivo Disposition and Activity of Selective Androgen Receptor Modulators", The Journal of Pharmacology and Experimental Therapeutics, vol. 315, No. 1, pp. 230-239.

Kirkovsky et al. "125I-Radioiodinated Bicalutamide Analogs as Potential Imaging Agents for Prostate Cancer" National Amer. Chem. Soc, Mtg., Las Vegas, NV, MEDI-155,1997.

Kirkovsky et al. "Approaches to Irreversible Non-Steroidal Chiral Antiandrogens" Southeast Regional Amer. Chem. Soc. Mtg., Memphis, TN, Nov. 29-Dec. 1, 1995.

Kirkovsky et al. "Chiral Nonsteroidal Affinity Ligands for the Androgen Receptor. 1. Bicalutamide Analogs bearing Electrophilic Groups at the Aromatic Ring B." Journal of Medicinal Chemistry, 43: 581-590, 2000.

Kirkovsky et al. "Chiral Non-Steroidal Antiandrogen Analogs of Hydroxyflutamide" National. Amer. Chem. Soc. Mtg., New Orleans, LA, 1996.

Kirkovsky et al., "[125I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.

Kori et al. "Early Phase II Study of Combination Chemotherapy of Docetaxel and Carboplatin in Patients With Postoperative Recurrent Adenocarcinoma of the Lung", Apr. 20, 2002, Japanese Journal of Jung Cancer, vol. 42, No. 2, pp. 85-91.

Korkaya et al.; "Activation of an IL6 inflammatory loop mediates trastuzumab resistance in HER2+ breast cancer by expanding the cancer stem cell population", Molecular cell. 2012; 47:570-84.

Koski et al.; "Cutting edge: innate immune system discriminates between RNA containing bacterial versus eukaryotic structural features that prime for high-level IL-12 secretion by dendritic cells",. J Immunol. Apr. 1, 2004;172(7):3989-93.

Laaksonen et al., "Sex hormones, inflammation and the metabolic syndrome: a population-based study", European Journal of Endocrinology, Dec. 2003, vol. 149, No. 6, pp. 601-608.

Lain et al. "Research resource: progesterone receptor targetome underlying mammary gland branching morphogenesis" Molecular Endocrinology. Aug. 26, 2013;27(10):1743-61.

Langer, "New Methods of Drug Delivery", Science 249:1627-1633 (1990).

Lea et al.; "Improved measurement of androgen receptors in human breast cancer", Cancer Research, 49:7162-7167, 1989.

Li et al.; "2-Arylthiazolidine-4-carboxylic acid amides (ATCAA) target dual pathways in cancer cells: 5'-AMP-acticated protein kinase (AMPK)/mTOR and PI3K/Akt/mTOR pathways", Int. J. Oncol. 37(4), 1023-30, 2010.

Lonnquist et al., 1995, Nature Med. 1:950.

Lopez-Berestein, in Liposomes in the Therapy of Infectious Disease and Cancer, Lopez-Berestein and Fidler (eds.), Liss, New York, pp. 317-327 (1989).

MacDonald et al.; "Understanding and managing cancer cachexia", J. American College of Surgeons, vol. 197, pp. 143-161, 2003.

Marhefka et al. "Design, synthesis, and biological characterization of metabolically stable selective androgen receptor modulators" Journal of Medicinal Chemistry, 47(4):993-998, Feb. 12, 2004.

Marhefka et al. "Homology Modeling Using Multiple Molecular Dynamics Simulations and Docking Studies of the Human Androgen Receptor Ligand Binding Domain Bound to Testosterone and Nonsteroidal Ligands" Journal of Medicinal Chemistry, 44: 1729-1740, 2001.

Matsumoto, "Hormonal therapy of male hypogonadism", Endocrinol. Met. Clin. N. Am. 23:857-75 (1994).

McKillop, et al., "Enantioselective metabolism and pharmacokinetics of Casodex in the male rat", Xenobiotica, 1995, vol. 25, No. 6, 623-634.

Miller et al. Men's Health. In: Foye '5 Principles of Medicinal Chemistry; Sixth Edition. Lemke TL, Williams DA, Roche VF, and Zito SW (Eds.), Lippincott, Williams and Wilkins, New York, NY, pp. 1265-1299, 2007.

Miller et al. "Chiral Epoxides as Irreversible Probe for the Androgen Receptor" National Amer, Chem. Soc. Mtg., Las Vegas, NV, MED1-222, 1997.

Miller et al., "Principles of Medicinal Chemistry", 5th Edition. Foye WO, Lemke TI, and Williams DA (Eds.), Williams and Wilkins, Baltimore, MD, pp. 653-717, 2008.

Mishra et al. "Expression of androgen receptor in breast cancer & its correlation with other steroid receptors & growth factors", Indian J Med Res. Jun. 2012;135(6):843-52.

Misiti et al. "Proteomic profiles in hyperandrogenic syndromes. Journal of endocrinological investigation" Mar. 1, 2010;33(3):156-64.

Mohammed et al. "Progesterone receptor modulates ER [agr] action in breast cancer" Nature. Jul. 16, 2015;523(7560):313-7.

Mohler et al., "Nonsteroidal tissue selective androgen receptor modulators: a promising class of clinical Candidates", Expert Opin. Ther Patents (2005) 15( 11), pp. 1-21.

Mohler et al.; "Estrogen Receptor-β Selective Nonsteroidal Estrogens: Seeking Tissue Specificity", Expert Opinion in Therapeutic Patents. 20 (4), 507-534, 2010.

Monaco et al. "Cloning of the Duchenne/Becker muscular dystrophy locus", Adv Hum Genet. 1988;17:61-98.

(56) References Cited

OTHER PUBLICATIONS

Mukherjee et al.; "Enantioselective Binding of Casodex to the Androgen Receptor", Xenobiotica 26(2): 117-122, 1996.
Mukherjee et al. "Alkylation of the Androgen Receptor with Nonsteroidal Affinity Ligands and Determination of their Functional Activity" Pharmaceutical Res., 14(11):S393, 1997.
Mukherjee et al. "Affinity Labeling of the Androgen Receptor with Nonsteroidal Chemoaffinity Ligands" Biochemical Pharmacology, 58: 1259-1267, 1999.
Mukherjee et al. "Development of Nonsteroidal Androgen Receptor Ligands for Imaging Prostate Tumors" PharmSci, 1(1): S-681, 1998.
Mukherjee et al. "Enantioselective Androgen Receptor Binding of Casodex" Pharmaceutical Res., 12(9):S378, 1995.
Mukherjee et al. "Evaluation of Novel Radioiodinated Imaging Agents for Prostate Cancer: Androgen Receptor Binding and Pharmacokinetics in Rats" Pharmaceutical Res., 14(11):S77, 1997.
Mukherjee et al. "In Vitro Pharmacologic Characterization of Non-steroidal Affinity Ligands for the Androgen Receptor" Pharmaceutical Res., 13(9):S491, 1996.
Nair et al.; "Synthesis of irreversibly binding bicalutamide analogs for imaging studies" Tetrahedron Letters, 46:4821-4823, May 31, 2005.
Nair et al. "Synthesis of Novel Iodo Derived Bicalutamide Analogs" Tetrahedron Letters, 45: 9475-9477, 2004.
Nair et al. "Synthesis of oxazolidinedione derived bicalutamide analogs" Tetrahedron Letters, 47 (23): 3953-3955, 2006.
Narayanan et al. "Molecular Mechanism for the Tissue Selectivity of a Novel Non-Steroidal Selective Androgen Receptor Modulator: Genome-Wide Mapping of Androgen Receptor Binding Sites" The Endocrine Society, Boston, Abstract # OR49-1, Jun. 2006.
Narayanan et al.; "Cyclin-dependent kinase activity is required for progesterone receptor function: novel role for cyclin A/Cdk2 as a progesterone receptor coactivator", Mol. Cell Biol. 25(1):264-77, 2005.
Narayanan et al.; "Discovery and mechanistic characterization of a novel selective nuclear androgen receptor exporter for the treatment of prostate cancer", Cancer Res. 2010;70:842-51.
Narayanan et al.; "Human Progesterone Receptor Displays Cell Cycle Dependent Changes in Transcriptional Activity", Mol.Cell. Biol. 25(8):2885-98, 2005.
Narayanan et al.; "MicroRNAs are Mediators of Androgen Action in Prostate and Muscle", Plos. One. 5(10), e13637, 2010.
Narayanan et al.; "Selective androgen receptor modulators in preclinical and clinical development", Nuclear Receptor Signaling, 6, e010, 2008.
Narayanan et al.; "Steroidal Androgens and Nonsteroidal, Tissue Selective Androgen Receptor Modulators (SARM) Regulate Androgen Receptor Function Through Distinct Genomic and Non-Genomic Signaling Pathways", Mol. Endocrinol. 22(11), 2448-65, 2008.
Narayanan et al.; "The functional consequences of cross talk between the vitamin D receptor and Erk signaling pathways are retinoid X receptor isoform specific", J. Biol. Chem. 279(45):47298-310, 2004.
Narayanan et al.; "Vector-averaged Gravity-induced Changes in Cell Signaling and Vitamin D Receptor Activity in MG-63 Cells Are Reversed by a 1,25-(OH)2D3 Analog, EB1089", Bone. 31(3), 381-388, 2002.
Narita et al.; "Immunohistochemical expression of androgen receptor and prostate-specific antigen in breast cancer", Folia Histochemica Et Cytobiologica 44:165-172, 2006.
Narita et al.; "Prostate-specific antigen value as a marker in breast cancer", Neoplasma. 2006;53:161-7.
Negro-Vilar (1999) "Selective androgen receptor modulators (SARMs): a novel approach to androgen therapy for the new illennium." J. Clin. Endocrin Metabol. 84: 3459-3462.
Niemeier et.al.; "Androgen receptor in breast cancer: expression in estrogen receptor-positive tumors and in estrogen-negative tumors with apocrine differentiation", Modern Pathology 23:205-212, 2010.
Njelekela et al.; "Obesity and lipid Profiles in Middle Aged Men and Women in Tanzania", East African Medical Journal, Vo. 79 No. 2, Feb. 2002, pp. 58-64.
Oakes et al. The alveolar switch: coordinating the proliferative cues and cell fate decisions that drive the formation of lobuloalveoli from ductal epithelium. Breast Cancer Res. 2006;8(2):207.
Office Action for Japanese Application No. 2014-005551 dated Jan. 27, 2015.
Office Action dated Apr. 13, 2015 for Russian Patent Application No. 2012151846.
Osborne et al. "Mechanisms of endocrine resistance in breast cancer", Annu Rev Med. 2011;62:233-47.
Patani et al. "Bioisosterism: A Rational Approach in Drug Design", Chem. Rev. 1996, 96, 3147-3176.
Patil et al. "Cesium fluoride and tetra-n-butylammonium fluoride mediated 1,4-N—O shift of disubstituted phenyl ring of a bicalutamide derivative" Tetrahedron Letters, 47:3941-3944, Mar. 31, 2006.
Pelleymounter et al., 1995, "Effects of the obese gene product on body weight regulation in ob/ob mice." Science 269:540-543.
Perera et al. "Metabolism of a Novel Selective Androgen Receptor Modulator" PharmSci 5 (4): T3360, 2003.
Perera et al. "Pharmacokinetics of androxolutamide (GTx-007) in beagle dogs" The Endocrine Society, San Francisco, P2-488, Jun. 2002.
Perera et al.; "Pharmacokinetics and Allometric Scaling of Andarine", PharmSci 4(4): 2002.
Peters et al.; "Androgen receptor expression predicts breast cancer survival: the role of genetic and epigenetic events", BMC Cancer. 2012;12:132.
Peters et al.; "Androgen receptor inhibits estrogen receptor-alpha activity and is prognostic in breast cancer", Cancer Res. 2009;69:6131-40.
Peters et al. "Differential effects of exogenous androgen and an androgen receptor antagonist in the peri-and postpubertal murine mammary gland" Endocrinology. Aug. 16, 2011;152(10):3728-37.
Petz et al. Differential regulation of the human progesterone receptor gene through an estrogen response element half site and Sp1 sites. The Journal of steroid biochemistry and molecular biology. Feb. 29, 2004;88(2):113-22.
"Phase 2 study of GTx-024 in women with Metastic Breast Cancer", Clinical trials.gov. 1-15. Jun. 11, 2012 (Jun. 11, 2012), XP002754300, Retrieved from the internet: https://clinicaltrials.gov/archive/NCT01616758/2012_06_11.
Podo et al.; "Triple-negative breast cancer: present challenges and new perspectives", Mol Oncol. 2010;4:209-29.
Rios et al. "In situ identification of bipotent stem cells in the mammary gland" Nature. Feb. 20, 2014;506(7488):322-7.
Rosen et al. Intracellular receptors and signal transducers and activators of transcription superfamilies: novel targets for small-molecule drug discovery. J. Med. Chem., 38: 4855, 1995.
Rosen et al.; "Novel, non-steroidal, selective androgen receptor modulators (SARMs) with anabolic activity in bone and muscle and improved safety profile", J Musculoskel Neuron Interact 2002, 2(3):222-224.
Saudek et al., "A preliminary trial of the programmable implantable medication system for insulin delivery", N. Engl. J. Med. 321:674 (1989).
Sefton, "Implantable Pumps", CRC Crit. Ref. Biomed. Eng. 14:201-240 (1987).
Segal et al. "Therapeutic potential of the SARMs: revisiting the androgen receptor for drug discovery" Expert Opinion in Investigational Drugs. 15(4):377-87, 2006.
Sflomos et al. "A preclinical model for ERα-positive breast cancer points to the epithelial microenvironment as determinant of luminal phenotype and hormone response" Cancer cell. Mar. 14, 2016;29(3):407-22.
Sharifi et al.; "A bifunctional colchicinoid that binds to the androgen receptor" Molecular Cancer Therapeutics, 6(8):2328-2336, 2007.
Silverman, "The Organic Chemistry of Drug Design and Drug Action", Academic Press, 1992, pp. 15-22.

(56) References Cited

OTHER PUBLICATIONS

Singh et al., "Androgens Stimulate Myogenic Differentiation and Inhibit Adipogenesis in C3H 10T1/2 Pluripotent Cells through an Androgen Receptor-Mediated Pathway". Endocrinology, 2003, 144(11): 5081-5088.
Smith et al. "A morphologically distinct candidate for an epithelial stem cell in mouse mammary gland" Journal of cell science. May 1, 1988;90(1):173-83.
Stebbing et al.; "overview of drug development for metastatic breast cancer", Br J Nurs., 2012;21:S18-22.
Steinberger et al., Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320-28 (1977).
Sternlicht et al. "Hormonal and local control of mammary branching morphogenesis" Differentiation. Sep. 1, 2006;74(7):365-81.
Sullivan et al., "Does Androgen Insufficiency Cause Lacrimal Gland Inflammation and Aqueous Tear Deficiency?", IOVS, May 1999, vol. 40, No. 6, pp. 1261-1265.
Sundaram et al., "7 Alpha-Methyl-Nortestosterone (MENT): The Optimal Androgen for Male Contraception", Ann. Med., 25:199-205 (1993).
Supplementary European Search Report for European Application No. 13817231.7 dated Feb. 26, 2016.
Swamydas et al.; "Mesenchymal stem cell-derived CCL-9 and CCL-5 promote mammary tumor cell invasion and the activation of matrix metalloproteinases", Cell adhesion & migration. 2013;7:315-24.
Takagi et al.; "Increased intratumoral androgens in human breast carcinoma following aromatase inhibitor exemestane treatment", Endocrine-related cancer, 2010;17:415-30.
Tarulli et al. "Bringing androgens up a NOTCH in breast cancer" Endocrine-related cancer. Aug. 1, 2014;21(4):T183-202.
Tarulli et al. "Hormone-sensing cells require Wip1 for paracrine stimulation in normal and premalignant mammary epithelium" Breast Cancer Research. Jan. 31, 2013;15(1):R10.
Treat et al., in Liposomes in the Therapy of Infectious Disease and Cancer, Lopez-Berestein and Fidler (eds.), Liss, New York, pp. 363-366 (1989).
Tucker et al "Nonsteroidal antiandrogens. Synthesis and structure-activity relationships of 3-substituted derivatives of 2-hydroxypropionanilides." J. Med Chem (1988), 31, 954-959.
Tucker et al., "Resolution of the Nonsteroidal Antiandrogen—4'-Cyano-3-[(4-fluorophenyl)sulfonyl]-2-hydroxy-2-methyl-3'-(trifluoromethyl)-propionanilide and the Determination of the Absolute Configuration of the Active Enantiomer" J. Med Chem. 1988, 31, pp. 885-887.
Van Keymeulen et al. "Distinct stem cells contribute to mammary gland development and maintenance" Nature. Nov. 10, 2011;479(7372):189-93.
Vippagunta et al., "Crystalline solids", Adv Drug Deliv Rev. May 16, 2001;48(1):3-26.
Wahner, et al (1984) "Assesment of Bone Mineral Part 1" J Nucl. Medicine, 1134-1141.
Wahner, et al (1985) "Bone Mineral Density of the Radius" J. Nucl Medicine 26 13-39.
Wang et al. "Androgen Receptor Mediated Transcriptional Activation of SARMs is Enhanced by Nuclear Receptor Coactivators" The Endocrine Society, Philadelphia, Jun. 2003, Abstract #P2-95.
Watkins, "Cardiovascular disease, hypertension, and lipids", BMJ. Apr. 19, 2003;326(7394):874-6.
World Health Organization Task Force on Methods for the Regulation of Male Fertility, "Contraceptive efficacy of testosterone-induced azoospermia in normal men", The Lancet, vol. 336, Oct. 20, 1990, pp. 955-959and 1517-1518.
World Health Organization Task Force on Methods and Regulation of Male Fertility "Contraceptive Efficacy of Testosterone-Induced Azoospermia and Oligospermia in Normal Men", Fertility & Sterility 65:821-29 (1996).
Wu et al. "Electrospray LC/MS method using single-!on monitoring and a monolithic silica column for quantitation and preclinical pharmacokinetics of a novel selective androgen receptor modulator (SARM) in rats" American Society of Mass Spectrometry, Montreal, Canada, Jun. 2003.
Wu et al. "Favorable Effects of Weak Acids on Negative-Ion Electrospray Mass Spectrometry" Analytical Chemistry, 76(3):839-847, 2004.
Wu et al. "Peptide mapping of the human androgen receptor ligand-binding domain using mass spectrometry" American Society of Mass Spectrometry, Montreal, Canada, Jun. 2003.
Wu et al. "Pharmacokinetics and metabolism of a selective androgen receptor modulator (SARM) in rats—implication of molecular properties and intensive metabolic profile to investigate ideal pharmacokinetic characteristics of a propanamide in preclinical study" Drug Metabolism and Disposition, 34(3):483-494, 2006.
Wu et al. "Pharmacokinetics of a selective androgen receptor modulator (SARM), S-I, in rats" PharmSci 5 (4): W5267, 2003.
Wu et al. "Urinary Metabolites of S-I, A Novel Selective Androgen Receptor Modulator (SARM), in Rats" The AAPS Journal, vol. 6, No. 4, Abstract #W5300, Nov. 2004.
Wu, "Effects of Testosterone Enanthate in Normal Men: Experience From a Multicenter Contraceptive Efficacy Study," Fertility and Sterility 65:626-36 (1996).
Wu, "Male Contraception: Current Status and Future Prospects", Clinical Endocrinology, (1988), 29, pp. 443-465.
Wuidart et al. "Quantitative lineage tracing strategies to resolve multipotency in tissue-specific stem cells" Genes & development. Jun. 1, 2016;30(11):1261-77.
Xie et al. "Dissecting cell-type-specific roles of androgen receptor in prostate homeostasis and regeneration through lineage tracing" Nature Communications. 2017;8.
Xu et al.; "Pharmacodynamics of Electrophilic Androgen Receptor Ligands in Prostate Cancer Cell Lines", PharmSci 4(4): 2002.
Xu et al. "In Vitro and In Vivo Anticancer Activity of S-NTBA for Prostate Cancer" PharmSci 5 (4): T2378, 2003.
Yalcin-Ozuysal et al. "Antagonistic roles of Notch and p63 in controlling mammary epithelial cell fates" Cell Death & Differentiation. Oct. 1, 2010;17(10):1600-12.
Yang et al. "Preclinical pharmacology of a nonsteroidal ligand for androgen receptor mediated imaging of prostate cancer" Journal of Pharmacology and Experimental Therapeutics, 317(1):402-408, Jan. 20, 2006.
Yang et al.; "IFN induces miR-21 through a signal transducer and activator of transcription 3-dependent pathway as a suppressive negative feedback on IFN-induced apoptosis", Cancer Res. 2010;70:8108-16.
Yepuru et al.; "Estrogen Receptor-β Selective Ligand Alleviates High Fat Diet- and Ovariectomy-Induced Obesity", J. Biol. Chem. 285(41), 31292-303, 2010.
Yepuru et al.; "Steroidogenic Enzyme AKR1C3 is a Novel Androgen Receptor-Selective Coactivator that Promotes Prostate Cancer Growth", Clinical cancer research: an official journal of the American Association for Cancer Research, 2013.
Yepuru, et al "An Angrogen Receptor-b Specific Selective Estrogen Receptor Modulator (SERM) Inhibits the Growth of the Prostate Cancer Cells and Stromal-Epithilial Tumor Xenograft." The Endocrine Society—Programs and Abstracts—89th Annual Meeting—Paper OR6-3.
Yin D, et al "Pharmacodynamics of Selective Androgen Receptor Modulators." Journal of Pharmacology and Experimental Therapeutics, 304(3):1334-1340, 2003.
Yin et al "Key Structural Features of Nonsteroidal Ligands for Binding and Activation of the Androgen Receptor." Molecular Pharmacology, 63:211-223, 2003.
Yin et al. "In Vitro Pharmacology and In Vivo Pharmacokinetics of® Para-Acetamido-Bicalutamide" PharmSci, 1(4):S3185, 1999.
Yin et al. "Metabolism of (R)-Para-Acetamido Bicalutamide in Rats" PharmSci 2(4):2000.
Yin et al. "Pharmacology, Pharmacokinetics and Metabolism of Acetothiolutamide, A Novel Nonsteroidal Agonist for the Androgen Receptor" Journal of Pharmacology and Experimental Therapeutics, 304(3):1323-1333, 2003.

(56) References Cited

OTHER PUBLICATIONS

Zhi et al.; "Switching androgen receptor antagonists to agonists by modifying C-ring substituents on piperidino[3,2-g]quinolone", Bioorg. Med. Chem. Lett., 9: 1009, 1999.

Zhou, et al., "Specificity of ligand-dependent androgen receptor stabilization: receptor domain interactions influce ligand dissociation and receptor stability", Molec. Endocrinol. 9:208-18 (1995).

Zilbermint et al., "Nonsteroidal selective androgen receptor modulator Ostarine in cancer cachexia", Future Oncol. (2009) 5(8) pp. 1211-1220.

Fuqua, et al; "Estrogen Receptor (ER) Mutations in Breast Cancer: Hidden in Plain Sight", Breast Cancer Res Treat. Feb. 2014; 144(1): pp. 1-17.

Bach, et al, "Prevention of Pulmonary Morbidity for Patients with Duchenne Muscular Dystrophy", Chest 1997; vol. 112: 1024-1028.

Aleskandarany M., et al., "Clinicopathologic and molecular significance of phospho-Akt expression in early invasive breast cancer"; Breast Cancer Res Treat. Jun. 2011; vol. 127, 407-16.

Sergeev P.V., Short course in molecular pharmacology, Moscow, 1975, p. 10.

Official Action dated Jul. 11, 2019 in respect of corresponding Russian Application No. 2017141776.

Official Action dated Sep. 25, 2018 in respect of corresponding Russian Application No. 2017141776.

Office Action dated Apr. 9, 2019 in respect of corresponding Mexican Application No. MX/a/2015/000572.

Notice of Allowance dated Aug. 22, 2018 in respect of corresponding Korean Application No. 10-2016-7030518.

Official Action dated Sep. 8, 2017 in respect of corresponding Japanese Application No. 2017-046924.

* cited by examiner

Figure 1A
Figure 1B
| IC$_{50}$ in AR positive cells | | |
|---|---|---|
| | Virus (µL) | IC$_{50}$ (nM) |
| DHT | 200 | 0.8 |
| | 500 | 0.7 |
| Formula IX | 200 | 32 |
| | 500 | 14 |
Figure 1C
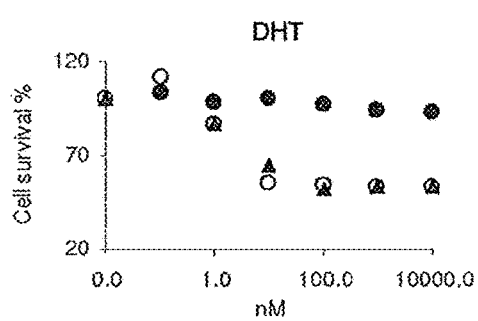
Figure 1D
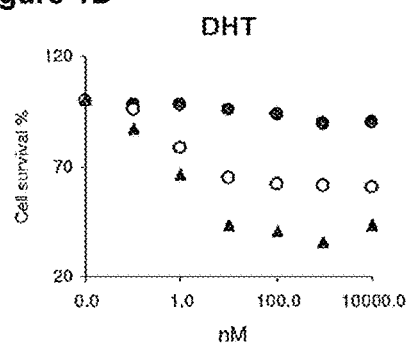
Figure 1E
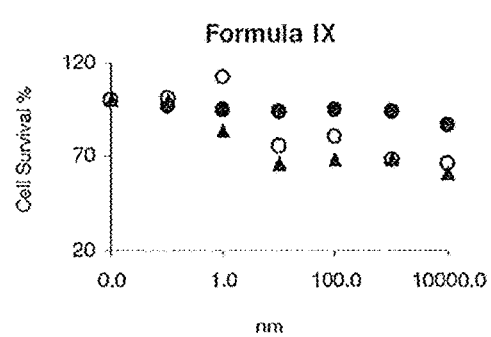
Figure 1F
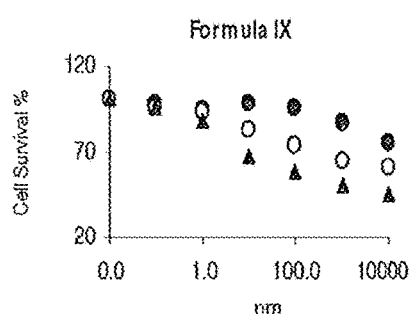
Figure 1G
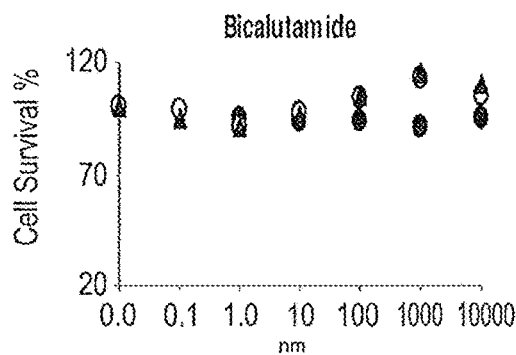
Figure 1H
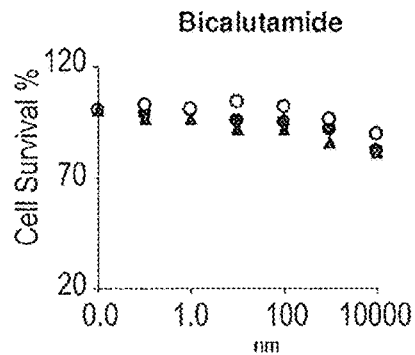

Figure 1I
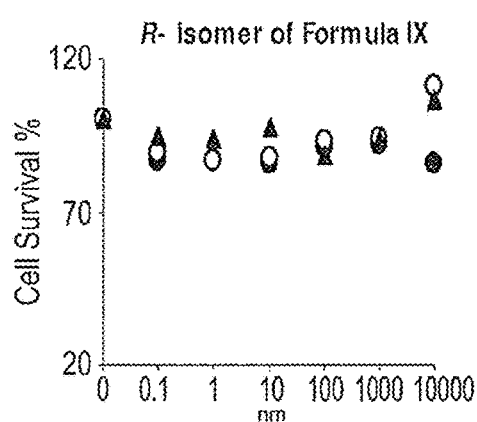
Figure 1J
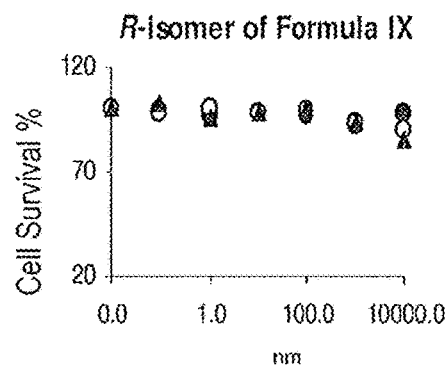
Figure 2A
Figure 2B
| IC$_{50}$ in AR positive cells | | |
|---|---|---|
| | Virus (µL) | IC$_{50}$ (nM) |
| DHT | 200 | 0.9 |
| | 500 | 1.3 |
| Formula IX | 200 | 637 |
| | 500 | 34 |
Figure 2C
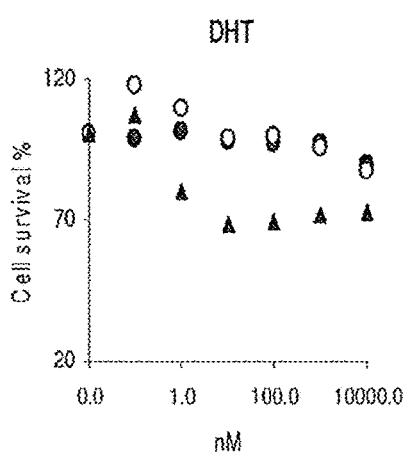
Figure 2D
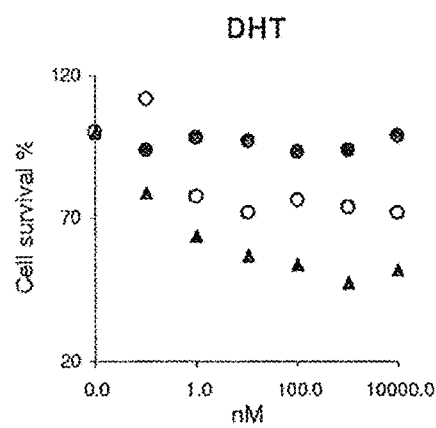

Figure 3A
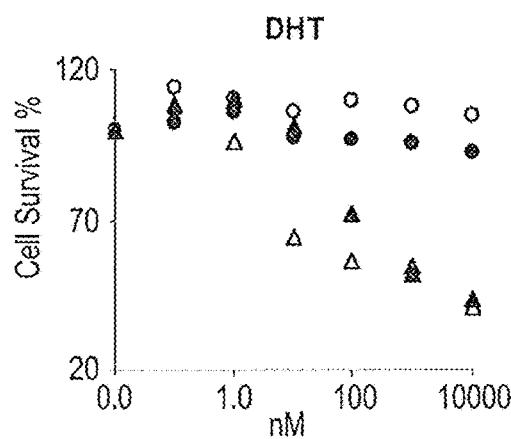
Figure 3B
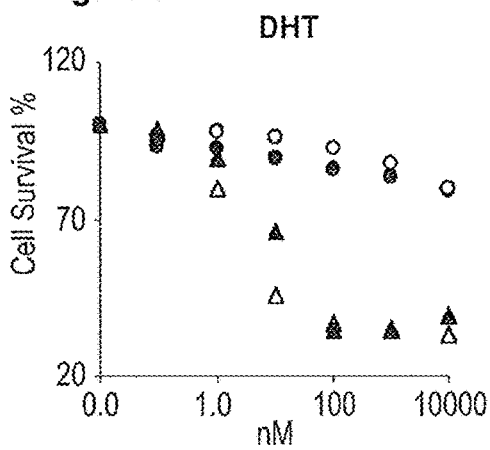
Figure 3C
Figure 3D
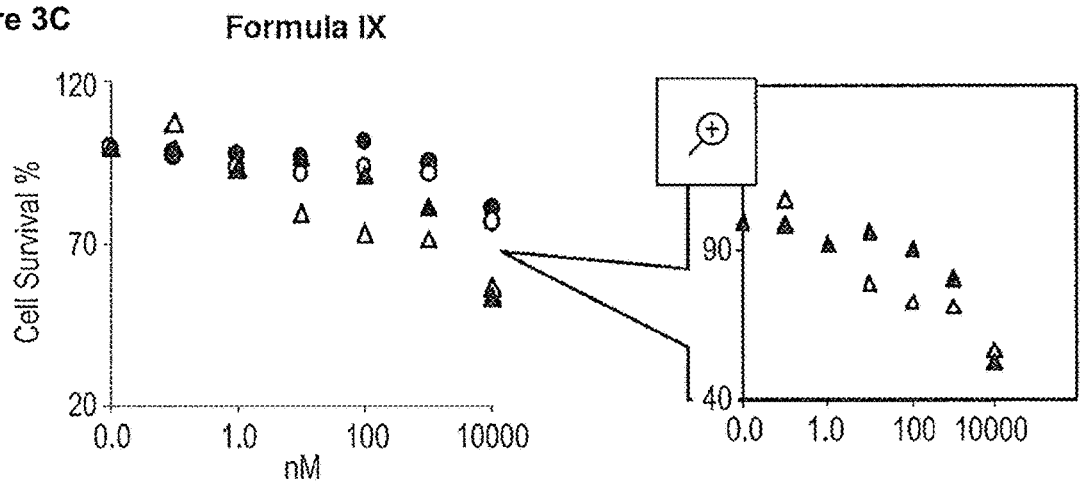
Figure 3E
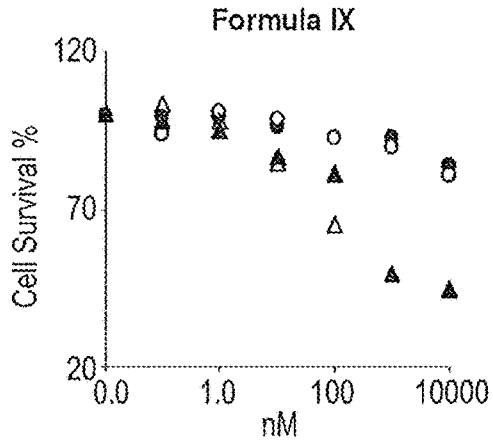
IC$_{50}$ in AR positive cells
| Compound | Pretreatment | IC$_{50}$ (nM) |
|---|---|---|
| DHT | 10 µM Bical | 9 |
|  | - | 2 |
| Formula IX | 10 µM Bical | 213 |
|  | - | 40 |

Figure 4Q

IC$_{50}$ values (nM)

| | Activity | | Cell growth | | |
|---|---|---|---|---|---|
| | EC$_{50}$ | IC$_{50}$ | Trial 1 | Trial 2 | Mean ± SD |
| DHT | 0.2 | | 1.2 | 1.0 | 1 ± 0.1 |
| Formula X | 9 | | 566 | 407 | 486 ± 113 |
| Formula IX | 1 | | 88 | 65 | 77 ± 16 |
| Formula XIV | | | | | |
| Formula XIV | 5 | | 184 | 85 | 134 ± 70 |
| Formula XIII | 1 | | 61 | 94 | 77 ± 23 |
| Formula VIII | 2 | | 77 | 86 | 81 ± 6 |
| Bicalutamide | | 22.4 | | | |

BR-0001 TNBC

BR-0001 TNBC

AR negative TNBC

Experiment 1

Experiment 2

Vehicle

Formula IX

Z-Score

| | | | |
|---|---|---|---|
| MYBL2 | 10.786 | FOXC1 | 8.200 |
| FOXA1 | 6.225 | MMP11 | 6.886 |
| UBE2T | 8.864 | BCL2 | 6.359 |
| MELK | 8.990 | UBE2C | 9.551 |
| NUF2 | 8.425 | EXO1 | 8.743 |
| CCNB1 | 8.232 | MLPH | 6.786 |
| CDC6 | 7.750 | SFRP1 | 6.524 |
| TYMS | 10.085 | BLVRA | 7.044 |
| MDM2 | 7.874 | EGFR | 7.281 |
| CEP55 | 9.049 | ERBB2 | 7.210 |
| PTTG1 | 7.217 | FGFR4 | 7.513 |
| NDC80 | 9.503 | MAPT | 7.305 |
| CENPF | 9.237 | CDH3 | 7.010 |
| SLC39A6 | 9.076 | KRT14 | 6.149 |
| MKI67 | 10.185 | KRT5 | 5.658 |
| CCNE1 | 9.170 | CXXC5 | 8.983 |
| CDC20 | 10.919 | PGR | 5.765 |
| ANLN | 10.149 | TMEM45B | 6.581 |
| RRM2 | 8.969 | GPR160 | 5.583 |
| ACTR3B | 7.099 | GRB7 | 5.739 |
| KIF2C | 8.531 | ORC6 | 7.284 |
| PHGDH | 9.006 | SLC35A5 | 8.264 |
| ESR1 | 6.174 | VPS29 | 7.608 |
| MYC | 9.153 | SNX16 | 8.043 |
| KRT17 | 6.872 | TMLHE | 9.121 |

| Bonferroni's Multiple Comparison Test | Mean Diff. | t | Significant P <0.05 | 95% CI of diff |
|---|---|---|---|---|
| BL1 vs LAR | -0.2479 | 3.532 | Yes | -0.4539 to -0.04183 |
| BL2 vs LAR | -0.524 | 5.999 | Yes | -0.7804 to -0.2675 |
| IM vs LAR | -0.6731 | 11.27 | Yes | -0.8484 to -0.4977 |
| LAR vs M | 0.5733 | 8.817 | Yes | 0.3823 to 0.7642 |
| LAR vs MSL | -0.01136 | 0.2499 | No | -0.1449 to 0.1222 |

ER positive

PR positive

Her2 positive

AR positive

ER positive

PR positive

HER2 positive

AR positive

HCI-13 PDX growth is not dependent on circulating estrogens

| I.D. | HCI-13 | 2005 | 1075 | 1074 | 1073 | 1053 | 1050 | 1045 | 1005 |
|---|---|---|---|---|---|---|---|---|---|
| AR | 1 | 0.002 | 0.03 | 0.05 | 0.05 | 0.05 | 0.02 | 0.2 | 0.02 |
| ER | 1 | 0.0001 | 0.08 | 0.01 | 0.04 | 0.03 | 0.01 | 0.4 | 0.009 |

| Canonical pathway | P-Value | Upstream regulator | P-Value | Diseases | P-Value |
|---|---|---|---|---|---|
| Glutamyl cycle | 4.45E-04 | ESR1 | 6.66E-11 | Mammary tumor | 1.02E-12 |
| Tocopherol degradation | 1.92E-03 | NUPR1 | 1.78E-07 | Breast cancer | 1.65E-12 |
| Glutathione-detox | 2.13E-03 | AR | 2.83E-07 | Breast/ovarian cancer | 4.09E-10 |
| Aryl H receptor signal | 2.43E-03 | E2F3 | 3.26E-07 | Carcinoma of breast | 2.31E-08 |
| Unfold protein response | 2.76E-03 | CTR9 | 5.67E-07 | Bening neoplasm | 1.96E-06 |

Each of the plots above is graphed from -2.0 to 2.0 kb as annotated for the far left plot.
The intensity legend along the right border above is labeled 0.0-1.4 in increments of 0.2.

Down-regulated sites     Enriched sites

Up-Regulated Motifs (ER)

SEQ ID NO: 1
ARE (1e-69)

SEQ ID NO: 2
GRE (1e-58)

SEQ ID NO: 3
FOXA1 (1e-38)

Down-Regulated Motifs (ER)

SEQ ID NO: 4
ERE (1e-87)

SEQ ID NO: 5
FOXA1 (1e-30)

SEQUENCE LISTING

<160> NUMBER OF SEQ ID NOS: 5

<210> SEQ ID NO 1
<211> LENGTH: 16
<212> TYPE: DNA
<213> ORGANISM: Artificial Sequence
<220> FEATURE:
<223> OTHER INFORMATION: response element motif

```
<220> FEATURE:
<221> NAME/KEY: misc_feature
<222> LOCATION: (1)..(1)
<223> OTHER INFORMATION: n is a, g, or t
<220> FEATURE:
<221> NAME/KEY: misc_feature
<222> LOCATION: (2)..(2)
<223> OTHER INFORMATION: n is a, or g
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, g, or t
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, or t
<220> FEATURE:
<221> NAME/KEY: misc_feature
<222> LOCATION: (12)..(12)
<223> OTHER INFORMATION: n is a, c, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (14)..(14)
<223> OTHER INFORMATION: n is c, or t
<220> FEATURE:
<221> NAME/KEY: misc_feature
<222> LOCATION: (15)..(15)
<223> OTHER INFORMATION: n is a, c, or t
<220> FEATURE:
<221> NAME/KEY: misc_feature
<222> LOCATION: (16)..(16)
<223> OTHER INFORMATION: n is a, c, g, or t

<400> SEQUENCE: 1
nnnncnnnnn gnnnnn                                                     16

<210> SEQ ID NO 2
<211> LENGTH: 15
<212> TYPE: DNA
<213> ORGANISM: Artificial Sequence
<220> FEATURE:
<223> OTHER INFORMATION: response element motif
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (2)..(2)
<223> OTHER INFORMATION: n is a, g, or t
<220> FEATURE:
<221> NAME/KEY: misc_feature
<222> LOCATION: (3)..(3)
<223> OTHER INFORMATION: n is a, or g
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, g, or t
<220> FEATURE:
<221> NAME/KEY: misc_feature
<222> LOCATION: (8)..(8)
```

```
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, or t
<220> FEATURE:
<221> NAME/KEY: misc_feature
<222> LOCATION: (13)..(13)
<223> OTHER INFORMATION: n is a, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, or t

<400> SEQUENCE: 2
nnnnacnnnn ngnnn                                                     15

<210> SEQ ID NO 3
<211> LENGTH: 10
<212> TYPE: DNA
<213> ORGANISM: Artificial Sequence
<220> FEATURE:
<223> OTHER INFORMATION: response element motif
<220> FEATURE:
<221> NAME/KEY: misc_feature
<222> LOCATION: (1)..(1)
<223> OTHER INFORMATION: n is a, or t
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(3)
<223> OTHER INFORMATION: n is a, g, or t
<220> FEATURE:
<221> NAME/KEY: misc_feature
<222> LOCATION: (4)..(4)
<223> OTHER INFORMATION: n is a, or g
<220> FEATURE:
<221> NAME/KEY: misc_feature
<222> LOCATION: (5)..(5)
<223> OTHER INFORMATION: n is c, or t
<220> FEATURE:
<221> NAME/KEY: misc_feature
<222> LOCATION: (6)..(6)
<223> OTHER INFORMATION: n is a, or c
<220> FEATURE:
<221> NAME/KEY: misc_feature
<222> LOCATION: (7)..(7)
<223> OTHER INFORMATION: n is a, or c
<220> FEATURE:
<221> NAME/KEY: misc_feature
<222> LOCATION: (9)..(9)
<223> OTHER INFORMATION: n is c, or t

<400> SEQUENCE: 3 nnnnnnnana                                                           10

<210> SEQ ID NO 4
<211> LENGTH: 15
<212> TYPE: DNA
<213> ORGANISM: Artificial Sequence
```

-continued

```
<220> FEATURE:
<223> OTHER INFORMATION: response element motif
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (2)..(2)
<223> OTHER INFORMATION: n is a, g, or t
<220> FEATURE:
<221> NAME/KEY: misc_feature
<222> LOCATION: (3)..(3)
<223> OTHER INFORMATION: n is a, g, or t
<220> FEATURE:
<221> NAME/KEY: misc_feature
<222> LOCATION: (4)..(4)
<223> OTHER INFORMATION: n is a, or g
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (6)..(6)
<223> OTHER INFORMATION: n is c, g, or t
<220> FEATURE:
<221> NAME/KEY: misc_feature
<222> LOCATION: (7)..(7)
<223> OTHER INFORMATION: n is a, or t
<220> FEATURE:
<221> NAME/KEY: misc_feature
<222> LOCATION: (8)..(10)
<223> OTHER INFORMATION: n is a, c, g, or t
<220> FEATURE:
<221> NAME/KEY: misc_feature
<222> LOCATION: (11)..(11)
<223> OTHER INFORMATION: n is a, or t
<220> FEATURE:
<221> NAME/KEY: misc_feature
<222> LOCATION: (12)..(12)
<223> OTHER INFORMATION: n is a, or g
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, or t

<400> SEQUENCE: 4 nnnnnnnnn nnnnn                                                15

<210> SEQ ID NO 5
<211> LENGTH: 10
<212> TYPE: DNA
<213> ORGANISM: Artificial Sequence
<220> FEATURE:
<223> OTHER INFORMATION: response element motif
<220> FEATURE:
<221> NAME/KEY: misc_feature
<222> LOCATION: (1)..(1)
<223> OTHER INFORMATION: n is a, or t
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (3)..(3)
<223> OTHER INFORMATION: n is a, g, or t
<220> FEATURE:
```

```
<221> NAME/KEY: misc_feature
<222> LOCATION: (4)..(4)
<223> OTHER INFORMATION: n is a, or g
<220> FEATURE:
<221> NAME/KEY: misc_feature
<222> LOCATION: (5)..(5)
<223> OTHER INFORMATION: n is c, or t
<220> FEATURE:
<221> NAME/KEY: misc_feature
<222> LOCATION: (6)..(6)
<223> OTHER INFORMATION: n is a, or c
<220> FEATURE:
<221> NAME/KEY: misc_feature
<222> LOCATION: (7)..(7)
<223> OTHER INFORMATION: n is a, or c
<220> FEATURE:
<221> NAME/KEY: misc_feature
<222> LOCATION: (9)..(9)
<223> OTHER INFORMATION: n is c, or t

<400> SEQUENCE: 5 nnnnnnnana                                                              10
```

METHOD OF TREATING ER MUTANT EXPRESSING BREAST CANCERS WITH SELECTIVE ANDROGEN RECEPTOR MODULATORS (SARMS)

CROSS REFERENCE TO RELATED APPLICATIONS

This Application is a Continuation-In-Part of U.S. patent application Ser. No. 15/371,104, filed Dec. 6, 2016; which is a Continuation-In-Part of U.S. patent application Ser. No. 15/075,373, filed Mar. 21, 2016; which is a Continuation-In-Part of U.S. patent application Ser. No. 14/798,208, filed Jul. 13, 2015, now U.S. Pat. No. 9,744,149; which is a Continuation-In-Part of U.S. patent application Ser. No. 14/293,632, filed Jun. 2, 2014, now U.S. Pat. No. 9,622,992; which is a Continuation-In-Part of U.S. patent application Ser. No. 13/953,492, filed Jul. 29, 2013, now U.S. Pat. No. 9,969,683; which is a Continuation-In-Part of U.S. patent application Ser. No. 13/789,005, filed Mar. 7, 2013, now U.S. Pat. No. 9,604,916; which claims the benefit of U.S. Provisional Ser. No. 61/671,366, filed Jul. 13, 2012 and the benefit of U.S. Provisional Ser. No. 61/726,274, filed Nov. 14, 2012, which are all incorporated in their entirety herein by reference.

FIELD OF INVENTION

This invention relates to the treatment of androgen receptor-positive breast cancer in a subject, for example a female subject. Accordingly, this invention provides methods of: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of estrogen receptor (ER), progesterone receptor (PR), and/or human epidermal growth factor receptor 2 (HER2); i) treating a subject suffering from triple negative breast cancer (TNBC); j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP) bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, comprising administering to the subject a therapeutically effective amount of a selective androgen receptor modulator (SARM) compound.

BACKGROUND OF THE INVENTION

Breast cancer is a disease that kills over 45,000 women each year in the United States alone. Over 180,000 new cases of breast cancer are diagnosed annually, and it is estimated that one in eight women will develop breast cancer. These numbers indicate that breast cancer is one of the most dangerous diseases facing women today. Cancer research has been unable to determine the cause of breast cancer, and has not found a suitable method of therapy or prevention.

Genotyping has long been used to screen women who may be genetically predisposed to developing breast cancer. It is another diagnostic or prognostic tool that can be used to determine the availability of therapies. Certain women are predisposed to develop breast cancer based on the presence of germline (i.e., inherited) mutations in the breast cancer susceptibility genes (BRCA) type 1 (BRCA1) or BRCA2. A couple of SERMs, tamoxifen in 1999 and raloxifene in 2007, were approved for the primary prevention of breast cancer in patient populations that are high risk based on family history and/or genotype considerations. However, hysterectomy or prophylactic mastectomy was often considered in these patients as a more definite preventative. In 2018, olaparib (Lynparza), an inhibitor of the enzyme poly ADP ribose polymerase (PARP), was approved for metastatic ER-positive and HER2-negative breast cancer patients with certain inherited BRCA mutations who have received chemotherapy (and hormone therapy if ER-positive).

The standard of care currently includes screening the tumor for the expression levels of the hormone receptors, estrogen receptor (ER) and progesterone receptor (PR), and the human epidermal growth factor receptor 2 (HER2) kinase. Currently, a woman diagnosed with breast cancer may be treated preliminarily with surgery, chemotherapy (optional in some cases), and radiation before targeted therapy is initiated. Hormone receptor-positive breast cancers are susceptible to hormone therapies (also referred to as endocrine therapies) with selective estrogen receptor modulators or SERMs (e.g., tamoxifen, toremifene, raloxifene), aromatase inhibitors (e.g., anastrozole), or selective estrogen receptor degraders or SERDs (e.g., fulvestrant). Hormone therapies such as gonadotropin-releasing hormone (GnRH) agonists (typically used in pre- and peri-menopausal women) and aromatase inhibitors (AI) (typically used in post-menopausal women or together with GnRH agonists in pre- or peri-menopausal women) block production of estrogens in the body, whereas SERMs and SERDs block the proliferative action of estrogens on the breast cancer cells. While the prognosis of most early stage ER-positive breast cancer patients is relatively good compared to non-hormonal cancers, adjuvant hormone therapy failures do occur resulting in recurrence, including distant metastases (i.e, advanced breast cancer). Metastatic or advanced breast cancer, whether hormone naïve or progressive despite endocrine therapy, is often still ER-positive and still dependent on the ER axis for growth. The treatment of advanced breast cancer is rapidly evolving from the use of an endocrine monotherapy such as SERM or AI or fulvestrant, to combinations of an endocrine therapy with recently approved kinase inhibitors, including the cyclin-dependent kinase 4/6 (CDK4/6) inhibitors (palbociclib (approved 2015), ribociclib (approved 2017), or abemaciclib (approved 2017)), or mechanistic target of rapamycin (mTOR) inhibitor (everolimus (approved 2012)). These combination therapies delay progression of advanced breast cancer compared to endocrine therapy alone and are supplanting the use of endocrine therapy alone in late breast cancer.

Herein, we propose the use of tumor genotyping (deep DNA sequencing) as a means to determine the mutation status of the estrogen receptor in a breast cancer patient as basis for rational selection of therapies. Certain common mutations of the estrogen receptor alpha can be treatment emergent and confer resistance to the approved endocrine therapies even when combined with various kinase therapies as discussed above. We have discovered at least one mutation (e.g. Y537S) described herein which despite SERM, AI, and fulvestrant resistance is still sensitive to the androgen agonists of this invention. Consequently, even late stage ER-positive AR-positive breast cancer patients which have been exposed to the full endocrine- and directed-therapy milieu may still have further hormonal treatment options before being relegated to chemotherapies. If screening reveals certain ER mutants then their treatment can be personalized to include the use of SARMs to delay progression of the disease and/or regress tumors.

HER2-positive breast cancers are susceptible to HER2 kinase inhibitors (e.g., trastuzumab, lapatinib, and neratinib) and are generally used in metastatic disease. Anti-angiogenic therapy (bevacizumab) was also approved in metastatic disease, but the FDA removed this for bevacizumab in 2011. Despite these multiple tiers of targeted treatments, patients often have or develop refractory forms of breast cancer. Examples of refractory breast cancer include primary tumors which are triple-negative (lacking ER, PR, HER2), hormone resistant (SERM-, SERD-, or AI-resistant), or kinase inhibitor resistant (e.g., inhibitors of CDK 4/6, mTor, and/or HER2), or metastatic breast cancer tumors. Once the all the targeted therapies fail e.g., metastatic tumors are re-activated or tumors further metastasize, radiation and high dose chemotherapy are required to ablate the refractory breast cancer tumors. Current chemotherapies available for the treatment of refractory breast cancer include anthracyclines, taxanes, and epothilones, which are toxic, dangerous, costly, and often are ineffective, especially in the treatment of metastatic disease.

Abundant clinical evidence suggests that androgens normally inhibit breast growth. For instance, women with androgen deficits have an increased risk for developing breast cancer. Androgen signaling plays a crucial role in breast homeostasis, negating the proliferative effects of estrogen signaling in the breast. However, when steroidal androgens biotransform into estrogens (via aromatase pathway), they increase cell proliferation and mammary carcinogenesis risk. Historically, the steroidal androgen receptor agonists testosterone, fluoxymesterone, and calusterone were used in advanced breast cancer. These agents suffered from side effects such as excessive virilization, cross-reactivity with the estrogen receptor, and aromatization to estrogens. The use of steroidal androgens in advanced breast cancer pre-dates the screening of breast cancers for hormone and kinase receptors. Recently, it was found that the AR is expressed in 50-90% of breast tumors, providing a mechanism to use androgens as targeted therapy for AR-positive breast cancers.

Although the majority of breast cancers are considered hormone receptor-positive (ER, PR, or HER2), 15-20% of women diagnosed with breast cancer will have Triple Negative Breast Cancer (TNBC) which is characterized by a lack of expression of ER, PR, or HER2. TNBC occurs more frequently in younger patients (<50 years of age) and generally shows a more aggressive behavior. For those patients with advanced TNBC, standard palliative treatment options are limited to cytotoxic chemotherapy. However, even after initial response to chemotherapy, the duration of the response may be short and there is a higher likelihood of visceral metastases, rapidly progressive disease, and inferior survival compared to hormone receptor positive breast cancer. Therefore, research is focused on identifying therapeutic targets in TNBC. One such target is the androgen receptor (AR). The AR is the most highly expressed steroid receptor in breast cancer with up to 95% of ER-positive breast cancers expressing AR (see Example 9 infra). In TNBC, up to 30% of cancers may express AR. Historically, AR has been considered anti-proliferative and beneficial in hormone receptor positive breast cancers. In TNBC, data demonstrates that the presence of AR and androgen synthesizing enzymes is associated with lower proliferation, lower tumor grade, better overall survival, and more favorable clinical outcomes as compared to those patients with TNBC not expressing AR. Evidence also suggests that the AR target gene prostate specific antigen (PSA) is a favorable prognostic marker in breast cancer (not just TNBC). Based on these findings, research is focused on AR as a potential therapeutic target.

Prolonged treatment of cancers with estrogen synthesis inhibitors (AI or GnRH agonists) or ER antagonists (SERMs or SERDs) results in mutations in the target protein and activation of resistance pathways. For example, continued treatment of ER-positive breast cancers with ER antagonists or aromatase inhibitors (AI) results in resistance due to mutations in the ER ligand binding domain (LBD). Clinical studies have estimated that over 30% of breast cancers treated with tamoxifen become refractory and recur as a resistant cancer and over 40% of recurrent breast cancers express mutated ER. Treatment emergent mutant ERs have escaped inhibition of the hormonal axis fail to respond to endocrine therapy and, consequently, these patients will need to be treated with chemotherapeutic agents. Such cancers require new non- or less-toxic effective endocrine therapies. One possibility is the pharmacogenomic screening of tumors or circulating tumor cells for the present of mutant ERs that would confer resistance to current endocrine therapies. This could be done upon molecular phenotyping as ER-positive (i.e., early disease) or, alternatively, in patients that have failed endocrine therapies (i.e, late disease) such as SERM, AI, SERD and/or GnRH agonist whether or not combined with CDK 4/6 or mTor inhibitors.

Selective androgen receptor modulators (SARMs) are compounds which demonstrate AR-mediated tissue selective activity. Unlike their steroidal precursors, SARMs are non-aromatizable, generally demonstrate no activity at other steroidal receptors including ER and PR, and are non-virilizing. Further, SARMs may be beneficial in refractory breast cancer patients due to their hypermyoanabolic effects that should improve their tolerance of high-dose chemotherapy. Further, SARMs have beneficial osteoblastic and anti-osteoclastic effects in bones that may decrease the risk of metastasis to the bones or may decrease risk of osteoporosis during endocrine and/or chemotherapies.

New innovative approaches are urgently needed at both the basic science and clinical levels to develop compounds which are useful for: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; and/or p) prolonging progression-free survival of a subject with breast cancer; q) treating, preventing, suppressing or inhibiting AR-positive triple negative breast cancer; r) treating a subject suffering from HER2-positive breast cancer; s) treating a subject suffering from ER mutant expressing breast cancer, and/or t) treating a subject suffering from Y537S ER mutant expressing breast cancer.

SUMMARY OF THE INVENTION

In one embodiment, this invention is directed to a method of treating a subject suffering from ER mutant expressing breast cancer, comprising the step of administering to said subject a selective androgen receptor modulator (SARM) compound represented by a structure of Formula I:

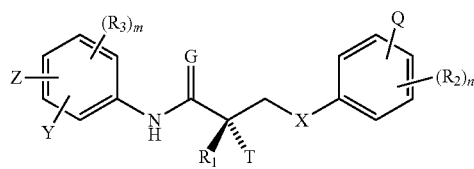

I

X is a bond, O, CH$_2$, NH, S, Se, PR, NO or NR;

G is O or S;

T is OH, OR, —NHCOCH$_3$, or NHCOR;

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;

R$_1$ is CH$_3$, CH$_2$F, CHF$_2$, CF$_3$, CH$_2$CH$_3$, or CF$_2$CF$_3$;

R$_2$ is H, F, Cl, Br, I, CH$_3$, CF$_3$, OH, CN, NO$_2$, NHCOCH$_3$, NHCOCF$_3$, NHCOR, alkyl, arylalkyl, OR, NH$_2$, NHR, N(R)$_2$, or SR;

R$_3$ is H, F, Cl, Br, I, CN, NO$_2$, COR, COOH, CONHR, CF$_3$, Sn(R)$_3$, or R$_3$ together with the benzene ring to which it is attached forms a fused ring system represented by the structure:

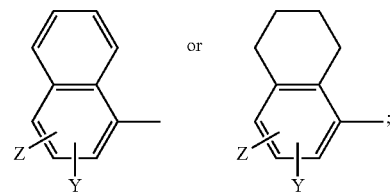

Z is NO$_2$, CN, COR, COOH, or CONHR;

Y is CF$_3$, F, Br, Cl, I, CN, or Sn(R)$_3$;

Q is CN, alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;

or Q together with the benzene ring to which it is attached is a fused ring system represented by structure A, B or C:

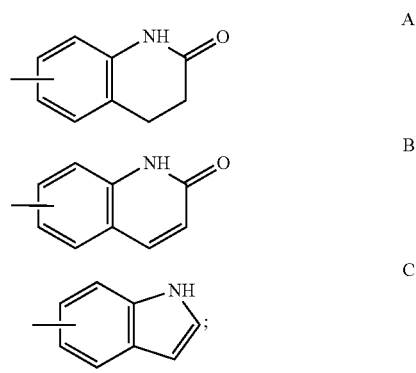

n is an integer of 1-4; and m is an integer of 1-3.

In another embodiment, the SARM compound is represented by a structure of Formula XIII:

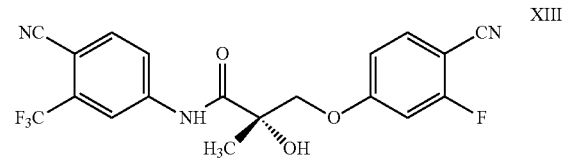 [SMILES: C[C@](O)(COc1ccc(C#N)c(F)c1)C(=O)Nc1ccc(C#N)c(C(F)(F)F)c1]

XIII or Formula XIV:

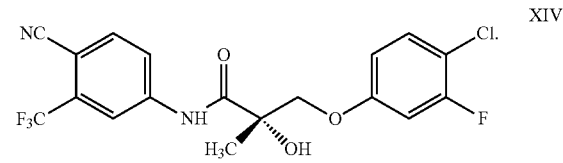

XIV

In another embodiment, the SARM compound is represented by a structure of Formula II:

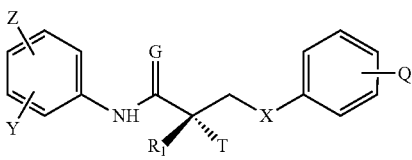

wherein X is a bond, O, CH$_2$, NH, Se, PR, or NR;
G is O or S;
T is OH, OR, —NHCOCH$_3$, or NHCOR;
Z is NO$_2$, CN, COR, COOH or CONHR;
Y is I, CF$_3$, Br, Cl, or Sn(R)$_3$;
Q is CN, alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;
or Q together with the benzene ring to which it is attached is a fused ring system represented by structure A, B or C:

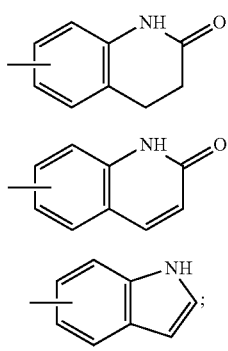

R is a C$_1$-C$_4$ alkyl, aryl, phenyl, alkenyl, hydroxyl, a C$_1$-C$_4$ haloalkyl, halogen, or haloalkenyl; and
R$_1$ is CH$_3$, CF$_3$, CH$_2$CH$_3$, or CF$_2$CF$_3$.
In another embodiment, said SARM compound is represented by a structure of Formula:

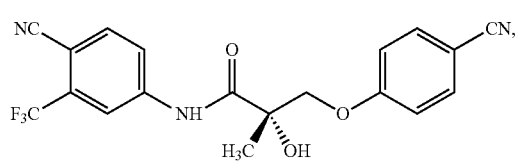

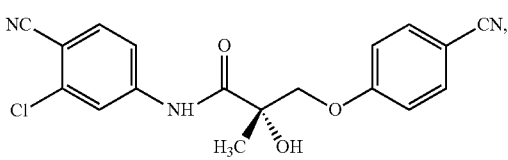

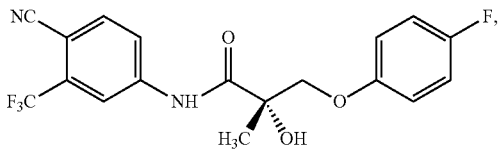

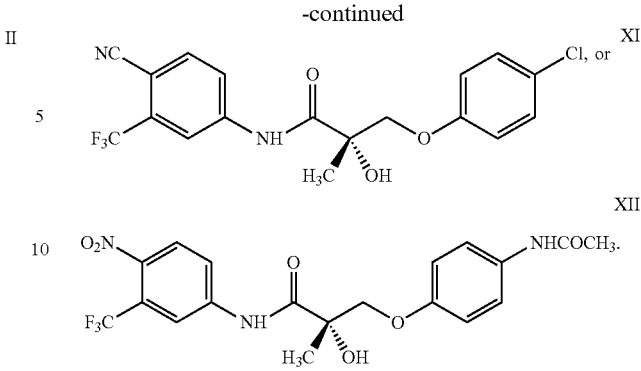

In one embodiment, the ER mutant expressing breast cancer is Y537S mutation expressing breast cancer.

In another embodiment, the method of this invention comprises administering an isomer, a racemic mixture containing a SARM compound of this invention, a metabolite, pharmaceutically acceptable salt, pharmaceutical product, hydrate, N-oxide, or crystal of said selective androgen receptor modulator, or any combination thereof.

In another embodiment, said administering comprises intravenously, intraarterially, or intramuscularly injecting to said subject said pharmaceutical product in liquid form; subcutaneously implanting in said subject a pellet containing said pharmaceutical product; orally administering to said subject said pharmaceutical product in a liquid or solid form; or topically applying to the skin surface of said subject said pharmaceutical product.

In another embodiment, said pharmaceutical product is a pellet, a tablet, a capsule, a solution, a suspension, an emulsion, an elixir, a gel, a cream, a suppository or a parenteral formulation.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A-FIG. 1J illustrate that DHT and a compound of Formula IX inhibit MDA-MB-231 triple negative breast cancer cell growth. FIG. 1A shows MDA-MB-231 cell expression of AR following transfection. FIG. 1B shows the IC$_{50}$ in AR-positive MDA-MB-231 cells. FIG. 1C-FIG. 1J show the effects of DHT, Formula IX, bicalutamide and the (R) enantiomer of Formula IX on percent (%) cell survival. (FIG. 1C, FIG. 1E, FIG. 1G and FIG. 1I cells were treated in charcoal stripped FBS. FIG. 1D, FIG. 1F, FIG. 1H and FIG. 1J cells were treated in full serum). • MDA-MB-231 with lacZ; ○ MDA-MB-231 with AR 200 µL; ▲ MDA-MB-231 with AR 500 µL.

FIG. 2A-FIG. 2H illustrate that DHT and Formula IX inhibit HCC-38 triple negative breast cancer cell growth. FIG. 2A shows HCC-38 cell expression of AR following transfection. FIG. 2B shows the IC$_{50}$ in AR-positive HCC-38 cells. FIG. 2A-FIG. 2H show the effects of DHT, Formula IX and Bicalutamide on percent (%) cell survival. (FIG. 2C, FIG. 2E and FIG. 2G cells were treated in charcoal stripped FBS.

FIG. 2D, FIG. 2F and FIG. 2H cells were treated in full serum). • HCC-38 with lacZ; ○ HCC-38 with AR 200 μL; ▲ HCC-38 with AR 500 μL.

FIG. 3A-FIG. 3E illustrate that the effect of DHT and Formula IX on MDA-MB-231 cells was reversed by bicalutamide. FIG. 3A-FIG. 3D show the effects of DHT or Formula IX in the presence or absence of bicalutamide, on percent (%) cell survival. (FIG. 3A and FIG. 3C cells were treated in charcoal stripped FBS. FIG. 3B and FIG. 3D cells were treated in full serum). • lacZ and with 10 μM bicalutamide; ○ lacZ; ▲ AR with 10 μM bicalutamide; Δ AR. FIG. 3E shows $IC_{50}$ values in AR-positive cells in the presence or absence of pretreatment with bicalutamide.

FIG. 4A-FIG. 4Q illustrate that AR agonists inhibit triple negative breast cancer cell growth. FIG. 4A, FIG. 4B, FIG. 4E, FIG. 4F, FIG. 4G, FIG. 4H, FIG. 4K, FIG. 4L, FIG. 4M, FIG. 4N, FIG. 4O and FIG. 4P show effect of AR agonists on percent (%) cell survival. FIG. 4A, FIG. 4C, FIG. 4E, FIG. 4G, FIG. 4I, FIG. 4M and FIG. 4O cells were treated in charcoal stripped FBS. FIG. 4B, FIG. 4D, FIG. 4F, FIG. 4H, FIG. 4J, FIG. 4L, FIG. 4N and FIG. 4P cells were treated in full serum. FIG. 4Q shows $EC_{50}$ and $IC_{50}$ values in AR-positive cells.

FIG. 6A and FIG. 6B show the expression of ERα or ERβ in MDA-MB-231 cells following transfection, respectively. FIG. 6C, FIG. 6D and FIG. 6E show the effects of estradiol (E2) or ICI 182,780 (ICI) on percent (%) cell survival. (FIG. 6C cells were treated in charcoal stripped serum. FIG. 6D and FIG. 6E cells were treated in full serum).

FIG. 25B and FIG. 25D show that adding AR (as opposed to Green Fluorescent Protein (GFP) as seen in FIGS. 25A and 25C) to MCF-7-AR cells increases the effects of estradiol (when unopposed) on the ER target genes PR and PS2, respectively. Adding AR to MCF-7-AR cells suppressed the activation of these ER targets in the presence of SARM alone or SARM+estradiol (E2) as compared to GFP transfected cells (i.e. no AR; FIG. 25A and FIG. 25C).

FIG. 25E shows that AR target genes are enhanced by SARM even in the presence of estradiol.

FIG. 27A provides results for Experiment 1, FIG. 27B provides results for Experiment 2 and FIG. 27C provides results for Experiment 2. BR-0001 TNBC fragments of 1 mm³ (approximately) were implanted subcutaneously in NOD scid gamma (NSG) mice. Once the tumors reach 100-200 mm³, the animals were randomized and treated with vehicle, 10 mg/kg/day Formula IX or enzalutamide orally. Tumor volume was measured thrice weekly. Animals were sacrificed and tumors were weighed.

FIG. 29 depicts Z-scores of 50 genes (PAM50) used to identify BR-0001. PAM50 is a set of 50 genes used to classify breast cancers. PAM50 gene expression data indicated that the BR-0001 tumor belonged to basal-like breast cancer (BLBC) subtype of TNBC. The expression (Z-score) of 50 genes required to classify the breast cancer is given here.

FIG. 33A: tumor volume changes (%) and FIG. 33B: tumor weight (g).

FIG. 34A depicts that Formula IX inhibited the proliferation of ZR-75-1 cells. ZR-75-1 breast cancer cells plated in growth medium (n=4/treatment) were treated with indicated doses of Formula IX for 6 days, with medium changed and re-treated on day 3. After 6 days of treatment, cells were harvested, and the number of cells was counted. FIG. 34B depicts that Formula IX inhibited proliferation of MCF-7 cells expressing AR. MCF-7 cells stably transfected with GFP (MCF-7-GFP) or the AR (MCF-7-AR) were plated in 96 well plates in growth medium (n=4/treatment) and treated with the indicated doses of Formula IX. Medium was changed after 3 days and re-treated. Cells were fixed after 6 days of treatment and the cell viability was measured by SRB assay. FIG. 34C depicts that breast cancer fibroblasts treated with AR agonists secreted factors that inhibited MCF-7-GFP cells lacking supplemented AR. Primary fibroblasts obtained from a breast cancer patient were cultured in growth medium and were treated in triplicates with vehicle, 10 nM DHT, 1 μM enzalutamide, or 1 μM Formula IX. Medium was changed, and the cells were re-treated on days 4 and 7. Medium was collected, pooled from triplicates, and stored in −80° C. After 10 days of treatment, cells were fixed, and cell viability was measured using SRB. MCF-7 cells stably transfected with GFP (MCF-7-GFP) were plated in growth medium. Twenty-four hours after plating, cells were fed with the conditioned medium obtained from patient-derived fibroblasts as indicated above. Cells were fed for 10 days with conditioned medium, with medium changed on days 4 and 7. After 10 days of treatment, cells were fixed, and the viability was measured by SRB assay. FIG. 34D depicts that AR ligands did not inhibit growth of ER-negative AR-positive HCI-9 PDX. AR-positive, but ER-negative HCI-9 PDX was surgically implanted as 1 mm³ fragments under the mammary fat pad in NSG mice (n=8-10/group). Once the tumors reached 100-200 mm³, the mice were randomized and treated with vehicle (DMSO:PEG-300 (15%:85%)), Formula IX (10 mpk p.o.), or enzalutamide (30 mpk p.o.). Tumor volume was measured thrice weekly. FIG. 34E depicts that HCI-13 ER-α was resistant to ER antagonists fulvestrant and tamoxifen (right pane) compared to wt-ER-α (left pane). ER-α from HCI-13 was cloned into pCR3.1 vector. Wildtype ER-α and HCI-13 ER-α, ERE-LUC, and CMV-LUC were transfected into COS-1 cells using lipofectamine. Cells were treated 24 hours after transfection with vehicle, 0.1 nM estradiol, 10 nM fulvestrant or 1 μM tamoxifen in combination with 0.1 nM estradiol. Twenty four hours after treatment cells were harvested and luciferase assay was performed. ER antagonists in wt-ER-α were significantly different than vehicle-treated wt-ER-α as depicted by *p<0.05. AR—androgen receptor; GFP—green fluorescent protein; DHT-5α—dihydrotestosterone; E2—17β-estradiol; ER—estrogen receptor; SARM—selective androgen receptor modulator; SRB—sulforhodamine B; mpk—milligram per kilogram body weight. Values are expressed as average±S.E. from n=3-4/data point.

FIG. 35A depicts that protein from HCI PDX (HCI-7, 9, or 13) tumor fragments was extracted and fractionated on a SDS-PAGE, and Western blotted for the AR. AR was also quantified at mRNA level and expressed as fold change from LNCaP prostate cancer cell AR (numbers provided under the blot). FIG. 35B (same as FIG. 32) and FIG. 35C depict that Formula IX inhibited HCI-7 tumor growth. AR-positive HCI-7 PDX expressing wildtype ER was surgically implanted as 1 mm³ fragments under the mammary fat pad in NSG mice (n=8-10/group). Once the tumors reached 100-200 mm³, the mice were randomized and treated with vehicle (DMSO:PEG-300 (15%:85%)), Formula IX (10 mpk p.o.), or enzalutamide (30 mpk p.o.). Tumor volume was measured weekly. At sacrifice, tumors were removed, weighed (FIG. 35C), and stored for further analysis. FIG. 35D depicts that MCF-7 cells (3 million cells/mouse) stably expressing AR (MCF-7-AR)

were implanted subcutaneously in ovariectomized mice supplemented with 17β-estradiol (n=8/group). Once the tumors reached 100-200 mm$^3$, the mice were randomized and treated with vehicle or Formula IX (10 mpk p.o.). Tumor volume was measured twice weekly. *=p<0.05; HCI—Huntsman Cancer Institute; AR—androgen receptor; ER—estrogen receptor; NSG—NOD SCID Gamma; PDX—patient-derived xenograft; OVX—ovariectomy; PR—progesterone receptor; mpk—milligram per kilogram body weight.

Figure 36A:
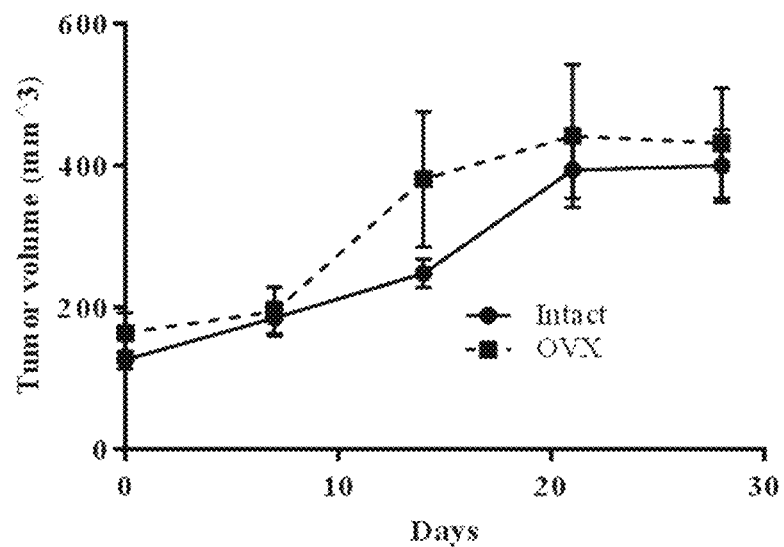
Figure 36B:
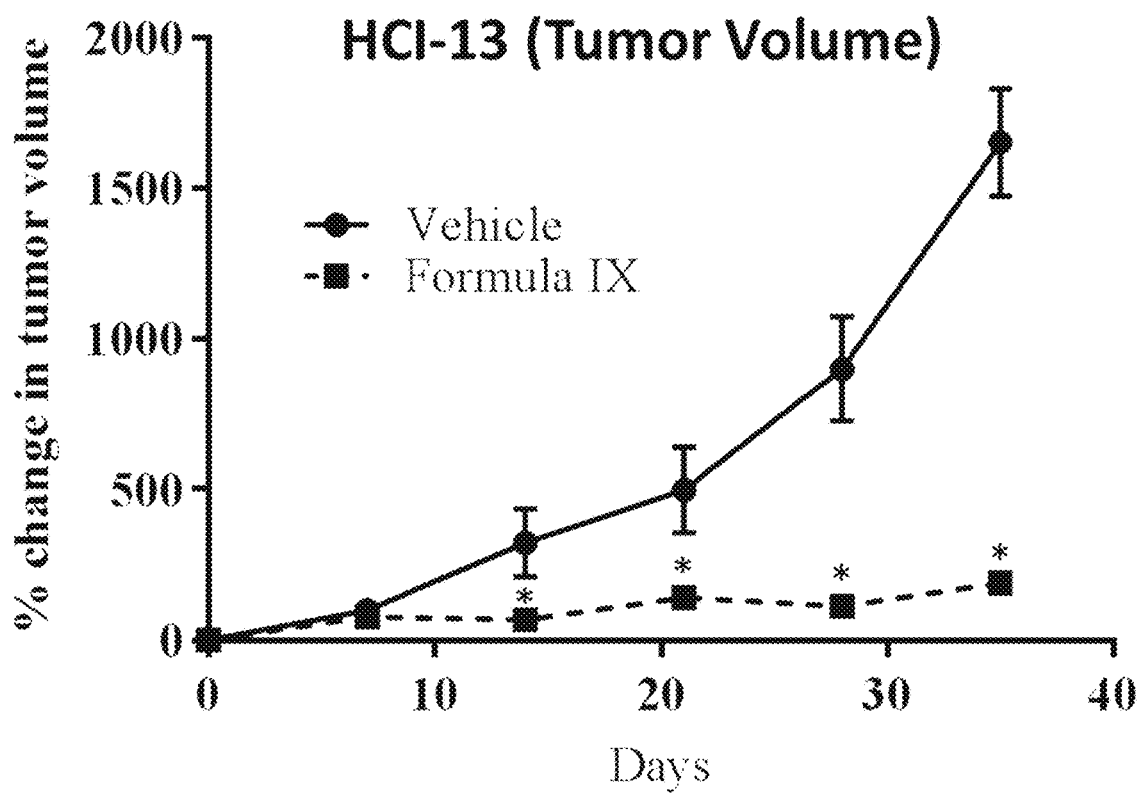
Figure 36C:
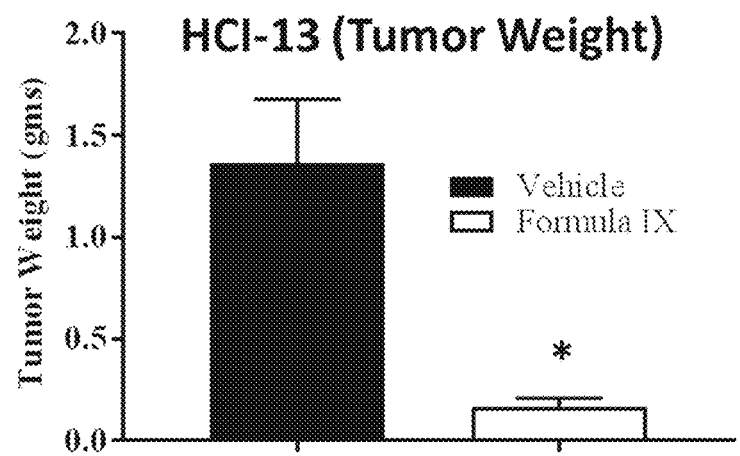
Figure 36D:
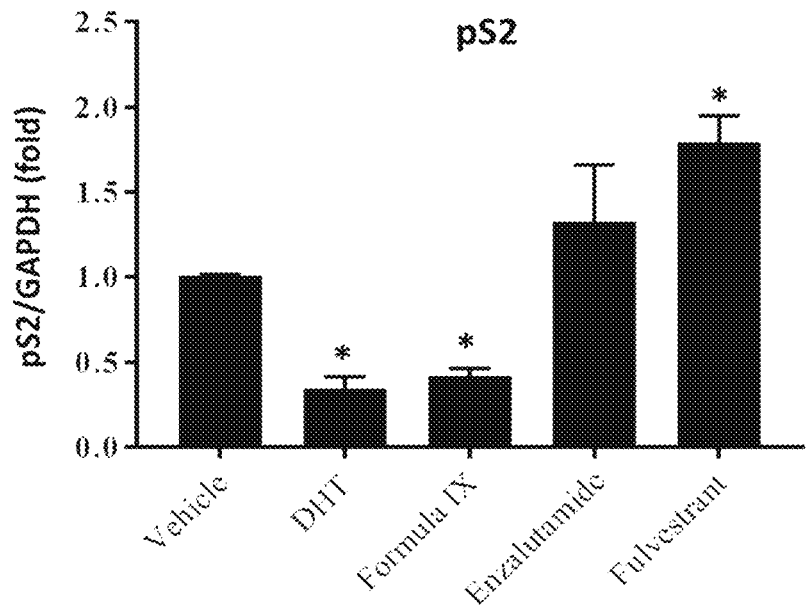
Figure 36E:
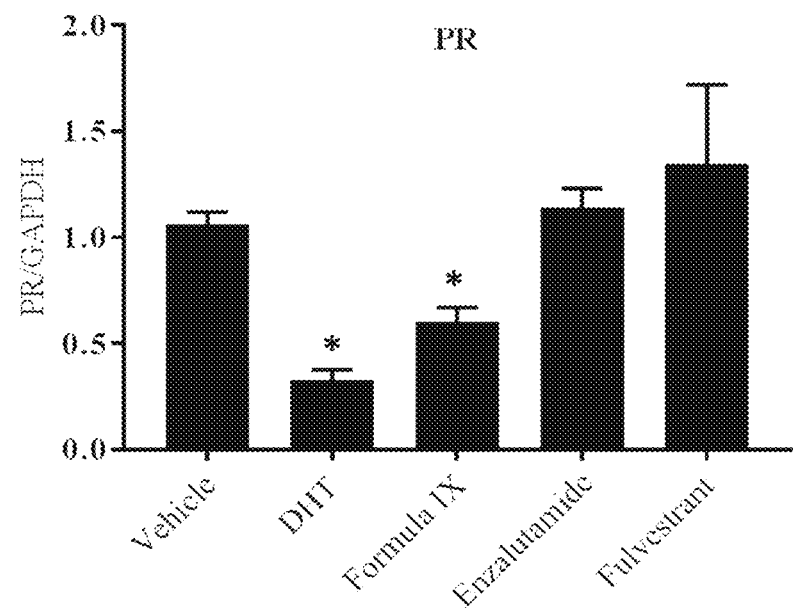
Figure 36F:
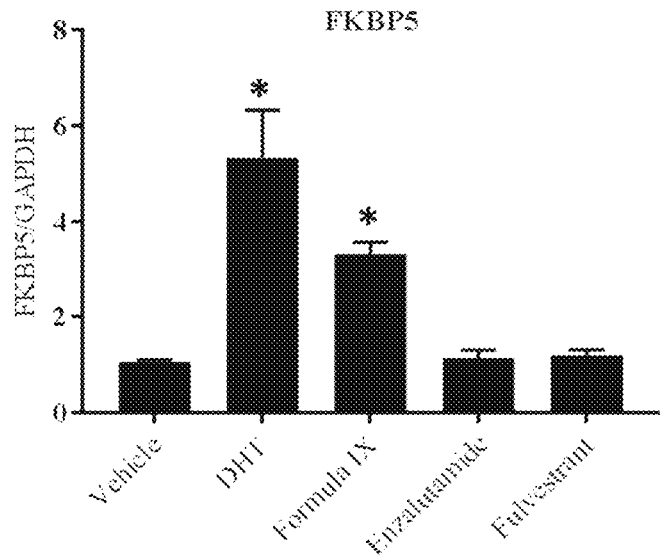
Figure 36G:
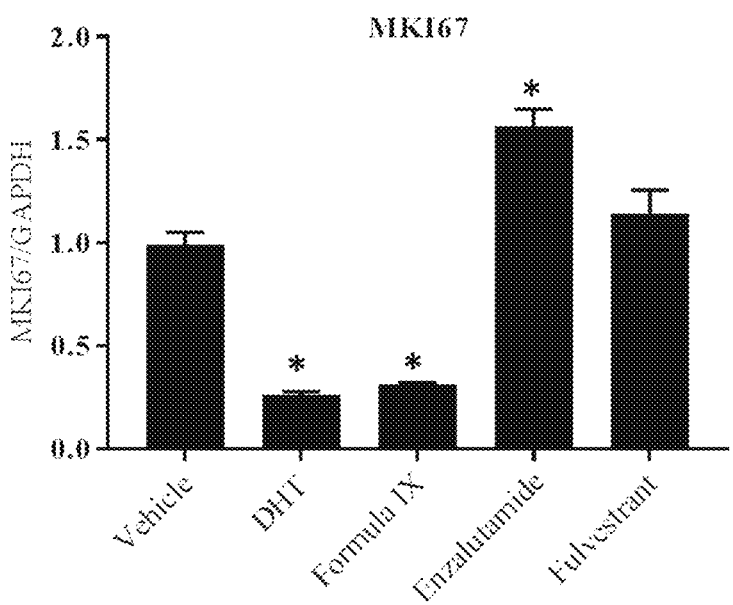
Figure 36H:
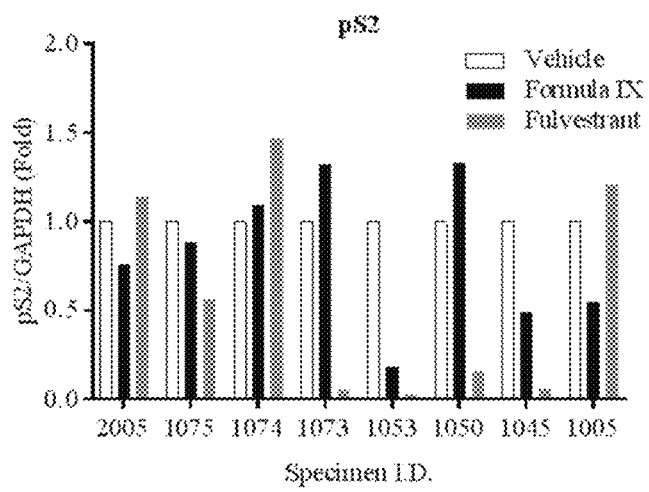
Figure 36I:
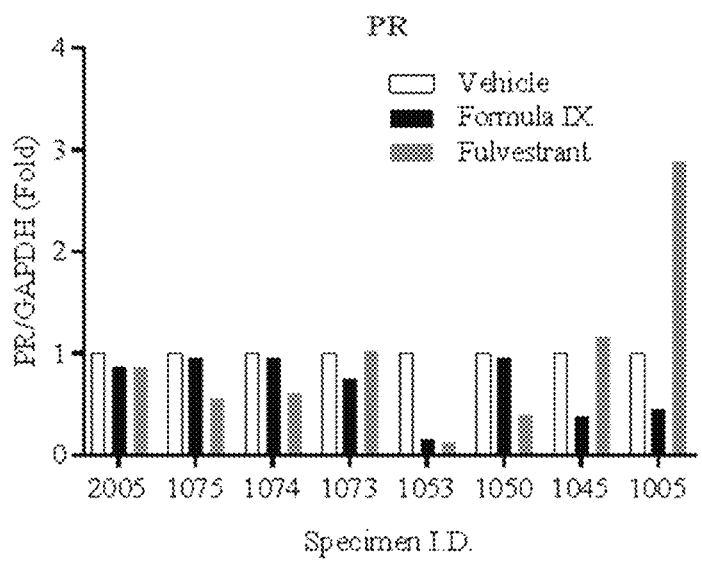
Figures 36J, 36K:
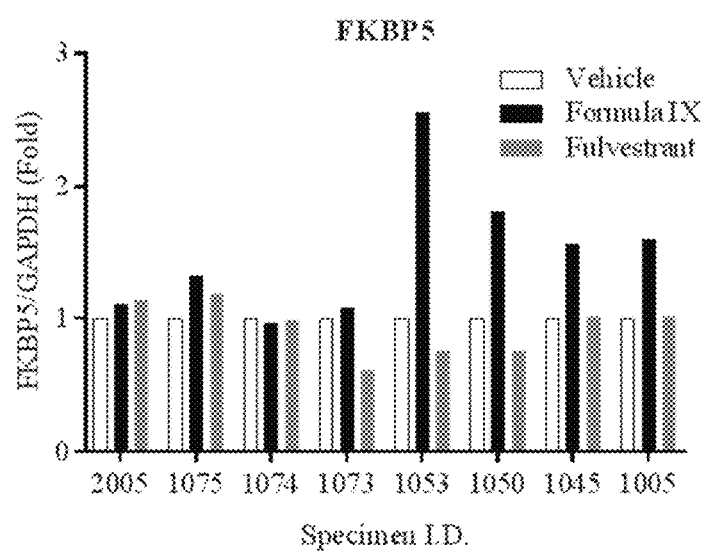

FIG. 36A-FIG. 36K depict that AR agonists inhibited proliferation and growth of mutant ER and AR-positive xenografts. FIG. 36A depicts that the growth of HCI-13 PDX was not dependent on circulating estrogens. HCI-13 PDX tumor fragments were surgically implanted as 1 mm$^3$ fragments under the mammary fat pad in NSG mice (n=6/group) that were sham operated or ovariectomized. Tumor volume was measured weekly. FIG. 36B and FIG. 36C depict that AR agonist (Formula IX) inhibited growth of HCI-13 PDX. AR-positive HCI-13 PDX expressing mutant ER was surgically implanted as 1 mm$^3$ fragments under the mammary fat pad in NSG mice (n=8-10/group). Once the tumors reached 100-200 mm$^3$, the mice were randomized and treated with vehicle (DMSO:PEG-300 (15%:85%)) or Formula IX (10 mpk p.o.). Tumor volume was measured weekly. At sacrifice, tumors were removed, weighed (FIG. 36C), and stored for further analysis. FIG. 36D-FIG. 36G depict that AR agonists, but not AR- or ER-antagonists, inhibited ER-target genes in HCI-13 ex vivo sponge culture. HCI-13 tumors (1 mm$^3$) were cultured on gelatin sponges (n=3/group; each n was obtained by pooling 5 fragments) in growth medium. Tissues were treated with vehicle, 10 nM DHT, 1 µM Formula IX, 1 µM enzalutamide, or 100 nM fulvestrant for three days. RNA was extracted from the tissues and expression of genes was measured by real time PCR and normalized to GAPDH. FIG. 36H-FIG. 36J depict the effect of Formula IX on ER-positive breast cancer patient specimens. Breast cancer specimens obtained from patients were cultured on gelatin sponges (n=1; each n was obtained from 5 tumor fragments). Tissues were treated with vehicle, 1 µM Formula IX, or 100 nM fulvestrant for three days. RNA was extracted from the tissues and expression of genes was measured by real time PCR and normalized to GAPDH. Table in FIG. 36K denotes the fold difference in the expression of AR and ER at the mRNA level compared to HCI-13 tumors. *=p<0.05; HCI—Huntsman Cancer Institute; AR—androgen receptor; ER—estrogen receptor; NSG—NOD SCID Gamma; PDX—patient-derived xenograft; MKI67—mRNA of Ki67 proliferative index protein; OVX—ovariectomy; PR—progesterone receptor; mpk—milligram per kilogram body weight.

Figure 37A:
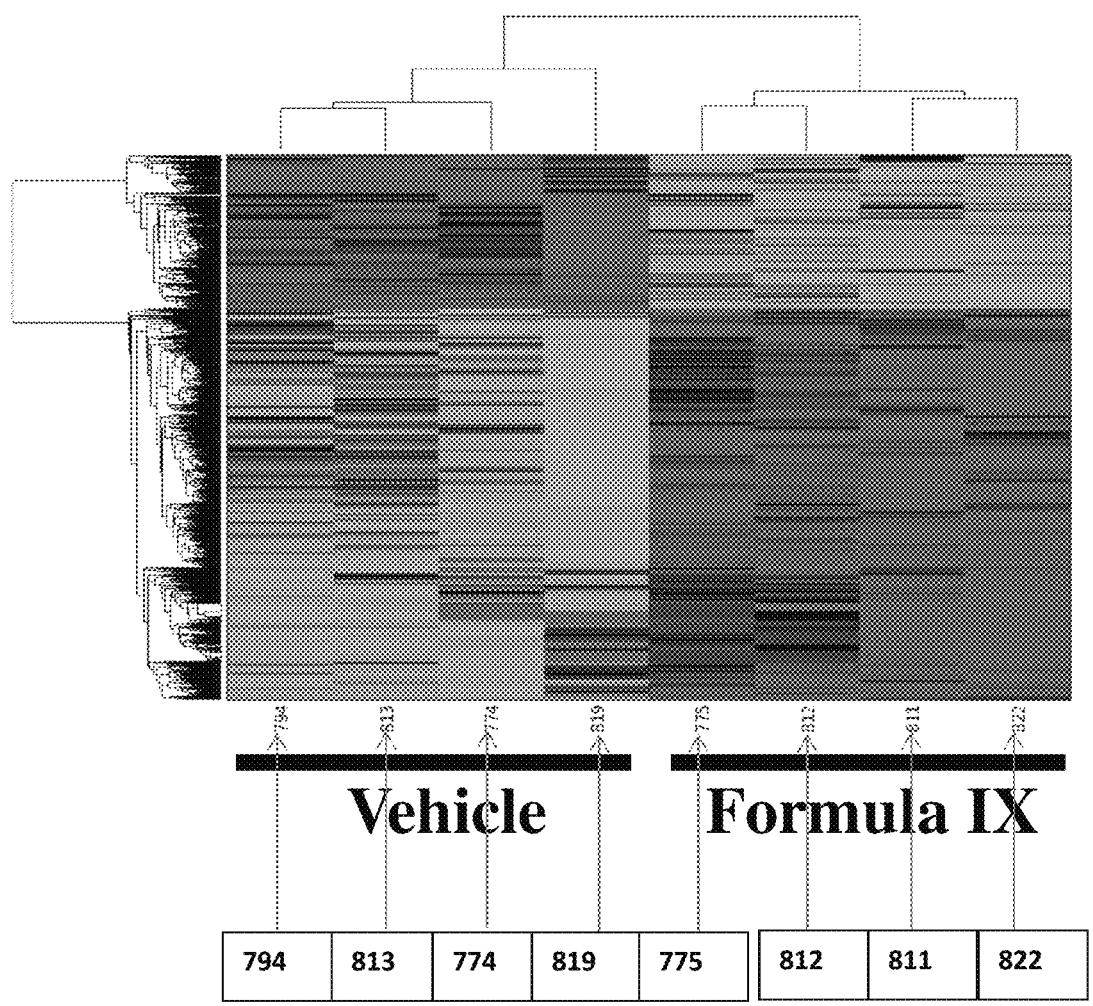
Figures 37B, 37C:
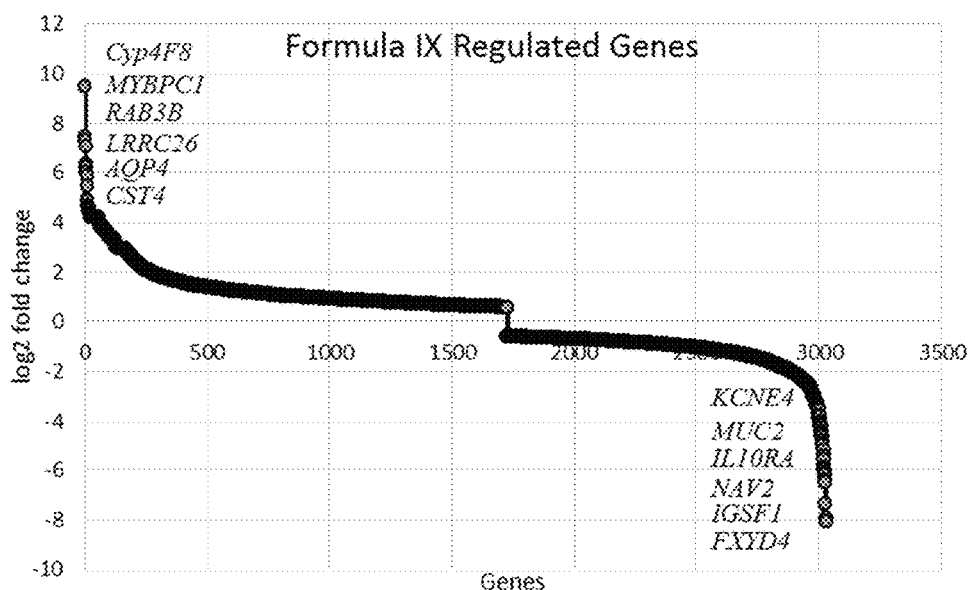
Figure 37D:
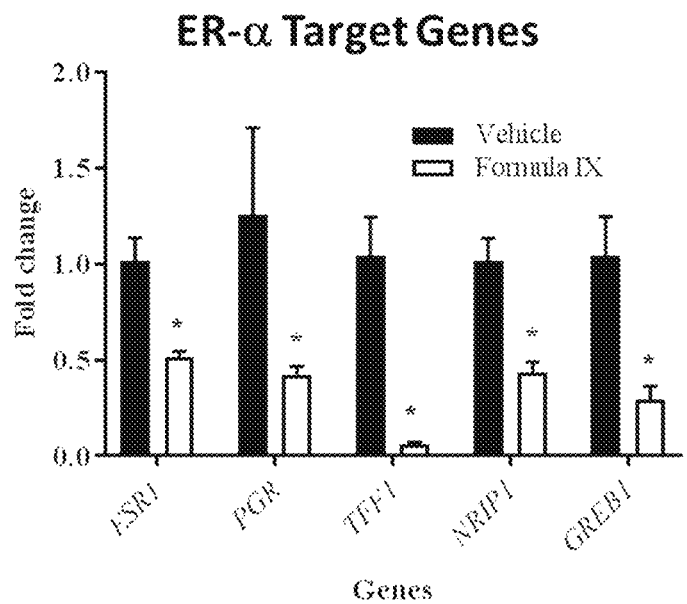
Figure 37E:
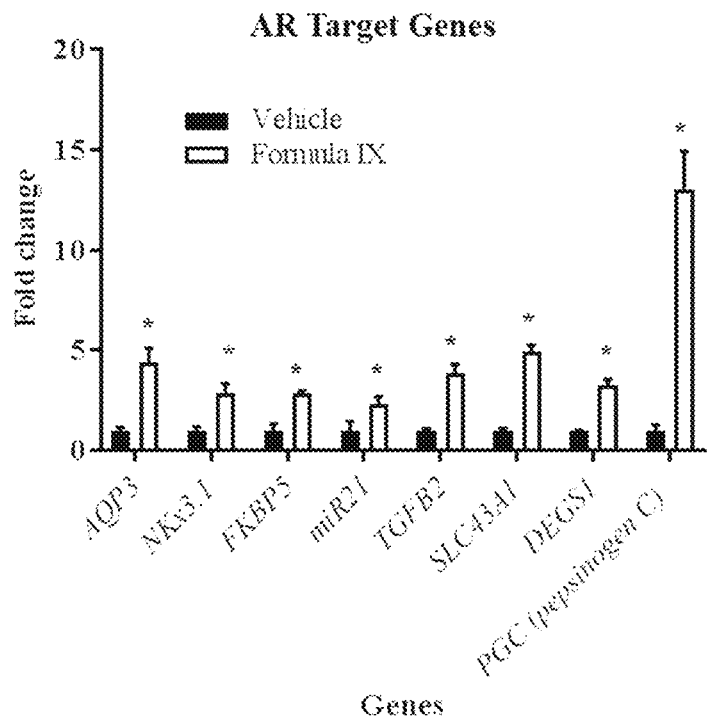
Figure 37F:
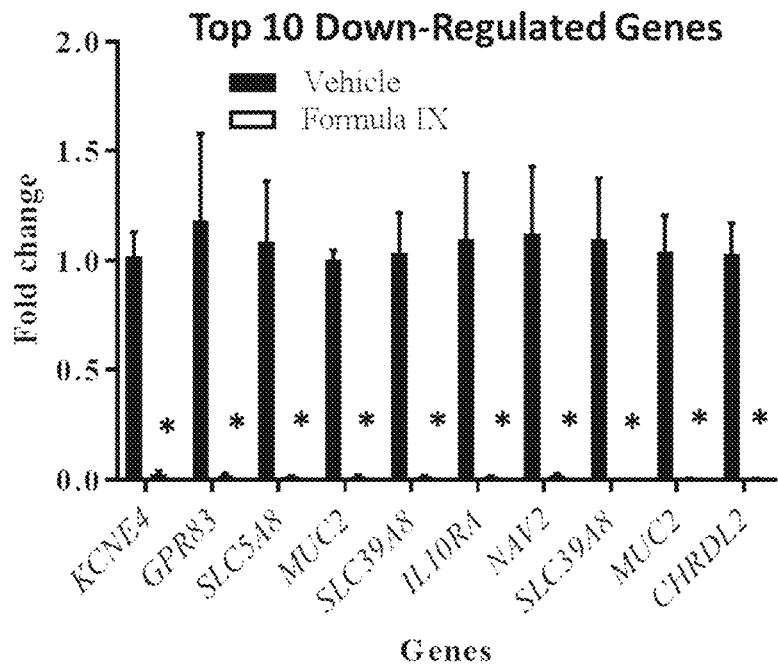
Figure 37G:
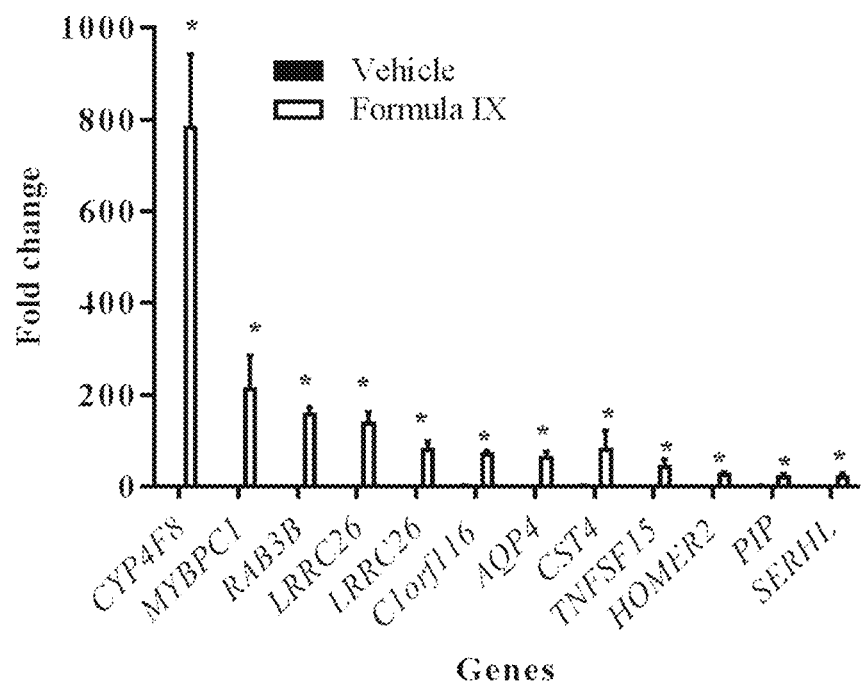
Figure 37H:
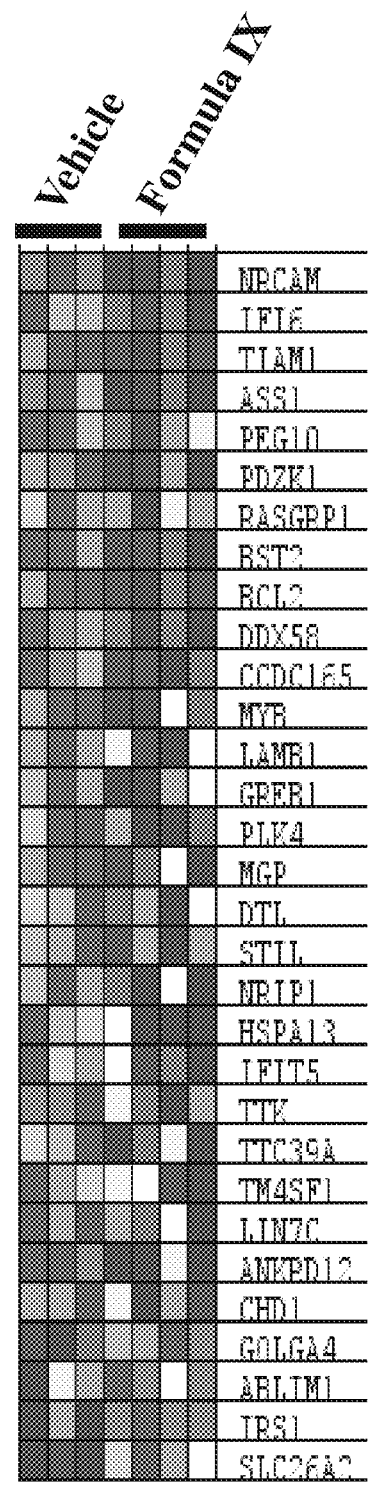

FIG. 37A-FIG. 37H depict a gene expression study in HCI-13 PDX that indicated the inhibition of the ER pathway by an AR agonist. RNA was isolated from HCI-13 PDX xenografts treated with vehicle or Formula IX (FIG. 36B-FIG. 36C) and microarray was performed (n=4/group). Genes that were different in Formula IX treated group (q<0.05) are represented in the heatmap (upper ⅕ of the left column (vehicle-treated) of the heatmap is predominantly upregulated (originally red) whereas lowered ⅘ of heatmap is predominantly downregulated (originally green); in contrast, the Formula IX treated column is just the opposite (green at top and red at bottom).) (FIG. 37A). Log fold change in expression with top up- and down-regulated was expressed in panel FIG. 37B. Canonical pathway, upstream regulators, and diseases represented by the enriched genes obtained from Ingenuity Pathway Analysis (IPA) were shown in panel FIG. 37C. Representative ER- and AR-target genes and the most up- and down-regulated genes were shown in panel FIG. 37D-FIG. 37G. FIG. 37H depicts that the GSEA KEGG pathway analysis provided ERBB2 (ERBB is abbreviated from erythroblastic oncogene B; also frequently called HER2 (from human epidermal growth factor receptor 2) or HER2/neu) pathway as one of the highly correlated pathway with Formula IX treatment (bottom four rows in the left column (vehicle treated) are downregulated genes (blue in the original color) whereas most of the rows are upregulated genes (red in the original color); in contrast, Formula IX treated column (right) is just the opposite). *=q<0.05; ER—estrogen receptor; AR—androgen receptor; PDX—patient-derived xenograft; GSEA—gene set enrichment analysis; KEGG—Kyoto encyclopedia of genes and genomes.

Figure 38A:
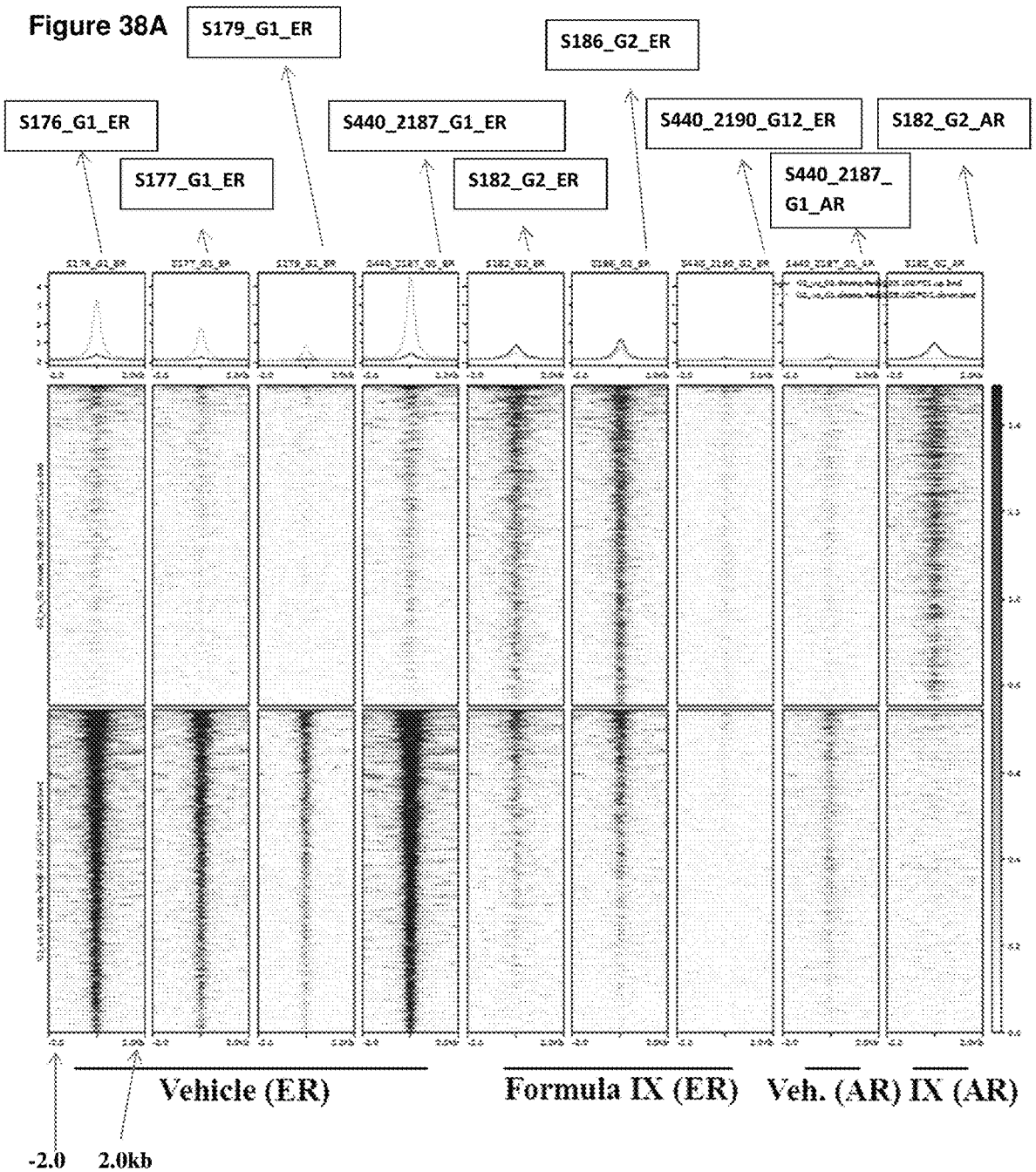
Figure 38B:
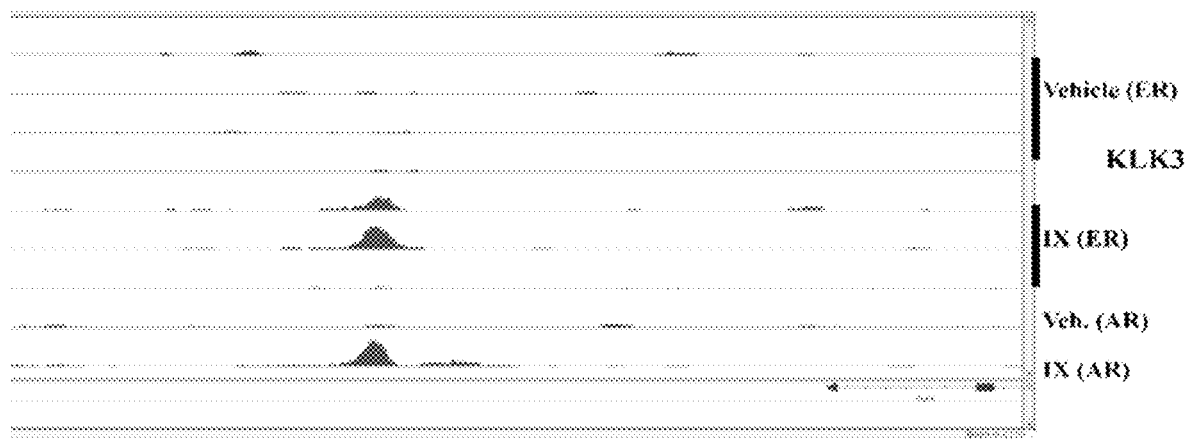
Figure 38C:
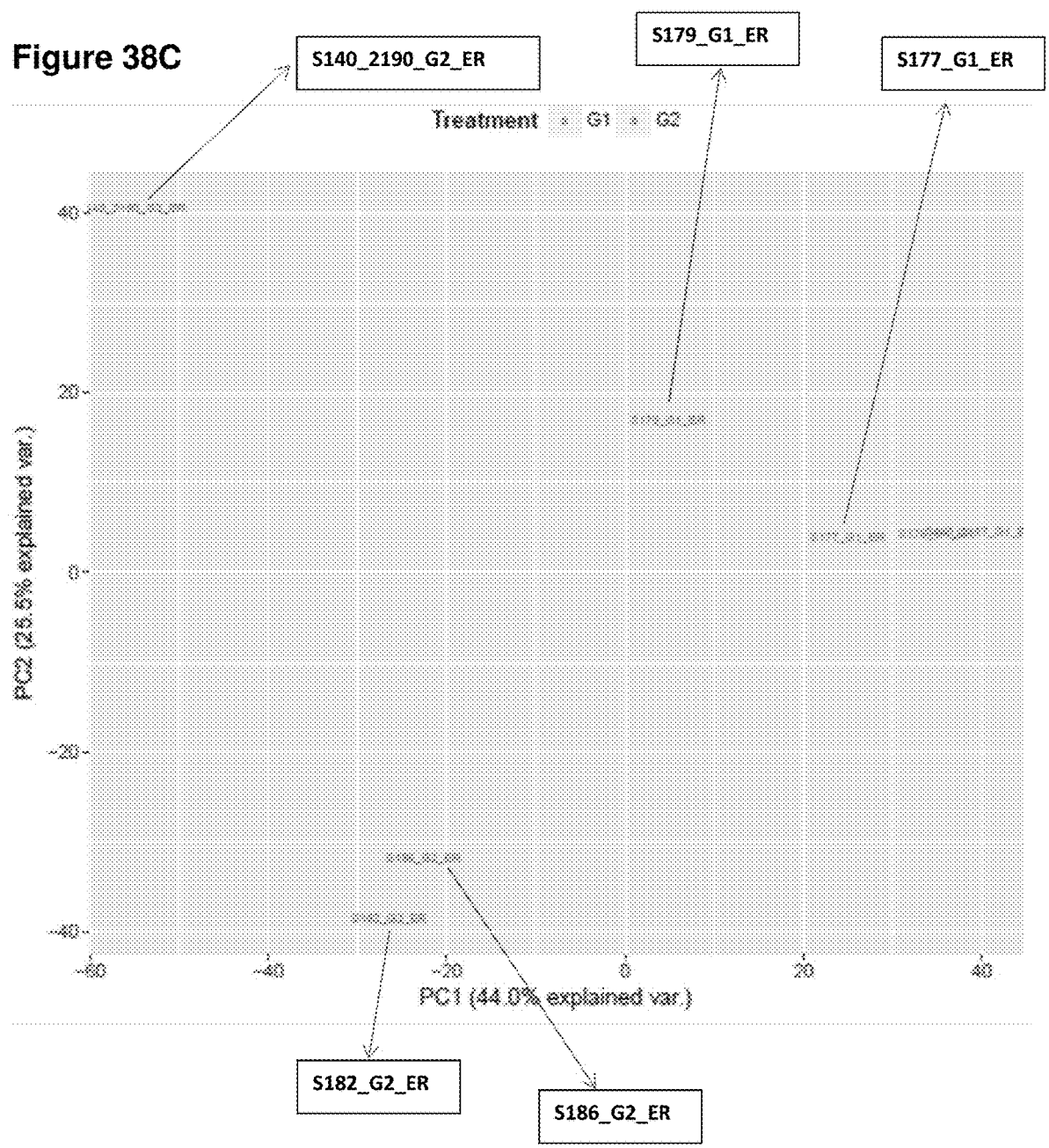
Figure 38D:
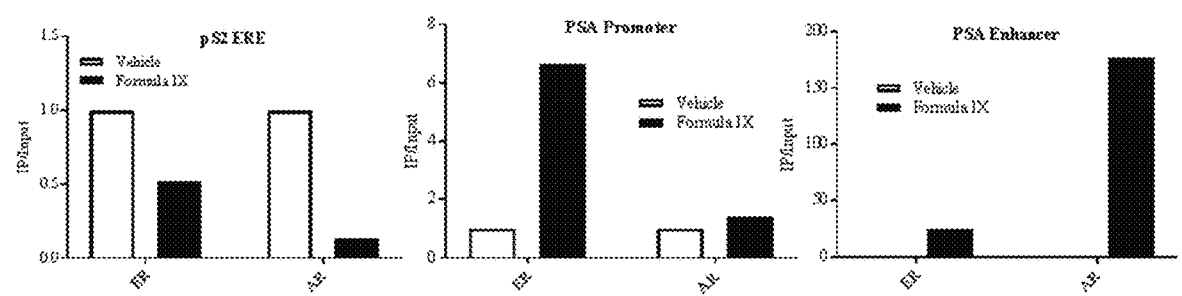
Figure 38E:
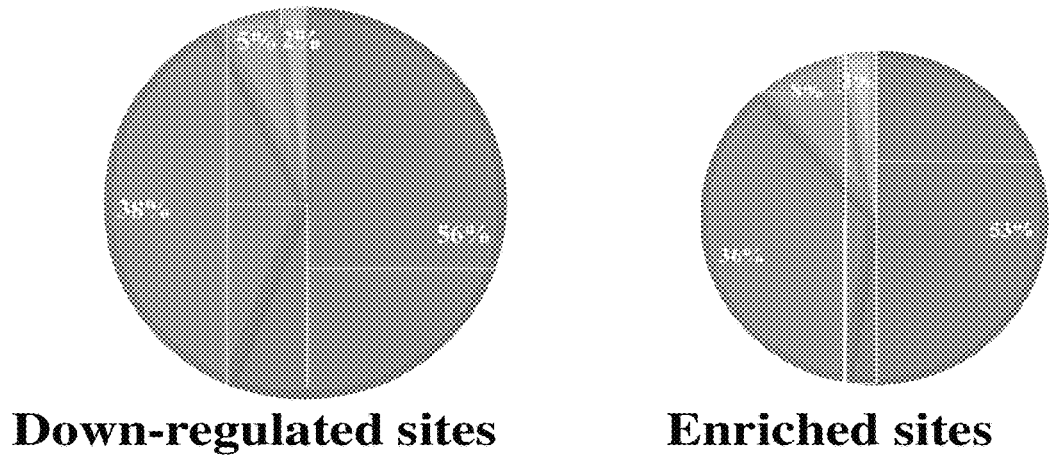
Figure 38F:
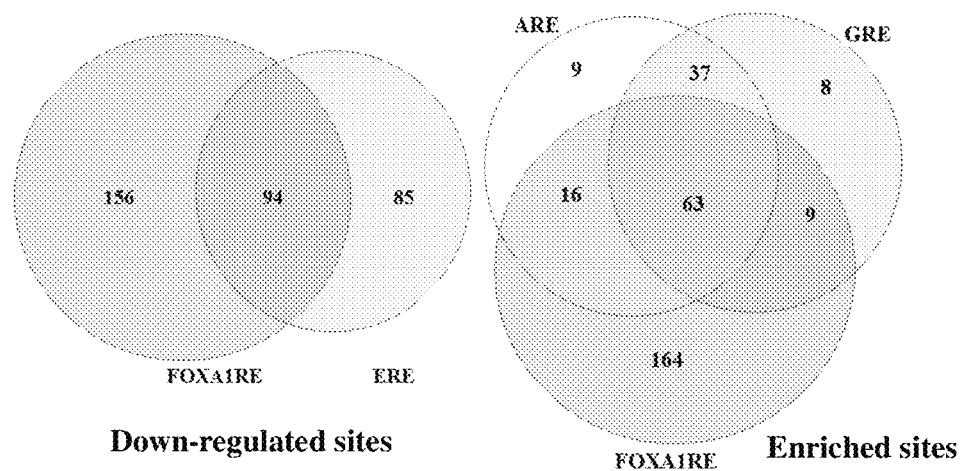
Figure 38G:
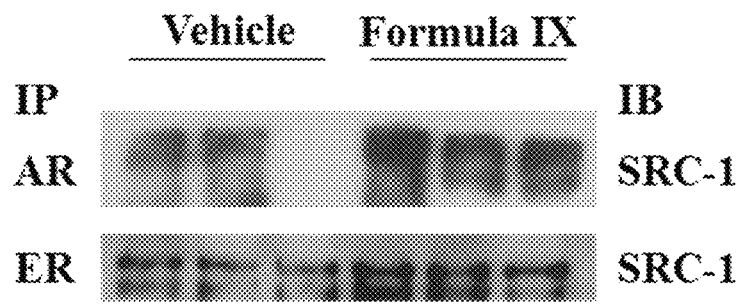
Figure 38H:
Figure 38H:
Figure 38H:
Figure 38H:
Figure 38H:

FIG. 38A-FIG. 38H depict that ChIP-Sequencing showed rearrangement of ER and AR binding to the DNA. FIG. 38A depicts that chromatin immunoprecipitation (ChIP) assay was performed with ER in tumors treated with vehicle (n=4) or 10 mg/kg/day Formula IX (n=3) or AR (n=1) (tumors from animals shown in FIG. 36B-FIG. 36C). Next-generation sequencing was performed to determine the genome-wide binding of ER and AR to the DNA. Heatmap of significantly different peaks (q<0.05 for ER and corresponding AR peaks) is shown. The top enriched motifs are shown in FIG. 38H. FIG. 38B shows representative peaks from KLK3 regulatory regions from ER and AR ChIP-Seq. FIG. 38C shows Principal Component Analysis (PCA) plot of vehicle- and Formula IX-treated samples that corresponds to ER-ChIP peaks. FIG. 38D depicts that ChIP assay was performed with AR or ER antibody in HCI-13 specimens treated with vehicle or Formula IX and real time PCR was performed with the primers and Taqman probe to the specified regions. FIG. 38E depicts pie charts showing the distribution of ER enrichment in Formula IX-treated HCI-13 samples. For downregulated sites (left pie), 'distal regulatory regions' represent 56%, introns 38%, exons 5%, and promoters 2%. For enriched sites (right pie), 'distal regulatory proteins' represent 53%, introns 36%, exons 8%, and promoters 3%. FIG. 38F depicts Venn diagrams showing the overlap between depleted FOXA1RE and ERE regions and enriched ARE, GRE, and FOXA1RE. FIG. 38G depicts that SRC-1 interacted with both AR and ER in response to Formula IX. Protein extracts from HCI-13 tumor samples treated with vehicle or Formula IX were immunoprecipitated with AR or ER antibodies and Western blot for SRC-1 was performed. AR—androgen receptor; ER—estrogen receptor; ChIP—chromatin immunoprecipitation; ARE—androgen response elements; ERE—estrogen response element; GRE—glucocorticoid response elements; SRC-1—steroid receptor coactivator-1, FOXA1RE—Forkhead box A1 response element. FIG. 38H depicts up-regulated motifs (ER).

Figure 39:
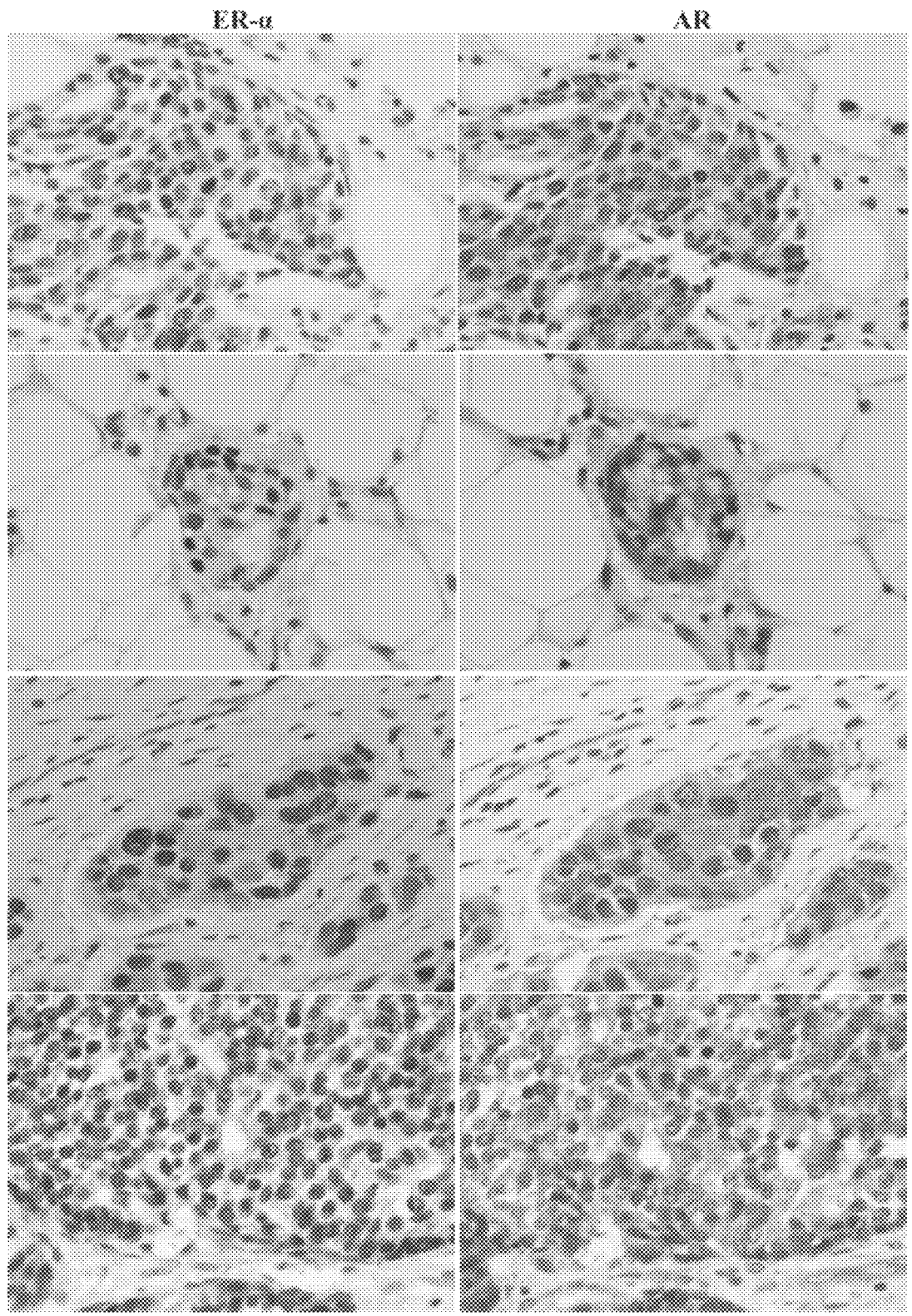

FIG. 39 depicts colocalization of AR and ER-α in luminal B breast cancer specimens.

Figure 40:
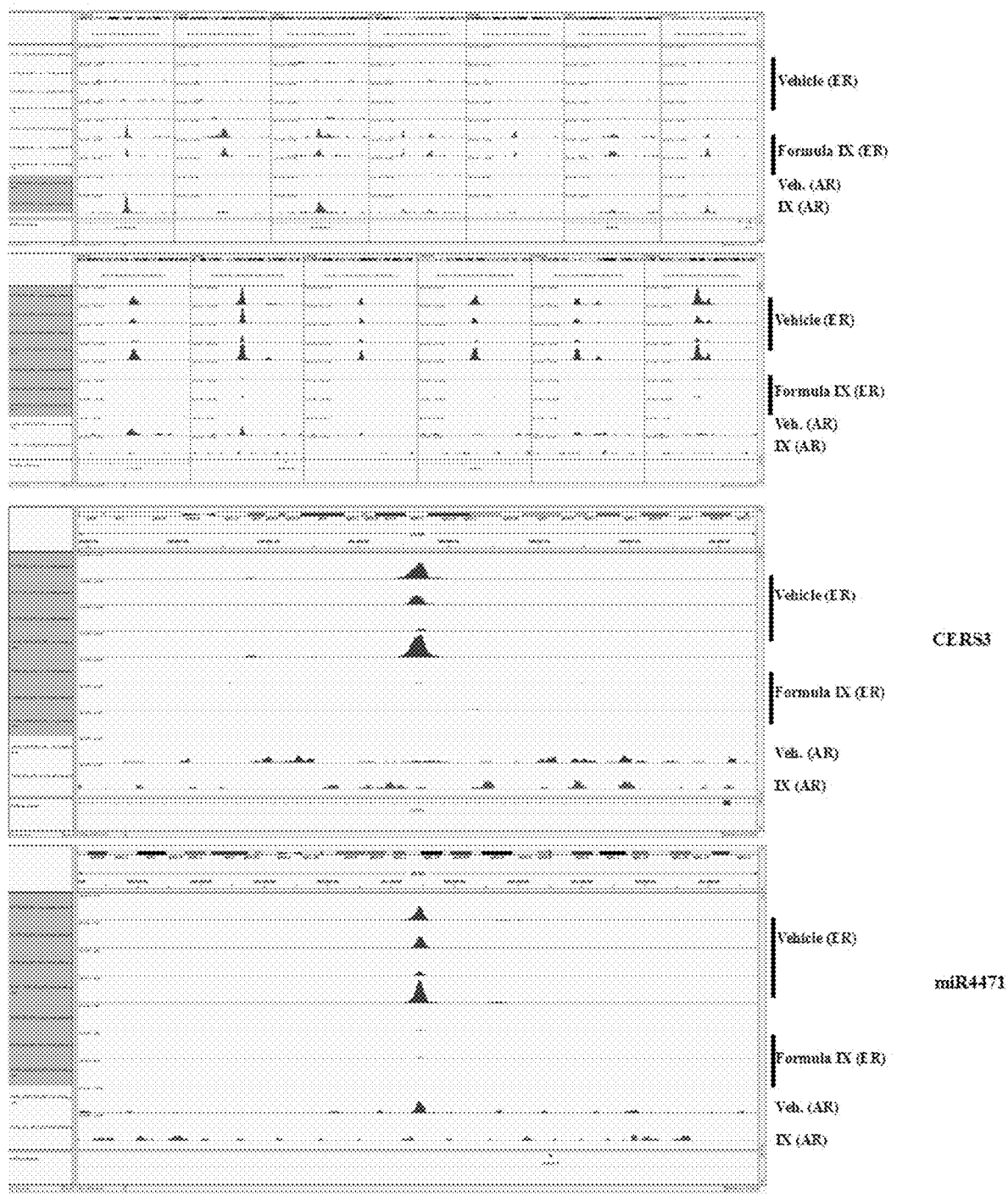

FIG. 40 depicts representative ChIP Seq peaks in the regulated regions of genes. The peaks are color coded with the top panel being predominantly upregulated (red), whereas the 2$^{nd}$ from top panel is downregulated (blue), 3$^{rd}$ panel from top (CERS3) is downregulated except for the last line (IX (AR)), and bottom panel (miR4471) is also downregulated except for the last line (IX (AR)).

Figure 41A:
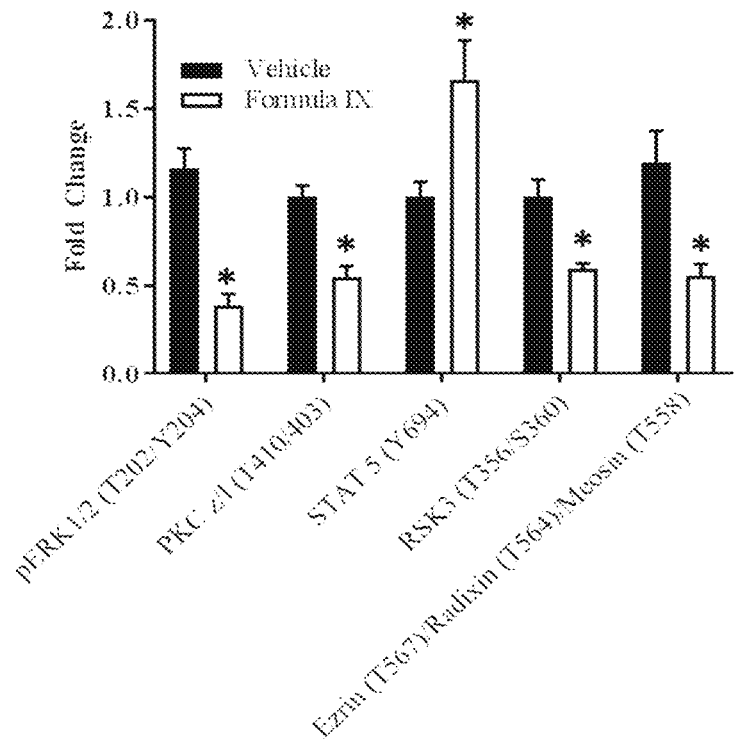
Figure 41B:
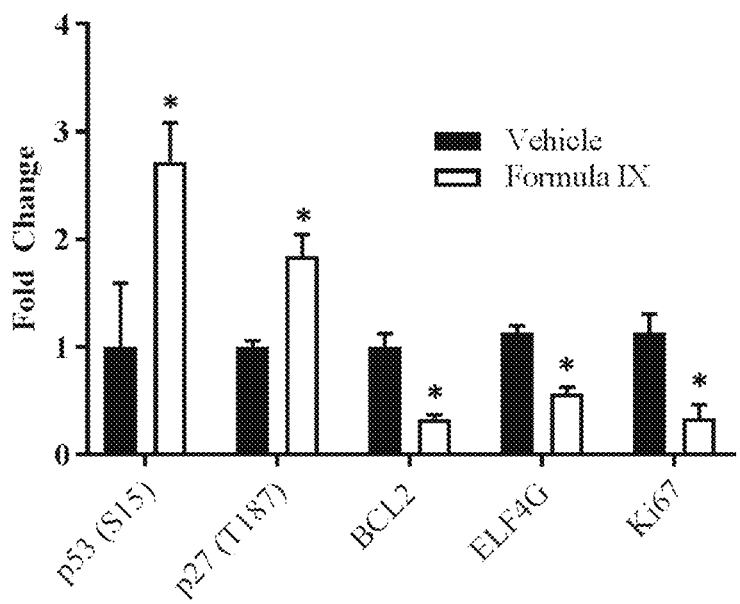
Figure 41C:
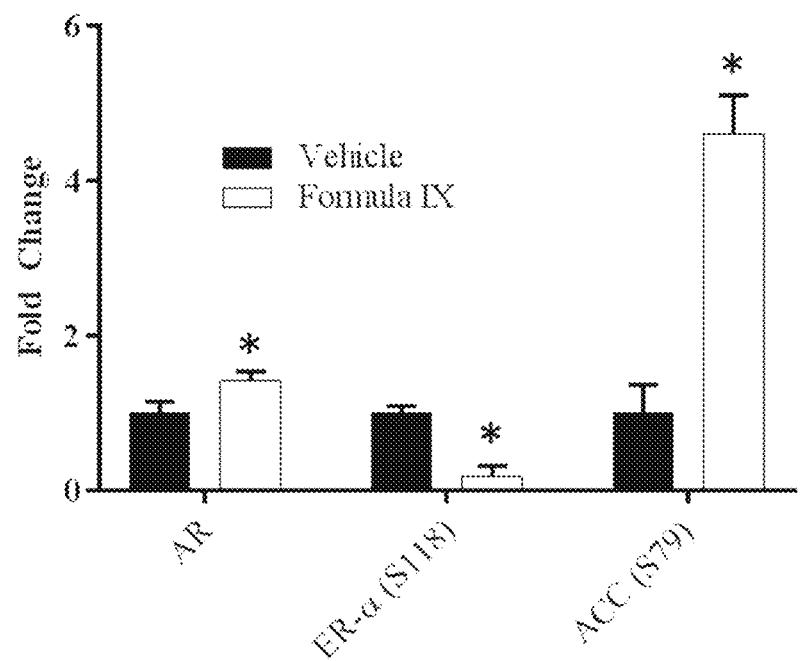
Figure 41D:
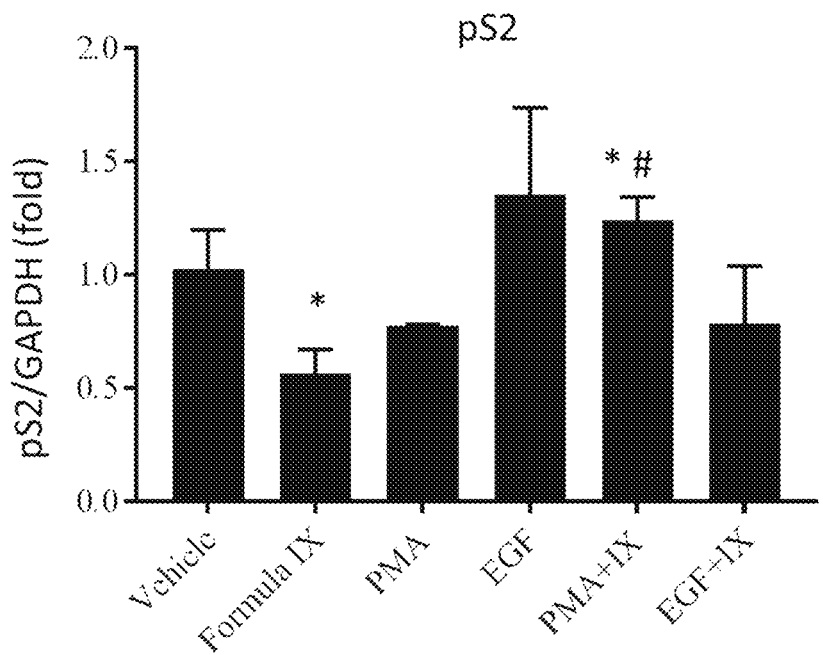
Figure 41E:
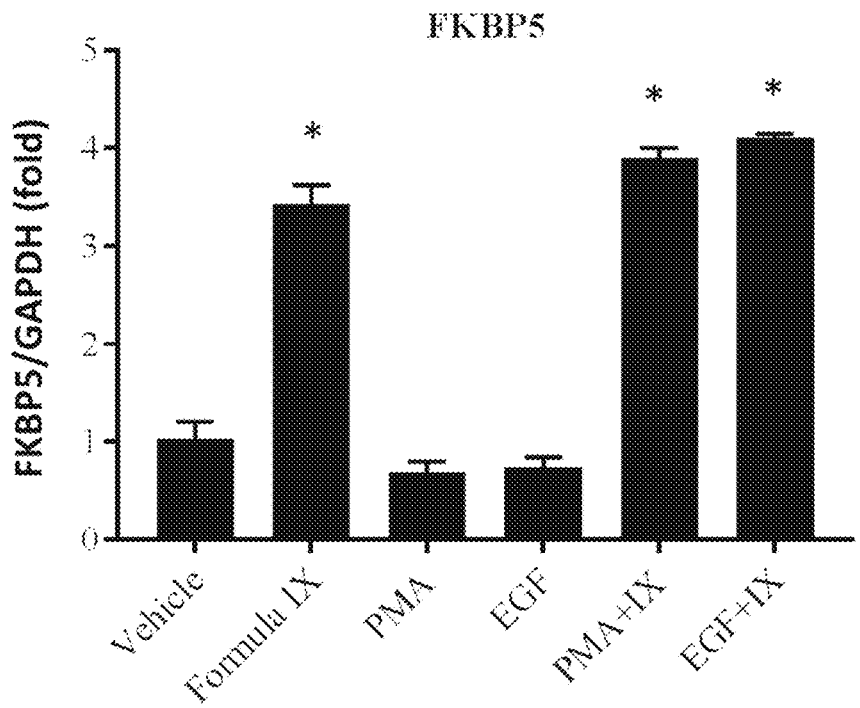

FIG. 41A-FIG. 41E depict a phospho-proteome analysis of HCI-13 PDX. FIG. 41A-FIG. 41C depict that lysates from HCI-13 tumor specimens (n=4) from PDX (as shown in FIG. 36B-FIG. 36C) were printed onto nitrocellulose coated slides. Arrays were probed with a total of 174 antibodies targeting a wide range of protein kinases and their activation via phosphorylation. Arrays were stained with an anti-rabbit or anti-mouse biotinylated secondary antibody. The signals were amplified and a streptavidin-conjugated IRDye680 were used as secondary signal detection agents. Images were acquired and quantified. FIG. 41D-FIG. 41E depict that activation of PKC overcame inhibition by Formula IX. HCI-13 tissues fragments were cultured on gelatin sponges and were treated with 100 nM phorbol 12-myristate 13-acetate (PMA) or 100 ng/mL EGF 30 minutes before addition of 1 µM Formula IX. EGF was treated twice daily due to its shorter stability. Tissues were harvested after 3 days of treatment, RNA isolated, and expression of various genes was measured by real time PCR. *$p<0.05$ from vehicle-treated samples; #$p<0.05$ from Formula IX-treated samples. n=3/group (each sample is obtained from 5 individual fragments). PMA—phorbol 12-myristate 13-acetate; EGF—epidermal growth factor; PDX—patient derived xenografts; HCI—Huntsman Cancer Institute.

Figure 42:
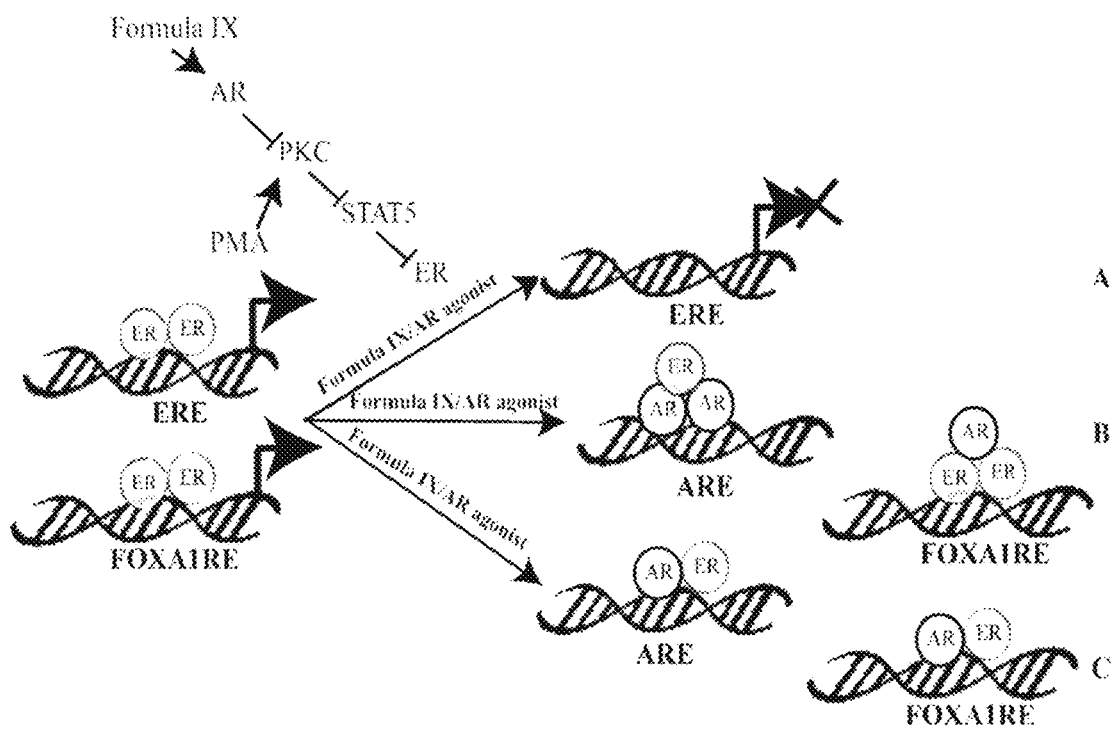

FIG. 42 shows a model depicting the regulation of ER function by AR agonist.

DETAILED DESCRIPTION OF THE INVENTION

In one embodiment, this invention relates to the treatment of androgen receptor-positive breast cancer in a subject. Accordingly, this invention provides methods of: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating, preventing, suppressing or inhibiting AR-positive triple negative breast cancer; r) treating a subject suffering from HER2-positive breast cancer; s) treating a subject suffering from ER mutant expressing breast cancer, and/or t) treating a subject suffering from Y537S ER mutant expressing breast cancer, by administering to the subject a therapeutically effective amount of a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a male. In one embodiment, the subject is a female.

In one embodiment of the present invention, a method is provided for treating a subject suffering from breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat breast cancer in the subject. In one embodiment, the subject is a female subject. In another embodiment, the subject is a male subject.

In another embodiment of the present invention, a method is provided for treating a subject suffering from metastatic breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat metastatic breast cancer in the subject. In one embodiment, the subject is a female subject. In another embodiment, the subject is a male subject.

In another embodiment of the present invention, a method is provided for treating a subject suffering from refractory breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat refractory breast cancer in the subject. In one embodiment, the subject is a female subject. In another embodiment, the subject is a male subject.

In another embodiment of the present invention, a method is provided for treating a subject suffering from AR-positive breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat AR-positive breast cancer in the subject. In one embodiment, the subject is a female subject. In another embodiment, the subject is a male subject.

In one embodiment, the AR-positive breast cancer is ER, PR and HER2-positive. In another embodiment, the AR-positive breast cancer is ER, PR and HER2-negative. In one embodiment, the AR-positive breast cancer is ER-positive, and PR and HER2-negative. In another embodiment, the AR-positive breast cancer is ER and PR-positive, and HER2-negative. In yet another embodiment, the AR-positive breast cancer is ER and HER2-positive, and PR-negative. In still another embodiment, the AR-positive breast cancer is ER-negative, and PR and HER2-positive. In a further embodiment, the AR-positive breast cancer is ER and PR-negative, and HER2-positive. In still a further embodiment, the AR-positive breast cancer is ER and HER2-negative, and PR-positive. In one embodiment, the AR-positive breast cancer is ER-negative. In another embodiment, the AR-positive breast cancer is ER-positive.

In another embodiment of the present invention, a method is provided for treating a subject suffering from AR-positive refractory breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat AR-positive refractory breast cancer in the subject. In one embodiment, the subject is a female subject. In another embodiment, the subject is a male subject.

In another embodiment of the present invention, a method is provided for treating a subject suffering from AR-positive metastatic breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat AR-positive metastatic breast cancer in the subject. In one embodiment, the subject is a female subject. In another embodiment, the subject is a male subject.

In another embodiment of the present invention, a method is provided for treating a subject suffering from AR-positive and ER-positive breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat AR-positive metastatic breast cancer in the subject. In one embodiment, the subject is a female subject. In another embodiment, the subject is a male subject.

In another embodiment of the present invention, a method is provided for treating a subject suffering from ER-positive breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat ER-positive breast cancer in the subject. In one embodiment, the subject is a female subject. In another embodiment, the subject is a male subject.

In one embodiment, the ER-positive breast cancer is AR-positive. In another embodiment, the ER-positive breast cancer is AR-negative. In one embodiment, ER-positive breast cancer is triple positive (ER, PR, HER2) breast cancer. In another embodiment, ER-positive breast cancer is not triple positive breast cancer.

In another embodiment of the present invention, a method is provided for treating a subject suffering from triple negative breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat triple negative breast cancer in the subject. In one embodiment, the subject is a female subject. In another embodiment, the subject is a male subject.

In another embodiment of the present invention, a method is provided for treating a subject suffering from AR-positive triple negative breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to AR-positive treat triple negative breast cancer in the subject. In one embodiment, the subject is a female subject. In another embodiment, the subject is a male subject.

In another embodiment of the present invention, a method is provided for treating a subject suffering from advanced breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat advanced breast cancer in the subject. In one embodiment, the subject is a female subject. In another embodiment, the subject is a male subject.

In another embodiment of the present invention, a method is provided for treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments in the subject. In one embodiment, the subject is a female subject. In another embodiment, the subject is a male subject.

In another embodiment this invention provides a method for treating a subject suffering from HER2-positive breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat HER2-positive breast cancer in the subject. In one embodiment, the subject is a female subject. In another embodiment, the subject is a male subject.

In one embodiment, the HER2-positive breast cancer is HER2-positive refractory breast cancer. In another embodiment, the HER2-positive breast cancer is HER2-positive metastatic breast cancer. In one embodiment, the HER2-positive breast cancer is ER-negative. In another embodiment, the HER2-positive breast cancer is ER-positive. In one embodiment, the HER2-positive breast cancer is PR-positive. In another embodiment, the HER2-positive breast cancer is PR-negative. In one embodiment, the HER2-positive breast cancer is AR-positive. In another embodiment, the HER2-positive breast cancer is AR-negative.

In certain embodiment, the HER2-positive breast cancer is ER-positive, PR-positive, and AR-positive. In another embodiment, the HER2-positive breast cancer is ER-positive, PR-negative, and AR-positive. In another embodiment, the HER2-positive breast cancer is ER-positive, PR-negative, and AR-negative. In other embodiment, the HER2-positive breast cancer is ER-positive, PR-positive, and AR-negative. In another embodiment, the HER2-positive breast cancer is ER-negative, PR-negative, and AR-positive. In another embodiment, the HER2-positive breast cancer is ER-negative, PR-positive, and AR-positive. In other embodiment, the HER2-positive breast cancer is ER-negative, PR-positive, and AR-negative. In certain embodiment, the HER2-positive breast cancer is ER-negative, PR-negative, and AR-negative. In certain embodiment, the HER2-positive breast cancer is triple-positive HER2 breast cancer.

In another embodiment this invention provides a method for treating a subject suffering from ER mutant expressing breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat ER mutant expressing breast cancer in the subject. In one embodiment, the subject is a female subject. In another embodiment, the subject is a male subject.

In a certain embodiment, the ER mutant expressing breast cancer is Y537S mutation expressing breast cancer.

In a certain embodiment, the ER mutant expressing breast cancer is D351Y mutation expressing breast cancer. In a certain embodiment, the ER mutant expressing breast cancer is E380Q mutation expressing breast cancer. In a certain embodiment, the ER mutant expressing breast cancer is V422del mutation expressing breast cancer. In a certain embodiment, the ER mutant expressing breast cancer is S432L mutation expressing breast cancer. In a certain embodiment, the ER mutant expressing breast cancer is G442A mutation expressing breast cancer. In a certain embodiment, the ER mutant expressing breast cancer is S463P mutation expressing breast cancer. In a certain embodiment, the ER mutant expressing breast cancer is L469V mutation expressing breast cancer. In a certain embodiment, the ER mutant expressing breast cancer is L536R mutation expressing breast cancer. In a certain embodiment, the ER mutant expressing breast cancer is L536H mutation expressing breast cancer. In a certain embodiment, the ER mutant expressing breast cancer is L536P mutation expressing breast cancer. In a certain embodiment, the ER mutant expressing breast cancer is L536Q mutation expressing breast cancer. In a certain embodiment, the ER mutant expressing breast cancer is Y537N mutation expressing breast cancer. In a certain embodiment, the ER mutant expressing breast cancer is Y537C mutation expressing breast cancer. In a certain embodiment, the ER mutant expressing breast cancer is Y537D mutation expressing breast cancer. In a certain embodiment, the ER mutant expressing breast cancer is D538G mutation expressing breast cancer. In a certain embodiment, the ER mutant expressing breast cancer is E542G mutation expressing breast cancer. In one embodiment, ER mutant expressing breast cancer refers to mutants of ER-alpha.

In a certain embodiment, the ER mutant expressing breast cancer is as described in Cancer Cell 2018, 33, 173-186; or in Nat Rev Cancer. 2018 June; 18(6):377-388, which are incorporated herein by reference. In one embodiment, ER mutant expressing breast cancer refers to mutants of ER-alpha.

As used herein, in one embodiment the term "treating" may refer to treating, delaying the progression, preventing the recurrence or treating the recurrence. In one embodiment, the term "treating" refers to a reduction in morbidity, mortality, or a combination thereof, in association with breast cancer.

The term "preventing" may refer to preventing the initial occurrence of a disorder, reducing risk factors, minimize the disability or potential health threat of a disorder.

As used herein, the term "breast cancer" may refer to breast cancer; advanced breast cancer; metastatic breast cancer; AR-positive breast cancer; ER-positive breast cancer; AR-positive breast cancer with or without expression of ER, PR and/or HER2; triple-positive breast cancer (ER, PR and HER2-positive), AR-positive breast cancer with or without expression of ER; ER-positive breast cancer with or without expression of AR; AR-positive and ER-positive breast cancer; refractory breast cancer; AR-positive refractory breast cancer; ER-positive refractory breast cancer; AR-positive metastatic breast cancer; ER-positive metastatic breast cancer; breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; or triple negative breast cancer; or any combination thereof.

In one embodiment, the term "breast cancer" refers to a condition characterized by anomalous rapid proliferation of abnormal cells in one or both breasts of a subject. The abnormal cells often are referred to as "neoplastic cells," which refers to, in some embodiments, transformed cells that can form a solid tumor. The term "tumor", in some embodiments, refers to an abnormal mass or population of cells (i.e. two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize.

In breast cancer, neoplastic cells may be identified in one or both breasts only and not in another tissue or organ, in one or both breasts and one or more adjacent tissues or organs (e.g. lymph node), or in a breast and one or more non-adjacent tissues or organs to which the breast cancer cells have metastasized.

The term "metastasis", in some embodiments, refers to a process in which cancer cells travel from one organ or tissue to another non-adjacent organ or tissue. Cancer cells in the breast(s) can spread to tissues and organs of a subject, and conversely, cancer cells from other organs or tissue can invade or metastasize to a breast. Cancerous cells from the breast(s) may invade or metastasize to any other organ or tissue of the body. Breast cancer cells often invade lymph node cells and/or metastasize to the liver, brain and/or bone and spread cancer in these tissues and organs. The term "invasion", in some embodiments, refers to the spread of cancerous cells to adjacent surrounding tissues.

As used herein, the term "advanced breast cancer" refers to cancer that has spread to other places in the body and usually cannot be cured or controlled with current treatment.

As used herein, the term "AR-positive breast cancer" may refer to breast cancer wherein at least a portion of the cancer cells express at least the androgen receptor (AR).

As used herein, the term "ER-positive breast cancer" may refer to breast cancer wherein at least a portion of the cancer cells express at least the estrogen receptor (ER).

As used herein, the term "triple negative breast cancer" may refer to breast cancer cells that do not have estrogen receptors (ER), progesterone receptors (PR), or large amounts of HER2/neu protein. "Triple negative breast cancer" may also be referred to herein as "ER-negative PR-negative HER2/neu-negative breast cancer".

As used herein, the term "triple positive breast cancer" may refer to breast cancer cells that express estrogen receptors (ER), progesterone receptors (PR), and large amounts of HER2/neu (HER2) protein. "Triple positive breast cancer" may also be referred to herein as "ER-positive PR-positive HER2/neu-positive breast cancer" or "ER, PR, and HER2 breast cancer".

As used herein, the term "refractory" may refer to breast cancer that does not respond to treatment. The breast cancer may be resistant at the beginning of treatment or it may become resistant during treatment. "Refractory breast cancer" may also be referred to herein as "resistant cancer".

As used herein, the term "HER2-positive breast cancer" may refer to breast cancers wherein at least a portion of the cancer cells express elevated levels of HER2 protein (HER2 (from human epidermal growth factor receptor 2) or HER2/neu) which promotes rapid growth of cells.

As used herein, the term "ER mutant expressing breast cancer" may refer to breast cancers that express estrogen receptor alpha (ER-α) with therapy resistance conferring mutations. Often these mutations are located within the ligand binding domain of ER-α, are treatment emergent, and/or confer resistance to certain or all endocrine therapies such as SERMs, AIs, SERDs, and/or GnRH agonists. As used herein, the term "Y537S ER mutant expressing breast cancer" may refer to breast cancers that express estrogen receptor alpha (ER-α) with the point mutation Y537S.

In another embodiment of the present invention, a method is provided for treating, preventing, suppressing or inhibiting metastasis in a subject suffering from breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat, prevent, suppress or inhibit metastasis in the subject. In one embodiment, the subject is a female subject. In another embodiment, the subject is a male subject.

In another embodiment of the present invention, a method is provided for prolonging the survival of a subject with breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to prolong the survival of a subject with breast cancer. In one embodiment, the subject is a female subject. In another embodiment, the subject is a male subject.

In another embodiment of the present invention, a method is provided for slowing the progression of breast cancer in a subject, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to slow the progression of breast cancer in the subject. In one embodiment, the subject is a female subject. In another embodiment, the subject is a male subject.

In another embodiment of the present invention, a method is provided for prolonging progression-free survival of a subject with breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to prolong progression-free survival of a subject with breast cancer. In one embodiment, the subject is a female subject. In another embodiment, the subject is a male subject.

In one embodiment, breast cancer of this invention refers to in one embodiment to ER-positive metastatic breast cancer; In another embodiment to ER-positive refractory breast cancer; In another embodiment to ER-positive PR-positive HER2-negative breast cancer; In another embodiment to AR-positive ER-positive breast cancer; In another embodiment to AR-positive ER-positive refractory breast cancer; In another embodiment to AR-positive ER-positive metastatic breast cancer; In another embodiment to triple positive breast cancer; In another embodiment to advanced ER-positive breast cancer; In another embodiment to AR-positive; In another embodiment to ER-positive breast cancer; and in another embodiment to breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments.

In another embodiment of the present invention, a method is provided for lowering biomarker levels in a subject with breast cancer comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to lower the biomarker level in said subject. In another embodiment, the method comprises administering a compound of Formulae I-XIV of this invention. As used herein, the term "biomarker" may refer to a substance used as an indicator of a process, event, or condition. A biomarker can be a biomolecule such as a nucleic acid molecule (e.g. microRNA, genomic DNA, etc.), a protein, a polysaccharide, and the like. Biomarkers include tumor antigens and tumor markers. In one embodiment, a biomarker indicates the presence of cancer, e.g., breast cancer. In one embodiment, a biomarker may be used to determine the efficacy of treatment. In one embodiment, a biomarker may be used to determine the progression of a condition, e.g., breast cancer.

The MUC-1 associated antigen, or CA 27.29, is a cancer antigen highly associated with breast cancer. As used herein, the term "CA27.29 biomarker" refers to a biomarker for breast cancer. In one embodiment, CA27.29 is a biomarker for advanced breast cancer.

"PSA (prostate-specific antigen) biomarker" is used as a biomarker for prostate cancer, however PSA was also found in the blood of women with breast cancer at higher levels compared to women without breast cancer. PSA is useful also as a biomarker for breast cancer.

"CTX biomarker" and "NTX biomarker" are the C-telopeptide and N-telopeptide of collagen type I, respectively, which are used as biomarkers of bone turnover. NTX and CTX biomarkers may be sensitive indicators of the presence of bone metastases in breast cancer patients.

In one embodiment, a method of this invention lowers CA27.29 biomarker in a subject. In one embodiment, a method of this invention lowers PSA in a subject. In one embodiment, a method of this invention lowers CTX biomarker in a subject. In one embodiment of this invention, a method of this invention lowers NTX biomarker in a subject. In another embodiment, a method of this invention maintains the level of CA27.29 in a subject. In another embodiment, a method of this invention maintains the level of PSA in a subject. In another embodiment, a method of this invention maintains the level of CTX biomarker in a subject. In another embodiment, a method of this invention maintains the level of NTX biomarker. In one embodiment, the subject has breast cancer. In one embodiment, the subject has advanced breast cancer. In another embodiment, the subject has refractory breast cancer. In yet another embodiment, the subject has AR-positive breast cancer. In still another embodiment, the subject has ER-positive breast cancer.

In one embodiment, the compound of this invention is an antagonist. In another embodiment, the compound of this invention is an agonist. In yet another embodiment, the compound of this invention is a partial agonist/partial antagonist. In one embodiment, a compound of this invention is an AR agonist. In another embodiment, a compound is an AR antagonist. In yet another embodiment, a compound is a partial AR agonist and AR antagonist. In one embodiment, a compound of this invention is a PR agonist. In another embodiment, a compound is a PR antagonist. In yet another embodiment, a compound is a partial PR agonist and PR antagonist.

In one embodiment, a compound of this invention is an AR agonist and a PR antagonist.

The SARM compounds of this invention may be useful, in some embodiments, for: a) treatment, prevention, delaying onset of, increasing time to first skeletal related event (SRE), suppression or inhibition of, or the reduction of the risk of developing a skeletal-related event (SRE), such as pathological bone fractures, surgery of the bone, radiation of the bone, spinal cord compression, new bone metastasis, and/or bone loss in a subject; b) treatment, prevention, suppression or inhibition of, or the reduction of the risk of developing a variety of hormone-related conditions in a subject, for example for increasing libido; and/or c) improving quality of life in a subject.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake. However, osteoporosis also occurs frequently in males. It is well established that the bone mineral density of males decreases with age. Decreased amounts of bone mineral content and density correlates with decreased bone strength, and predisposes to fracture. The molecular mechanisms underlying the pleiotropic effects of sex-hormones in non-reproductive tissues are only beginning to be understood, but it is clear that physiologic concentrations of androgens and estrogens play an important role in maintaining bone homeostasis throughout the life-cycle. Consequently, when androgen or estrogen deprivation occurs there is a resultant increase in the rate of bone remodeling that tilts the balance of resorption and formation to the favor of resorption that contributes to the overall loss of bone mass. In males, the natural decline in sex-hormones at maturity (direct decline in androgens as well as lower levels of estrogens derived from peripheral aromatization of androgens) is associated with the frailty of bones. This effect is also observed in males who have been castrated.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for: a) treating a bone related disorder; b) preventing a bone related disorder; c) suppressing a bone related disorder; d) inhibiting a bone related disorder; e) increasing a strength of a bone of a subject; f) increasing a bone mass in a subject; g) use for osteoclastogenesis inhibition; and/or h) use for osteoblastogenesis stimulation.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for: a) accelerating bone repair; b) treating bone disorders; c) treating bone density loss; d) treating low bone mineral density (BMD); e) treating reduced bone mass; f) treating metabolic bone disease; g) promoting bone growth or regrowth; h) promoting bone restoration; i) promoting bone fracture repair; j) promoting bone remodeling; k) treating bone damage following reconstructive surgery including of the face, hip, or joints; l) enhancing of bone strength and function; m) increasing cortical bone mass; n) increasing trabecular connectivity; o) preventing, inhibiting or delaying metastasis to the bone; and/or p) preventing, inhibiting or delaying the growth of metastatic tumors of the bone.

In one embodiment, the bone related disorder is a genetic disorder, or in another embodiment, is induced as a result of a treatment regimen for a given disease. For example, and in one embodiment, the compounds as herein described are useful in treating a bone-related disorder that arises as a result of cancer metastasis to bone, or in another embodiment, as a result of androgen-deprivation therapy, for example, given in response to prostate carcinogenesis in the subject.

As used herein, "estrogen-deprivation therapy" may refer to therapy which is given in response to breast cancer in a subject. Known treatments include treatment with GnRH agonists, SERMs, SERDs, or aromatase inhibitors (AI). For example, and in one embodiment, the compounds as herein described are useful in treating a bone-related disorder that arises as a result of cancer metastasis to bone, or in another embodiment, as a result of estrogen-deprivation therapy, for example, given in response to breast cancer in the subject. Menopause can also be induced using GnRH agonists such as gosarelin (Zoladex) which maintains endogeneous estrogens at low levels via inhibition of the hypothalamus-pituitary-gonadal axis.

In one embodiment, the bone-related disorder is a loss of bone mineral density (BMD). In another embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty. In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility.

In one embodiment, the osteoporosis results from androgen deprivation. In another embodiment, the osteoporosis follows androgen deprivation. In another embodiment, the osteoporosis results from estrogen-deprivation therapy. In another embodiment, the osteoporosis follows estrogen-deprivation therapy. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis. In another embodiment, osteoporosis can predispose a breast cancer patient to metastasis to the bones and/or predispose the patients toward the development of a skeletally related event.

In another embodiment, the primary osteoporosis is type I primary osteoporosis. In another embodiment, the primary osteoporosis is type II primary osteoporosis. Each type of osteoporosis represents a separate embodiment of the present invention.

According to this aspect of the invention and in one embodiment, the bone-related disorder is treated with a compound as herein described, or a combination thereof. In another embodiment, other bone-stimulating compounds can be provided to the subject, prior to, concurrent with or following administration of a compound or compounds as herein described. In one embodiment, such a bone stimulating compound may comprise natural or synthetic materials.

In one embodiment, the bone stimulating compound may comprise a bone morphogenetic protein (BMP), a growth factor, such as epidermal growth factor (EGF), a fibroblast growth factor (FGF), a transforming growth factor (TGF, an insulin growth factor (IGF), a platelet-derived growth factor (PDGF) hedgehog proteins such as sonic, indian and desert hedgehog, a hormone such as follicle stimulating hormone, parathyroid hormone, parathyroid hormone related peptide, activins, inhibins, follistatin, frizzled, frzb or frazzled proteins, BMP binding proteins such as chordin and fetuin, a cytokine such as IL-3, IL-7, GM-CSF, a chemokine, such as eotaxin, a collagen, osteocalcin, osteonectin and others, as will be appreciated by one skilled in the art.

In another embodiment, the compositions for use in treating a bone disorder of this invention may comprise a compound or compounds as herein described, an additional bone stimulating compound, or compounds, and osteogenic cells. In one embodiment, an osteogenic cell may be a stem cell or progenitor cell, which may be induced to differentiate into an osteoblast. In another embodiment, the cell may be an osteoblast. In another embodiment, nucleic acids which encode bone-stimulating compounds may be administered to the subject, which is to be considered as part of this invention.

In one embodiment, this invention provides for the treatment, prevention, suppression or inhibition of, or the reduction of the risk of developing a skeletal-related event (SRE), such as bone fractures, surgery of the bone, radiation of the bone, spinal cord compression, new bone metastasis, bone loss, or a combination thereof in a subject with cancer, comprising administering a compound as herein described and/or its analog, derivative, isomer, metabolite, pharmaceutically acceptable salt, pharmaceutical product, hydrate, N-oxide, or any combination thereof. The invention relates, inter alia, to treatment of an SRE with the compound of Formulae I-XIV of this invention: (a) in a subject with prostate cancer undergoing or having undergone androgen deprivation therapy (ADT); or (b) in a subject with breast cancer undergoing or having undergone estrogen-deprivation therapy.

In one embodiment, the skeletal-related events treated using the methods provided herein and/or utilizing the compositions provided herein, are fractures, which in one embodiment, are pathological fractures, non-traumatic fractures, vertebral fracture, non-vertebral fractures, morphometric fractures, or a combination thereof. In some embodiments, fractures may be simple, compound, transverse, greenstick, or comminuted fractures. In one embodiment, fractures may be to any bone in the body, which in one embodiment, is a fracture in any one or more bones of the arm, wrist, hand, finger, leg, ankle, foot, toe, hip, collar bone, or a combination thereof. In breast cancer, metastasis occurs most often to the hip and vertebrae. In one embodiment, the skeletal-related is fractures to the hip and/or vertebrae.

In another embodiment, the methods and/or compositions provided herein, are effective in treatment, prevention, suppression, inhibition or reduction of the risk of skeletal-related events such as pathologic fractures, spinal cord compression, hypercalcemia, bone-related pain, or their combination.

In another embodiment, the skeletal-related events sought to be treated using the methods provided herein and/or utilizing the compositions provided herein, comprise the necessity for bone surgery and/or bone radiation, which in some embodiments, is for the treatment of pain resulting in one embodiment from bone damage, or nerve compression. In another embodiment, the skeletal-related events sought to be treated using the methods provided herein and/or utilizing the compositions provided herein, comprise spinal cord compression, or the necessity for changes in antineoplastic therapy, including changes in hormonal therapy, in a subject. In some embodiments, skeletal-related events sought to be treated using the methods provided herein and/or utilizing the compositions provided herein, comprise treating, suppressing, preventing, reducing the incidence of, or delaying progression or severity of bone metastases, or bone loss. In one embodiment, bone loss may comprise osteoporosis, osteopenia, or a combination thereof. In one embodiment, skeletal-related events may comprise any combination of the embodiments listed herein.

In one embodiment, the methods provided herein and/or utilizing the compositions provided herein, are effective in reducing metastases to the bone, such as in terms of number of foci, the size of foci, or a combination thereof. According to this aspect of the invention and in one embodiment, provided herein is a method of preventing or inhibiting cancer metastasis to bone in a subject, comprising the step of administering to the subject a composition comprising toremifene, raloxifene, tamoxifen or an analogue, functional derivative, metabolite or a combination thereof, or a pharmaceutically acceptable salt thereof. In one embodiment, such metabolites may comprise ospemifene, fispemifene or their combination. In one embodiment, the cancer is prostate cancer. In one embodiment, the cancer is breast cancer.

In one embodiment, the skeletal-related events are a result of cancer therapy. In one embodiment, the skeletal-related events are a result of hormone deprivation therapy, while in another embodiment, they are a product of androgen deprivation therapy (ADT), and in another embodiment they are a product of estrogen-deprivation therapy As used herein, the term "libido", may refer to sexual desire, or as defined in Example 9.

As used herein, the term "quality of life" may refer to the focuses on the health and life of a subject suffering from a condition or disease, for example suffering from breast cancer, post treatment until the end of life. It covers the physical, psychosocial, and economic issues faced by the subject, beyond the diagnosis and treatment phases. The term "quality of life" may also be referred to herein as "survivorship". In one embodiment, survivorship includes issues related to the ability to get health care and follow-up treatment, late effects of treatment, second cancers, and quality of life. Family members, friends, and caregivers are also considered part of the survivorship experience.

In one embodiment, the methods of this invention are useful to a subject, which is a human. In one embodiment, the subject is male. In another embodiment, the subject is female. In some embodiments, while the methods as described herein may be useful for treating either males or females, females may respond more advantageously to administration of certain compounds, for certain methods. In other embodiments, while the methods as described herein may be useful for treating either males or females, males may respond more advantageously to administration of certain compounds, for certain methods.

Selective Androgen Receptor Modulator (SARM) Compounds

In one embodiment, the compound of this invention which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; and/or p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a structure of Formula I, and/or its analog, derivative, isomer, metabolite, pharmaceutically acceptable salt, pharmaceutical product, hydrate, N-oxide, crystal, polymorph, prodrug or any combination thereof:

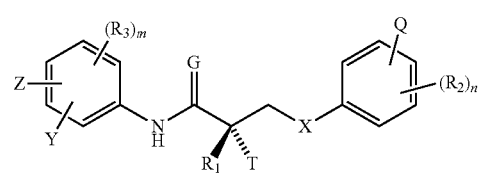

I

X is a bond, O, CH$_2$, NH, S, Se, PR, NO or NR;
G is O or S;
T is OH, OR, —NHCOCH$_3$, or NHCOR;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;
R$_1$ is CH$_3$, CH$_2$F, CHF$_2$, CF$_3$, CH$_2$CH$_3$, or CF$_2$CF$_3$;

$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;

$R_3$ is H, F, Cl, Br, I, CN, $NO_2$, COR, COOH, CONHR, $CF_3$, $Sn(R)_3$, or $R_3$ together with the benzene ring to which it is attached forms a fused ring system represented by the structure:

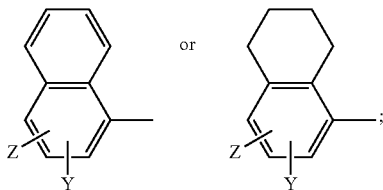

Z is $NO_2$, CN, COR, COOH, or CONHR;
Y is $CF_3$, F, Br, Cl, I, CN, or $Sn(R)_3$;
Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;
or Q together with the benzene ring to which it is attached is a fused ring system represented by structure A, B or C:

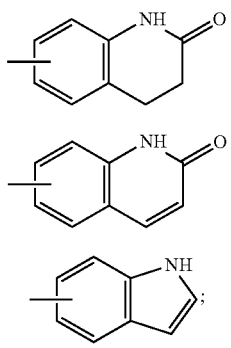

n is an integer of 1-4; and
m is an integer of 1-3.

In one embodiment, this invention relates to the treatment of androgen receptor-positive breast cancer in a subject, for example a female subject. Accordingly, this invention provides methods for: a) treating AR-positive breast cancer in a subject; b) treating metastatic AR-positive breast cancer, or advanced AR-positive breast cancer; c) treating refractory AR-positive breast cancer; d) treating, preventing, suppressing or inhibiting metastasis in a subject suffering from breast cancer; e) prolonging progression-free survival of a subject suffering from breast cancer; f) treating a subject suffering from ER-positive breast cancer; g) treating a subject suffering from metastatic ER-positive breast cancer; h) treating a subject suffering from refractory ER-positive breast cancer; i) treating a subject suffering from AR-positive ER-positive breast cancer; j) treating a subject suffering from AR-positive ER-positive refractory breast cancer; k) treating a subject suffering from AR-positive ER-positive metastatic breast cancer; l) treating a subject suffering from AR-positive and ER-positive breast cancer; m) treating a subject suffering from AR-positive ER-positive breast cancer with or without expression of PR, and/or HER2; n) treating a subject suffering from advanced ER-positive breast cancer; o) treating a subject suffering from ER-positive breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; p) treating, preventing, suppressing or inhibiting metastasis in a subject suffering from ER-positive breast cancer; q) prolonging survival of a subject with ER-positive breast cancer; r) slowing the progression of ER-positive breast cancer in a subject; s) prolonging progression-free survival of a subject with ER-positive breast cancer; t) treating a subject suffering from AR-positive HER2-positive breast cancer; u) treating a subject suffering from ER mutant expressing breast cancer, and/or v) treating a subject suffering from Y537S ER mutant expressing breast cancer, comprising administering to the subject a therapeutically effective amount of a selective androgen receptor modulator (SARM) compound represented by a compound of Formula I:

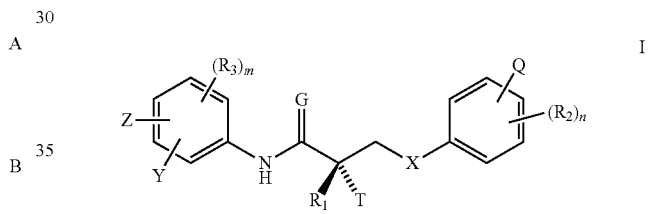

X is a bond, O, $CH_2$, NH, S, Se, PR, NO or NR;
G is O or S;
T is OH, OR, —$NHCOCH_3$, or NHCOR;
R is alkyl, haloalkyl, dihaloalkyl, trihaloalkyl, $CH_2F$, $CHF_2$, $CF_3$, $CF_2CF_3$, aryl, phenyl, halogen, alkenyl or OH;
$R_1$ is $CH_3$, $CH_2F$, $CHF_2$, $CF_3$, $CH_2CH_3$, or $CF_2CF_3$;
$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;
$R_3$ is H, F, Cl, Br, I, CN, $NO_2$, COR, COOH, CONHR, $CF_3$, $Sn(R)_3$, or $R_3$ together with the benzene ring to which it is attached forms a fused ring system represented by the structure:

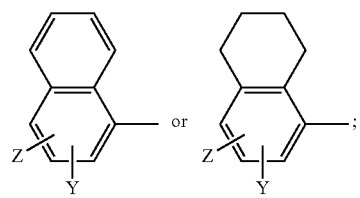

Z is $NO_2$, CN, COR, COOH, or CONHR;
Y is $CF_3$, F, Br, Cl, I, CN, or $Sn(R)_3$;
Q is CN, alkyl, halogen, $N(R)_2$, $NHCOCH_3$, $NHCOCF_3$, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R or SR;

or Q together with the benzene ring to which it is attached is a fused ring system represented by structure A, B or C:

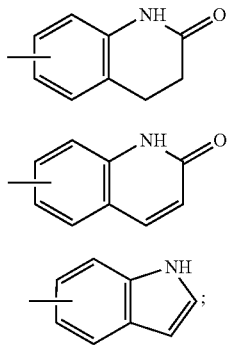

n is an integer of 1-4; and
m is an integer of 1-3;

and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In another embodiment, this invention provides methods for: a) treating a subject suffering from HER2-positive breast cancer; b) treating a subject suffering from HER2-positive refractory breast cancer; c) treating a subject suffering from HER2-positive metastatic breast cancer; d) treating a subject suffering from HER2-positive and ER-negative breast cancer; e) treating a subject suffering from HER2-positive and ER-positive breast cancer; f) treating a subject suffering from HER2-positive and PR-positive breast cancer; g) treating a subject suffering from HER2-positive and PR-negative breast cancer; h) treating a subject suffering from HER2-positive and AR-positive breast cancer; i) treating a subject suffering from HER2-positive and AR-negative breast cancer; j) treating a subject suffering from HER2-positive, ER-positive, PR-positive, and AR-positive breast cancer; k) treating a subject suffering from HER2-positive, ER-positive, PR-negative, and AR-positive breast cancer; l) treating a subject suffering from HER2-positive, ER-positive, PR-negative, and AR-negative breast cancer; m) treating a subject suffering from HER2-positive, ER-positive, PR-positive, and AR-negative breast cancer; n) treating a subject suffering from HER2-positive, ER-negative, PR-negative, and AR-positive breast cancer; o) treating a subject suffering from HER2-positive, ER-negative, PR-positive, and AR-positive breast cancer; p) treating a subject suffering from HER2-positive, ER-negative, PR-positive, and AR-negative breast cancer; and/or q) treating a subject suffering from HER2-positive, ER-negative, PR-negative, and AR-negative breast cancer; comprising administering to the subject a therapeutically effective amount of a selective androgen receptor modulator (SARM) compound represented by a compound of Formula I:

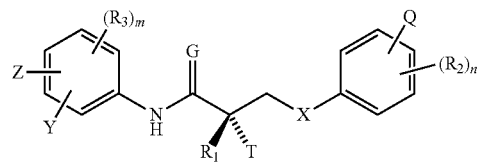

X is a bond, O, CH₂, NH, S, Se, PR, NO or NR;
G is O or S;
T is OH, OR, —NHCOCH₃, or NHCOR;
R is alkyl, haloalkyl, dihaloalkyl, trihaloalkyl, CH₂F, CHF₂, CF₃, CF₂CF₃, aryl, phenyl, halogen, alkenyl or OH;
R₁ is CH₃, CH₂F, CHF₂, CF₃, CH₂CH₃, or CF₂CF₃;
R₂ is H, F, Cl, Br, I, CH₃, CF₃, OH, CN, NO₂, NHCOCH₃, NHCOCF₃, NHCOR, alkyl, arylalkyl, OR, NH₂, NHR, N(R)₂, or SR;
R₃ is H, F, Cl, Br, I, CN, NO₂, COR, COOH, CONHR, CF₃, Sn(R)₃, or R₃ together with the benzene ring to which it is attached forms a fused ring system represented by the structure:

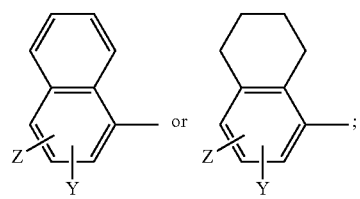

Z is NO₂, CN, COR, COOH, or CONHR;
Y is CF₃, F, Br, Cl, I, CN, or Sn(R)₃;
Q is CN, alkyl, halogen, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R or SR;

or Q together with the benzene ring to which it is attached is a fused ring system represented by structure A, B or C:

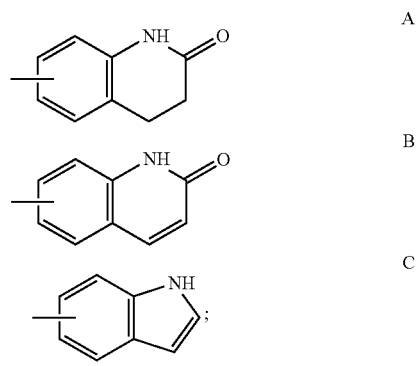

n is an integer of 1-4; and
m is an integer of 1-3;

and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In one embodiment, G in Formula I is O. In another embodiment, X in Formula I is O. In another embodiment, T in Formula I is OH. In another embodiment, R₁ in Formula I is CH₃. In another embodiment, Z in Formula I is NO₂. In another embodiment, Z in Formula I is CN. In another embodiment, Y in Formula I is CF₃. In another embodiment, Y in Formula I is Cl. In another embodiment, Q in Formula I is CN. In another embodiment, Q in Formula I is halogen. In another embodiment, Q in Formula I is F. In another embodiment, Q in Formula I is Cl. In another embodiment, Q in Formula I is NHCOCH₃. In another embodiment, Q in Formula I is CN and R₂ is F. In another embodiment, Q in Formula I is Cl and R₂ is F. In another embodiment, Q in Formula I is in the para position. In another embodiment, Z in Formula I is in the para position. In another embodiment, Y in Formula I is in the meta position.

The substituents Z, Y and R₃ can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituents Q and R₂ can be in any position of the ring carrying these substituents (hereinafter "B ring"). In one embodiment, the substituent Q is in the para position of the B ring. In another embodiment, the substituent R₂ is in the meta position of the B ring. In another embodiment, the substituent Q is CN and is in the para position of the B ring.

As contemplated herein, when the integers m and n are greater than one, the substituents R₂ and R₃ are not limited to one particular substituent, and can be any combination of the substituents listed above.

In another embodiment, the compound of this invention which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a compound of Formula II, and/or its analog, derivative, isomer, metabolite, pharmaceutically acceptable salt, pharmaceutical product, hydrate, N-oxide, crystal, polymorph, prodrug or any combination thereof:

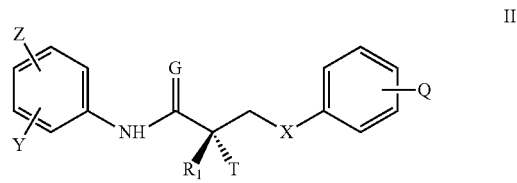

II wherein X is a bond, O, CH₂, NH, Se, PR, or NR;
G is O or S;
T is OH, OR, —NHCOCH₃, or NHCOR;
Z is NO₂, CN, COR, COOH or CONHR;
Y is I, CF₃, Br, Cl, or Sn(R)₃;
Q is CN, alkyl, halogen, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R or SR;
or Q together with the benzene ring to which it is attached is a fused ring system
represented by structure A, B or C:

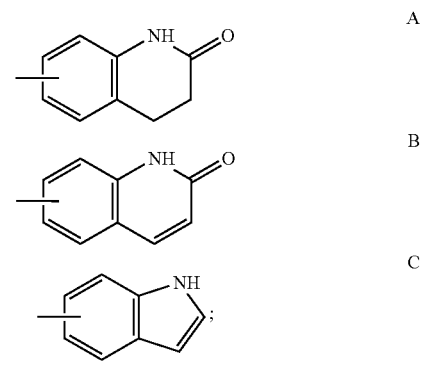

R is a C₁-C₄ alkyl, aryl, phenyl, alkenyl, hydroxyl, a C₁-C₄ haloalkyl, halogen, or haloalkenyl; and
R₁ is CH₃, CF₃, CH₂CH₃, or CF₂CF₃.

In one embodiment, this invention relates to the treatment of androgen receptor-positive breast cancer in a subject, for example a female subject. Accordingly, this invention provides methods for: a) treating AR-positive breast cancer in a subject; b) treating metastatic AR-positive breast cancer, or advanced AR-positive breast cancer; c) treating refractory AR-positive breast cancer; d) treating, preventing, suppressing or inhibiting metastasis in a subject suffering from breast cancer; e) prolonging progression-free survival of a subject suffering from breast cancer; f) treating a subject suffering from ER-positive breast cancer; g) treating a subject suffering from metastatic ER-positive breast cancer; h) treating a subject suffering from refractory ER-positive breast cancer; i) treating a subject suffering from AR-positive ER-positive breast cancer; j) treating a subject suffering from AR-positive ER-positive refractory breast cancer; k) treating a subject suffering from AR-positive ER-positive metastatic breast cancer; l) treating a subject suffering from AR-positive and ER-positive breast cancer; m) treating a subject suffering from AR-positive ER-positive breast cancer with or without expression of PR, and/or HER2; n) treating a subject suffering from advanced ER-positive breast cancer; o) treating a subject suffering from ER-positive breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; p) treating, preventing, suppressing or inhibiting metastasis in a subject suffering from ER-positive breast cancer; q) prolonging survival of a subject with ER-positive breast cancer; r) slowing the progression of ER-positive breast cancer in a subject; s) prolonging progression-free survival of a subject with ER-positive breast cancer; t) treating a subject suffering from AR-positive HER2-positive breast cancer; u) treating a subject suffering from ER mutant expressing breast cancer, and/or v) treating a subject suffering from Y537S ER mutant expressing breast cancer, comprising administering to the subject a therapeutically effective amount of a selective androgen receptor modulator (SARM) compound represented by a compound of Formula II:

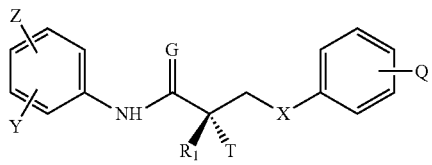

II wherein X is a bond, O, $CH_2$, NH, Se, PR, or NR;

G is O or S;

T is OH, OR, —$NHCOCH_3$, or NHCOR;

Z is $NO_2$, CN, COR, COOH or CONHR;

Y is I, $CF_3$, Br, Cl, or $Sn(R)_3$;

Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;

or Q together with the benzene ring to which it is attached is a fused ring system represented by structure A, B or C:

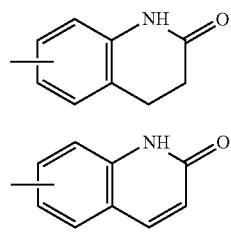

A

B

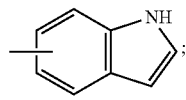

C

R is a $C_1$-$C_4$ alkyl, aryl, phenyl, alkenyl, hydroxyl, a $C_1$-$C_4$ haloalkyl, halogen, or haloalkenyl; and $R_1$ is $CH_3$, $CF_3$, $CH_2CH_3$, or $CF_2CF_3$;

and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In another embodiment, this invention provides methods for: a) treating a subject suffering from HER2-positive breast cancer; b) treating a subject suffering from HER2-positive refractory breast cancer; c) treating a subject suffering from HER2-positive metastatic breast cancer; d) treating a subject suffering from HER2-positive and ER-negative breast cancer; e) treating a subject suffering from HER2-positive and ER-positive breast cancer; f) treating a subject suffering from HER2-positive and PR-positive breast cancer; g) treating a subject suffering from HER2-positive and PR-negative breast cancer; h) treating a subject suffering from HER2-positive and AR-positive breast cancer; i) treating a subject suffering from HER2-positive and AR-negative breast cancer; j) treating a subject suffering from HER2-positive, ER-positive, PR-positive, and AR-positive breast cancer; k) treating a subject suffering from HER2-positive, ER-positive, PR-negative, and AR-positive breast cancer; l) treating a subject suffering from HER2-positive, ER-positive, PR-negative, and AR-negative breast cancer; m) treating a subject suffering from HER2-positive, ER-positive, PR-positive, and AR-negative breast cancer; n) treating a subject suffering from HER2-positive, ER-negative, PR-negative, and AR-positive breast cancer; o) treating a subject suffering from HER2-positive, ER-negative, PR-positive, and AR-positive breast cancer; p) treating a subject suffering from HER2-positive, ER-negative, PR-positive, and AR-negative breast cancer; and/or q) treating a subject suffering from HER2-positive, ER-negative, PR-negative, and AR-negative breast cancer; comprising administering to the subject a therapeutically effective amount of a selective androgen receptor modulator (SARM) compound represented by a compound of Formula II:

II wherein X is a bond, O, $CH_2$, NH, Se, PR, or NR;
G is O or S;
T is OH, OR, —$NHCOCH_3$, or NHCOR;
Z is $NO_2$, CN, COR, COOH or CONHR;
Y is I, $CF_3$, Br, Cl, or $Sn(R)_3$;
Q is CN, alkyl, halogen, $N(R)_2$, $NHCOCH_3$, $NHCOCF_3$, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R or SR;

or Q together with the benzene ring to which it is attached is a fused ring system represented by structure A, B or C:

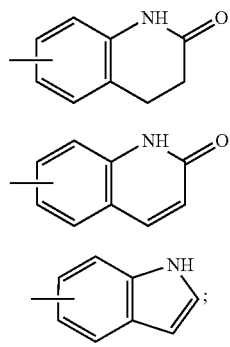

R is a $C_1$-$C_4$ alkyl, aryl, phenyl, alkenyl, hydroxyl, a $C_1$-$C_4$ haloalkyl, halogen, or haloalkenyl; and $R_1$ is $CH_3$, $CF_3$, $CH_2CH_3$, or $CF_2CF_3$;

and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In one embodiment, G in Formula II is O. In another embodiment, X in Formula II is O. In another embodiment, T in Formula II is OH. In another embodiment, $R_1$ in Formula II is $CH_3$. In another embodiment, Z in Formula II is $NO_2$. In another embodiment, Z in Formula II is CN. In another embodiment, Y in Formula II is $CF_3$. In another embodiment, Y in Formula II is halogen. In another embodiment, Y in Formula II is Cl. In another embodiment, Q in Formula II is CN. In another embodiment, Q in Formula II is halogen. In another embodiment, Q in Formula II is Cl. In another embodiment, Q in Formula II is F. In another embodiment, Q in Formula II is NHCOCH₃. In another embodiment, Q in Formula II is in the para position. In another embodiment, Z in Formula II is in the para position. In another embodiment, Y in Formula II is in the meta position. In another embodiment, G in Formula II is O, T is OH, $R_1$ is $CH_3$, X is O, Z is CN, Y is $CF_3$ or halogen and Q is CN or F. In another embodiment, G in Formula II is O, T is OH, $R_1$ is $CH_3$, X is O, Z is $NO_2$, Y is $CF_3$ and Q is NHCOCH₃, F or CL.

The substituents Z and Y can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituent Q can be in any position of the ring carrying this substituent (hereinafter "B ring"). In one embodiment, the substituent Q is in the para position of the B ring. In another embodiment, the substituent Q is CN and is in the para position of the B ring.

In another embodiment, the compound of this invention which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a structure of Formula III, and/or its analog, derivative, isomer, metabolite, pharmaceutically acceptable salt, pharmaceutical product, hydrate, N-oxide, crystal, polymorph, prodrug or any combination thereof:

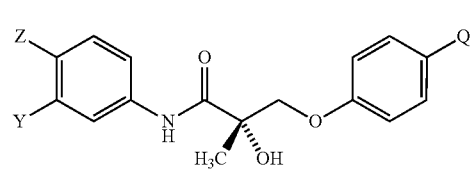

III wherein

Z is $NO_2$, CN, COOH, COR, NHCOR or CONHR;

Y is $CF_3$, F, I, Br, Cl, CN, $C(R)_3$ or $Sn(R)_3$;

Q is CN, alkyl, halogen, $N(R)_2$, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R or SR;

or Q together with the benzene ring to which it is attached is a fused ring system represented by structure A, B or C:

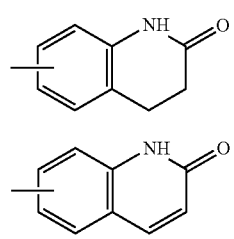

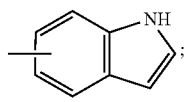

and

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH.

In one embodiment, this invention relates to the treatment of androgen receptor-positive breast cancer in a subject, for example a female subject. Accordingly, this invention provides methods for: a) treating AR-positive breast cancer in a subject; b) treating metastatic AR-positive breast cancer, or advanced AR-positive breast cancer; c) treating refractory AR-positive breast cancer; d) treating, preventing, suppressing or inhibiting metastasis in a subject suffering from breast cancer; e) prolonging progression-free survival of a subject suffering from breast cancer; f) treating a subject suffering from ER-positive breast cancer; g) treating a subject suffering from metastatic ER-positive breast cancer; h) treating a subject suffering from refractory ER-positive breast cancer; i) treating a subject suffering from AR-positive ER-positive breast cancer; j) treating a subject suffering from AR-positive ER-positive refractory breast cancer; k) treating a subject suffering from AR-positive ER-positive metastatic breast cancer; l) treating a subject suffering from AR-positive and ER-positive breast cancer; m) treating a subject suffering from AR-positive ER-positive breast cancer with or without expression of PR, and/or HER2; n) treating a subject suffering from advanced ER-positive breast cancer; o) treating a subject suffering from ER-positive breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; p) treating, preventing, suppressing or inhibiting metastasis in a subject suffering from ER-positive breast cancer; q) prolonging survival of a subject with ER-positive breast cancer; r) slowing the progression of ER-positive breast cancer in a subject; s) prolonging progression-free survival of a subject with ER-positive breast cancer; t) treating a subject suffering from AR-positive HER2-positive breast cancer; comprising administering to the subject a therapeutically effective amount of a selective androgen receptor modulator (SARM) compound represented by a compound of Formula III:

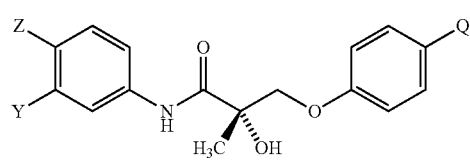

wherein
Z is NO$_2$, CN, COOH, COR, NHCOR or CONHR;
Y is CF$_3$, F, I, Br, Cl, CN, C(R)$_3$ or Sn(R)$_3$;

Q is CN, alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;

or Q together with the benzene ring to which it is attached is a fused ring system represented by structure A, B or C:

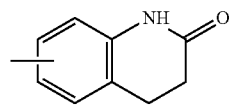

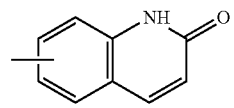

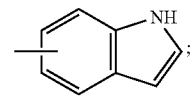

and

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;

and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In another embodiment, this invention provides methods for: a) treating a subject suffering from HER2-positive breast cancer; b) treating a subject suffering from HER2-positive refractory breast cancer; c) treating a subject suffering from HER2-positive metastatic breast cancer; d) treating a subject suffering from HER2-positive and ER-negative breast cancer; e) treating a subject suffering from HER2-positive and ER-positive breast cancer; f) treating a subject suffering from HER2-positive and PR-positive breast cancer; g) treating a subject suffering from HER2-positive and PR-negative breast cancer; h) treating a subject suffering from HER2-positive and AR-positive breast cancer; i) treating a subject suffering from HER2-positive and AR-negative breast cancer; j) treating a subject suffering from HER2-positive, ER-positive, PR-positive, and AR-positive breast cancer; k) treating a subject suffering from HER2-positive, ER-positive, PR-negative, and AR-positive breast cancer; l) treating a subject suffering from HER2-positive, ER-positive, PR-negative, and AR-negative breast cancer; m) treating a subject suffering from HER2-positive, ER-positive, PR-positive, and AR-negative breast cancer; n) treating a subject suffering from HER2-positive, ER-negative, PR-negative, and AR-positive breast cancer; o) treating a subject suffering from HER2-positive, ER-negative, PR-positive, and AR-positive breast cancer; p) treating a subject suffering from HER2-positive, ER-negative, PR-positive, and AR-negative breast cancer; and/or q) treating a subject suffering from HER2-positive, ER-negative, PR-negative, and AR-negative breast cancer; comprising administering to the subject a therapeutically effective amount of a selective androgen receptor modulator (SARM) compound represented by a compound of Formula III:

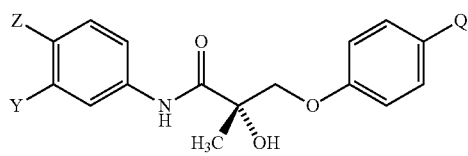

wherein
Z is NO$_2$, CN, COOH, COR, NHCOR or CONHR;
Y is CF$_3$, F, I, Br, Cl, CN, C(R)$_3$ or Sn(R)$_3$;
Q is CN, alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;
or Q together with the benzene ring to which it is attached is a fused ring system represented by structure A, B or C:

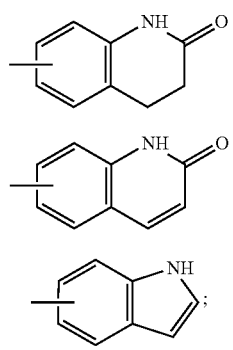

and
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;
and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In one embodiment, Z in Formula III is NO$_2$. In another embodiment, Z in Formula III is CN. In another embodiment, Y in Formula III is CF$_3$. In another embodiment, Y in Formula III is Cl. In another embodiment, Y in Formula III is halogen. In another embodiment, Q in Formula III is CN. In another embodiment, Q in Formula III is halogen. In another embodiment, Q in Formula III is F. In another embodiment, Q in Formula III is Cl. In another embodiment, Q in Formula III is NHCOCH$_3$. In another embodiment, Z is CN, Y is CF$_3$ or halogen, and Q is CN or F. In another embodiment, Z is NO$_2$, Y is CF$_3$, and Q is NHCOCH$_3$, F or Cl.

In another embodiment, the compound of this invention which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a structure of Formula IV, and/or its analog, derivative, isomer, metabolite, pharmaceutically acceptable salt, pharmaceutical product, hydrate, N-oxide, crystal, polymorph, prodrug or any combination thereof:

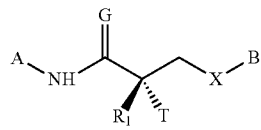

wherein X is a bond, O, CH$_2$, NH, S, Se, PR, NO or NR;
G is O or S;
R$_1$ is CH$_3$, CH$_2$F, CHF$_2$, CF$_3$, CH$_2$CH$_3$, or CF$_2$CF$_3$;
T is OH, OR, —NHCOCH$_3$, or NHCOR;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;
A is a ring selected from:

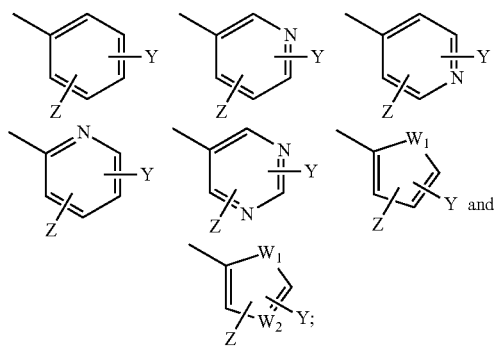

B is a ring selected from:

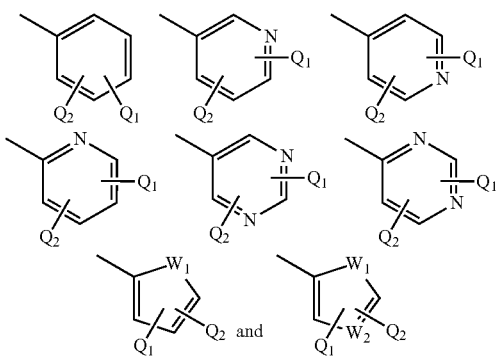

wherein A and B cannot simultaneously be a benzene ring;

Z is $NO_2$, CN, COOH, COR, NHCOR or CONHR;

Y is $CF_3$, F, I, Br, Cl, CN, $C(R)_3$ or $Sn(R)_3$;

$Q_1$ and $Q_2$ are independently hydrogen, alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, or

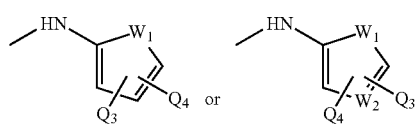

$Q_3$ and $Q_4$ are independently of each other a hydrogen, alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;

$W_1$ is O, NH, NR, NO or S; and $W_2$ is N or NO.

In one embodiment, this invention relates to the treatment of androgen receptor-positive breast cancer in a subject, for example a female subject. Accordingly, this invention provides methods for: a) treating AR-positive breast cancer in a subject; b) treating metastatic AR-positive breast cancer, or advanced AR-positive breast cancer; c) treating refractory AR-positive breast cancer; d) treating, preventing, suppressing or inhibiting metastasis in a subject suffering from breast cancer; e) prolonging progression-free survival of a subject suffering from breast cancer; f) treating a subject suffering from ER-positive breast cancer; g) treating a subject suffering from metastatic ER-positive breast cancer; h) treating a subject suffering from refractory ER-positive breast cancer; i) treating a subject suffering from AR-positive ER-positive breast cancer; j) treating a subject suffering from AR-positive ER-positive refractory breast cancer; k) treating a subject suffering from AR-positive ER-positive metastatic breast cancer; l) treating a subject suffering from AR-positive and ER-positive breast cancer; m) treating a subject suffering from AR-positive ER-positive breast cancer with or without expression of PR, and/or HER2; n) treating a subject suffering from advanced ER-positive breast cancer; o) treating a subject suffering from ER-positive breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; p) treating, preventing, suppressing or inhibiting metastasis in a subject suffering from ER-positive breast cancer; q) prolonging survival of a subject with ER-positive breast cancer; r) slowing the progression of ER-positive breast cancer in a subject; s) prolonging progression-free survival of a subject with ER-positive breast cancer; t) treating a subject suffering from AR-positive HER2-positive breast cancer; u) treating a subject suffering from ER mutant expressing breast cancer, and/or v) treating a subject suffering from Y537S ER mutant expressing breast cancer, comprising administering to the subject a therapeutically effective amount of a selective androgen receptor modulator (SARM) compound represented by a compound of Formula IV:

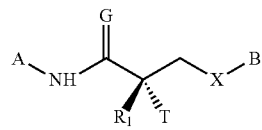

wherein X is a bond, O, $CH_2$, NH, S, Se, PR, NO or NR;

G is O or S;

$R_1$ is $CH_3$, $CH_2F$, $CHF_2$, $CF_3$, $CH_2CH_3$, or $CF_2CF_3$;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl or OH;

A is a ring selected from:

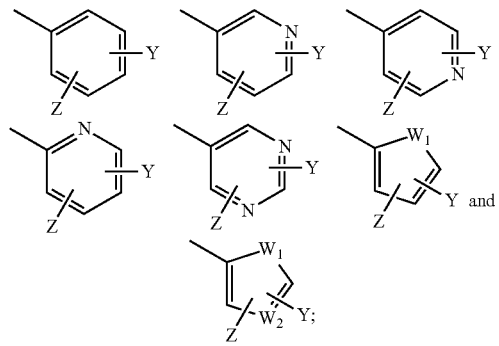

B is a ring selected from:

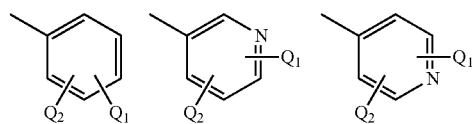

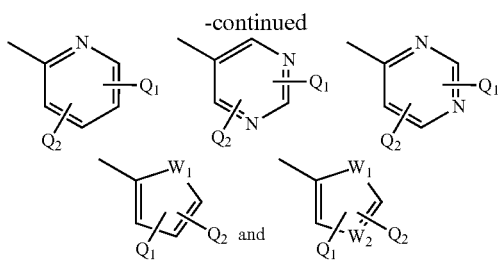

wherein A and B cannot simultaneously be a benzene ring;

Z is NO₂, CN, COOH, COR, NHCOR or CONHR;

Y is CF₃, F, I, Br, Cl, CN, C(R)₃ or Sn(R)₃; $Q_1$ and $Q_2$ are independently hydrogen, alkyl, halogen, CF₃, CN, C(R)₃, Sn(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, or

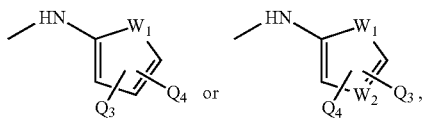

$Q_3$ and $Q_4$ are independently of each other a hydrogen, alkyl, halogen, CF₃, CN, C(R)₃, Sn(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R or SR;

$W_1$ is O, NH, NR, NO or S; and $W_2$ is N or NO;

and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In another embodiment, this invention provides methods for: a) treating a subject suffering from HER2-positive breast cancer; b) treating a subject suffering from HER2-positive refractory breast cancer; c) treating a subject suffering from HER2-positive metastatic breast cancer; d) treating a subject suffering from HER2-positive and ER-negative breast cancer; e) treating a subject suffering from HER2-positive and ER-positive breast cancer; f) treating a subject suffering from HER2-positive and PR-positive breast cancer; g) treating a subject suffering from HER2-positive and PR-negative breast cancer; h) treating a subject suffering from HER2-positive and AR-positive breast cancer; i) treating a subject suffering from HER2-positive and AR-negative breast cancer; j) treating a subject suffering from HER2-positive, ER-positive, PR-positive, and AR-positive breast cancer; k) treating a subject suffering from HER2-positive, ER-positive, PR-negative, and AR-positive breast cancer; l) treating a subject suffering from HER2-positive, ER-positive, PR-negative, and AR-negative breast cancer; m) treating a subject suffering from HER2-positive, ER-positive, PR-positive, and AR-negative breast cancer; n) treating a subject suffering from HER2-positive, ER-negative, PR-negative, and AR-positive breast cancer; o) treating a subject suffering from HER2-positive, ER-negative, PR- positive, and AR-positive breast cancer; p) treating a subject suffering from HER2-positive, ER-negative, PR-positive, and AR-negative breast cancer; and/or q) treating a subject suffering from HER2-positive, ER-negative, PR-negative, and AR-negative breast cancer; comprising administering to the subject a therapeutically effective amount of a selective androgen receptor modulator (SARM) compound represented by a compound of Formula IV:

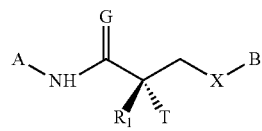

wherein X is a bond, O, CH₂, NH, S, Se, PR, NO or NR;

G is O or S;

$R_1$ is CH₃, CH₂F, CHF₂, CF₃, CH₂CH₃, or CF₂CF₃;

T is OH, OR, —NHCOCH₃, or NHCOR;

R is alkyl, haloalkyl, dihaloalkyl, trihaloalkyl, CH₂F, CHF₂, CF₃, CF₂CF₃, aryl, phenyl, halogen, alkenyl or OH;

A is a ring selected from:

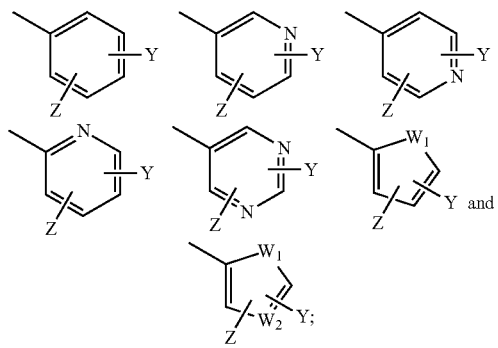

B is a ring selected from:

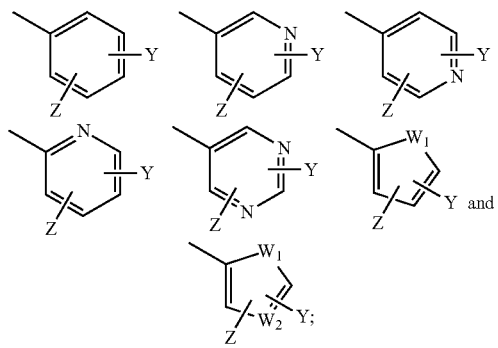

wherein A and B cannot simultaneously be a benzene ring;

Z is NO₂, CN, COOH, COR, NHCOR or CONHR;

Y is CF₃, F, I, Br, Cl, CN, C(R)₃ or Sn(R)₃;

$Q_1$ and $Q_2$ are independently hydrogen, alkyl, halogen, CF₃, CN, C(R)₃, Sn(R)₃, N(R)₂, NHCOCH₃, NHCOCF₃, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, or

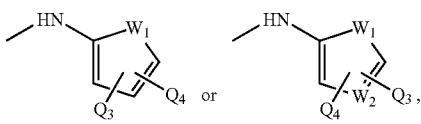

Q$_3$ and Q$_4$ are independently of each other a hydrogen, alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;

W$_1$ is O, NH, NR, NO or S; and

W$_2$ is N or NO;

and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In one embodiment, G in Formula IV is O. In another embodiment, X in Formula IV is O. In another embodiment, T in Formula IV is OH. In another embodiment, R$_1$ in Formula IV is CH$_3$. In another embodiment, Z in Formula IV is NO$_2$. In another embodiment, Z in Formula IV is CN. In another embodiment, Y in Formula IV is CF$_3$. In another embodiment, Y in Formula IV is halogen. In another embodiment, Y in Formula IV is Cl. In another embodiment, Q$_1$ in Formula II is CN. In another embodiment, Q$_1$ in Formula IV is F. In another embodiment, Q$_1$ in Formula IV is Cl. In another embodiment, Q$_1$ in Formula II is NHCOCH$_3$. In another embodiment, Q$_1$ in Formula IV is in the para position. In another embodiment, Z in Formula IV is in the para position. In another embodiment, Y in Formula IV is in the meta position. In another embodiment, G in Formula IV is O, T is OH, R$_1$ is CH$_3$, X is O, Z is NO$_2$ or CN, Y is CF$_3$ or halogen and Q$_1$ is CN, F, Cl, or NHCOCH$_3$.

The substituents Z and Y can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituents Q$_1$ and Q$_2$ can be in any position of the ring carrying these substituents (hereinafter "B ring"). In one embodiment, the substituent Q$_1$ is in the para position of the B ring. In another embodiment, the substituent is Q$_2$ is H. In another embodiment, the substituent Q$_1$ is in the para position of the B ring and the substituent Q$_2$ is H. In another embodiment, the substituent Q$_1$ is CN and is in the para position of the B ring, and the substituent is Q$_2$ is H.

As contemplated herein, other specific embodiments of compounds included within the scope of the present invention, and which are useful in: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, are Formula V or VI. It is understood that included within the scope of the present invention are analogs, derivatives, metabolites, isomers, pharmaceutically acceptable salts, pharmaceutical products, hydrates, N-oxides, polymorphs, crystals, prodrugs or combinations thereof of these compounds:

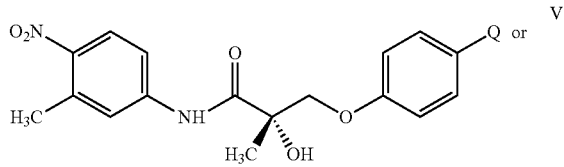

V

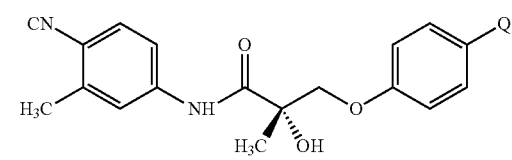

VI wherein Q is CN, alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;

or Q together with the benzene ring to which it is attached is a fused ring system represented by structure A, B or C:

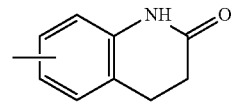

A

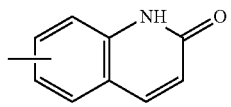

B

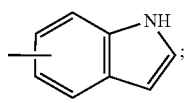

C and

R is alkyl, haloalkyl, dihaloalkyl, trihaloalkyl, $CH_2F$, $CHF_2$, $CF_3$, $CF_2CF_3$, aryl, phenyl, halogen, alkenyl or OH.

In one embodiment, this invention relates to the treatment of androgen receptor-positive breast cancer in a subject, for example a female subject. Accordingly, this invention provides methods for: a) treating AR-positive breast cancer in a subject; b) treating metastatic AR-positive breast cancer, or advanced AR-positive breast cancer; c) treating refractory AR-positive breast cancer; d) treating, preventing, suppressing or inhibiting metastasis in a subject suffering from breast cancer; e) prolonging progression-free survival of a subject suffering from breast cancer; f) treating a subject suffering from ER-positive breast cancer; g) treating a subject suffering from metastatic ER-positive breast cancer; h) treating a subject suffering from refractory ER-positive breast cancer; i) treating a subject suffering from AR-positive ER-positive breast cancer; j) treating a subject suffering from AR-positive ER-positive refractory breast cancer; k) treating a subject suffering from AR-positive ER-positive metastatic breast cancer; l) treating a subject suffering from AR-positive and ER-positive breast cancer; m) treating a subject suffering from AR-positive ER-positive breast cancer with or without expression of PR, and/or HER2; n) treating a subject suffering from advanced ER-positive breast cancer; o) treating a subject suffering from ER-positive breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; p) treating, preventing, suppressing or inhibiting metastasis in a subject suffering from ER-positive breast cancer; q) prolonging survival of a subject with ER-positive breast cancer; r) slowing the progression of ER-positive breast cancer in a subject; s) prolonging progression-free survival of a subject with ER-positive breast cancer; t) treating a subject suffering from AR-positive HER2-positive breast cancer; u) treating a subject suffering from ER mutant expressing breast cancer, and/or v) treating a subject suffering from Y537S ER mutant expressing breast cancer, comprising administering to the subject a therapeutically effective amount of a selective androgen receptor modulator (SARM) compound represented by the following structures of Formula V or VI:

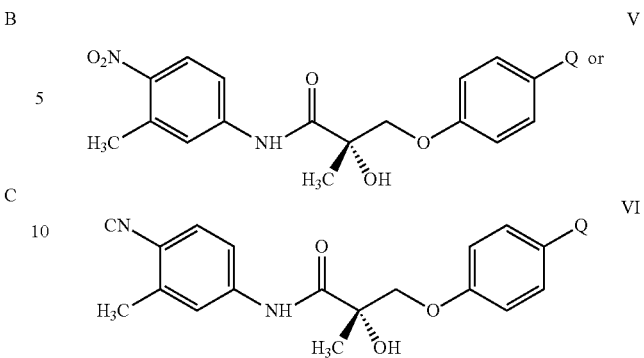

wherein Q is CN, alkyl, halogen, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;

or Q together with the benzene ring to which it is attached is a fused ring system represented by structure A, B or C:

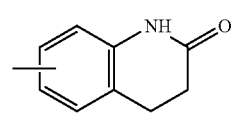

A

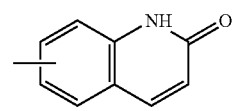

B

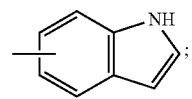

C and

R is alkyl, haloalkyl, dihaloalkyl, trihaloalkyl, $CH_2F$, $CHF_2$, $CF_3$, $CF_2CF_3$, aryl, phenyl, halogen, alkenyl or OH;

and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In another embodiment, this invention provides methods for: a) treating a subject suffering from HER2-positive breast cancer; b) treating a subject suffering from HER2-positive refractory breast cancer; c) treating a subject suffering from HER2-positive metastatic breast cancer; d) treating a subject suffering from HER2-positive and ER-negative breast cancer; e) treating a subject suffering from HER2-positive and ER-positive breast cancer; f) treating a subject suffering from HER2-positive and PR-positive breast cancer; g) treating a subject suffering from HER2-positive and PR-negative breast cancer; h) treating a subject suffering from HER2-positive and AR-positive breast cancer; i) treating a subject suffering from HER2-positive and AR-negative breast cancer; j) treating a subject suffering from HER2-positive, ER-positive, PR-positive, and AR-positive breast cancer; k) treating a subject suffering from HER2-positive, ER-positive, PR-negative, and AR-positive breast cancer; l) treating a subject suffering from HER2-positive, ER-positive, PR-negative, and AR-negative breast cancer; m) treating a subject suffering from HER2-positive, ER-positive, PR-positive, and AR-negative breast cancer; n) treating a subject suffering from HER2-positive, ER-negative, PR-negative, and AR-positive breast cancer; o) treating a subject suffering from HER2-positive, ER-negative, PR-positive, and AR-positive breast cancer; p) treating a subject suffering from HER2-positive, ER-negative, PR-positive, and AR-negative breast cancer; and/or q) treating a subject suffering from HER2-positive, ER-negative, PR-negative, and AR-negative breast cancer; comprising administering to the subject a therapeutically effective amount of a selective androgen receptor modulator (SARM) compound represented by a compound of Formula V or VI:

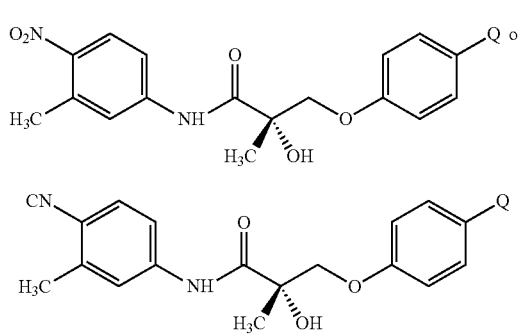

wherein Q is CN, alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;

or Q together with the benzene ring to which it is attached is a fused ring system represented by structure A, B or C:

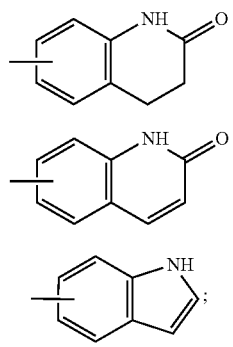

and
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;
and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In one embodiment, Q in Formula V or VI is CN. In one embodiment, Q in Formula V or VI is halogen. In one embodiment, Q in Formula V or VI is F. In one embodiment, Q in Formula V or VI is Cl. In one embodiment, Q in Formula V or VI is NHCOCH$_3$.

In another embodiment, the compound of this invention which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a structure of Formula VII, and/or its analog, derivative, isomer, metabolite, pharmaceutically acceptable salt, pharmaceutical product, hydrate, N-oxide, crystal, polymorph, prodrug or any combination thereof:

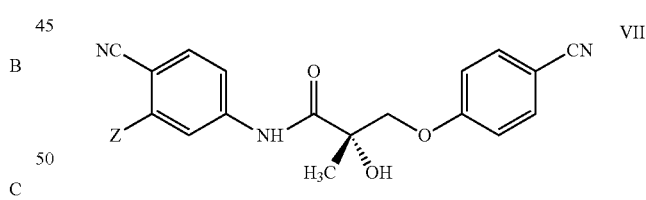

wherein Z is Cl or CF$_3$.

In one embodiment, this invention relates to the treatment of androgen receptor-positive breast cancer in a subject, for example a female subject. Accordingly, this invention provides methods for: a) treating AR-positive breast cancer in a subject; b) treating metastatic AR-positive breast cancer, or advanced AR-positive breast cancer; c) treating refractory AR-positive breast cancer; d) treating, preventing, suppressing or inhibiting metastasis in a subject suffering from breast cancer; e) prolonging progression-free survival of a subject suffering from breast cancer; f) treating a subject suffering from ER-positive breast cancer; g) treating a subject suffering from metastatic ER-positive breast cancer; h) treating a subject suffering from refractory ER-positive breast cancer; i) treating a subject suffering from AR-positive ER-positive breast cancer; j) treating a subject suffering from AR-positive ER-positive refractory breast cancer; k) treating a subject suffering from AR-positive ER-positive metastatic breast cancer; l) treating a subject suffering from AR-positive and ER-positive breast cancer; m) treating a subject suffering from AR-positive ER-positive breast cancer with or without expression of PR, and/or HER2; n) treating a subject suffering from advanced ER-positive breast cancer; o) treating a subject suffering from ER-positive breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; p) treating, preventing, suppressing or inhibiting metastasis in a subject suffering from ER-positive breast cancer; q) prolonging survival of a subject with ER-positive breast cancer; r) slowing the progression of ER-positive breast cancer in a subject; s) prolonging progression-free survival of a subject with ER-positive breast cancer; t) treating a subject suffering from AR-positive HER2-positive breast cancer; and/or u) treating a subject suffering from ER mutant expressing breast cancer, and/or v) treating a subject suffering from Y537S ER mutant expressing breast cancer, comprising administering to the subject a therapeutically effective amount of a selective androgen receptor modulator (SARM) compound represented by the following structures of Formula VII:

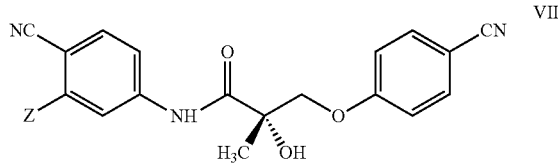

wherein Z is Cl or CF$_3$;
and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject In another embodiment, this invention provides methods for: a) treating a subject suffering from HER2-positive breast cancer; b) treating a subject suffering from HER2-positive refractory breast cancer; c) treating a subject suffering from HER2-positive metastatic breast cancer; d) treating a subject suffering from HER2-positive and ER-negative breast cancer; e) treating a subject suffering from HER2-positive and ER-positive breast cancer; f) treating a subject suffering from HER2-positive and PR-positive breast cancer; g) treating a subject suffering from HER2-positive and PR-negative breast cancer; h) treating a subject suffering from HER2-positive and AR-positive breast cancer; i) treating a subject suffering from HER2-positive and AR-negative breast cancer; j) treating a subject suffering from HER2-positive, ER-positive, PR-positive, and AR-positive breast cancer; k) treating a subject suffering from HER2-positive, ER-positive, PR-negative, and AR-positive breast cancer; l) treating a subject suffering from HER2-positive, ER-positive, PR-negative, and AR-negative breast cancer; m) treating a subject suffering from HER2-positive, ER-positive, PR-positive, and AR-negative breast cancer; n) treating a subject suffering from HER2-positive, ER-negative, PR-negative, and AR-positive breast cancer; o) treating a subject suffering from HER2-positive, ER-negative, PR-positive, and AR-positive breast cancer; p) treating a subject suffering from HER2-positive, ER-negative, PR-positive, and AR-negative breast cancer; and/or q) treating a subject suffering from HER2-positive, ER-negative, PR-negative, and AR-negative breast cancer; comprising administering to the subject a therapeutically effective amount of a selective androgen receptor modulator (SARM) compound represented by a compound of Formula VII:

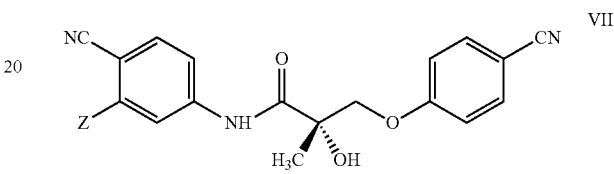

wherein Z is Cl or CF$_3$;
and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In another embodiment, the compound which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a structure of Formula VIII, and/or its analog, derivative, isomer, metabolite, pharmaceutically acceptable salt, pharmaceutical product, hydrate, N-oxide, crystal, polymorph, prodrug or any combination thereof:

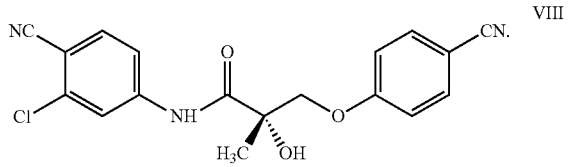 [SMILES: C[C@](O)(COc1ccc(C#N)cc1)C(=O)Nc1ccc(C#N)c(Cl)c1]

VIII

In another embodiment, the compound which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a structure of Formula IX, and/or its analog, derivative, isomer, metabolite, pharmaceutically acceptable salt, pharmaceutical product, hydrate, N-oxide, crystal, polymorph, prodrug or any combination thereof:

IX

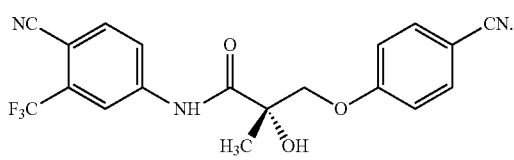

In another embodiment, the compound which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a structure of Formula X, and/or its analog, derivative, isomer, metabolite, pharmaceutically acceptable salt, pharmaceutical product, hydrate, N-oxide, crystal, polymorph, prodrug or any combination thereof:

X

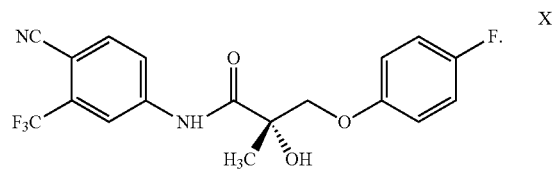 [SMILES: C[C@](O)(COc1ccc(F)cc1)C(=O)Nc1ccc(C#N)c(C(F)(F)F)c1]

In another embodiment, the compound which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a structure of Formula XI, and/or its analog, derivative, isomer, metabolite, pharmaceutically acceptable salt, pharmaceutical product, hydrate, N-oxide, crystal, polymorph, prodrug or any combination thereof:

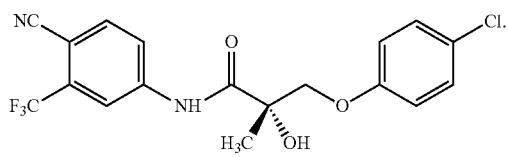

In another embodiment, the compound which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a structure of Formula XII, and/or its analog, derivative, isomer, metabolite, pharmaceutically acceptable salt, pharmaceutical product, hydrate, N-oxide, crystal, polymorph, prodrug or any combination thereof:

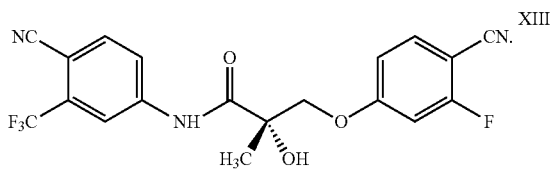 [SMILES: C[C@](O)(COc1ccc(C#N)c(F)c1)C(=O)Nc1ccc(C#N)c(C(F)(F)F)c1]

In another embodiment, the compound which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a compound of Formula XIII, and/or its analog, derivative, isomer, metabolite, pharmaceutically acceptable salt, pharmaceutical product, hydrate, N-oxide, crystal, polymorph, prodrug or any combination thereof:

In another embodiment, the compound which is effective at: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h)

treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, is a compound represented by a structure of Formula XIV, and/or its analog, derivative, isomer, metabolite, pharmaceutically acceptable salt, pharmaceutical product, hydrate, N-oxide, crystal, polymorph, prodrug or any combination thereof:

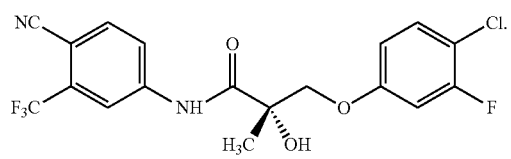

In one embodiment, this invention relates to the treatment of androgen receptor-positive breast cancer in a subject, for example a female subject. Accordingly, this invention provides methods for: a) treating AR-positive breast cancer in a subject; b) treating metastatic AR-positive breast cancer, or advanced AR-positive breast cancer; c) treating refractory AR-positive breast cancer; d) treating, preventing, suppressing or inhibiting metastasis in a subject suffering from breast cancer; e) prolonging progression-free survival of a subject suffering from breast cancer; f) treating a subject suffering from ER-positive breast cancer; g) treating a subject suffering from metastatic ER-positive breast cancer; h) treating a subject suffering from refractory ER-positive breast cancer; i) treating a subject suffering from AR-positive ER-positive breast cancer; j) treating a subject suffering from AR-positive ER-positive refractory breast cancer; k) treating a subject suffering from AR-positive ER-positive metastatic breast cancer; l) treating a subject suffering from AR-positive and ER-positive breast cancer; m) treating a subject suffering from AR-positive ER-positive breast cancer with or without expression of PR, and/or HER2; n) treating a subject suffering from advanced ER-positive breast cancer; o) treating a subject suffering from ER-positive breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; p) treating, preventing, suppressing or inhibiting metastasis in a subject suffering from ER-positive breast cancer; q) prolonging survival of a subject with ER-positive breast cancer; r) slowing the progression of ER-positive breast cancer in a subject; s) prolonging progression-free survival of a subject with ER-positive breast cancer; and/or t) treating a subject suffering from AR-positive HER2-positive breast cancer; u) treating a subject suffering from ER mutant expressing breast cancer, and/or v) treating a subject suffering from Y537S ER mutant expressing breast cancer, comprising administering to the subject a therapeutically effective amount of a selective androgen receptor modulator (SARM) compound represented by the following structures of Formulae VIII, IX, X, XI, XII, XIII or XIV:

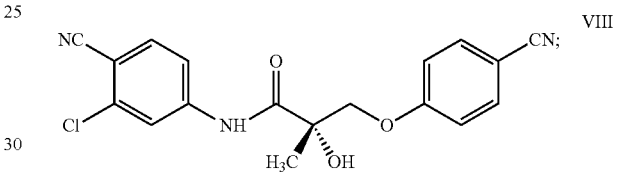

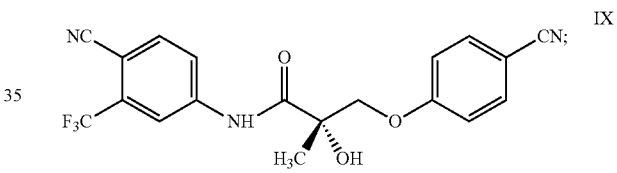

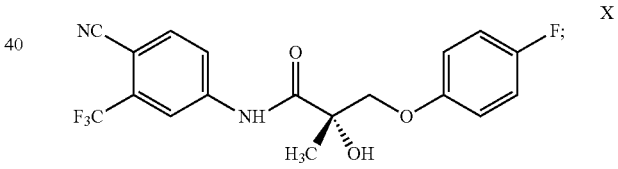

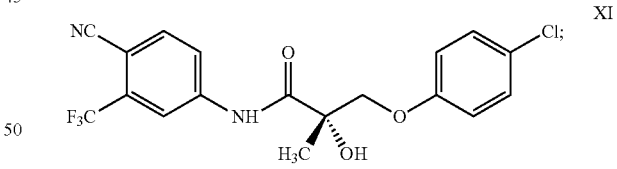

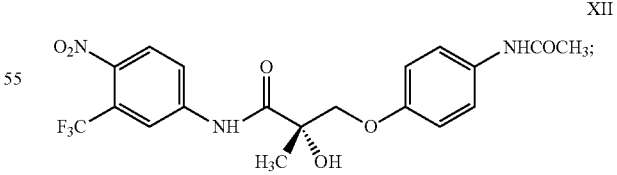

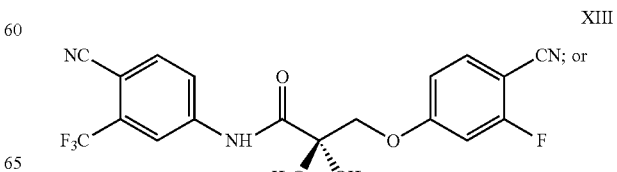

-continued

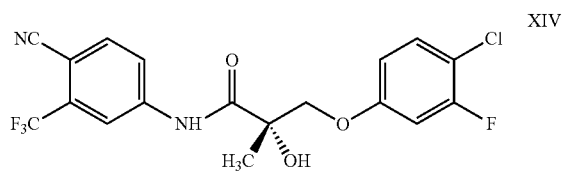 [SMILES: C[C@](O)(COc1ccc(Cl)c(F)c1)C(=O)Nc1ccc(C#N)c(C(F)(F)F)c1]

and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In another embodiment, this invention provides methods for: a) treating a subject suffering from HER2-positive breast cancer; b) treating a subject suffering from HER2-positive refractory breast cancer; c) treating a subject suffering from HER2-positive metastatic breast cancer; d) treating a subject suffering from HER2-positive and ER-negative breast cancer; e) treating a subject suffering from HER2-positive and ER-positive breast cancer; f) treating a subject suffering from HER2-positive and PR-positive breast cancer; g) treating a subject suffering from HER2-positive and PR-negative breast cancer; h) treating a subject suffering from HER2-positive and AR-positive breast cancer; i) treating a subject suffering from HER2-positive and AR-negative breast cancer; j) treating a subject suffering from HER2-positive, ER-positive, PR-positive, and AR-positive breast cancer; k) treating a subject suffering from HER2-positive, ER-positive, PR-negative, and AR-positive breast cancer; l) treating a subject suffering from HER2-positive, ER-positive, PR-negative, and AR-negative breast cancer; m) treating a subject suffering from HER2-positive, ER-positive, PR-positive, and AR-negative breast cancer; n) treating a subject suffering from HER2-positive, ER-negative, PR-negative, and AR-positive breast cancer; o) treating a subject suffering from HER2-positive, ER-negative, PR-positive, and AR-positive breast cancer; p) treating a subject suffering from HER2-positive, ER-negative, PR-positive, and AR-negative breast cancer; and/or q) treating a subject suffering from HER2-positive, ER-negative, PR-negative, and AR-negative breast cancer; comprising administering to the subject a therapeutically effective amount of a selective androgen receptor modulator (SARM) compound represented by the following structures of Formulae VIII, IX, X, XI, XII, XIII or XIV:

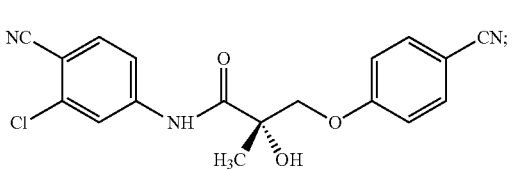

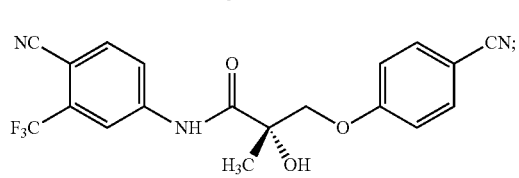

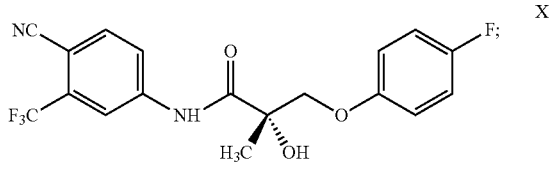

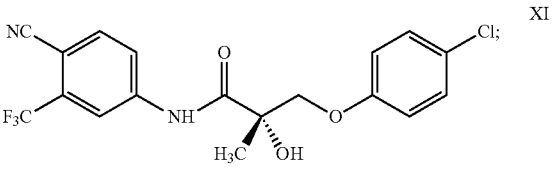

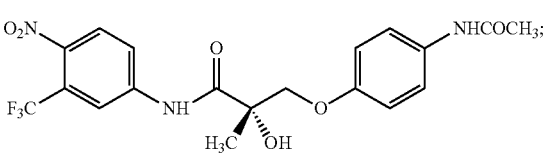

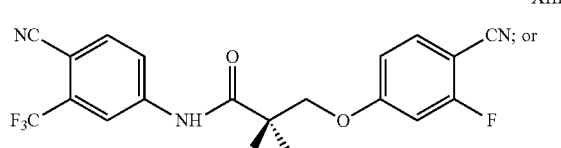

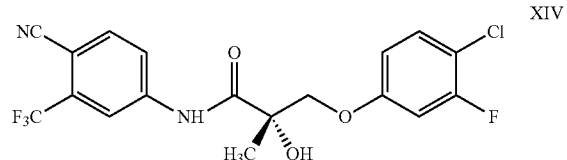

and/or its analog, derivative, isomer, metabolite, pharmaceutically acceptable salt, pharmaceutical product, hydrate, N-oxide, crystal, polymorph, prodrug or any combination thereof, as described herein. In one embodiment, the subject is a female subject. In one embodiment, the subject is a male subject.

In one embodiment, the methods of this invention make use of a compound of Formula VIII. In one embodiment, the methods of this invention make use of a compound of Formula IX. In one embodiment, the methods of this invention make use of a compound of Formula X. In one embodiment, the methods of this invention make use of a compound of Formula XI. In one embodiment, the methods of this invention make use of a compound of Formula XII. In one embodiment, the methods of this invention make use of a compound of Formula XIII. In one embodiment, the methods of this invention make use of a compound of Formula XIV.

In one embodiment, the methods of the present invention comprise administering an analog of the compound of Formulae I-XIV. In another embodiment, the methods of the present invention comprise administering a derivative of the compound of Formulae I-XIV. In another embodiment, the methods of the present invention comprise administering an isomer of the compound of Formulae I-XIV. In another embodiment, the methods of the present invention comprise administering a metabolite of the compound of Formulae I-XIV. In another embodiment, the methods of the present invention comprise administering a pharmaceutically acceptable salt of the compound of Formulae I-XIV. In another embodiment, the methods of the present invention comprise administering a pharmaceutical product of the compound of Formulae I-XIV. In another embodiment, the methods of the present invention comprise administering a hydrate of the compound of Formulae I-XIV. In another embodiment, the methods of the present invention comprise administering an N-oxide of the compound of Formulae I-XIV. In another embodiment, the methods of the present invention comprise administering a polymorph of the compound of Formulae I-XIV. In another embodiment, the methods of the present invention comprise administering a crystal of the compound of Formulae I-XIV. In another embodiment, the methods of the present invention comprise administering a prodrug of the compound of Formulae I-XIV. In another embodiment, the methods of the present invention comprise administering a combination of any of an analog, derivative, metabolite, isomer, pharmaceutically acceptable salt, pharmaceutical product, hydrate, N-oxide, polymorph, crystal or prodrug of the compound of Formulae I-XIV.

In one embodiment, the methods of this invention comprise administering a compound of Formulae I-XIV. In another embodiment, the methods of this invention comprise administering a compound of Formula I. In another embodiment, the methods of this invention comprise administering a compound of Formula II. In another embodiment, the methods of this invention comprise administering a compound of Formula III. In another embodiment, the methods of this invention comprise administering a compound of Formula IV. In another embodiment, the methods of this invention comprise administering a compound of Formula V. In another embodiment, the methods of this invention comprise administering a compound of Formula VI. In another embodiment, the methods of this invention comprise administering a compound of Formula VII. In another embodiment, the methods of this invention comprise administering a compound of Formula VIII. In another embodiment, the methods of this invention comprise administering a compound of Formula IX. In another embodiment, the methods of this invention comprise administering a compound of Formula X. In another embodiment, the methods of this invention comprise administering a compound of Formula XI. In another embodiment, the methods of this invention comprise administering a compound of Formula XII. In another embodiment, the methods of this invention comprise administering a compound of Formula XIII. In another embodiment, the methods of this invention comprise administering a compound of Formula XIV.

The compounds of the present invention, either alone or as a pharmaceutical composition, are useful for: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) prolonging survival of a subject with ER-positive breast cancer; r) slowing the progression of ER-positive breast cancer in a subject; s) prolonging progression-free survival of a subject with ER-positive breast cancer; t) treating a subject suffering from AR-positive HER2-positive breast cancer, u) treating a subject suffering from ER mutant expressing breast cancer, and/or v) treating a subject suffering from Y537S ER mutant expressing breast cancer.

The compounds of the present invention offer a significant advance over steroidal androgen treatment since treatment of breast cancer with these compounds will not be accompanied by serious side effects, inconvenient modes of administration, or high costs and still have the advantages of oral bioavailability, lack of cross-reactivity with other steroid receptors, lack of aromatizability, and long biological half-lives.

In one embodiment, this invention relates to the treatment of androgen receptor-positive breast cancer in a subject. Accordingly, this invention provides methods of: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; and/or p) prolonging progression-free survival of a subject with breast cancer; q) treating a subject suffering from HER2-positive breast cancer; r) treating a subject suffering from ER mutant expressing breast cancer, and/or s) treating a subject suffering from Y537S ER mutant expressing breast cancer, by administering to the subject a therapeutically effective amount of a selective androgen receptor modulator of Formulae I-XIV of this invention, and/or its analog, derivative, isomer, metabolite, pharmaceutically acceptable salt, pharmaceutical product, hydrate, N-oxide, crystal, polymorph, prodrug or any combination thereof, as described herein.

As defined herein, the term "isomer" includes, but is not limited to, optical isomers and analogs, structural isomers and analogs, conformational isomers and analogs, and the like. As used herein, the term "isomer" may also be referred to herein as an "enantiomer" having all of the qualities and properties of an "isomer".

In one embodiment, this invention encompasses the use of various optical isomers of the selective androgen receptor modulator. It will be appreciated by those skilled in the art that the selective androgen receptor modulators of the present invention contain at least one chiral center. Accordingly, the selective androgen receptor modulators used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or any combination thereof, which form possesses properties useful in the treatment of androgen-related conditions described herein. In one embodiment, the selective androgen receptor modulators are the pure (R)-isomers. In another embodiment, the selective androgen receptor modulators are the pure (S)-isomers. In another embodiment, the selective androgen receptor modulators are a mixture of the (R) and the (S) isomers. In another embodiment, the selective androgen receptor modulators are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the compounds of this invention, which may be produced, by reaction of a compound of this invention with an acid or base.

The invention includes pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

Suitable pharmaceutically acceptable salts of the compounds of Formulae I-XIV may be prepared from an inorganic acid or from an organic acid. In one embodiment, examples of inorganic salts of the compounds of this invention are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of the compounds of this invention may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoate, hydrofluorate, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

This invention further includes derivatives of the selective androgen receptor modulators. The term "derivatives" includes but is not limited to ether derivatives, acid derivatives, amide derivatives, ester derivatives and the like. In addition, this invention further includes hydrates of the selective androgen receptor modulators. The term "hydrate" includes but is not limited to hemihydrate, monohydrate, dihydrate, trihydrate and the like.

This invention further includes metabolites of the selective androgen receptor modulators. The term "metabolite" means any substance produced from another substance by metabolism or a metabolic process.

This invention further includes pharmaceutical products of the selective androgen receptor modulators. The term "pharmaceutical product" means a composition suitable for pharmaceutical use (pharmaceutical composition), as defined herein.

This invention further includes prodrugs of the selective androgen receptor modulators. The term "prodrug" means a substance which can be converted in vivo into a biologically active agent by such reactions as hydrolysis, esterification, de-esterification, activation, salt formation and the like.

This invention further includes crystals of the selective androgen receptor modulators. Furthermore, this invention provides polymorphs of the selective androgen receptor modulators. The term "crystal" means a substance in a crystalline state. The term "polymorph" refers to a particular crystalline state of a substance, having particular physical properties such as X-ray diffraction, IR spectra, melting point, and the like.

In one embodiment of the present invention, a method is provided for treating a subject suffering from breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat breast cancer in the subject. In one embodiment, the subject is a female subject. In another embodiment, the subject is a male subject.

In another embodiment of the present invention, a method is provided for treating a subject suffering from metastatic breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat metastatic breast cancer in the subject. In one embodiment, the subject is a female subject. In another embodiment, the subject is a male subject.

In another embodiment of the present invention, a method is provided for treating a subject suffering from refractory breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat refractory breast cancer in the subject. In one embodiment, the subject is a female subject. In another embodiment, the subject is a male subject.

In another embodiment of the present invention, a method is provided for treating a subject suffering from AR-positive breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat AR-positive breast cancer in the subject. In one embodiment, the subject is a female subject. In another embodiment, the subject is a male subject.

In one embodiment, the AR-positive breast cancer is ER, PR and HER2-positive. In another embodiment, the AR-positive breast cancer is ER, PR and HER2-negative. In one embodiment, the AR-positive breast cancer is ER-positive, and PR and HER2-negative. In another embodiment, the AR-positive breast cancer is ER and PR-positive, and HER2-negative. In yet another embodiment, the AR-positive breast cancer is ER and HER2-positive, and PR-negative. In still another embodiment, the AR-positive breast cancer is ER-negative, and PR and HER2-positive. In a further embodiment, the AR-positive breast cancer is ER and PR-negative, and HER2-positive. In still a further embodiment, the AR-positive breast cancer is ER and HER2-negative, and PR-positive. In one embodiment, the AR-positive breast cancer is ER-negative. In another embodiment, the AR-positive breast cancer is ER-positive.

In another embodiment of the present invention, a method is provided for treating a subject suffering from AR-positive refractory breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat AR-positive refractory breast cancer in the subject. In one embodiment, the subject is a female subject. In another embodiment, the subject is a male subject.

In another embodiment of the present invention, a method is provided for treating a subject suffering from AR-positive metastatic breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat AR-positive metastatic breast cancer in the subject. In one embodiment, the subject is a female subject. In another embodiment, the subject is a male subject.

In another embodiment of the present invention, a method is provided for treating a subject suffering from ER-positive breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat ER-positive breast cancer in the subject. In one embodiment, the subject is a female subject. In another embodiment, the subject is a male subject.

In another embodiment of the present invention, a method is provided for treating a subject suffering from AR-positive and ER-positive breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat AR-positive metastatic breast cancer in the subject. In one embodiment, the subject is a female subject. In another embodiment, the subject is a male subject.

In another embodiment of the present invention, a method is provided for treating a subject suffering from ER-positive refractory breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat ER-positive refractory breast cancer in the subject. In one embodiment, the subject is a female subject. In another embodiment, the subject is a male subject.

In another embodiment of the present invention, a method is provided for treating a subject suffering from ER-positive metastatic breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat ER-positive metastatic breast cancer in the subject. In one embodiment, the subject is a female subject. In another embodiment, the subject is a male subject.

In one embodiment, an ER-positive breast cancer is AR-positive. In another embodiment, an ER-positive breast cancer is AR-negative.

In another embodiment of the present invention, a method is provided for treating a subject suffering from advanced breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat advanced breast cancer in the subject. In one embodiment, the subject is a female subject. In another embodiment, the subject is a male subject.

In another embodiment of the present invention, a method is provided for treating a subject suffering from AR-positive and ER-positive breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat AR-positive and ER-positive refractory breast cancer in the subject. In one embodiment, the subject is a female subject. In another embodiment, the subject is a male subject.

In another embodiment of the present invention, a method is provided for treating a subject suffering from AR-positive and ER-negative breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat AR-positive and ER-negative metastatic breast cancer in the subject. In one embodiment, the subject is a female subject. In another embodiment, the subject is a male subject.

In another embodiment of the present invention, a method is provided for treating a subject suffering from triple negative breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat triple negative breast cancer in the subject. In one embodiment, the subject is a female subject. In another embodiment, the subject is a male subject.

In another embodiment of the present invention, a method is provided for treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments in the subject. In one embodiment, the subject is a female subject. In another embodiment, the subject is a male subject.

In another embodiment of the present invention, a method is provided for treating, preventing, suppressing or inhibiting metastasis in a subject suffering from breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat, prevent, suppress or inhibit metastasis in the subject. In one embodiment, the subject is a female subject. In another embodiment, the subject is a male subject.

In another embodiment of the present invention, a method is provided for treating and/or preventing skeletal related events in a subject suffering, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat and/or prevent skeletal related events in the subject. In one embodiment, the subject is a female subject. In another embodiment, the subject is a male subject.

In another embodiment of the present invention, a method is provided for improving libido in a subject, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to improve libido in the subject. In one embodiment, the subject is a female subject. In another embodiment, the subject is a male subject.

In another embodiment of the present invention, a method is provided for improving quality of life in a subject, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to quality of life in the subject. In one embodiment, the subject is a female subject. In another embodiment, the subject is a male subject.

In another embodiment of the present invention, a method is provided for treating, preventing, suppressing or inhibiting metastasis in a subject suffering from breast cancer, comprising the step of administering to the subject a selective androgen receptor modulator of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat, prevent, suppress or inhibit metastasis in the subject. In one embodiment, the subject is a female subject. In another embodiment, the subject is a male subject.

In another embodiment of the present invention, a method is provided for treating a subject suffering from HER2-positive breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat HER2-positive breast cancer in the subject. In one embodiment, the subject is a female subject. In another embodiment, the subject is a male subject.

In one embodiment, the HER2-positive breast cancer is HER2-positive refractory breast cancer. In another embodiment, the HER2-positive breast cancer is HER2-positive metastatic breast cancer. In one embodiment, the HER2-positive breast cancer is ER-negative. In another embodiment, the HER2-positive breast cancer is ER-positive. In one embodiment, the HER2-positive breast cancer is PR-positive. In another embodiment, the HER2-positive breast cancer is PR-negative. In one embodiment, the HER2-positive breast cancer is AR-positive. In another embodiment, the HER2-positive breast cancer is AR-negative.

In certain embodiment, the HER2-positive breast cancer is ER-positive, PR-positive, and AR-positive. In another embodiment, the HER2-positive breast cancer is ER-positive, PR-negative, and AR-positive. In another embodiment, the HER2-positive breast cancer is ER-positive, PR-negative, and AR-negative. In other embodiment, the HER2-positive breast cancer is ER-positive, PR-positive, and AR-negative. In another embodiment, the HER2-positive breast cancer is ER-negative, PR-negative, and AR-positive. In another embodiment, the HER2-positive breast cancer is ER-negative, PR-positive, and AR-positive. In other embodiment, the HER2-positive breast cancer is ER-negative, PR-positive, and AR-negative. In certain embodiment, the HER2-positive breast cancer is ER-negative, PR-negative, and AR-negative.

In another embodiment of the present invention, a method is provided for treating a subject suffering from ER mutant expressing breast cancer, comprising the step of administering to the subject a compound of Formulae I-XIV of this invention and/or its analog, derivative, isomer, metabolite, pharmaceutically acceptable salt, pharmaceutical product, hydrate, N-oxide, crystal, polymorph, prodrug or any combination thereof, in an amount effective to treat ER mutant expressing breast cancer in the subject. In one embodiment, the subject is a female subject. In another embodiment, the subject is a male subject.

In certain embodiment, the ER mutant expressing breast cancer is Y537S mutation expressing breast cancer. In a certain embodiment, the ER mutant expressing breast cancer is D351Y mutation expressing breast cancer. In a certain embodiment, the ER mutant expressing breast cancer is E380Q mutation expressing breast cancer. In a certain embodiment, the ER mutant expressing breast cancer is V422del mutation expressing breast cancer. In a certain embodiment, the ER mutant expressing breast cancer is S432L mutation expressing breast cancer. In a certain embodiment, the ER mutant expressing breast cancer is G442A mutation expressing breast cancer. In a certain embodiment, the ER mutant expressing breast cancer is S463P mutation expressing breast cancer. In a certain embodiment, the ER mutant expressing breast cancer is L469V mutation expressing breast cancer. In a certain embodiment, the ER mutant expressing breast cancer is L536R mutation expressing breast cancer. In a certain embodiment, the ER mutant expressing breast cancer is L536H mutation expressing breast cancer. In a certain embodiment, the ER mutant expressing breast cancer is L536P mutation expressing breast cancer. In a certain embodiment, the ER mutant expressing breast cancer is L536Q mutation expressing breast cancer. In a certain embodiment, the ER mutant expressing breast cancer is Y537N mutation expressing breast cancer. In a certain embodiment, the ER mutant expressing breast cancer is Y537C mutation expressing breast cancer. In a certain embodiment, the ER mutant expressing breast cancer is Y537D mutation expressing breast cancer. In a certain embodiment, the ER mutant expressing breast cancer is D538G mutation expressing breast cancer. In a certain embodiment, the ER mutant expressing breast cancer is E542G mutation expressing breast cancer. In one embodiment, ER mutant expressing breast cancer refers to mutants of ER-alpha.

In a certain embodiment, the ER mutant expressing breast cancer is as described in Cancer Cell 2018, 33, 173-186; or in Nat Rev Cancer. 2018 June; 18(6):377-388, which are incorporated herein by reference. In one embodiment, ER mutant expressing breast cancer refers to mutants of ER-alpha.

The substituent R is defined herein as an alkyl, haloalkyl, dihaloalkyl, trihaloalkyl, $CH_2F$, $CHF_2$, $CF_3$, $CF_2CF_3$; aryl, phenyl, halogen, alkenyl, or hydroxyl (OH).

An "alkyl" group refers to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, e.g. by F, Cl, Br or I.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxyl or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. An "alkenyl" group refers to a group having at least one carbon to carbon double bond. A halo group refers to F, Cl, Br or I.

An "arylalkyl" group refers to an alkyl bound to an aryl, wherein alkyl and aryl are as defined above. An example of an aralkyl group is a benzyl group.

Biological Activity of Selective Androgen Receptor Modulators

The selective androgen receptor modulators provided herein are a new class of compounds, which suppress growth of AR-positive breast cancers. The compounds of this invention have a tissue-selective myoanabolic activity profile of a nonsteroidal ligand for the androgen receptor. Furthermore compounds of the present invention are non-aromatizable, non-virilizing, and are not commonly cross-reactive with ER and PR. In addition, in one embodiment, the selective androgen receptor modulators (SARMs) of the present invention are beneficial to refractory breast cancer patients undergoing chemotherapy due to anabolism.

As contemplated herein, the appropriately substituted selective androgen receptor modulators of the present invention are useful for: a) treating a subject suffering from breast cancer; b) treating a subject suffering from metastatic breast cancer; c) treating a subject suffering from refractory breast cancer; d) treating a subject suffering from AR-positive breast cancer; e) treating a subject suffering from AR-positive refractory breast cancer; f) treating a subject suffering from AR-positive metastatic breast cancer; g) treating a subject suffering from AR-positive and ER-positive breast cancer; h) treating a subject suffering from AR-positive breast cancer with or without expression of ER, PR, and/or HER2; i) treating a subject suffering from triple negative breast cancer; j) treating a subject suffering from advanced breast cancer; k) treating a subject suffering from breast cancer that has failed selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments; l) treating a subject suffering from ER-positive breast cancer; m) treating, preventing, suppressing or inhibiting metastasis in a subject suffering from breast cancer; n) prolonging survival of a subject with breast cancer; o) slowing the progression of breast cancer in a subject; p) prolonging progression-free survival of a subject with breast cancer; q) treating HER2-positive breast cancer; r) treating ER mutant expressing breast cancer, and/or s) treating a subject suffering from Y537S ER mutant expressing breast cancer.

In one embodiment, a "refractory breast cancer" is a breast cancer that has not responded to treatment. In another embodiment, a "refractory breast cancer" is a breast cancer resistant to treatment. In one embodiment, refractory breast cancer is refractory metastatic breast cancer. In one embodiment, refractory breast cancer has not responded to treatment with anthracyclines, taxanes, capecitabine, ixabepilone, selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), and/or fulvestrant treatments or any combination thereof.

In one embodiment, a "triple negative breast cancer" is defined by lack of expression of estrogen, progesterone, and ErbB2 (also known as human epidermal growth factor receptor 2 (HER2)) receptors. This subgroup accounts for 15% of all types of breast cancer. This subtype of breast cancer is clinically characterized as more aggressive and less responsive to standard treatment and associated with poorer overall patient prognosis.

In one embodiment, the methods of this invention are directed to treating a subject suffering from AR-positive breast cancer, regardless of grade, stage or prior treatments.

In one embodiment, the methods of this invention are directed to treating a subject suffering from HER2-positive breast cancer, regardless of grade, stage or prior treatments.

In one embodiment, the methods of this invention are first, second, third, or fourth line therapies for breast cancer. A first line therapy refers to a medical therapy recommended for the initial treatment of a disease, sign or symptom. A second line therapy therapy is given when initial treatment (first-line therapy) does not work, or stops working. Third line therapy is given when both initial treatment (first-line therapy) and subsequent treatment (second-line therapy) does not work, or stop working, etc.

As used herein, "kinases" are a group of enzymes that catalyze the transfer of a phosphate group from a donor, such as ADP or ATP, to an acceptor. In one embodiment, phosphorylation results in a functional change of the target protein (substrate) by changing enzyme activity, cellular location, or association with other protein kinases. Kinases regulate the majority of cellular pathways, especially those involved in signal transduction. In one embodiment, deregulated kinase activity is a frequent cause of disease, in particular cancer, wherein kinases regulate many aspects that control cell growth, movement and death. In one embodiment, drugs that inhibit specific kinases are used to treat kinase-related diseases, including cancer. In one embodiment, HER2-positive breast cancers are susceptible to HER2 kinase inhibitors (e.g., trastuzumab and lapatinib) and are generally used in metastatic disease. However, some breast cancers are refractory to HER2 kinase inhibitor treatment.

As used herein, receptors for extracellular signaling molecules are collectively referred to as "cell signaling receptors". Many cell signaling receptors are transmembrane proteins on a cell surface; when they bind an extracellular signaling molecule (i.e., a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell.

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include but are not limited to progesterone receptors, estrogen receptors, androgen receptors, glucocorticoid receptors, and mineralocorticoid receptors. In one embodiment, the present invention is directed to androgen receptors. In one embodiment, the present invention is directed to androgen receptor agonists. In one embodiment, the present invention is directed to progesterone receptors. In one embodiment, the present invention is directed to progesterone receptor antagonists.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration. The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cells, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors may form. In some cases, this leads to a change in the configuration of the receptor, which is enough to begin the activation process (called signal transduction).

In one embodiment, the compounds of this invention inhibit the intratumoral expression of genes and pathways that promote breast cancer development through their actions on the AR. In one embodiment, a compound of this invention inhibits intratumoral expression of Muc1, SLUG, VCAM1, SPARC or MMP2, or any combination thereof. In another embodiment, Formula VIII inhibits gene expression that promotes breast cancer.

In one embodiment, a receptor antagonist is a substance which binds receptors and inactivates them. In one embodiment, a selective androgen receptor modulator is a molecule that exhibits in vivo tissue selectivity, activating signaling activity of the androgen receptor (AR) in anabolic (muscle, bone, etc.) tissues to a greater extent than in the androgenic tissues. Thus, in one embodiment, the selective androgen receptor modulators of the present invention are useful in binding to and activating steroidal hormone receptors. In one embodiment, the SARM compound of the present invention is an agonist which binds the androgen receptor. In another embodiment, the compound has high affinity for the androgen receptor.

Assays to determine whether the compounds of the present invention are AR agonists or antagonists are well known to a person skilled in the art. For example, AR agonistic activity can be determined by monitoring the ability of the selective androgen receptor modulators to maintain and/or stimulate the growth of AR containing androgenic tissue such as prostate and seminal vesicles, as measured by weight, in castrated animals. AR antagonistic activity can be determined by monitoring the ability of the selective androgen receptor modulators to inhibit the growth of AR containing tissue in intact animals or counter the effects of testosterone in castrated animals.

An androgen receptor (AR) is an androgen receptor of any species, for example a mammal. In one embodiment, the androgen receptor is an androgen receptor of a human. Thus, in another embodiment, the selective androgen receptor modulators bind reversibly to an androgen receptor of a human. In another embodiment, the selective androgen receptor modulators bind reversibly to an androgen receptor of a mammal.

As contemplated herein, the term "selective androgen receptor modulator" (SARM) refers to, in one embodiment, a molecule that exhibits in vivo tissue selectivity, activating signaling activity of the androgen receptor in anabolic (muscle, bone, etc.) tissues to a greater extent than in the androgenic tissues. In another embodiment, a selective androgen receptor modulator selectively binds the androgen receptor. In another embodiment, a selective androgen receptor modulator selectively affects signaling through the androgen receptor. In one embodiment, the SARM is a partial agonist. In one embodiment, the SARM is a tissue-selective agonist, or in some embodiments, a tissue-selective antagonist.

In one embodiment, a SARM of this invention exerts its effects on the androgen receptor in a tissue-dependent manner. In one embodiment, a SARM of this invention will have an $IC_{50}$ or $EC_{50}$ with respect to AR, as determined using AR transactivation assays, as known in the art, or, in other embodiments, as described herein.

The term "$IC_{50}$" refers, in some embodiments, to a concentration of the SARM which reduces the activity of a target (e.g., AR) to half-maximal level.

The term "$EC_{50}$" refers, in some embodiments, to a concentration of the SARM that produces a half-maximal effect.

Figure 5:
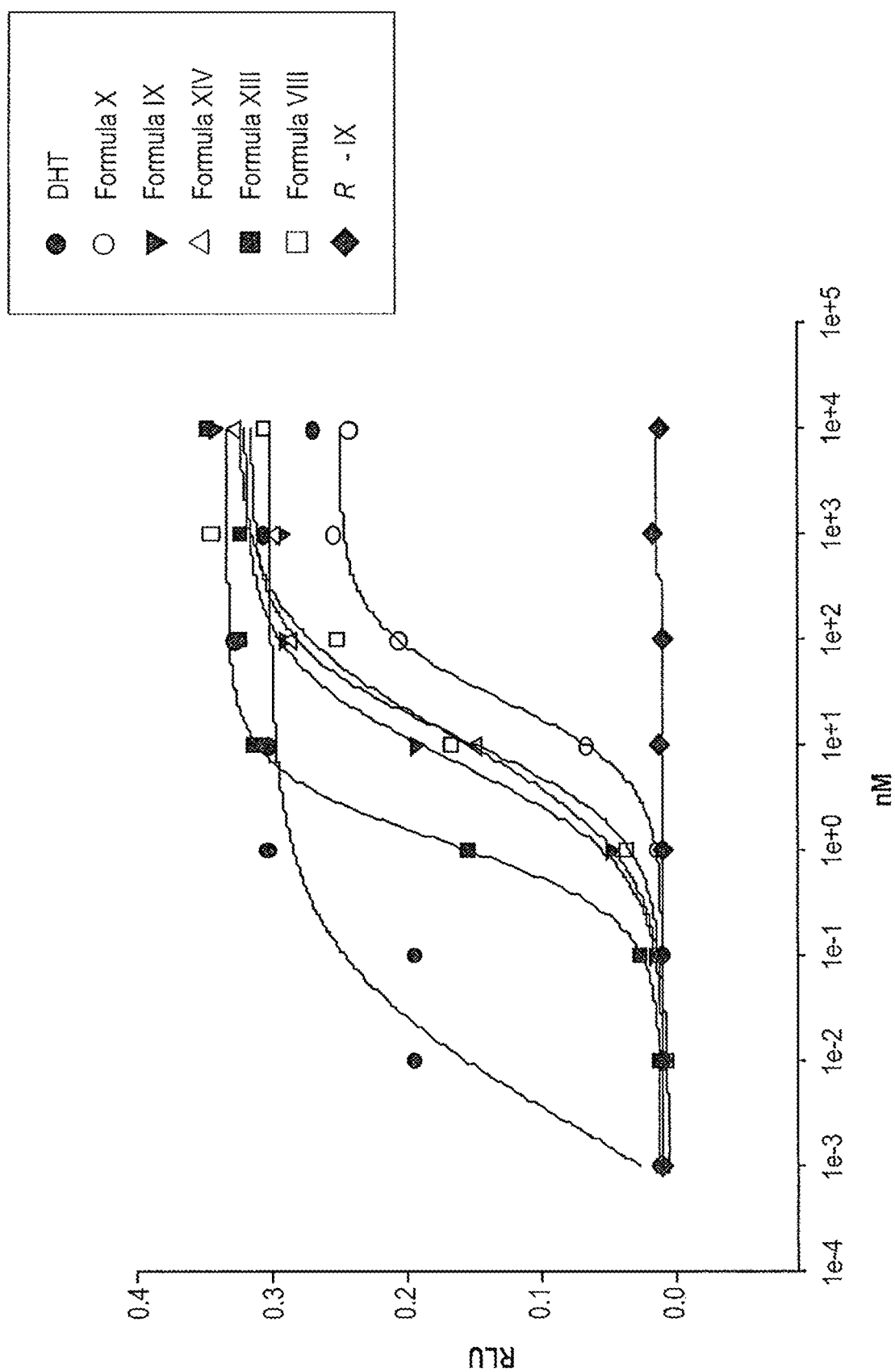
FIG. 5 illustrates that growth inhibitory ligands are AR agonists in MDA-MB-231 cells.

For example, utilizing transactivation assays, FIG. 5 shows that compounds of this invention exhibit AR agonist activity in MDA-MB-231 cells transfected with AR.

As defined herein, "contacting" means that the selective androgen receptor modulators of the present invention are introduced into a sample containing the receptor in a test tube, flask, tissue culture, chip, array, plate, microplate, capillary, or the like, and incubated at a temperature and time sufficient to permit binding of the selective androgen receptor modulators to the receptor. Methods for contacting the samples with the selective androgen receptor modulators or other specific binding components are known to those skilled in the art and may be selected depending on the type of assay protocol to be run. Incubation methods are also standard and are known to those skilled in the art.

In another embodiment, the term "contacting" means that the selective androgen receptor modulators of the present invention are introduced into a subject receiving treatment, and the selective androgen receptor modulator is allowed to come in contact with the androgen receptor in vivo.

As used herein, the term "treating" includes disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission. As used herein, the term "delaying" means stopping, hindering, slowing down, postponing, holding up or setting back. As used herein, the term "metastasis" refers to the transfer of a disease from one organ or part thereof to another not directly connected with it. Metastasis can occur for example as a result of transfer of malignant cells from one organ (for example breast) to other organs.

In one embodiment, "treating" refers to reducing tumor growth by 75%, as demonstrated in, e.g., Example 8. In another embodiment, treating refers to reducing tumor growth by at least 75%. In another embodiment, treating refers to reducing tumor growth by at least 50%. In another embodiment, treating refers to reducing tumor growth by at least 25%. In another embodiment, treating refers to reducing tumor growth by 50-100%. In another embodiment, treating refers to reducing tumor growth by 70-80%. In another embodiment, treating refers to reducing tumor growth by 25-125%.

In another embodiment, "treating" refers to reducing tumor weight by 50%, as demonstrated in, e.g., Example 8. In another embodiment, treating refers to reducing tumor weight by at least 50%. In another embodiment, treating refers to reducing tumor weight by at least 40%. In another embodiment, treating refers to reducing tumor weight by at least 30%. In another embodiment, treating refers to reducing tumor weight by at least 20%. In another embodiment, treating refers to reducing tumor weight by 25-75%. In another embodiment, treating refers to reducing tumor weight by 25-100%.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, a compound of the present invention is administered to a subject once a week. In another embodiment, a compound of the present invention is administered to a subject twice a week. In another embodiment, a compound of the present invention is administered to a subject three times a week. In another embodiment, a compound of the present invention is administered to a subject four times a week. In another embodiment, a compound of the present invention is administered to a subject five times a week. In another embodiment, a compound of the present invention is administered to a subject daily. In another embodiment, a compound of the present invention is administered to a subject weekly. In another embodiment, a compound of the present invention is administered to a subject bi-weekly. In another embodiment, a compound of the present invention is administered to a subject monthly.

In one embodiment, the methods of the present invention comprise administering a selective androgen receptor modulator as the sole active ingredient. However, also encompassed within the scope of the present invention are methods for hormone therapy, for treating breast cancer, for delaying the progression of breast cancer, and for preventing and treating the recurrence of breast cancer and/or breast cancer metastasis, which comprise administering the selective androgen receptor modulators in combination with one or more therapeutic agents. These agents include, but are not limited to: selective estrogen receptor modulator (SERM) (tamoxifen, toremifene, raloxifene), gonadotropin-releasing hormone (GnRH) agonist (goserelin), aromatase inhibitor (AI) (letrozole, anastrozole, exemestane), cyclin-dependent kinase 4/6 (CDK 4/6) inhibitor (palbociclib (Ibrance), ribociclib (Kisqali), abemaciclib (Vorzenio)), mTOR inhibitor (everolimus), trastuzumab (Herceptin, ado-trastuzumab emtansine), pertuzumab (Perjeta), lapatinib, neratinib (Nerlynx), olaparib (Lynparza) (an inhibitor of the enzyme poly ADP ribose polymerase (PARP)), bevacizumab (Avastin), SERD (fulvestrant) HDAC inhibitors (entinostat), PI3K inhibitors (buparlisib, tapelisib, alpelisib), vaccines and immune stimulants or adjuvants (NeuVax®), CTLA-4 (cytotoxic T-lymphocyte associated protein-4) inhibitors (tramelimumab), PD-1 inhibitors (pembrolizumab), PD-L1 inhibitors (atezolizumb, avelumab, durvalumab), chemotherapeutic agents, taxanes, anthracyclines, epothilones, LHRH analogs, reversible antiandrogens, antiestrogens, anticancer drugs, 5-alpha reductase inhibitors, progestins, agents acting through other nuclear hormone receptors such as progesterone and estrogen receptors, estrogens, progestins, PDE5 inhibitors, apomorphine, bisphosphonate, growth factor inhibitors (such as those that inhibit VEGF, IGF and the like), or one or more additional selective androgen receptor modulators (SARMs).

Additional therapeutic agents that may be administered in combination with a selective androgen receptor modulator compound of this invention include, but are not limited to: abemaciclib, Abitrexate® (methotrexate), Abraxane® (paclitaxel albumin-stabilized nanoparticle formulation), ado-trastuzumab emtansine, adriamycin PFS (doxorubicin hydrochloride), adriamycin RDF (doxorubicin hydrochloride), Adrucil® (fluorouracil), Afinitor® (everolimus), alpelisib, anastrozole, Arimidex® (anastrozole), Aromasin® (exemestane), velumab, atezolizumb, bicalutamide, buparlisib, Caelyx® (pegylated liposomal doxorubicin), capecitabine, carboplatin, cisplatin, Clafen® (cyclophosphamide), cyclophosphamide, Cytoxan® (cyclophosphamide), docetaxel, doxorubicin hydrochloride, durvalumab, Efudex® (fluorouracil), Ellence® (epirubicin hydrochloride), entinostat, enzalutamide, epirubicin hydrochloride, eribulin, ethynyl estradiol, everolimus, Evista® (raloxifene), exemestane, Fareston® (toremifene), Faslodex® (fulvestrant), Femara® (letrozole), Fluoroplex® (5-fluorouracil), fluorouracil, fluoxymesterone, Folex® (methotrexate), Folex PFS® (methotrexate), fulvestrant, gemcitabine hydrochloride, Gemzar® (gemcitabine hydrochloride), Halaven® (eribulin mesylate), Herceptin® (trastuzumab), ixabepilone, Ixempra® (ixabepilone), lapatinib ditosylate, letrozole, megestrol acetate, methotrexate, methotrexate LPF (methotrexate), Mexate® (methotrexate), Mexate-AQ® (methotrexate), Neosar® (cyclophosphamide), NeuVax® (nelipepimut-S), Nolvadex® (tamoxifen citrate), paclitaxel, paclitaxel albumin-stabilized nanoparticle formulation, palbociclib, pembrolizumab, Perjeta® (pertuzumab), pertuzumab, raloxifene, ribociclib, tamoxifen citrate, taselisib, Taxol® (paclitaxel), Taxotere® (docetaxel), trastuzumab, tremelimumab, toremifene, Tykerb® (lapatinib ditosylate), vinorelbine, and Xeloda® (capecitabine).

Thus, in one embodiment, the methods of the present invention comprise administering the selective androgen receptor modulator, in combination with a selective estrogen receptor modulator. Thus, in one embodiment, the methods of the present invention comprise administering the selective androgen receptor modulator, in combination with a selective estrogen receptor degrader (fulvestrant). Thus, in one embodiment, the methods of the present invention comprise administering the selective androgen receptor modulator, in combination with a CDK4/6 inhibitor (palbociclib, ribociclib, abemaciclib). Thus, in one embodiment, the methods of the present invention comprise administering the selective androgen receptor modulator, in combination with a HER2 inhibitor (lapatinib, trastuzumab, neratinib). Thus, in one embodiment, the methods of the present invention comprise administering the selective androgen receptor modulator, in combination with a VEGF-A inhibitor (bevacizumab). Thus, in one embodiment, the methods of the present invention comprise administering the selective androgen receptor modulator, in combination with a chemotherapeutic agent. In one embodiment, the chemotherapeutic agent is a taxane. In another embodiment, the chemotherapeutic agent is an anthracycline. In one embodiment, the chemotherapeutic agent is an epothilone (ixabepilone). Thus, in one embodiment, the methods of the present invention comprise administering the selective androgen receptor modulator, in combination with an LHRH analog. In another embodiment, the methods of the present invention comprise administering a selective androgen receptor modulator, in combination with a reversible antiandrogen. In another embodiment, the methods of the present invention comprise administering a selective androgen receptor modulator, in combination with an antiestrogen. In another embodiment, the methods of the present invention comprise administering a selective androgen receptor modulator, in combination with an anticancer drug. In another embodiment, the methods of the present invention comprise administering a selective androgen receptor modulator, in combination with a 5-alpha reductase inhibitor. In another embodiment, the methods of the present invention comprise administering a selective androgen receptor modulator of this invention, in combination with an aromatase inhibitor. In another embodiment, the methods of the present invention comprise administering a selective androgen receptor modulator of this invention, in combination with a progestin. In another embodiment, the methods of the present invention comprise administering a selective androgen receptor modulator of this invention, in combination with an agent acting through other nuclear hormone receptors. In another embodiment, the methods of the present invention comprise administering a selective androgen receptor modulator of this invention, in combination with a selective estrogen receptor modulators (SERM). In another embodiment, the methods of the present invention comprise administering a selective androgen receptor modulator of this invention, in combination with a progestin or antiprogestin. In another embodiment, the methods of the present invention comprise administering a selective androgen receptor modulator, in combination with an estrogen. In another embodiment, the methods of the present invention comprise administering a selective androgen receptor modulator of this invention, in combination with a PDE5 inhibitor. In another embodiment, the methods of the present invention comprise administering a selective androgen receptor modulator of this invention, in combination with apomorphine. In another embodiment, the methods of the present invention comprise administering a selective androgen receptor modulator of this invention, in combination with a bisphosphonate (pamidronate, zoledronic acid). In another embodiment, the methods of the present invention comprise administering a selective androgen receptor modulator of this invention, in combination with a denosumab (Xgeva®). In another embodiment, the methods of the present invention comprise administering a selective androgen receptor modulator of this invention, in combination with a growth factor inhibitor. In another embodiment, the methods of the present invention comprise administering a selective androgen receptor modulator of this invention, in combination with one or more additional selective androgen receptor modulators (SARMs).

In another embodiment, the methods of the present invention comprise administering a selective androgen receptor modulator of this invention, in combination with Abitrexate® (methotrexate). In another embodiment, the methods of the present invention comprise administering a selective androgen receptor modulator of this invention, in combination with Abraxane® (paclitaxel albumin-stabilized nanoparticle formulation). In another embodiment, the methods of the present invention comprise administering a selective androgen receptor modulator of this invention, in combination with ado-trastuzumab emtansine. In another embodiment, the methods of the present invention comprise administering a selective androgen receptor modulator of this invention, in combination with Adriamycin PFS® (doxorubicin hydrochloride). In another embodiment, the methods of the present invention comprise administering a selective androgen receptor modulator of this invention, in combination with Adriamycin RDF® (doxorubicin hydrochloride). In another embodiment, the methods of the present invention comprise administering a selective androgen receptor modulator of this invention, in combination with Adrucil® (fluorouracil). In another embodiment, the methods of the present invention comprise administering a selective androgen receptor modulator of this invention, in combination with Afinitor® (everolimus). In another embodiment, the methods of the present invention comprise administering a selective androgen receptor modulator of this invention, in combination with anastrozole. In another embodiment, the methods of the present invention comprise administering a selective androgen receptor modulator of this invention, in combination with Arimidex® (anastrozole). In another embodiment, the methods of the present invention comprise administering a selective androgen receptor modulator of this invention, in combination with Aromasin® (exemestane). In another embodiment, the methods of the present invention comprise administering a selective androgen receptor modulator of this invention, in combination with capecitabine. In another embodiment, the methods of the present invention comprise administering a selective androgen receptor modulator of this invention, in combination with Clafen® (cyclophosphamide). In another embodiment, the methods of the present invention comprise administering a selective androgen receptor modulator of this invention, in combination with cyclophosphamide. In another embodiment, the methods of the present invention comprise administering a selective androgen receptor modulator of this invention, in combination with Cytoxan® (cyclophosphamide). In another embodiment, the methods of the present invention comprise administering a selective androgen receptor modulator of this invention, in combination with docetaxel. In another embodiment, the methods of the present invention comprise administering a selective androgen receptor modulator of this invention, in combination with doxorubicin hydrochloride. In another embodiment, the methods of the present invention comprise administering a selective androgen receptor modulator of this invention, in combination with Efudex® (fluorouracil). In another embodiment, the methods of the present invention comprise administering a selective androgen receptor modulator of this invention, in combination with Ellence® (epirubicin hydrochloride). In another embodiment, the methods of the present invention comprise administering a selective androgen receptor modulator of this invention, in combination with epirubicin hydrochloride. In another embodiment, the methods of the present invention comprise administering a selective androgen receptor modulator of this invention, in combination with everolimus. In another embodiment, the methods of the present invention comprise administering a selective androgen receptor modulator of this invention, in combination with exemestane. In another embodiment, the methods of the present invention comprise administering a selective androgen receptor modulator of this invention, in combination with Fareston® (toremifene). In another embodiment, the methods of the present invention comprise administering a selective androgen receptor modulator of this invention, in combination with Evista® (raloxifene). In another embodiment, the methods of the present invention comprise administering a selective androgen receptor modulator of this invention, in combination with Faslodex® (fulvestrant). In another embodiment, the methods of the present invention comprise administering a selective androgen receptor modulator of this invention, in combination with Femara® (letrozole).

In another embodiment, the methods of the present invention comprise administering a selective androgen receptor modulator of this invention, in combination with Fluoroplex® (5-fluorouracil). In another embodiment, the methods of the present invention comprise administering a selective androgen receptor modulator of this invention, in combination with fluorouracil. In another embodiment, the methods of the present invention comprise administering a selective androgen receptor modulator of this invention, in combination with Folex® (methotrexate). In another embodiment, the methods of the present invention comprise administering a selective androgen receptor modulator of this invention, in combination with Folex PFS® (methotrexate). In another embodiment, the methods of the present invention comprise administering a selective androgen receptor modulator of this invention, in combination with fulvestrant. In another embodiment, the methods of the present invention comprise administering a selective androgen receptor modulator of this invention, in combination with gemcitabine hydrochloride. In another embodiment, the methods of the present invention comprise administering a selective androgen receptor modulator of this invention, in combination with Gemzar® (gemcitabine hydrochloride). In another embodiment, the methods of the present invention comprise administering a selective androgen receptor modulator of this invention, in combination with Herceptin® (trastuzumab). In another embodiment, the methods of the present invention comprise administering a selective androgen receptor modulator of this invention, in combination with Ibrance (palbociclib). In another embodiment, the methods of the present invention comprise administering a selective androgen receptor modulator of this invention, in combination with ixabepilone. In another embodiment, the methods of the present invention comprise administering a selective androgen receptor modulator of this invention, in combination with Ixempra® (ixabepilone). In another embodiment, the methods of the present invention comprise administering a selective androgen receptor modulator of this invention, in combination with lapatinib ditosylate. In another embodiment, the methods of the present invention comprise administering a selective androgen receptor modulator of this invention, in combination with letrozole. In another embodiment, the methods of the present invention comprise administering a selective androgen receptor modulator of this invention, in combination with methotrexate. In another embodiment, the methods of the present invention comprise administering a selective androgen receptor modulator of this invention, in combination with methotrexate LPF (methotrexate). In another embodiment, the methods of the present invention comprise administering a selective androgen receptor modulator of this invention, in combination with Mexate® (methotrexate). In another embodiment, the methods of the present invention comprise administering a selective androgen receptor modulator of this invention, in combination with Mexate-AQ® (methotrexate). In another embodiment, the methods of the present invention comprise administering a selective androgen receptor modulator of this invention, in combination with Neosar® (cyclophosphamide). In another embodiment, the methods of the present invention comprise administering a selective androgen receptor modulator of this invention, in combination with Nolvadex® (tamoxifen citrate). In another embodiment, the methods of the present invention comprise administering a selective androgen receptor modulator of this invention, in combination with paclitaxel. In another embodiment, the methods of the present invention comprise administering a selective androgen receptor modulator of this invention, in combination with paclitaxel albumin-stabilized nanoparticle formulation. In another embodiment, the methods of the present invention comprise administering a selective androgen receptor modulator of this invention, in combination with Perjeta® (pertuzumab). In another embodiment, the methods of the present invention comprise administering a selective androgen receptor modulator of this invention, in combination with pertuzumab. In another embodiment, the methods of the present invention comprise administering a selective androgen receptor modulator of this invention, in combination with tamoxifen citrate. In another embodiment, the methods of the present invention comprise administering a selective androgen receptor modulator of this invention, in combination with Taxol® (paclitaxel). In another embodiment, the methods of the present invention comprise administering a selective androgen receptor modulator of this invention, in combination with Taxotere® (docetaxel). In another embodiment, the methods of the present invention comprise administering a selective androgen receptor modulator of this invention, in combination with trastuzumab. In another embodiment, the methods of the present invention comprise administering a selective androgen receptor modulator of this invention, in combination with oremifene. In another embodiment, the methods of the present invention comprise administering a selective androgen receptor modulator of this invention, in combination with Tykerb® (lapatinib ditosylate). In another embodiment, the methods of the present invention comprise administering a selective androgen receptor modulator of this invention, in combination with Xeloda® (capecitabine).

In one embodiment, the methods of the present invention comprise administering a pharmaceutical composition (or pharmaceutical preparation, used herein interchangeably) comprising the selective androgen receptor modulator of the present invention and/or its analog, derivative, isomer, metabolite, pharmaceutical product, hydrate, N-oxide, polymorph, crystal, prodrug or any combination thereof; and a suitable carrier or diluent.

Pharmaceutical Compositions:

As used herein, "pharmaceutical composition" means therapeutically effective amounts of the selective androgen receptor modulator together with suitable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20®, Tween 80®, Pluronic F68®, bile acid salts), solubilizing agents (e.g., glycerol, polyethylene glycerol), anti-oxidants (e.g., ascorbic acid, sodium metabisulfite), preservatives (e.g., Thimerosal®, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multi-lamellar vesicles, erythrocyte ghosts, or spheroplasts). Such compositions will influence the physical state, solubility, stability, rate of in vivo release, and rate of in vivo clearance. Controlled or sustained release compositions include formulation in lipophilic depots (e.g., fatty acids, waxes, oils).

In one embodiment, the pharmaceutical compositions comprising the compounds of this invention make use in the methods of this invention of a dosage of between 1 and 50 mg of a compound of this invention. In another embodiment, the dosage is 1 mg, 3 mg, 9 mg, 10 mg, 18 mg or 30 mg of the compound of this invention. In another embodiment, the pharmaceutical compositions comprising the compounds of this invention make use in the methods of this invention of a dosage of 1 mg of a compound of this invention. In another embodiment, the pharmaceutical compositions comprising the compounds of this invention make use in the methods of this invention of a dosage of 3 mg of a compound of this invention. In another embodiment, the pharmaceutical compositions comprising the compounds of this invention make use in the methods of this invention of a dosage of 9 mg of a compound of this invention. In another embodiment, the pharmaceutical compositions comprising the compounds of this invention make use in the methods of this invention of a dosage of 10 mg of a compound of this invention. In another embodiment, the pharmaceutical compositions comprising the compounds of this invention make use in the methods of this invention of a dosage of 18 mg of a compound of this invention. In another embodiment, the pharmaceutical compositions comprising the compounds of this invention make use in the methods of this invention of a dosage of 30 mg of a compound of this invention.

Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitoneally, intraventricularly, intravaginally, intracranially and intratumorally.

Further, as used herein "pharmaceutically acceptable carriers" are well known to those skilled in the art and include, but are not limited to, 0.01-0.1 M and preferably 0.05 M phosphate buffer or about 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions of the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The pharmaceutical preparation can comprise the selective androgen receptor modulator alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the selective androgen receptor modulator can be administered to a subject by, for example, subcutaneous implantation of a pellet; in a further embodiment, the pellet provides for controlled release of selective androgen receptor modulator over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository.

The pharmaceutical preparations of the invention can be prepared by known dissolving, mixing, granulating, or tablet-forming processes. For oral administration, the selective androgen receptor modulators or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the selective androgen receptor modulators or their physiologically tolerated derivatives such as salts, esters, N-oxides, and the like are converted into a solution, suspension, or emulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions can be prepared as aerosols of the active component delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the selective androgen receptor modulators or their physiologically tolerated derivatives such as salts, esters, N-oxides, and the like are prepared and applied as solutions, suspensions, or emulsions in a physiologically acceptable diluent with or without a pharmaceutical carrier.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

For use in medicine, the salts of the selective androgen receptor modulator will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In one embodiment, the term "about", refers to a deviance of between 0.0001-5% from the indicated number or range of numbers. In one embodiment, the term "about", refers to a deviance of between 1-10% from the indicated number or range of numbers. In one embodiment, the term "about", refers to a deviance of up to 25% from the indicated number or range of numbers.

In some embodiments, the term "comprise" or grammatical forms thereof, refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components, which exert a therapeutic effect via a mechanism distinct from that of the indicated active ingredient. In some embodiments, the term "consisting essentially of" may refer to components, which exert a therapeutic effect and belong to a class of compounds distinct from that of the indicated active ingredient. In some embodiments, the term "consisting essentially of" may refer to components, which exert a therapeutic effect and belong to a class of compounds distinct from that of the indicated active ingredient, by acting via a different mechanism of action, for example, and representing an embodiment of this invention, polypeptides comprising T cell epitopes present in a composition may be specifically combined with polypeptides comprising B cell epitopes. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

Further, as used herein, the term "comprising" is intended to mean that the system includes the recited elements, but not excluding others which may be optional. By the phrase "consisting essentially of" it is meant a method that includes the recited elements but exclude other elements that may have an essential significant effect on the performance of the method. "Consisting of" shall thus mean excluding more than traces of other elements. Embodiments defined by each of these transition terms are within the scope of this invention.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the term "a" or "one" or "an" refers to at least one. In one embodiment the phrase "two or more" may be of any denomination, which will suit a particular purpose. In one embodiment, "about" may comprise a deviance from the indicated term of +1%, or in some embodiments, −1%, or in some embodiments, ±2.5%, or in some embodiments, ±5%, or in some embodiments, ±7.5%, or in some embodiments, ±10%, or in some embodiments, ±15%, or in some embodiments, ±20%, or in some embodiments, ±25%.

The following examples are presented in order to more fully illustrate the preferred embodiments of the invention. They should in no way be construed, however, as limiting the broad scope of the invention.

EXPERIMENTAL DETAILS SECTION

General Experimental Methods
Cell Growth Conditions

HCC 1937, HCC 1954, HCC 38, T47D-Kbluc, MDA-MB-453, and MDA-MB-231 cells were grown in RPMI-1640 medium containing 2 mM L-glutamine supplemented with 10% fetal bovine serum (FBS). Cells were maintained in a 5% $CO_2$/95% air humidified atmosphere at 37° C. MCF-7 cells were grown in Minimum Essential Medium supplemented with 10% FBS.

Breast cancer tumors typically express AR 70-90% of the time, however breast cancer cell lines typically do not express AR. This makes development of a preclinical model for the study of androgen effects on breast cancer very difficult. Consequently, the AR has been introduced by adenoviral infection (stably incorporated into the genome) into some breast cancer cell lines used in the studies below.

Sulforhodamine B (SRB) Assay

The SRB assay was used to determine cell number during cytotoxocity experiments. The following protocol was used:
1. Cells were detached with 0.25% trypsin.
2. Experimental cultures were cultured in 96-well microtiter plates (200 uL growth medium per well; 1,000-200,000 cells per well).
3. Cultures were fixed with 50 uL 50% TCA (4° C.). (see cell fixation protocol for details).
4. Fixed cells were stained with 50 uL 0.4% (wt/vol) SRB in 1% acetic acid for 10 minutes.
5. SRB was removed and the cultures were quickly* rinsed 5 times with 1% acetic acid to remove unbound dye.**

*quickly performing rinsing process was to prevent desorption of protein-bound SRB
   **completely removed residual wash solution by sharply flicking plates over sink.

6. Cultures were air-dried overnight until there was no visible moisture.
7. The cellular protein-bound SRB was dissolved with 200 uL unbuffered Tris base (10 mM, pH 10.5) for 30 minutes on a rocking platform shaker.
8. Absorbance was read at 540 nm.

Fixation of Cells Attached to the Plastic Substratum

The following protocol was used for fixing cells:
a. 50 uL of 50% TCA (4° C.) was gently layered on the top of growth medium in each well to make a final TCA concentration of 10%.
b. Cultures were incubated at 4° C. for 1 hour.
c. Cultures were washed 5 times with tap water to remove TCA, growth medium, low-molecular-weight metabolites, and serum protein.
d. Plates were air-dried until there was no visible moisture.

Example 1

Effect of Formula IX on Growth in Different Breast Cancers Cell Lines Expressing Androgen Receptor Materials and Methods MDA-MB-231 and HCC-38 triple negative breast cancer cells were used to analyze growth effects of various compounds.

MDA-MB-231 and HCC-38 triple negative breast cancer cells were infected with 200 μL or 500 μL adenovirus containing LacZ (negative control) or AR, and were treated with various AR ligands (agonists: DHT and Formula IX, and antagonist: bicalutamide) or a non-AR binder that is structurally similar to Formula IX, R-enantiomer of Formula IX. Cells were treated in charcoal stripped FBS (FIGS. 1C, 1E, 1G and 1I; 2C, 2E and 2G or full serum (FIGS. 1D, 1F, 1H and 1J; 2D, 2F and 2H for 3 days, fixed and stained with sulforhodamine blue (SRB) to measure cell viability. $IC_{50}$ values were calculated.

Results

Figure 2E:
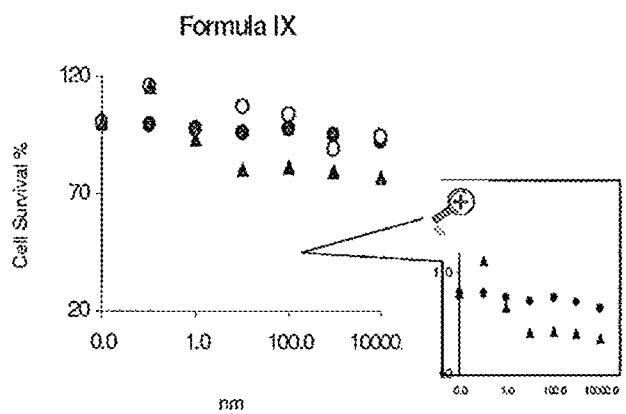
Figure 2F:
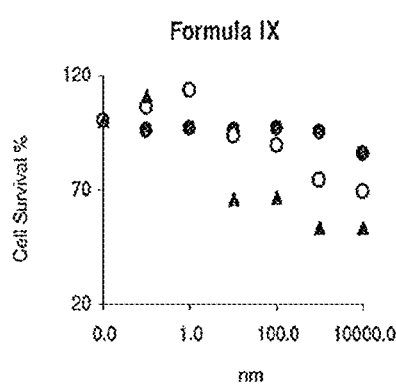
Figure 2G:
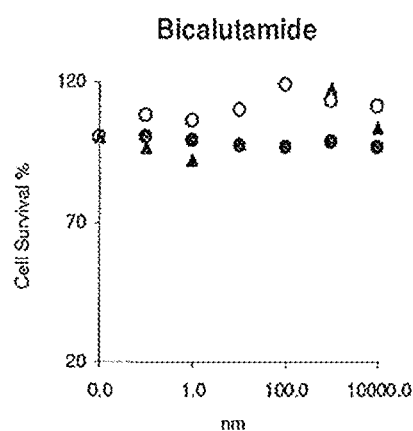
Figure 2H:
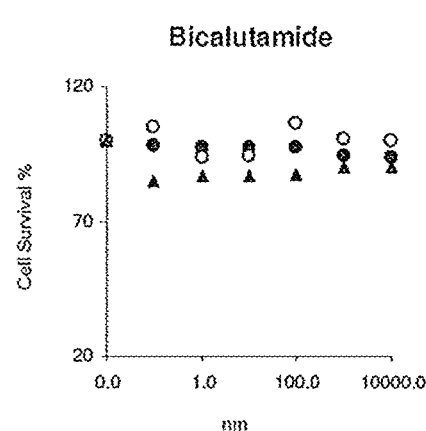

Expression of AR in cells infected with AR or LacZ was evaluated using Western blotting (FIG. 1A and FIG. 2A).

Only the AR agonists, DHT and Formula IX, inhibited MDA-MB-231 and HCC-38 triple negative breast cancer cell growth (FIGS. 1C, 1D, 1E, 1F and FIGS. 2C, 2D, 2E and 2F). This inhibition was observed only in the presence of AR (compare w/lacZ and w/AR). $IC_{50}$ values in AR-positive cells for DHT and Formula IX are presented in FIG. 1B and FIG. 2B.

Example 2

Reversal of Effect of Formula IX on Growth

Materials and Methods

To determine if the growth inhibition observed with DHT and Formula IX in AR-positive cells is AR dependent, MDA-MB-231 cells were infected with adenovirus containing LacZ (negative control) or AR and were treated with AR agonists, DHT or Formula IX, in the presence or absence of the AR antagonist, bicalutamide. Cells were treated in charcoal stripped FBS (FIGS. 3A and 3C or full serum (FIGS. 3B and 3D for 3 days, fixed and stained with sulforhodamine blue (SRB) to measure cell viability. $IC_{50}$ values were calculated.

Results

Both DHT and Formula IX required AR to inhibit MDA-MB-231 cell growth, as demonstrated by the weakened growth inhibitory effects in the presence of bicalutamide (FIGS. 3A-3D). $IC_{50}$ values for DHT and Formula IX in AR-positive cells pretreated with or without bicalutamide are presented in FIG. 3E.

Example 3

Effect of AR Ligands on Breast Cancer Cell Growth

Materials and Methods

To determine if all AR ligands inhibit the growth of triple negative breast cancer cells, MDA-MB-231 cells were infected with adenovirus containing LacZ or AR and were treated with various AR ligands (agonists: DHT, Formula VIII, Formula IX, Formula X, Formula XIII, Formula XIV; antagonist: bicalutamide) and a non-AR-binder: R-enantiomer of Formula IX. Cells were treated in charcoal stripped FBS (FIGS. 4A, 4C, 4E, 4G, 4I, 4K, 4M and 4O) or full serum (FIGS. 4B, 4D, 4F, 4H, 4J, 4L, 4N and 4P) for 3 days, fixed and stained with sulforhodamine blue (SRB) to measure cell viability. Anti-proliferative $IC_{50}$ values were calculated in breast cancer cells and compared to transactivation values, i.e., $EC_{50}$ (agonists) and $IC_{50}$ (antagonists) values, generated in HEK-293 cells. The growth regulatory properties in breast cancer cells of these molecules in breast cancer cells are comparable to the transactivation values obtained in HEK-293 cells.

Results

Figure 4A:
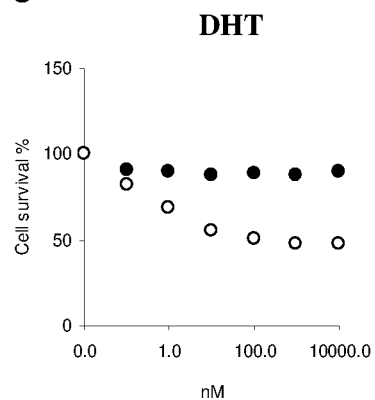
Figure 4B:
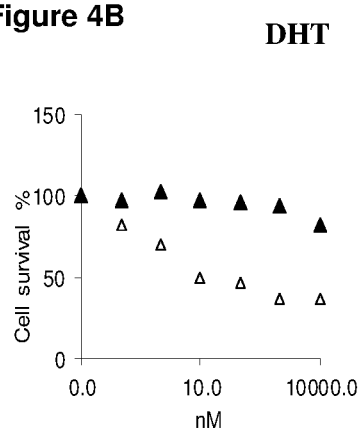
Figure 4C:
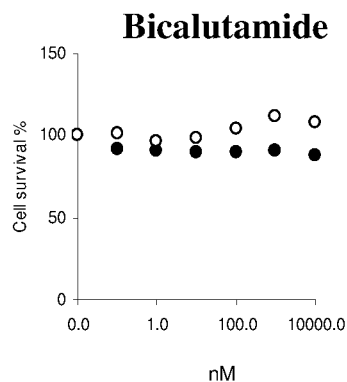
FIG. 4C and FIG. 4D show the effect of AR antagonist on percent (%) cell survival.
Figure 4D:
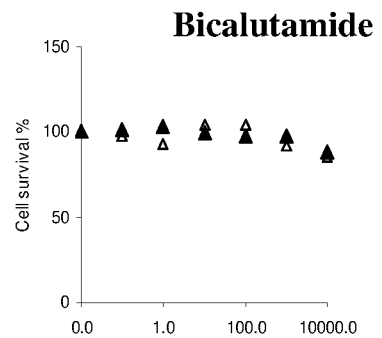
Figure 4E:
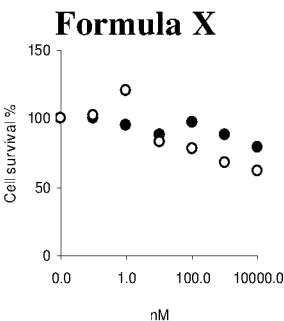
Figure 4F:
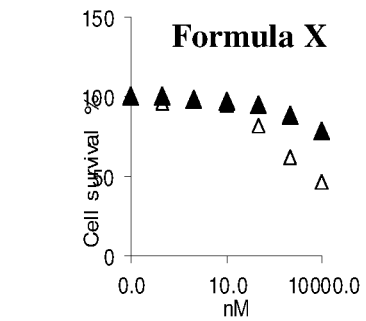
Figure 4G:
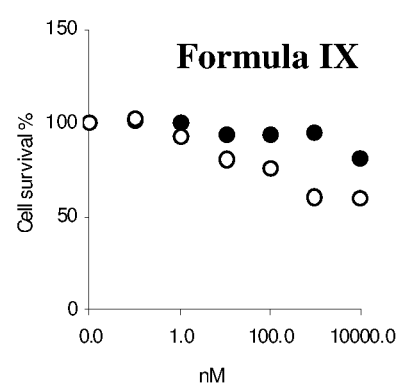
Figure 4H:
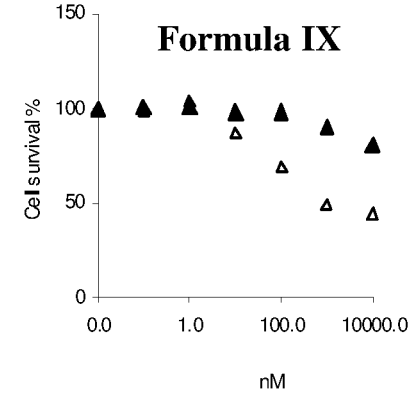
Figure 4I:
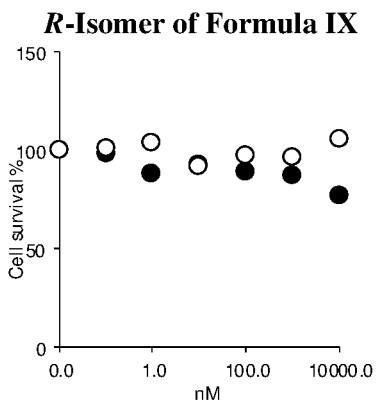
FIG. 4I and FIG. 4J show the effect of AR non-binder on percent (%) cell survival.
Figure 4J:
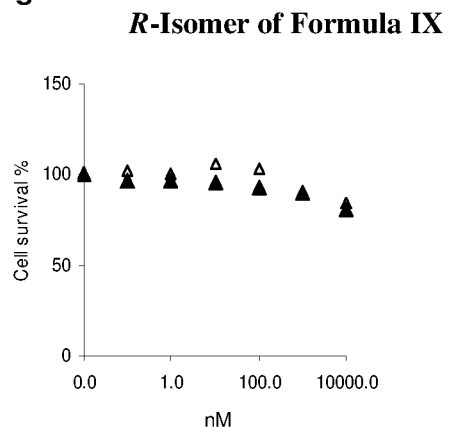
Figure 4K:
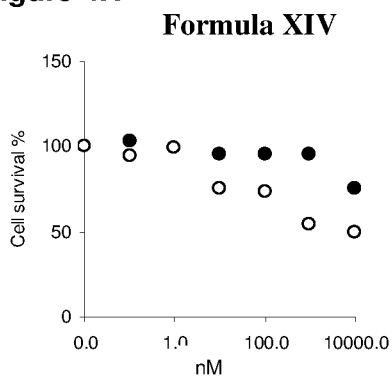
Figure 4L:
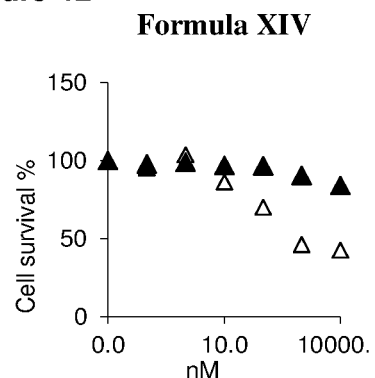
Figure 4M:
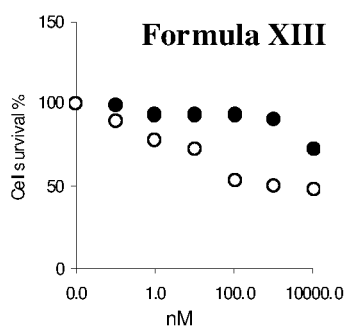
Figure 4N:
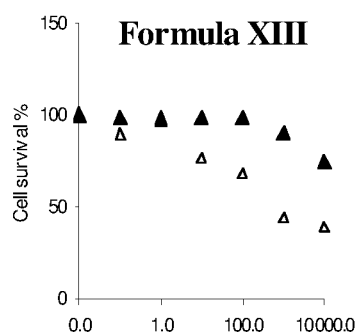
Figure 4O:
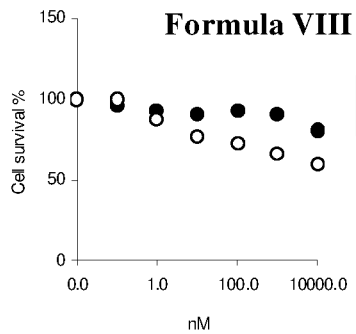
Figure 4P:
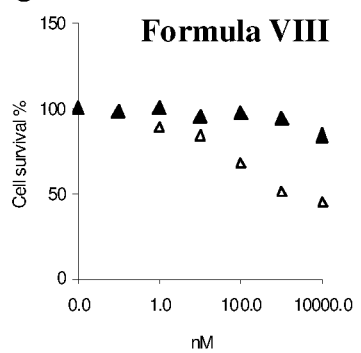

Only AR agonists inhibited the growth of MDA-MB-231 cells (FIGS. 4A, 4B, 4E-4H, and 4K-4P) and the growth inhibitory potential of these ligands rank order with their agonistic activity observed in HEK-293 cells (FIG. 4Q).

Example 4 demonstrates as well that AR agonists inhibited the proliferation of MDA-MB-231 cells stably transfected with AR.

Example 4

AR Transactivation Assays in Breast Cancer Cells

Materials and Methods

To ensure that the ligands that elicited growth inhibitory properties are agonists in MDA-MB-231 cells, AR transactivation assays were performed in MDA-MB-231 cells. Though AR transactivation assay was performed in HEK-293 cells, the ability of ligands to function as agonists or antagonists depends on cellular microenvironment. Hence, MDA-MB-231 cells were transfected using lipofectamine with AR, GRE-LUC and CMV-LUC as normalization control. The cells were treated 24 h after transfection and luciferase assay performed 48 h after transfection.

Results

FIG. 5 shows that all AR ligands that elicited anti-proliferative activity are agonists in MDA-MB-231 cells transfected with AR and their agonist and growth inhibitory properties compare well. In other words, growth inhibitory ligands are AR agonists in MDA-MB-231 cells transfected with AR.

Example 5

Analysis of Growth Inhibitory Effects in Breast Cancer Cells Expressing Estrogen Receptor Materials and Methods To ensure that growth inhibitory effects in MDA-MB-231 cells are selective to AR, and to determine if the ligand dependent growth inhibitory effects are exclusive to AR and also to ensure that the effects are not artifacts of adenoviral infection, MDA-MB-231 triple negative breast cancer cells were infected with ER-α or ER-β adenovirus constructs and were treated with ER agonist: 17β-estradiol (E2) or ER antagonist: ICI 182,780 (ICI) in charcoal stripped serum (FIG. 6C)

or full serum (FIGS. 6D and 6E) for 3 days. Cells were fixed and stained with sulforhodamine blue (SRB) to measure cell viability. Expression of ER in infected cells was evaluated using Western blotting.

Results

Figure 6A:
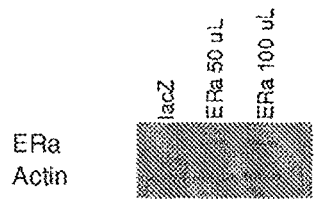
FIG. 6A-FIG. 6E illustrate that growth inhibitory effects in MDA-MB-231 cells are selective to AR.
Figure 6B:
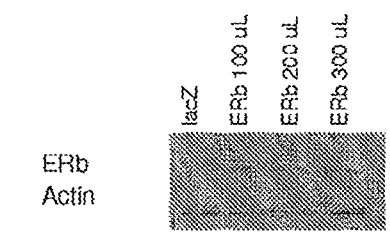
Figure 6C:
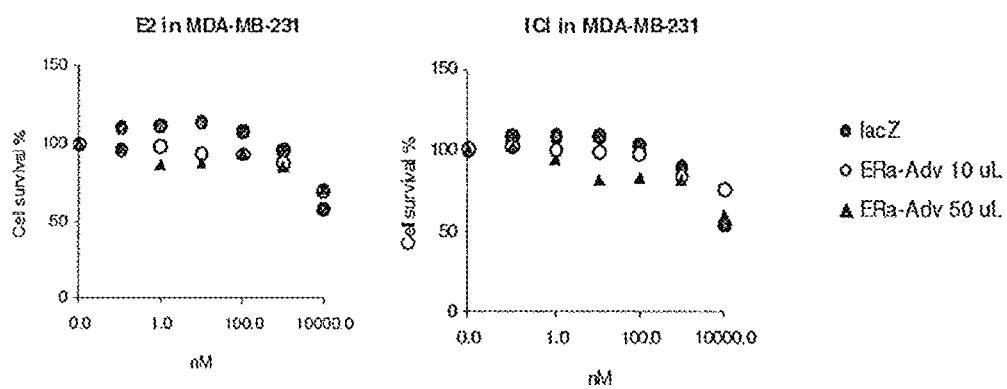
Figure 6D:
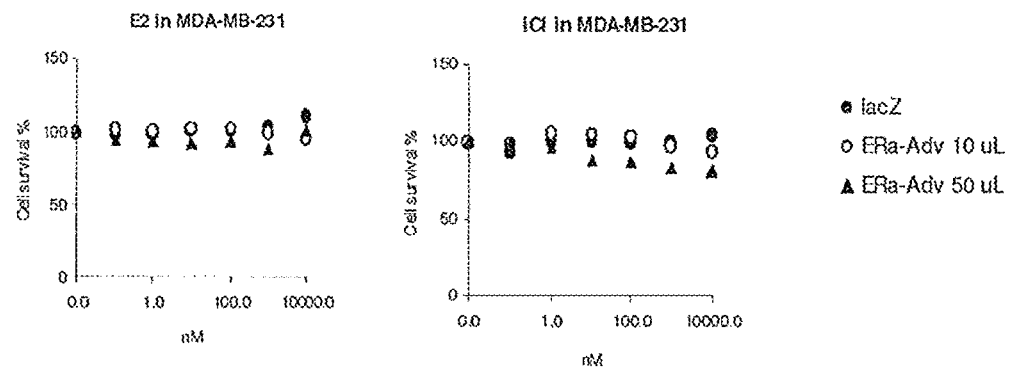
Figure 6E:
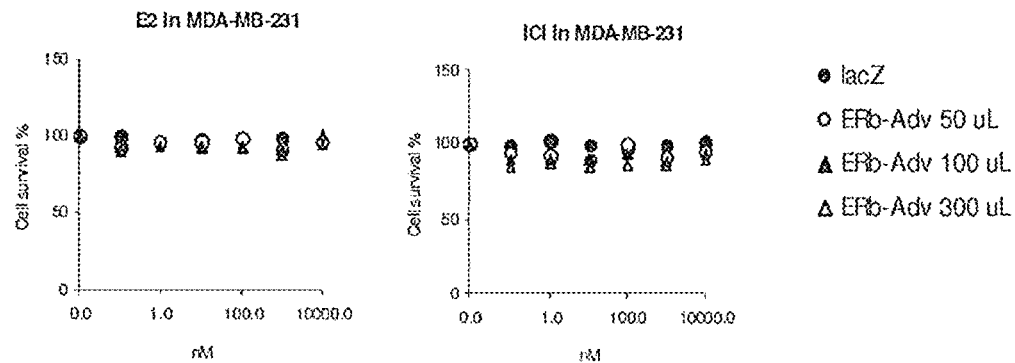

FIGS. 6A-6B show the presence or absence of ERα or ERβ in MDA-MB-231 cells following transfection. These results show that the anti-proliferative effects observed with androgens is unique to ligand activated AR and not an artifact of adenovirus. FIGS. 6C-6E show that over-expression of ER-α or ER-β in MDA-MB-231 cells failed to promote growth inhibition either in the presence of ER agonists or antagonists. Thus, the observed growth inhibitory effects in MDA-MB-231 cells are selective to the presence of the AR and AR agonists.

Example 6

Effect of AR Agonist on Morphology of Breast Cancer Cells

Materials and Methods

MDA-MB-231 cells were stably transfected with AR using lentivirus. Following transfection, cells were treated for 3 days with the indicated concentrations of DHT or bicalutamide. Live cells were visualized using a light-microscope and photographed. The cells were imaged at the same magnification and under the same microscopic conditions.

Results

Figure 7:
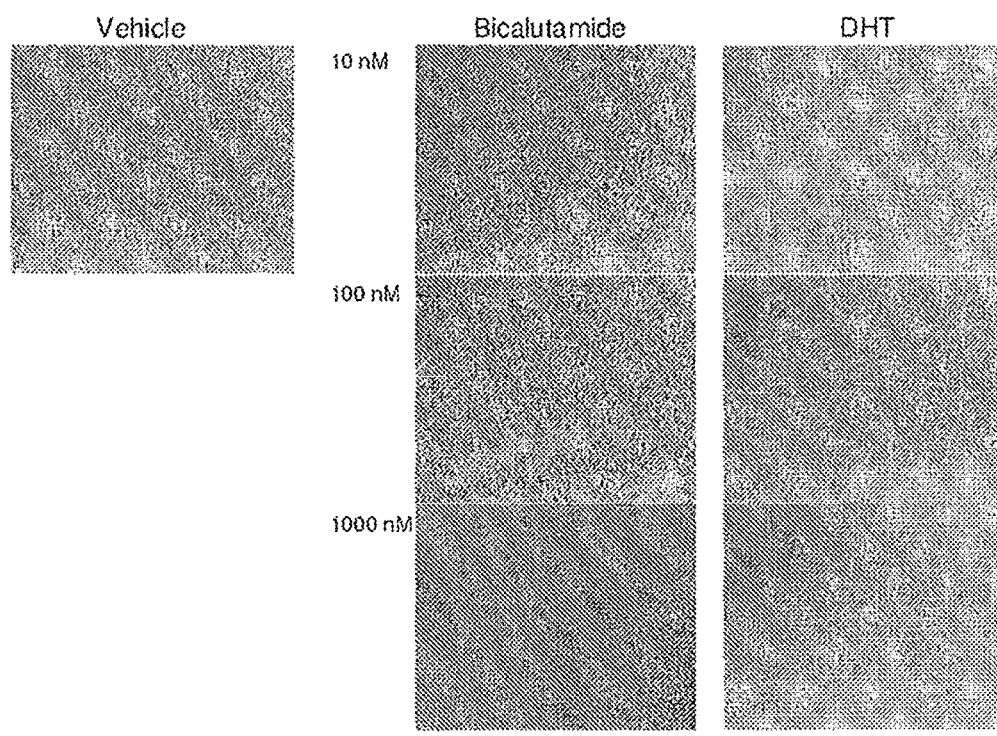
FIG. 7 shows DHT alters the morphology of MDA-MB-231 cells.

FIG. 7 shows that DHT altered the morphology of MDA-MB-231 cells into more anchorage dependent and differentiated cells, indicating that AR agonist-bound AR expressing breast cancer cells will have less invasive and migratory properties (e.g., less likely to metastasize).

DHT and SARMs alter the morphology of AR-positive MDA-MB-231 cells. MDA-MB-231 cells were stably transfected with AR using lentivirus and were treated with vehicle or AR agonists at the indicated concentrations. At the end of 3 days of incubation, the cells were imaged under a microscope (40×).

Figure 12:
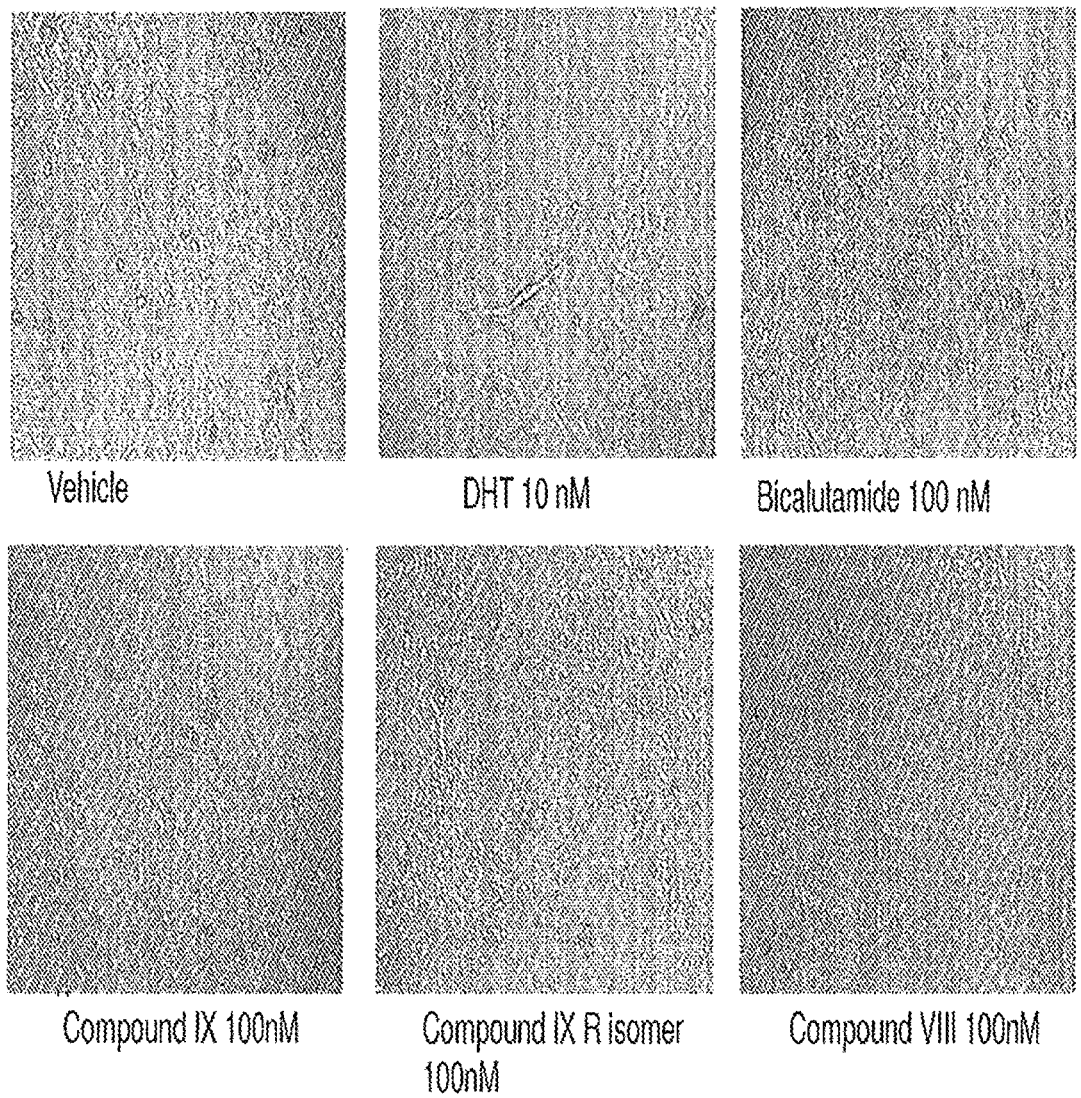
FIG. 12 demonstrates the morphology of MDA-MB-231 breast cancer cells stably transfected with AR (MDA-MB-231-AR cells). The results indicate that AR agonists, DHT, Formula IX, and Formula VIII altered the morphology into a more anchored phenotype compared to vehicle, bicalutamide or an inactive isomer of Formula IX. This may be indicative of a less metastatic breast cancer phenotype.

DHT and SARMs, but not the AR antagonist, bicalutamide (data not shown), or the inactive isomer of Formula IX, altered the morphology of the cells into a more anchorage-dependent phenotype (FIG. 12).

Example 7

Cross-Reactivity of Formula VIII with Other Nuclear Hormone Receptors

In order to determine whether compounds of this invention affected other nuclear hormone receptor signaling, the ability of a compound represented by Formula VIII to stimulate (agonist) or inhibit (antagonist) ERα-, ERβ-, GR-, PR-, or MR-mediated transcriptional activation, was analyzed.

Materials and Methods

Transient Transfection

Rat GR, MR, PR, ER-α and ER-β were individually cloned into a pCR3.1 vector backbone. Sequencing was performed to verify the absence of any mutations. HEK-293 cells were plated at 90,000 cells per well of a 24 well plate in Dulbecco's Minimal Essential Media supplemented with 5% charcoal-stripped FBS. The cells were transfected using Lipofectamine (Invitrogen, Carlsbad, Calif.) with 0.25 µg GRE-LUC for GR, MR and PR and ERE-LUC for ER-α and ER-β, 0.5 ng CMV-LUC (renilla luciferase) and 12.5-25 ng of the respective expression vector for each receptor. The cells were treated 24 h after transfection with Formula VIII in the absence (agonist mode) and presence (antagonist mode) of known agonists (17β-estradiol for ER; dexamethasone for GR; aldosterone for MR; progesterone for PR) as controls. Luciferase assays were performed 48 h after transfection. Transcriptional activation values are represented as firefly luciferase normalized to renilla luciferase.

Results

Figure 8:
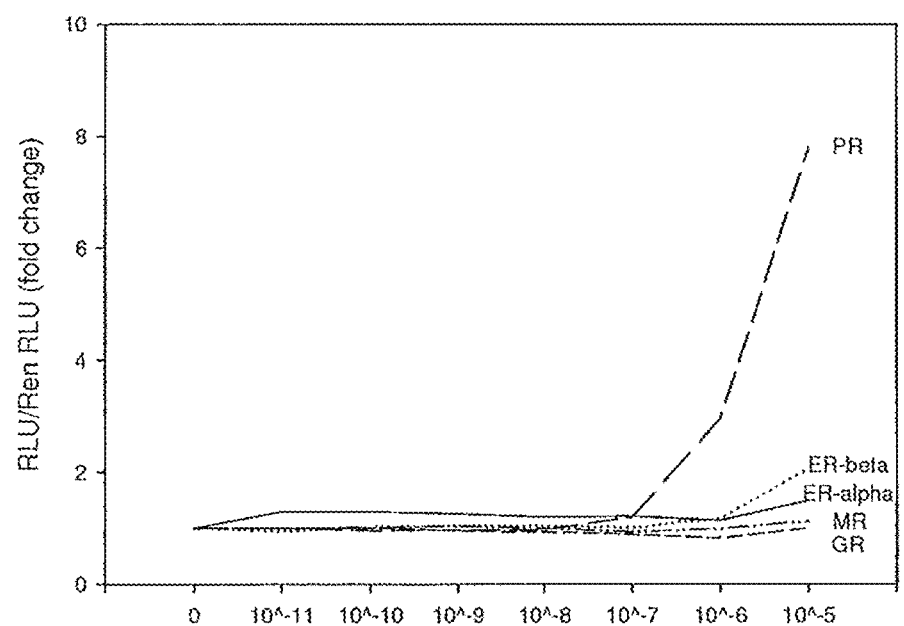
FIG. 8 illustrates the effect of Formula VIII on steroid receptor transactivation (agonist mode).

The agonist effects of Formula VIII on ER-β, ER-α, GR, PR and MR were tested and compared to the activities of the known ligands, as well (FIG. 8). A compound of Formula VIII failed to activate ER-β or ER-α even at the highest tested concentration (1 μM) whereas 1 nM 17β-estradiol induced ERα- and ERβ-mediated transactivation by 3- and 5-fold, respectively. A compound of Formula VIII failed to activate GR- or MR-mediated transactivation. A compound of Formula VIII at all the tested concentrations did not induce GR- or MR-mediated transactivation, whereas the known ligands (dexamethasone and aldosterone) induced the activities of GR or MR by 70- and 60-fold, respectively, at a concentration of 1 nM. However, a compound of Formula VIII increased the transactivation of PR at 1 μM and 10 μM by 3 and 8 fold, respectively. Progesterone activated PR by 23 fold at a 1 nM concentration, indicating that a compound of Formula VIII is greater than 10,000-fold weaker than the endogenous agonist for PR.

The ability of a compound of Formula VIII to inhibit the effects of a known agonist for each of the above mentioned receptors was tested as well.

Co-incubation of HEK 293 cells with the indicated concentrations of Formula VIII failed to alter the 17β-estradiol-induced ER-β or ER-α activity, dexamethasone-induced GR-mediated transactivation or aldosterone-induced MR-mediated transactivation.

Figure 9:
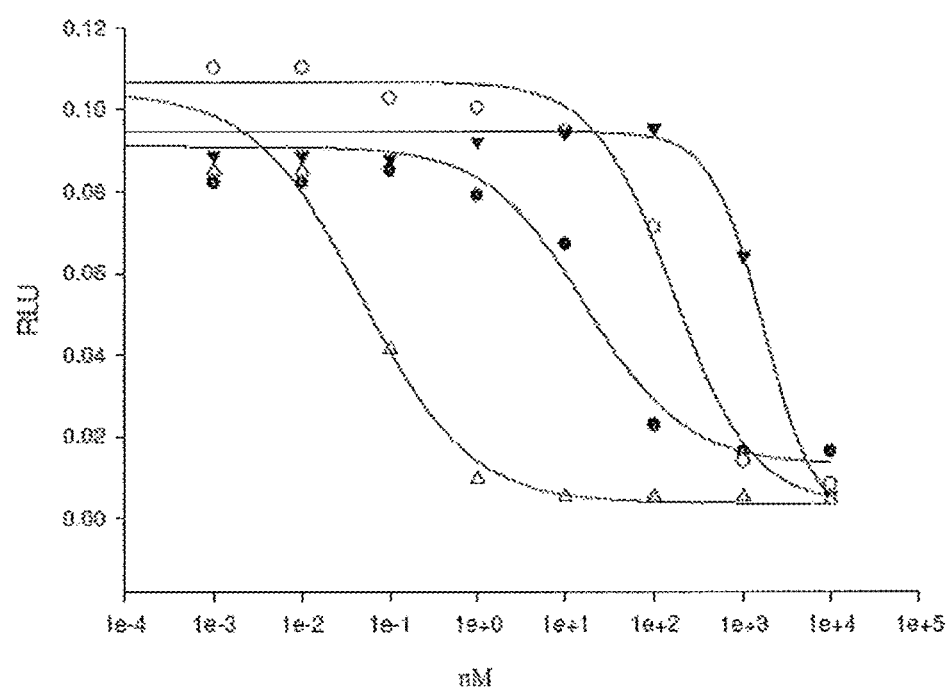
FIG. 9 depicts a dose response curve of PR activity (antagonist mode) for compound of Formula VIII, Formula IX, R-enantiomer of Formula IX and RU486. The closed circles (•) correspond to Formula VIII data points ($IC_{50}$=17.05 nM); open circles (○) correspond to Formula IX ($IC_{50}$=162.9 nM); closed triangles (▼) correspond to R-enantiomer of Formula IX ($IC_{50}$=1689 nM); and open triangles (Δ) correspond to RU486 ($IC_{50}$=0.048 nM).

A dose response curve for a compound of Formula VIII in antagonist mode demonstrated potent partial inhibition of PR activity (FIG. 9). In comparison to Formula IX, Formula VIII is was 10-times more potent, and 100-times more potent than R-enantiomer of Formula IX. In comparison to RU486, Formula VIII was about 1,000 fold weaker as a PR antagonist, than RU486.

Compounds of Formulae VIII and IX are specific for the AR and do not stimulate or inhibit receptor-mediated transactivation of ERα, ERβ, GR, or MR. Unexpectedly, Formula VIII exhibited moderate potency partial agonist activity for PR, and potent PR partial antagonism (see FIG. 9). Combined AR-agonism and PR-antagonism will be beneficial in certain breast cancers (e.g., PR-positive breast cancers).

Example 8

Formula VIII and Formula IX Inhibit Triple Negative Breast Cancer Cell Tumor Growth in Mice Materials and Methods MDA-MB-231-AR triple negative breast cancer cells (2 million cells/mouse; MDA-MB-231 cells stably transfected with AR using lentivirus) were mixed with matrigel (1:1) and injected subcutaneously into the flanks of intact female nude mice (n=5/group). When the tumors reached 150-200 mm$^3$, the animals were separated into two groups, one receiving vehicle and the other receiving 30 mg/kg Formula VIII orally. Tumor volume was measured thrice weekly and % tumor growth inhibition (TGI) was calculated. At the end of 35 days of treatment, the animals were sacrificed, tumors excised, weighed, and collected for various analyses. Blood was collected and serum separated for drug concentration measurement.

Results

Figure 10A:
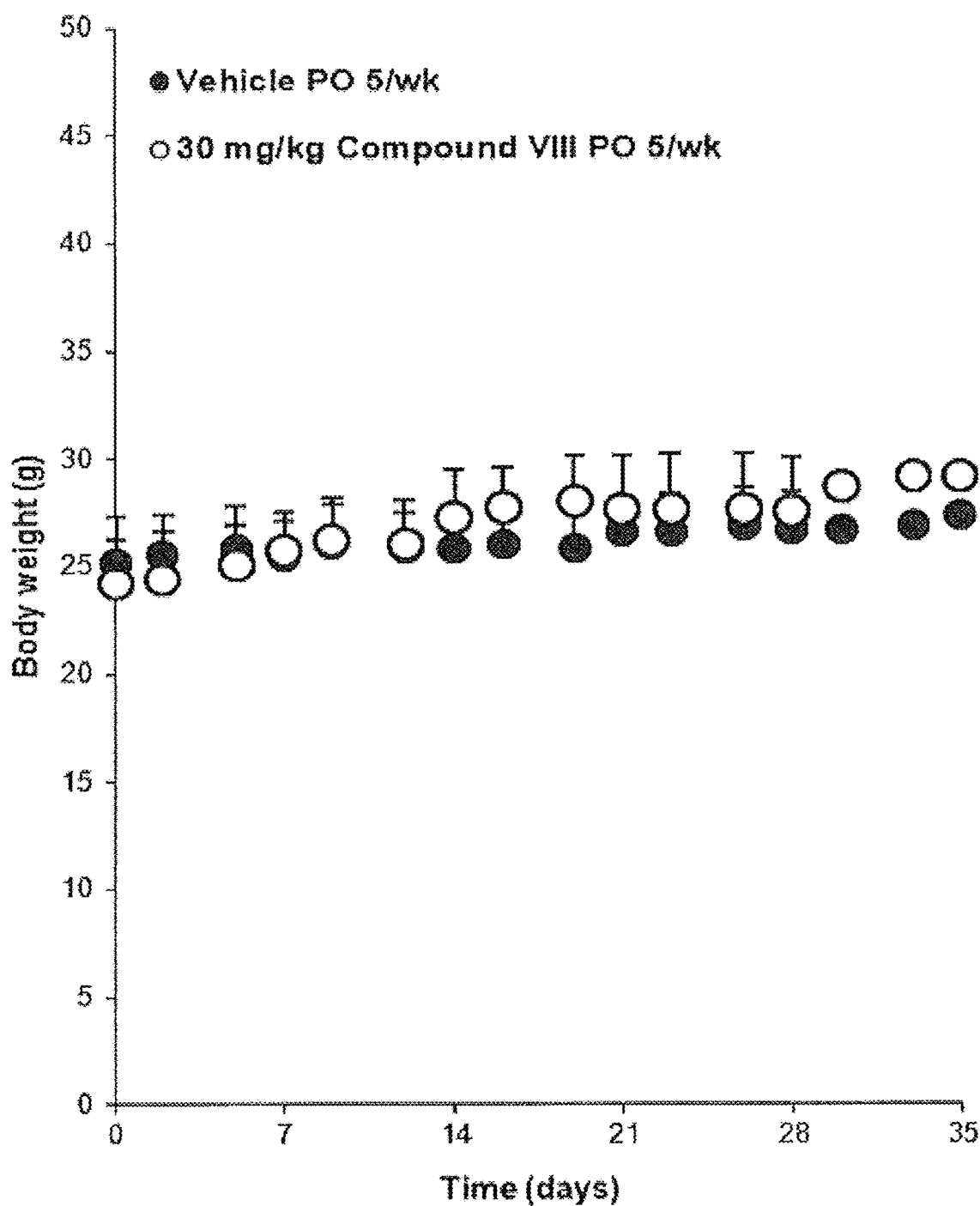
FIG. 10A-FIG. 10B demonstrate that SARM (Formula VIII) inhibits MDA-MB-231-AR tumor growth. Body weight (10A) and tumor size (10B) were measured for 35 days in intact female nude mice having 150-200 mm³ tumors from MDA-MB-231-AR triple negative breast cancer cells and then orally administered vehicle (✱) or 30 mg/kg of Formula VIII (•).
Figure 10B:
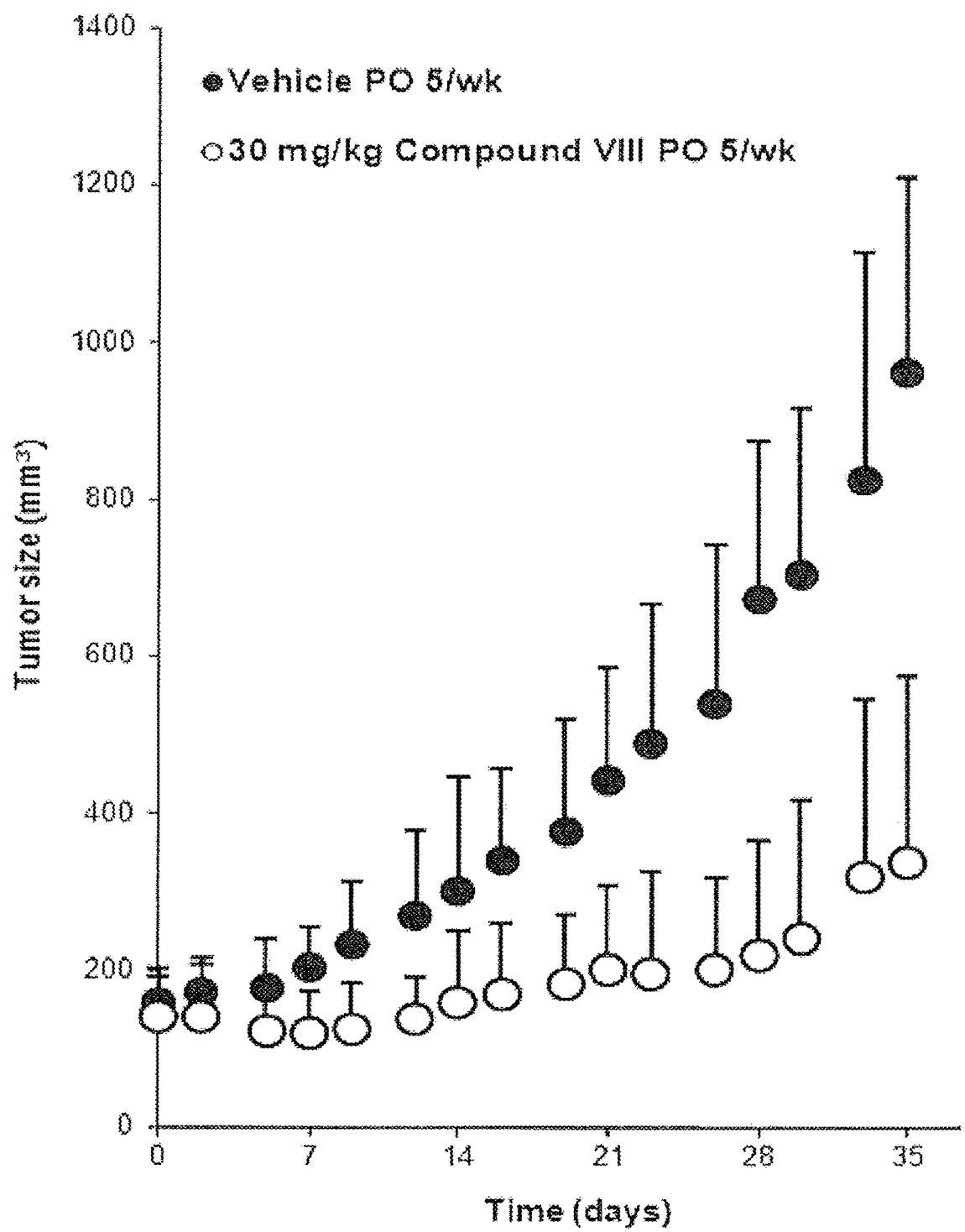
Figure 11:
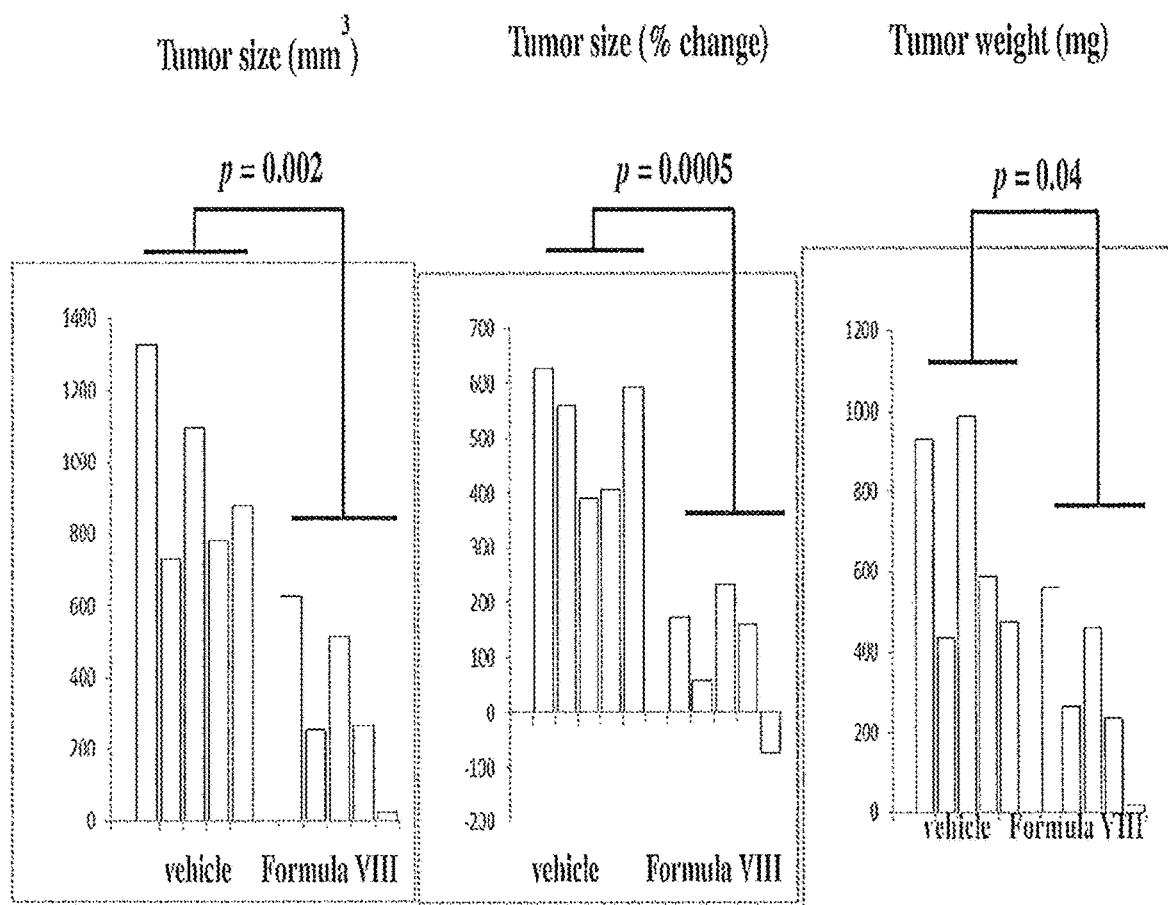
FIG. 11 demonstrates that SARM (Formula VIII) inhibits MDA-MB-231-AR tumor growth. Tumor size in mm³ (left pane) and % change in tumor size (middle pane), as well as tumor weight (right pane) were measured after 35 days in intact female nude mice having 150-200 mm³ tumors from MDA-MB-231-AR triple negative breast cancer cells and then receiving oral administration of vehicle or 30 mg/kg of Formula VIII.

Formula VIII significantly reduced the tumor growth with TGI of ~75% (FIG. 10B). Tumor weights were also reduced by more than 50% by Formula VIII treatment (FIG. 11, right panel) as were tumor size (FIG. 11, left panel (mm$^3$) and middle panel (% change)). Formula VIII elicited these results without any associated toxicity or changes in body weight (FIG. 10A). Uterus weight also increased in response to Formula VIII treatment (not shown), indicative of in vivo androgenic response.

Figure 24:
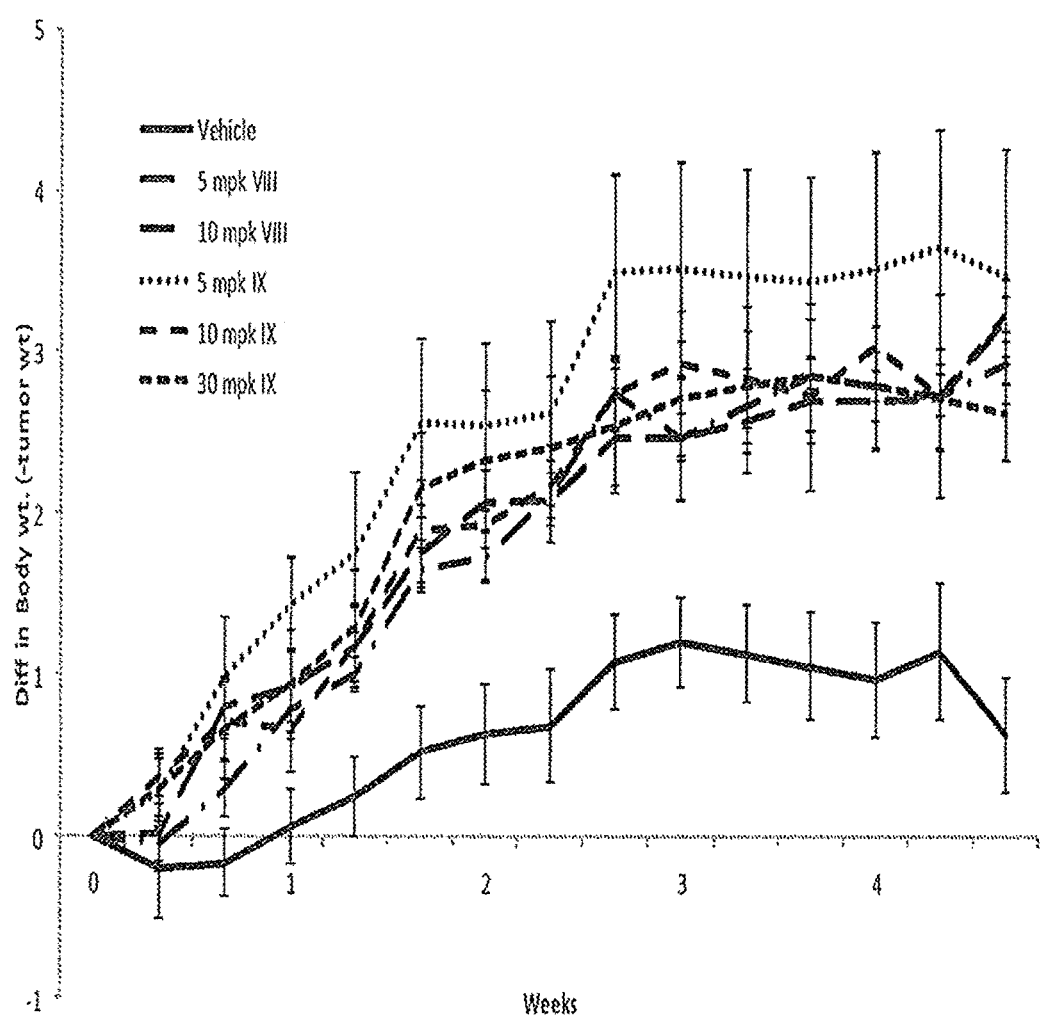
FIG. 24 shows increased body weight by the SARMs at all doses of Formula VIII and Formula IX, indicative of healthy growth and a lack of toxicity. By comparison, the vehicle treated animals did not grow as robustly.

The results presented in FIG. 24 shows the increase of body weight by the SARMs at all doses of Formula VIII and Formula IX, indicative of healthy growth and a lack of toxicity. By comparison, the vehicle treated animal did not grow as robustly.

In summary, the Formula VIII SARM is extremely effective in regressing the growth of AR expressing triple negative breast cancer xenografts in mice, and is likely to be effective in a wide variety of AR-positive breast cancers in humans, as described supra and infra.

Example 9

Effect of Formula IX in Women with Metastatic or ER and/or AR-Positive Refractory Breast Cancer This clinical trial assessed the safety and efficacy of 9 mg of the compound represented by the structure of Formula IX (Formula IX), in 22 post-menopausal women who have estrogen receptor (ER) positive metastatic breast cancer, and who have responded previously to adjuvant and/or salvage endocrine therapy. The goal of this study was to determine the importance of the AR status as a therapeutic target in women with ER-positive metastatic breast cancer (MBC) that had previously responded to hormone therapy. The treatment was continued until disease progression (PD).

Primary endpoint was clinical benefit response (CBR) by 6 months (m) defined as patients having a complete response (CR), partial response (PR), or stable disease (SD). CBR will be correlated with AR status of metastatic tumor biopsy.

Serum prostate specific antigen (PSA) was evaluated as a biomarker of AR activity.

Results: Formula IX was well-tolerated, with no drug related serious adverse events and none exceeding Grade 3. Conclusions: Formula IX demonstrated promise as a novel targeted therapy for AR-positive MBC. The primary endpoint has been achieved, with 6/17 AR+ patients meeting statistical threshold for success, as outlined in the Tables 1-5 herein below. Serum PSA appeared to be a surrogate marker for AR activity and disease response.

Materials and Methods

Subject Population

Female subjects with ER-positive metastatic breast cancer who have previously been treated with up to 3 prior hormonal therapies for the treatment of breast cancer. Subjects must have been treated with and responded to previous adjuvant therapy for ≥3 years or hormonal therapy for metastatic disease for ≥6 months prior to progression. Details of subject selection criteria are presented below:

To be eligible for participation in this study, subjects must meet all of the following criteria, including give voluntary, signed informed consent in accordance with institutional policies; be a woman that has been diagnosed with ER-positive metastatic breast cancer; and be clinically confirmed as postmenopausal. Subjects must have undergone the onset of spontaneous, medical or surgical menopause prior to the start of this study. (Spontaneous menopause is defined as the natural cessation of ovarian function as indicated by being amenorrheic for at least 12 months. If the subject has been amenorrheic for ≥6 months but <12 months they must have a serum FSH concentration of ≥50 mIU/mL and an 17β-estradiol concentration of ≤25 pg/mL; medical menopause is defined as treatment with a luteinizing hormone receptor hormone agonist; and surgical menopause is defined as bilateral oophorectomy).

Additional requirement that subjects must meet include that they have been treated and responded to previous adjuvant hormonal therapy for ≥3 years or previous hormonal therapy for metastatic disease for ≥6 months prior to disease progression; that they have not had radiation therapy for breast cancer within 2 weeks of randomization in this study and are not planned to have radiation therapy during participation in this study. Subjects must be willing to provide tissue sample from a biopsy of a metastatic tumor lesion(s) for determination of AR and ER status. Tissue samples from a biopsy of a primary tumor lesion will also be provided if available. Further subjects must have ECOG score ≤2 and be age ≥18 years.

Subjects with any of the following exclusion criteria will NOT be eligible for enrollment in this study: have triple negative breast cancer; have, in the judgment of the Investigator, a clinically significant concurrent illness or psychological, familial, sociological, geographical or other concomitant condition that would not permit adequate follow-up and compliance with the study protocol; have uncontrolled hypertension, congestive heart failure or angina; have Stage 4 chronic obstructive pulmonary disease (COPD); have positive screen for hepatitis B consisting of HBsAg (Hepatitis B Surface Antigen), unless subject was diagnosed >10 years prior to enrollment and no evidence of active liver disease; have ALT/SGOT or AST/SGPT above 1.5 times the upper limit of normal (ULN); have positive screen for hepatitis A antibody IgM or HIV; have received chemotherapy for metastatic breast cancer within the 3 months prior to enrollment in the study or be expected to receive chemotherapy for metastatic breast cancer during the study; be currently taking testosterone, methyltestosterone, oxandrolone (Oxandrin®), oxymetholone, danazol, fluoxymesterone (Halotestin®), testosterone-like agents (such as dehydroepiandrosterone (DHEA), androstenedione, and other androgenic compounds, including herbals), or antiandrogens; previous therapy with testosterone and testosterone-like agents is acceptable with a 30-day washout (if previous testosterone therapy was long term depot within the past 6 months, the site should contact the medical monitor for this study to determine appropriate washout period); have untreated or uncontrolled brain metastasis; have been diagnosed with or treated for cancer within the previous two years, other than breast cancer or non-melanoma carcinoma of the skin Androgen receptor (AR) status was assessed in all subjects from primary and/or metastatic lesions after enrollment. It was observed that the majority (17/19) of subjects with ER-positive breast cancer also expressed AR) in their primary tumor samples, which correlated well with previous literature which predicted 70-95% would be AR-positive (Niemeier L A, et. al. Androgen receptor in breast cancer: expression in estrogen receptor-positive tumors and in estrogen-negative tumors with apocrine differentiation. *Modern Pathology* 23:205-212, 2010; Narita D, et al. Immunohistochemical expression of androgen receptor and prostate-specific antigen in breast cancer. *Folia Histochemica Et Cytobiologica* 44:165-172, 2006). High percentages (72-84%) of metastatic lesions obtained from women with advanced breast cancer have also been found to be AR-positive (Lea O A. et al. Improved measurement of androgen receptors in human breast cancer. *Cancer Research* 49:7162-7167, 1989).

As 70% or greater of the women with ER-positive breast cancer were expected to have tumors that are AR-positive, the study was designed to enroll approximately 27 subjects (of 40 originally intended to be enrolled) with AR-positive breast cancer in each dose arm, enabling assessment of the primary endpoint in AR-positive subjects, as well as the secondary and tertiary endpoints in subsets based on AR status (i.e., all subjects, AR-positive subjects, and AR-negative subjects).

At the time of this writing, patient demographics were: mean age 63.7 years, mean time from diagnosis 11.0 years, 72.7% prior chemotherapy, 89% (17/19) AR+, 41% detectable baseline PSA and 86.4% previous radiation.

TABLE 1

The baseline characteristic by response was as follows:

| Clinical Benefit at Best Response | Clinical Benefit at 6 Months | Progressive Disease at 6 Months or Prior |
|---|---|---|
| N = 9 | N = 7 | N = 12 |
| Mean age 65.5 | Mean age 64.6 | Mean age 60.5 |
| AR status 7/7 AR+ | AR status 6/6 AR+ | AR status 8/10 AR+ |
| Years from Diagnosis (Dx) | Years from Diagnosis (Dx) | Years from Diagnosis (Dx) |
| Mean 13.7 | Mean 15.7 | Mean 8.6 |
| Median 11.4 | Median 15.0 | Median 7.8 |
| (5.1-27.2) | (8.5-27.2) | (1.9-22.8) |
| Years from Dx to Metastasis (Mets) | Years from Dx to Metastasis (Mets) | Years from Dx to Metastasis (Mets) |
| Mean 8.6 | Mean 9.8 | Mean 4.4 |
| Median 9.3 (0-15.8) | Median 9.8 (0-15.8) | Median 4.1 (0-17.2) |
| Chemotherapy (NA + A): 6/9 | Chemotherapy (NA + A): 5/7 | Chemotherapy (NA + A): 9/12 |
| Everolimus: 0/9 | Everolimus: 0/7 | Everolimus: 4/12 |
| Bone only disease: 4/9 | Bone only disease: 4/7 | Bone only disease: 1/12 |
| Visceral only disease: 2/9 | Visceral only disease: 2/7 | Visceral only disease: 2/12 |

TABLE 2

Table of Subjects Assessed as Having Clinical Benefit as Best Response

| Subject | Age | AR | Time (y) From Initial BC Dx | Time (y) From Dx to Metastatic Disease | Time (y) From Metastatic Dx to Enrollment | Number of Lines of Previous Hormonal Therapy | Metastases |
|---|---|---|---|---|---|---|---|
| 22 | 73.9 | + | 8.7 | 8.5 | 0.2 | 2 | Lymph Nodes, Bone |
| 07 | 64.1 |  | 5.1 | 0 | 5.1 | 2 | Peritoneum, Bone |
| 08 | 52.5 | + | 11.4 | 9.8 | 1.6 | 2 | Bone |
| 14 | 65.6 | + | 27.2 | 13.5 | 13.7 | 5 | Liver, Bone |

TABLE 2-continued

Table of Subjects Assessed as Having Clinical Benefit as Best Response

| Subject | Age | AR | Time (y) From Initial BC Dx | Time (y) From Dx to Metastatic Disease | Time (y) From Metastatic Dx to Enrollment | Number of Lines of Previous Hormonal Therapy | Metastases |
|---|---|---|---|---|---|---|---|
| 16 | 80.1 | + | 21.6 | 12.5 | 9.1 | 3 | Lung, Chest Wall, Skin |
| 19 | 67.6 | + | 9.5 | 8 | 1.5 | 4 | Bone |
| 18 | 54.4 | + | 15 | 9.3 | 5.7 | 4 | Bone |
| 03 | 62.8 | + | 16.6 | 15.8 | 0.8 | 1 | Bone |
| 11 | 69 | | 8.5 | 0 | 8.5 | 2 | Liver |

TABLE 3

Table of Subjects Assessed as Having Clinical Benefit at 6 Months

| Subject | Age | AR | Time (y) From Initial BC Dx | Time (y) From Dx to Metastatic Disease | Time (y) From Metastatic Dx to Enrollment | Number of Lines of Previous Hormonal Therapy | Metastases |
|---|---|---|---|---|---|---|---|
| 08 | 52.5 | + | 11.4 | 9.8 | 1.6 | 2 | Bone |
| 14 | 65.6 | + | 27.2 | 13.5 | 13.7 | 5 | Liver, Bone |
| 16 | 80.1 | + | 21.6 | 12.5 | 9.1 | 3 | Lung, Chest Wall, Skin |
| 19 | 67.6 | + | 9.5 | 8 | 1.5 | 4 | Bone |
| 18 | 54.4 | + | 15 | 9.3 | 5.7 | 4 | Bone |
| 03 | 62.8 | + | 16.6 | 15.8 | 0.8 | 1 | Bone |
| 11 | 69 | | 8.5 | 0 | 8.5 | 2 | Liver |

TABLE 4

Table of Subjects Assessed as Having Progressive Disease at 6 Months or Prior

| Subject | Age | AR | Time (y) From Initial BC Dx | Time (y) From Dx to Metastatic Disease | Time (y) From Metastatic Dx to Enrollment | Number of Lines of Previous Hormonal Therapy | Metastases |
|---|---|---|---|---|---|---|---|
| 20 | 66.9 | + | 1.9 | 0.1 | 1.8 | 5 | Lymph Nodes, Bone |
| 07 | 64.1 | | 5.1 | 0 | 5.1 | 2 | Peritoneum, Bone |
| 06 | 49.1 | + | 7.6 | 5.1 | 2.5 | 3 | Pleura, Liver, Lymph Nodes |
| 09 | 67.3 | + | 7.9 | 4 | 3.9 | 3 | Lymph Nodes, Liver, Bone |
| 12 | 48.5 | | 14.4 | 4.1 | 10.3 | 5 | Lung, Liver, Bone |
| 13 | 63.5 | + | 5.8 | 0 | 5.8 | 3 | Abd Wall, Lung, Bone, Skin |
| 21 | 56.3 | | 3.7 | 0 | 3.7 | 2 | Liver, Bone |
| 01 | 67.3 | + | 3.7 | | | 2 | Lung, Liver, Bone |
| 02 | 62.1 | − | 8.3 | 5.3 | 3 | 4 | Bone, Adrenal Nodule |
| 04 | 45.7 | − | 5.3 | 0 | 5.3 | 6 | Bone |
| 17 | 84.7 | + | 22.8 | 17.2 | 5.6 | 4 | Bone, Pleura |
| 10 | 50.8 | + | 16 | 12.7 | 3.3 | 3 | Lymph Nodes, Neck |

Treatment

Subjects received 9 mg daily dose of Formula IX, with baseline and regular on study assessments of safety and efficacy.

Measurable and non-measurable lesions (primary and/or metastatic) were identified and assessed by a modified Response Evaluation Criteria In Solid Tumors (RECIST 1.1) classification over the course of this study (described in detail below).

Study Duration

Each subject enrolled into this study received intervention until a progression free survival (PFS) endpoint has been reached (tumor progression or death). Subjects will be followed after treatment has been discontinued for vital status only.

Efficacy Endpoints

The primary efficacy analysis was the clinical benefit in subjects with AR-positive breast cancer at 6 months as measured by a modified Response Evaluation Criteria In Solid Tumors (RECIST 1.1) classification. Key secondary endpoints of clinical benefit in all subjects and AR-negative subjects, as well as objective response rate, progression free survival, time to progression, duration of response, incidence of SREs, and time to first SRE in subsets based on AR status (i.e., all subjects, AR-positive subjects, and AR-negative subjects) was also assessed. Effects on CA 27-29, PSA, bone turnover markers, QOL, and libido were assessed as tertiary endpoints.

Primary Endpoint

Clinical benefit in a subject is defined as a complete response [CR], a partial response [PR] or stable disease [SD] as measured by modified RECIST 1.1, which is described in detail below. (Eisenhauer E A et al. New response evaluation criteria in solid tumors: revised RECIST guideline (version 1.1). *European Journal of Cancer* 45:228-247, 2009).

For subjects with non-measurable (non-target) disease only at baseline, SD was defined as those with non-CR/non-PD combined response. The primary endpoint of the study was to assess the proportion of subjects with clinical benefit (PCB) at 6 months (CR+PR+SD) in subjects with AR-positive breast cancer.

Secondary Endpoints

The secondary efficacy endpoints include:

To assess the clinical benefit in all subjects with breast cancer treated with Formula IX. The clinical benefit is defined as the proportion of subjects with complete response [CR]+partial response [PR]+stable disease [SD] as measured by modified RECIST 1.1 (Eisenhauer E A et al. New response evaluation criteria in solid tumors: revised RECIST guideline (Version 1.1). *European Journal of Cancer* 45: 228-247, 2009).

For subjects with non-measurable (non-target) disease only at baseline, SD was defined as those with non-CR/non-PD combined response.

To assess objective response rate (ORR) in subjects with breast cancer treated with Formula IX. Objective response rate is defined as the proportion of subjects with a CR or PR at 6 months as measured by modified RECIST 1.1. For subjects with non-measurable (non-target) disease only at baseline, ORR is defined as the proportion of subjects with a CR at 6 months as measured by modified RECIST 1.1.

To assess progression free survival (PFS) in subjects with breast cancer treated with Formula IX. PFS is defined as the time elapsed between treatment initiation and tumor progression as measured by modified RECIST 1.1 OR death.

To assess time to progression (TTP) in subjects with breast cancer treated with Formula IX. Time to tumor progression is defined as the time elapsed between treatment initiation and tumor progression as measured by modified RECIST 1.1.

To assess duration of response in subjects with breast cancer treated with Formula IX.

To assess incidence of skeletal related events (SREs) in subjects treated with Formula IX.

To assess time to first skeletal related event (SRE) in subjects treated with Formula IX.

Tertiary Endpoints

To assess serum CA 27-29 changes in subjects with breast cancer treated with Formula IX.

To assess serum PSA changes in subjects with breast cancer treated with Formula IX.

To assess changes in bone turnover markers (serum osteocalcin, serum collagen type I cross linked C-telopeptide [CTX], serum collagen type I cross linked N-telopeptide [NTX], serum bone specific alkaline phosphatase, and urinary NTX in subjects treated with Formula IX.

To assess the effect of Formula IX on quality of life (QOL) as measured by FACIT-F questionnaire in subjects treated with Formula IX.

To assess the effect of Formula IX on libido as measured by female sexual function index (FSFI) questionnaire in subjects treated with Formula IX.

To explore the relationship of various levels of AR expression as determined by immunohistochemistry with primary, secondary and tertiary objectives.

Results:

After a median follow-up of 81 days (d) (range 7-304 d), preliminary results of the 22 patients were as follows: 9 SD was observed as best response, median duration 212 d. Current disposition of all patients: 15 PD after a median 80 d (range 15-304 d), 4 SD, and 3 early discontinuations (d 7, 28, 255). Among patients who reached 6 m, six are AR-positive with SD and increased PSA. 1 has yet to reach 6 m and no CR or PR has been observed. Formula LX was well-tolerated, with no drug related serious adverse events and none exceeding Grade 3.

No useful trends were seen with the biomarkers of bone turnover: bone specific alkaline phosphatase, C-telopeptides, N-telopeptides, and osteocalcin. Likewise breast cancer biomarker CA 27-29 did not demonstrate any useful trends.

PSA levels appeared to increase in response to Formula IX treatment as was observed in 20 of the 22 patients measured, but correlation with clinical benefit or disease progression is not yet evident.

The following non serous adverse events were observed:

A-fib (1); anxiety/emotional changes (5), arthralgia (6), bloating (2), bruising (1), cellulitis (1), chills (1), constipation (2), cough (1), dehydration (1), diarrhea (3), dizziness (2), dysgeusia (1), dyspepsia (1), dyspnea (3), edema (2), fatigue (14), fever (1), flatulence (1), glaucoma (1), headache (4), hot flash night sweats (7), hypertension (2), infection (1), insomnia (2), myalgia (5), nail discoloration (1), nausea (11), pain (22), paresthesia (1), pleural effusion (1), polyuria (1), post menopausal bleeding (3), rash/acne (3), stiffness (1), tendonitis (1), vision changes (3), vomiting (2), weight gain (2), and weight loss (2).

The liver enzymes (ALT, AST and bilirubin) returned to baseline with no interruption of therapy and no increase in total bilirubin.

Conclusions: Formula IX demonstrated promise as a novel targeted therapy for AR-positive MBC. The primary endpoint was achieved, with 6/17 AR-positive patients meeting statistical threshold for success. Serum PSA appeared to be a surrogate marker for AR activity and disease response.

TABLE 5

AR Status and Patient Disposition

| Patient # | Day 84 RECIST | Day 168 RECIST | Current Disposition | Days on Study | Primary Lesion H Score | Primary Lesion ER % | Metastatic Lesion H Score | Metastatic Lesion ER % | PSA Day 0 | MAX PSA F/U |
|---|---|---|---|---|---|---|---|---|---|---|
| 01 | PD | N/A | Deceased | 100 | 245 | 40 | 270 | 90 | 0.220 | 0.046 |
| 02 | PD | N/A | PD | 91 | 200 | 50 | 0 | 0 | <0.007 | 0.092 |
| 03 | SD | SD | D/C | 255 | 260 | 80 | 265 | 90 | 0.010 | 2.430 |
| 04 | PD | N/A | PD | 105 | 0 | 20 | 0 | 60 | <0.007 | 0.058 |
| 05 | D/C SAE (D2) | N/A | D/C | 7 | 300 | 100 | 300 | 100 | <0.007 | 0.008 |
| 06 | PD (D15) | N/A | Deceased | 18 | | | 55 | 70 | <0.007 | <0.007 |
| 07 | SD | PD | PD | 158 | | | | | <0.007 | 0.078 |
| 08 | SD | SD | PD | 308 | | | 120 | 95 | 0.104 | 0.217 |
| 09 | PD SAE (D52) | N/A | Deceased | 52 | | | 150 | 70 | 0.009 | 9.610 |
| 10 | PD | N/A | PD | 63 | | | 195 | 40 | <0.007 | 0.450 |
| 11 | SD | SD | PD | 230 | 300 | 100 | | | 0.104 | 3.540 |
| 12 | PD | N/A | PD | 84 | | | | | <0.007 | 0.238 |
| 13 | PD | N/A | PD | 84 | | | 210 | 100 | 0.023 | 8.180 |
| 14 | SD (D56) | SD (D140) | PD | 252 | | | 95 | 1 | <0.007 | 0.548 |

TABLE 5-continued

AR Status and Patient Disposition

| Patient # | Day 84 RECIST | Day 168 RECIST | Current Disposition | Days on Study | Primary Lesion | | Metastatic Lesion | | PSA Day 0 | MAX PSA F/U |
| --- | --- | --- | --- | --- | --- | --- | --- | --- | --- | --- |
| | | | | | H Score | ER % | H Score | ER % | | |
| 15 | D/C | N/A | Deceased | 28 | | | 160 | 95 | <0.007 | 0.062 |
| 16 | SD | SD | SD | 239 | | | 240 | 95 | <0.007 | 0.024 |
| 17 | PD | N/A | PD | 86 | | | 70 | 30 | 2.850 | 13.160 |
| 18 | SD | SD | SD | 202 | | | 285 | 90 | <0.007 | 0.069 |
| 19 | SD | SD | SD | 190 | | | 110 | | <0.007 | 0.031 |
| 20 | PD | N/A | PD | 99 | | | 300 | 100 | 0.080 | 0.795 |
| 21 | PD | N/A | PD | 84 | | | 160 | 100 | 0.298 | 0.301 |
| 22 | SD | SD | | 137 | | | 285 | 90 | <0.007 | 0.028 |

Subject 02 and 04 were the only two AR-negative subjects on trial. Subjects 03, 07, 08, 11, 14, 16, 18, 19 and 22 were assessed as having clinical benefit as their best response (9 of 22 total subjects). Subjects with clinical benefit at Day 168 (6 months which was the clinical endpoint) were 03, 08, 14, 16, 18, and 19 (6 of 19 AR-positive subjects). Subject 11 was missing a metastasis biopsy and hence could not be counted toward the primary endpoint. Subject 22 has not yet reached the 6 month (day 168) on study date such that she could be counted toward the primary endpoint.

Modified RECIST 1.1

The modified RECIST 1.1 definitions described below was applied:

Measurable Lesions

A measurable lesion is defined as one lesion whose longest diameter (LD) can be accurately measured as ≥10 mm CT or MRI technique by using a 5 mm contiguous reconstruction algorithm.

Measurable lesions must be at least 2 times the slice thickness or at least two times the size of the CT scan interval cut.

Lesions seen on chest x-ray but not confirmed by CT or MRI scan are not acceptable as measurable lesions for this study.

To be considered pathologically enlarged and measurable, a lymph node must be >15 mm in short axis when assessed by CT scan (CT scan slice thickness recommended to be no greater than 5 mm). At baseline and in follow-up, only the short axis will be measured and followed.

Measurable disease is defined as the presence of at least one measurable lesion.

All measurements will be taken and recorded in millimeters using an electronic measurement method.

Non-Measurable Lesions

Non-measurable lesions are defined as any lesion(s) that are smaller than the criteria for measurable lesions stated above (non-nodal lesions with longest diameter <10 mm or pathological lymph nodes with ≥10 mm to <15 mm in short axis) or truly non measurable lesions (or sites of disease). Lesions considered to be truly non-measurable are bone lesions (lytic lesions or mixed lytic-blastic lesions without identifiable soft tissue components, and blastic lesions), leptomeningeal disease, ascites, pleural/pericardial effusions, lymphangitis cutis/pulmonis, inflammatory breast disease, abdominal masses not confirmed by imaging techniques, and cystic lesions.

Target Lesions

Target lesions must be measurable lesions.

All target lesions up to a maximum of two lesions per organ and five lesions in total, representative of all involved organs, will be selected/confirmed as target lesions, recorded and measured at baseline.

Target lesions should be selected on the basis of their size (lesions with the longest diameter) and their suitability for accurate repetitive measurements by CT/MRI imaging techniques and be most representative of the subject's tumor burden.

Target lesions will be measured in one dimension by the size estimation of their diameter. A sum of the diameters (longest for non-nodal lesions and shortest for nodal lesions) for all target lesions will be calculated and reported for each time point. The baseline sum of diameters will be used as reference to further characterize the objective tumor response of the measurable dimension of the disease.

Non-Target Lesions

All other lesions (or sites of disease) and any measurable lesions that were not selected as target lesions should be identified as non-target lesions and indicated as present at baseline.

Measurements of the non-target lesions may be performed, however the continued presence or absence as well as the disappearance or progression status of these lesions will be noted throughout follow-up assessments.

New Lesions

New lesions will be called at follow-up visits regardless of whether they occur in anatomic regions that were routinely subjected to follow-up, or in regions without disease at baseline and for which a follow-up scan is performed for clinical suspicion of new disease. New lymph nodes need to have a minimum size of 10 mm in their shortest axis. New non-nodal lesions need not to be measurable or to have a minimum size. Measurements of new lesions may be performed.

Response Criteria Definitions

The following response criteria will be applied for target and non-target lesions:

Target Lesion Response Criteria

Complete Response (CR): Disappearance of all target lesions. Target lymph node lesions that become <10 mm in their shortest diameter will be considered to be normal (non-pathologic) and their actual measurement will be recorded. Thus, it follows that if all target node lesions have become <10 mm, and all other non-nodal lesions have disappeared (whether target or non-target type), the overall response will be considered to be a CR.

Partial Response (PR): At least a 30% decrease in the sum of diameters of target lesions, taking as reference the baseline sum of the diameters.

Stable Disease (SD): Neither sufficient shrinkage to qualify for PR nor sufficient increase to qualify for PD taking as reference the smallest sum of diameters (nadir).

Progressive Disease (PD): At least a 20% increase in the sum of the diameters of target lesions taking as reference the smallest sum of diameters (nadir) recorded since the treatment started. In addition to the relative increase of 20%, the sum of diameters must also demonstrate an absolute increase of at least 5 mm.

Not evaluable (NE): NE can be applied if repeated measurements cannot be assessed for reasons such as inadequate or missing imaging.

Non-Target Lesion Response Criteria

Complete Response (CR): Disappearance of all non-target lesions. All lymph nodes must be non-pathological in size (<10 mm short axis). Disappearance of bone lesions identified on bone scintigraphy.

Non-CR/Non-PD: Persistence of one or more non-target lesions. Stability, decrease, or mild increase in uptake of bone lesions on bone scintigraphy.

Progressive Disease (PD): Unequivocal progression of existing non-target lesions. A perceived increase in bone disease in a preexisting area will not be considered progression. For bone scintigraphy, at least two new lesions are required to conclude to a definite presence of new lesions unless one or more of these lesions are confirmed by radiography, CT or MRI.

Not Evaluable (NE): NE can be applied if repeated evaluations cannot be assessed for reasons such as inadequate or missing imaging.

Definitions of Combined Response at Each Time Point

Determination of an overall response for each time point is based on the combination of responses for target, non-target, and the presence or absence of new lesions using the algorithm outlined on tables C1 and C2 below.

TABLE C1

Summary of Definitions of Response for Patients with Measurable (Target) Disease at Baseline Response of Combined Lesion Types

| Target Lesions | Non-Target Lesions | New Lesions | Combined Response |
|---|---|---|---|
| CR | CR | No | CR |
| CR | Non-CR/non-PD or NE | No | PR |
| PR | CR, non-CR/non-PD, or NE | No | PR |
| SD | CR, non-CR/non-PD, or NE | No | SD |
| PD | Any | Yes or No | PD |
| Any | PD | Yes or No | PD |
| Any | Any | Yes | PD |
| NE | Non-PD | No | NE |
| Non-PD | Non-PD | NE | NE |

TABLE C2

Summary of Definitions of Response for Patients with Non-Measurable (Non-Target) Disease only at Baseline Response of Combined Lesion Types

| Non-Target Lesions | New Lesions | Combined Response |
|---|---|---|
| CR | No | CR |
| Non-CR/non-PD | No | Non-CR/non-PD |
| NE | No | NE |
| PD | Yes or No | PD |
| Any | Yes | PD |

Example 10

Synthesis of (S) Enantiomer of Formula VIII

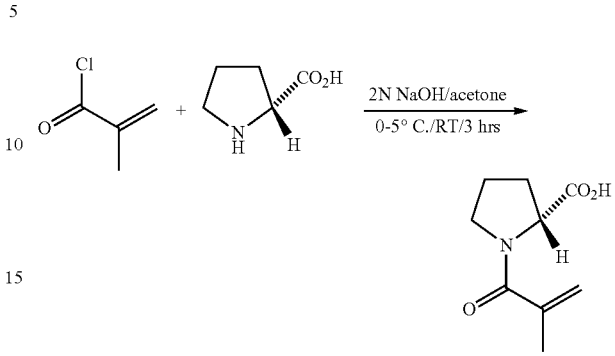

(2R)-1-Methacryloylpyrrolidin-2-carboxylic Acid

D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102-103° C.; the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[\alpha]_D^{26}$ +80.8° (c=1, MeOH); Anal. Calcd. for $C_9H_{13}NO_3$: C, 59.00, H, 7.15, N, 7.65. Found: C, 59.13, H, 7.19, N, 7.61.

(3R,8aR)-3-Bromomethyl-3-methyl-tetrahydro-pyrrolo[2,1-c][1,4]oxazine-1,4-dione A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 g (81%) (smaller weight when dried ~34%) of the titled compound as a yellow solid: mp 152-154° C.; $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$ +124.5° (c=1.3, chloroform); Anal. Calcd. for C$_9$H$_{12}$BrNO$_3$: C, 41.24, H, 4.61, N, 5.34. Found: C, 41.46, H, 4.64, N, 5.32.

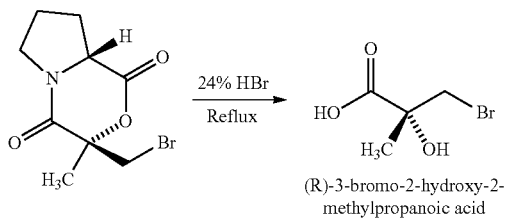

(2R)-3-Bromo-2-hydroxy-2-methylpropanoic Acid

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite, and evaporated in vacuo to dryness. Recrystallization from toluene afforded 10.2 g (86%) of the desired compound as colorless crystals: mp 107-109° C.; $^1$H NMR (300 MHz, DMSO-$d_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[α]_D^{26}$ +10.5° (c=2.6, MeOH); Anal. Calcd. for C$_4$H$_7$BrO$_3$: C, 26.25, H, 3.86. Found: C, 26.28, H, 3.75.

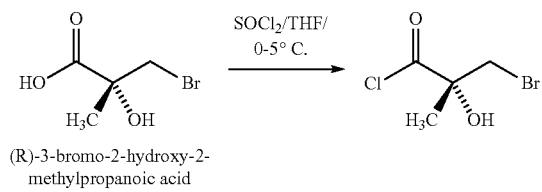

R-18

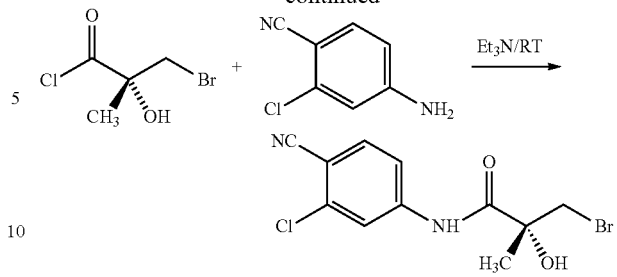

Synthesis of (2R)-3-bromo-N-(3-chloro-4-cyanophenyl)-2-hydroxy-2-methylpropanamide Thionyl chloride (7.8 g, 65.5 mmol) was added dropwise to a cooled solution (less than 4° C.) of (R)-3-bromo-2-hydroxy-2-methylpropanoic acid (9.0 g, 49.2 mmol) in 50 mL of THF under an argon atmosphere. The resulting mixture was stirred for 3 h under the same condition. To this was added Et$_3$N (6.6 g, 65.5 mol) and stirred for 20 min under the same condition. After 20 min, 4-amino-2-chlorobenzonitrile (5.0 g, 32.8 mmol) and 100 mL of THF were added and then the mixture was allowed to stir overnight at room temperature. The solvent was removed under reduced pressure to give a solid which was treated with 100 mL of H$_2$O, extracted with EtOAc (2×150 mL). The combined organic extracts were washed with saturated NaHCO$_3$ solution (2×100 mL) and brine (300 mL), successively. The organic layer was dried over MgSO$_4$ and concentrated under reduced pressure to give a solid which was purified from column chromatography using EtOAc/hexane (50:50) to give 7.7 g (49.4%) of target compound as a brown solid.

$^1$H NMR (CDCl$_3$/TMS) δ 1.7 (s, 3H, CH$_3$), 3.0 (s, 1H, OH), 3.7 (d, 1H, CH), 4.0 (d, 1H, CH), 7.5 (d, 1H, ArH), 7.7 (d, 1H, ArH), 8.0 (s, 1H, ArH), 8.8 (s, 1H, NH). MS: 342.1 (M+23). Mp 129° C.

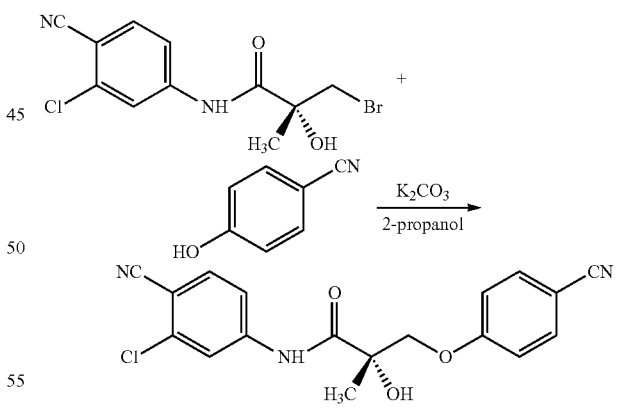

Synthesis of (S)—N-(3-chloro-4-cyanophenyl)-3-(4-cyanophenoxy)-2-hydroxy-2-methylpropanamide (Formula VIII)

A mixture of bromoamide (2.0 g, 6.3 mmol), anhydrous K$_2$CO$_3$ (2.6 g, 18.9 mmol) in 50 mL of acetone was heated to reflux for 2 h and then concentrated under reduced pressure to give a solid. The resulting solid was treated with 4-cyanophenol (1.1 g, 9.5 mmol) and anhydrous K$_2$CO$_3$ (1.7 g, 12.6 mmol) in 50 mL of 2-propanol was heated to reflux for 3 h and then concentrated under reduced pressure to give a solid. The residue was treated with 100 mL of H₂O and then extracted with EtOAc (2×100 mL). The combined EtOAc extracts were washed with 10% NaOH (4×100 mL) and brine, successively. The organic layer was dried over MgSO₄ and then concentrated under reduced pressure to give an oil which was purified by column chromatography using EtOAc/hexane (50:50) to give a solid. The solid was recrystallized from CH₂Cl₂/hexane to give 1.4 g (61.6%) of (S)—N-(3-chloro-4-cyanophenyl)-3-(4-cyanophenoxy)-2-hydroxy-2-methylpropanamide as a colorless solid.

¹H NMR (CDCl₃/TMS) δ 1.61 (s, 3H, CH₃), 3.25 (s, 1H, OH), 4.06 (d, J=9.15 Hz, 1H, CH), 4.50 (d, J=9.15 Hz, 1H, CH), 6.97-6.99 (m, 2H, ArH), 7.53-7.59 (m, 4H, ArH), 7.97 (d, J=2.01 Hz, 1H, ArH), 8.96 (s, 1H, NH). Calculated Mass: 355.1, [M+Na]⁺378.0. Mp: 103-105° C.

Example 11

Synthesis of (S) Enantiomer of Formula IX

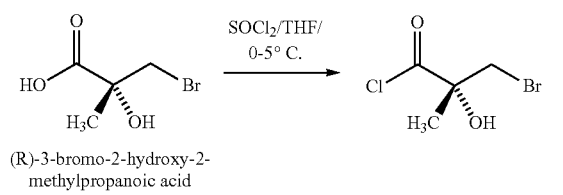

(R)-3-bromo-2-hydroxy-2-methylpropanoic acid

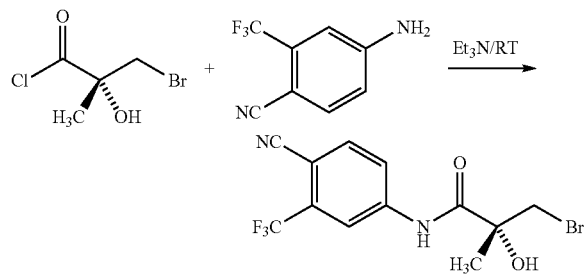

Synthesis of (2R)-3-Bromo-N-[4-cyano-3-(trifluoromethyl)phenyl]-2-hydroxy-2-methylpropanamide Thionyl chloride (46.02 g, 0.39 mol) was added dropwise to a cooled solution (less than 4° C.) of (R)-3-bromo-2-hydroxy-2-methylpropanoic acid (51.13 g, 0.28 mol) in 300 mL of THF under an argon atmosphere. (R)-3-Bromo-2-hydroxy-2-methylpropanoic acid was prepared as described in Example 10. The resulting mixture was stirred for 3 h under the same condition. To this was added Et₃N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H₂O, extracted with EtOAc (2×400 mL). The combined organic extracts were washed with saturated NaHCO₃ solution (2×300 mL) and brine (300 mL). The organic layer was dried over MgSO₄ and concentrated under reduced pressure to give a solid which was purified from column chromatography using CH₂Cl₂/EtOAc (80:20) to give a solid. This solid was recrystallized from CH₂Cl₂/hexane to give 55.8 g (73.9%) of (2R)-3-bromo-N-[4-cyano-3-(trifluoromethyl)phenyl]-2-hydroxy-2-methylpropanamide as a light-yellow solid.

¹H NMR (CDCl₃/TMS) δ 1.66 (s, 3H, CH₃), 3.11 (s, 1H, OH), 3.63 (d, J=10.8 Hz, 1H, CH₂), 4.05 (d, J=10.8 Hz, 1H, CH₂), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M-H]⁻ 349.0. M.p.: 124-126° C.

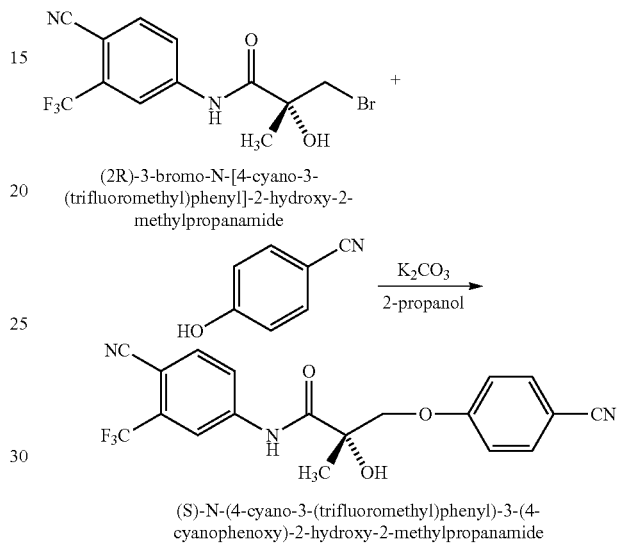

Synthesis of (S)—N-(4-Cyano-3-(trifluoromethyl)phenyl)-3-(4-cyanophenoxy)-2-hydroxy-2-methylpropanamide (Formula IX)

A mixture of bromoamide ((2R)-3-bromo-N-[4-cyano-3-(trifluoromethyl)phenyl]-2-hydroxy-2-methylpropanamide, 50 g, 0.14 mol), anhydrous K₂CO₃ (59.04 g, 0.43 mol), 4-cyanophenol (25.44 g, 0.21 mol) in 500 mL of 2-propanol was heated to reflux for 3 h and then concentrated under reduced pressure to give a solid. The resulting residue was treated with 500 mL of H₂O and then extracted with EtOAc (2×300 mL). The combined EtOAc extracts were washed with 10% NaOH (4×200 mL) and brine. The organic layer was dried over MgSO₄ and then concentrated under reduced pressure to give an oil which was treated with 300 mL of ethanol and an activated carbon. The reaction mixture was heated to reflux for 1 h and then the hot mixture was filtered through Celite®. The filtrate was concentrated under reduced pressure to give an oil. This oil was purified by column chromatography using CH₂Cl₂/EtOAc (80:20) to give an oil which was crystallized from CH₂Cl₂/hexane to give 33.2 g (59.9%) of (S)—N-(4-cyano-3-(trifluoromethyl)phenyl)-3-(4-cyanophenoxy)-2-hydroxy-2-methylpropanamide as a colorless solid (a cotton type).

¹H NMR (CDCl₃/TMS) δ 1.63 (s, 3H, CH₃), 3.35 (s, 1H, OH), 4.07 (d, J=9.04 Hz, 1H, CH), 4.51 (d, J=9.04 Hz, 1H, CH), 6.97-6.99 (m, 2H, ArH), 7.57-7.60 (m, 2H, ArH), 7.81 (d, J=8.55 Hz, 1H, ArH), 7.97 (dd, J=1.95, 8.55 Hz, 1H, ArH), 8.12 (d, J=1.95 Hz, 1H, ArH), 9.13 (bs, 1H, NH). Calculated Mass: 389.10, [M-H]⁺ 388.1. Mp: 92-94° C.

Example 12

Synthesis of (R) Enantiomer of Formula IX

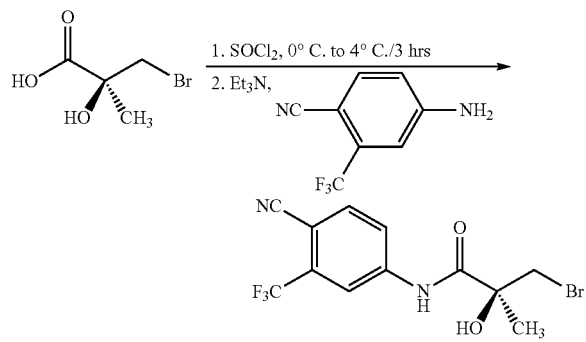

Synthesis of (2S)-3-bromo-N-[4-cyano-3-(trifluoromethyl)phenyl]-2-hydroxy-2-methylpropanamide (Precursor to R-enantiomer of Formula IX)

Thionyl chloride (46.02 g, 0.39 mol) was added dropwise to a cooled solution (less than 4° C.) of (S)-3-bromo-2-hydroxy-2-methylpropanoic acid (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from EtOAc/hexane to give 55.8 g (73.9%) of target compound as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M-H]$^-$ 349.0. Mp: 124-126° C.

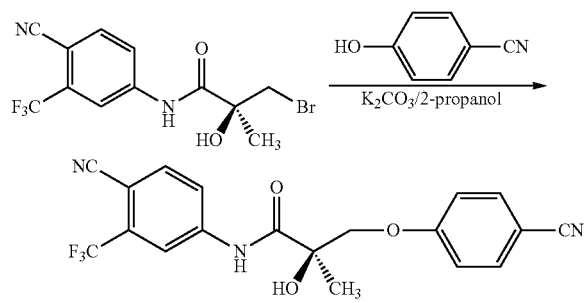

Synthesis of (R)—N-(4-cyano-3-(trifluoromethyl)phenyl)-3-(4-cyanophenoxy)-2-hydroxy-2-methylpropanamide (R-enantiomer of Formula IX)

A mixture of bromoamide (50.0 g, 0.14 mol), anhydrous K$_2$CO$_3$ (59.04 g, 0.43 mol), 4-cyanophenol (25.44 g, 0.21 mol) in 500 mL of 2-propanol was heated to reflux for 3 h and then concentrated under reduced pressure to give a solid. The resulting residue was treated with 500 mL of H$_2$O and then extracted with EtOAc (2×300 mL). The combined EtOAc extracts were washed with 10% NaOH (4×200 mL) and brine. The organic layer was dried over MgSO$_4$ and then concentrated under reduced pressure to give an oil which was treated with 300 mL of ethanol and an activated carbon. The reaction mixture was heated to reflux for 1 h and then the hot mixture was filtered through Celite®. The filtrate was concentrated under reduced pressure to give an oil. This oil was purified by column chromatography using hexane/EtOAc (20:80) to give an oil which was crystallized from EtOAc/hexane to give 33.2 g (59.9%) of (R)—N-(4-cyano-3-(trifluoromethyl)phenyl)-3-(4-cyanophenoxy)-2-hydroxy-2-methylpropanamide (R-isomer of Formula IX) as a colorless solid.

$^1$H NMR (CDCl$_3$/TMS) δ 1.63 (s, 3H, CH$_3$), 3.44 (s, 1H, OH), 4.07 (d, J=9.16 Hz, 1H, CH), 4.51 (d, J=9.16 Hz, 1H, CH), 6.97-6.99 (m, 2H, ArH), 7.57-7.59 (m, 2H, ArH), 7.81 (d, J=8.54 Hz, 1H, ArH), 7.97 (dd, J=2.07, 8.54 Hz, 1H, ArH), 8.12 (d, J=2.07 Hz, 1H, ArH), 9.15 (bs, 1H, NH). Calculated Mass: 389.10, [M-H]$^-$ 388.1. Mp: 92-94° C.

Example 13

Synthesis of (S) Enantiomer of Formula X

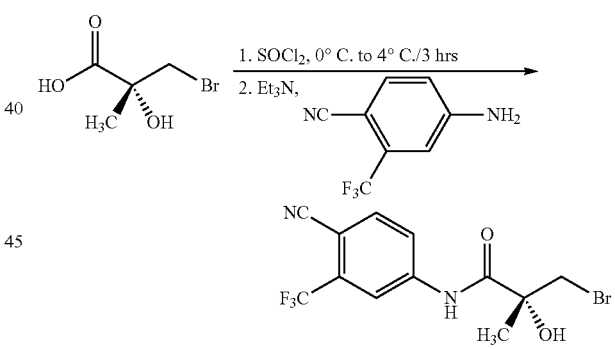

Synthesis of (2R)-3-bromo-N-[4-cyano-3-(trifluoromethyl)phenyl]-2-hydroxy-2-methylpropanamide Thionyl chloride (46.02 g, 0.39 mol) was added dropwise to a cooled solution (less than 4° C.) of (R)-3-bromo-2-hydroxy-2-methylpropanoic acid (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified by column chromatography using CH$_2$Cl$_2$/EtOAc (80:20) to give a solid. This solid was recrystallized from CH$_2$Cl$_2$/hexane to give a target compound (55.8 g, 73.9%) as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M-H]$^-$ 349.0. Mp: 124-126° C.

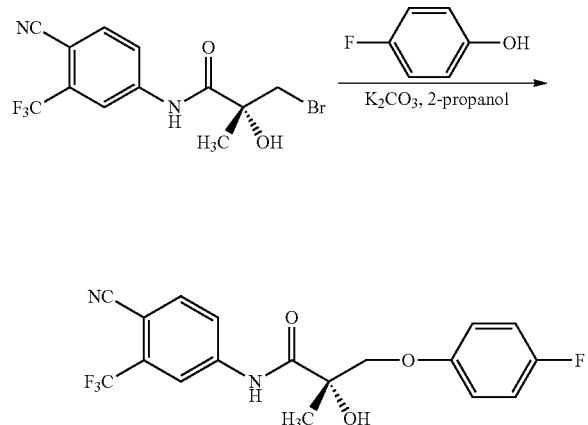

Example 14

Synthesis of (S) Enantiomer of Formula XIII

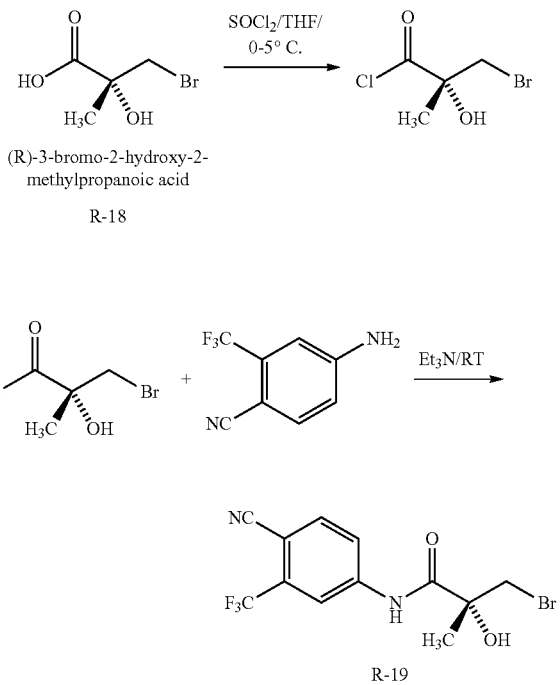

Synthesis of (S)—N-(4-cyano-3-(trifluoromethyl) phenyl)-3-(4-fluorophenoxy)-2-hydroxy-2-methyl-propanamide (Formula X)

A mixture of bromoamide (10.0 g, 28.5 mmol), anhydrous K$_2$CO$_3$ (11.8 g, 85.4 mmol) in 150 mL of acetone was heated to reflux for 1 h and then concentrated under reduced pressure to give a solid. The resulting residue was treated with 4-fluorophenol (4.8 g, 42.7 mmol), anhydrous K$_2$CO$_3$ (7.9 g, 57.0 mmol), 150 mL of 2-propanol and then heated to reflux for 2 h. The resulting mixture was concentrated under reduced pressure to give a solid. This solid was treated with 300 mL of H$_2$O and extracted with EtOAc (2×250 mL). The combined EtOAc extracts were washed with a saturated NaHCO$_3$ solution (2×250 mL) and brine. The organic layer was dried over MgSO$_4$ and then concentrated under reduced pressure to give an oil which was purified by column chromatography using CH$_2$Cl$_2$/EtOAc (80:20) to give a solid. This solid was recrystallized from CH$_2$Cl$_2$/hexane to give (S)—N-(4-cyano-3-(trifluoromethyl)phenyl)-3-(4-fluorophenoxy)-2-hydroxy-2-methylpropanamide (Formula X, 10.04 g, 92.2%) as a colorless solid.

$^1$H NMR (CDCl$_3$/TMS) δ 1.59 (s, 3H, CH$_3$), 3.36 (s, 1H, OH), 3.95 (d, J=9.00 Hz, 1H, CH), 4.43 (d, J=9.00 Hz, 1H, CH), 6.87-6.88 (m, 2H, ArH), 6.96-7.02 (m, 2H, ArH), 7.81 (d, J=8.45 Hz, 1H, ArH), 7.94-7.98 (m, 1H, ArH), 8.10 (d, J=1.79 Hz, 1H, ArH), 9.11 (s, 1H, NH). Calculated Mass: 382.31, [M-H]$^-$ 380.9. Mp: 139-141° C.

Synthesis of (2R)-3-Bromo-N-[4-cyano-3-(trifluoromethyl)phenyl]-2-hydroxy-2-methylpropanamide Thionyl chloride (46.02 g, 0.39 mol) was added dropwise to a cooled solution (less than 4° C.) of R-18 (51.13 g, 0.28 mol) in 300 mL of THF under an argon atmosphere. R-18 is (R)-3-bromo-2-hydroxy-2-methylpropanoic acid was prepared as described in Example 10. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl) phenyl]-2-hydroxy-2-methylpropanamide (R-19) as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M-H]$^-$ 349.0. M.p.: 124-126° C.

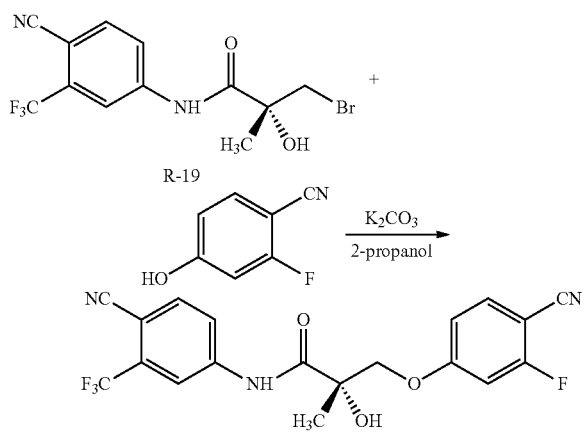

Synthesis of (S)—N-(4-cyano-3-(trifluoromethyl) phenyl)-3-(4-cyano-3-fluorophenoxy)-2-hydroxy-2-methylpropanamide (Formula XIII)

A mixture of bromoamide ((2R)-3-bromo-N-[4-cyano-3-(trifluoromethyl)phenyl]-2-hydroxy-2-methylpropanamide R-19 (2.0 g, 5.70 mmol)), anhydrous K₂CO₃ (2.4 g, 17.1 mmol) in 50 mL of acetone was heated to reflux for 2 h and then concentrated under reduced pressure to give a solid. The resulting solid was treated with 2-fluoro-4-hydroxybenzonitrile (1.2 g, 8.5 mmol) and anhydrous K₂CO₃ (1.6 g, 11.4 mmol) in 50 mL of 2-propanol was heated to reflux for 3 h and then concentrated under reduced pressure to give a solid. The residue was treated with 100 mL of H₂O and then extracted with EtOAc (2×100 mL). The combined EtOAc extracts were washed with 10% NaOH (4×100 mL) and brine, successively. The organic layer was dried over MgSO₄ and then concentrated under reduced pressure to give an oil which was crystallized from CH₂Cl₂/hexane to give 0.5 g (23%) of (S)—N-(4-cyano-3-(trifluoromethyl)phenyl)-3-(4-cyano-3-fluorophenoxy)-2-hydroxy-2-methylpropanamide as a colorless solid.

¹H NMR (CDCl₃/TMS) δ 1.63 (s, 3H, CH₃), 3.34 (bs, 1H, OH), 4.08 (d, J=9.17 Hz, 1H, CH), 4.50 (d, J=9.17 Hz, 1H, CH), 6.74-6.82 (m, 2H, ArH), 7.50-7.55 (m, 1H, ArH), 7.81 (d, J=8.50 Hz, 1H, ArH), 7.97 (q, J=2.03, 8.50 Hz, 1H, ArH), 8.11 (d, J=2.03 Hz, 1H, ArH), 9.12 (s, 1H, NH). Calculated Mass: 407.1, [M+Na]⁺430.0. Mp: 124-125° C.

Example 15

Synthesis of (S) Enantiomer of Formula XIV

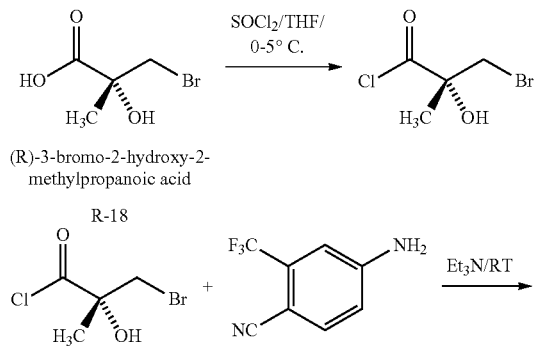

Synthesis of (2R)-3-Bromo-N-[4-cyano-3-(trifluoromethyl)phenyl]-2-hydroxy-2-methylpropanamide Thionyl chloride (46.02 g, 0.39 mol) was added dropwise to a cooled solution (less than 4° C.) of R-18 (51.13 g, 0.28 mol) in 300 mL of THF under an argon atmosphere. R-18 is (R)-3-bromo-2-hydroxy-2-methylpropanoic acid was prepared as described in Example 10. The resulting mixture was stirred for 3 h under the same condition. To this was added Et₃N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H₂O, extracted with EtOAc (2×400 mL). The combined organic extracts were washed with saturated NaHCO₃ solution (2×300 mL) and brine (300 mL). The organic layer was dried over MgSO₄ and concentrated under reduced pressure to give a solid, which was purified from column chromatography using CH₂Cl₂/EtOAc (80:20) to give a solid. This solid was recrystallized from CH₂Cl₂/hexane to give 55.8 g (73.9%) of (2R)-3-bromo-N-[4-cyano-3-(trifluoromethyl)phenyl]-2-hydroxy-2-methylpropanamide (R-19) as a light-yellow solid.

¹H NMR (CDCl₃/TMS) δ 1.66 (s, 3H, CH₃), 3.11 (s, 1H, OH), 3.63 (d, J=10.8 Hz, 1H, CH₂), 4.05 (d, J=10.8 Hz, 1H, CH₂), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M-H]⁻ 349.0. M.p.: 124-126° C.

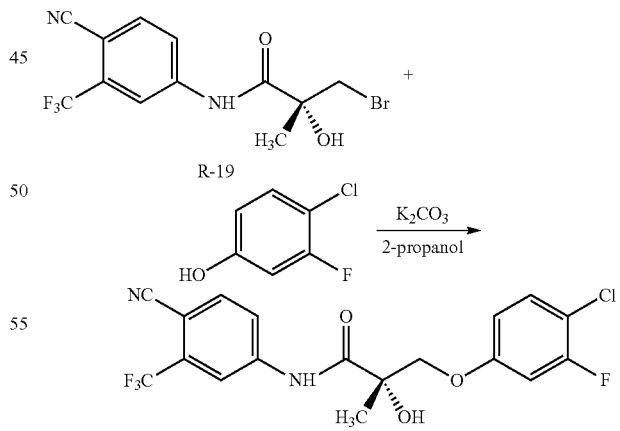

Synthesis of (S)-3-(4-chloro-3-fluorophenoxy)-N-(4-cyano-3-(trifluoromethyl)phenyl)-2-hydroxy-2-methylpropanamide (Formula XIV)

A mixture of bromoamide ((2R)-3-bromo-N-[4-cyano-3-(trifluoromethyl)phenyl]-2-hydroxy-2-methylpropanamide (R-19) 2.0 g, 5.70 mmol)), anhydrous K$_2$CO$_3$ (2.4 g, 17.1 mmol) was heated to reflux for 2 h and then concentrated under reduced pressure to give a solid. The resulting solid was treated with 4-chloro-3-fluorophenol (1.3 g, 8.5 mmol) and anhydrous K$_2$CO$_3$ (1.6 g, 11.4 mmol) in 50 mL of 2-propanol was heated to reflux for 3 h and then concentrated under reduced pressure to give a solid. The residue was treated with 100 mL of H$_2$O and then extracted with EtOAc (2×100 mL). The combined EtOAc extracts were washed with 10% NaOH (4×100 mL) and brine, successively. The organic layer was dried over MgSO$_4$ and then concentrated under reduced pressure to give an oil which was purified by column chromatography using EtOAc/hexane (50:50) to give a solid which was recrystallized from CH$_2$Cl$_2$/hexane to give 1.7 g (70.5%) of (S)-3-(4-chloro-3-fluorophenoxy)-N-(4-cyano-3-(trifluoromethyl)phenyl)-2-hydroxy-2-methylpropanamide as a colorless solid.

$^1$H NMR (CDCl$_3$/TMS) δ 1.60 (s, 3H, CH$_3$), 3.28 (s, 1H, OH), 3.98 (d, J=9.05 Hz, 1H, CH), 6.64-6.76 (m, 2H, ArH), 7.30 (d, J=8.67 Hz, 1H, ArH), 7.81 (d, J=8.52 Hz, 1H, ArH), 7.96 (q, J=2.07, 8.52 Hz, 1H, ArH), 8.10 (d, J=2.07 Hz, 1H, ArH), 9.10 (s, 1H, NH). Calculated Mass: [M-H]$^-$ 414.9. Mp: 132-134° C.

Example 16

Binding and Transactivation of SARMs in Breast Cancer Cells

In order to determine whether compounds of this invention are agonists in breast cancer cells, HEK-293 or MDA-MB-231 cells were transfected with 0.25 μg GRE-LUC, 10 ng CMV-renilla LUC, and 25 ng CMV-hAR using lipofectamine. Twenty four hours after transfection, the cells were treated with DHT, compound of Formula VIII or compound of Formula IX and luciferase assay was performed 48 hrs after transfection. Competitive binding of DHT, compound of Formula VIII and compound of Formula IX were measured using an in vitro competitive radioligand binding assay with [17α-methyl-$^3$H]-mibolerone ([$^3$H] MIB), a known steroidal and high affinity AR ligand, and purified AR-LBD protein.

Results

Figure 13A:
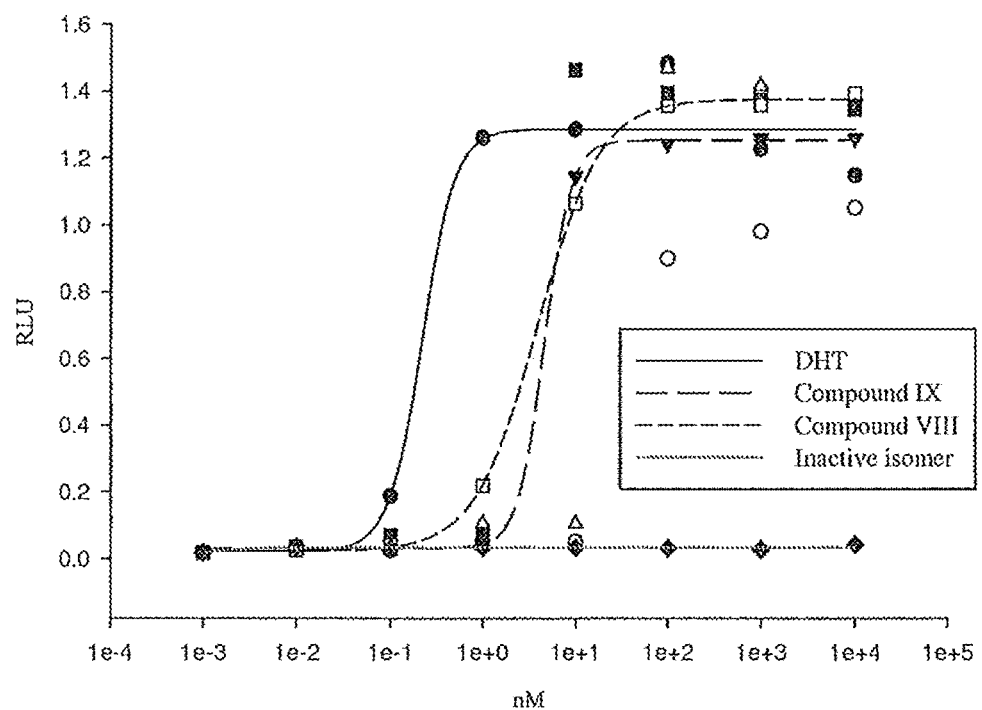
FIG. 13A-FIG. 13C demonstrate binding and transactivation of the indicated ligands to HEK-293 (13A) or MDA-MB-231 (13B & 13C) cells. DHT, Formula IX and Formula VIII are agonists of AR in breast cancer cells. (Example 16)
Figure 13B:
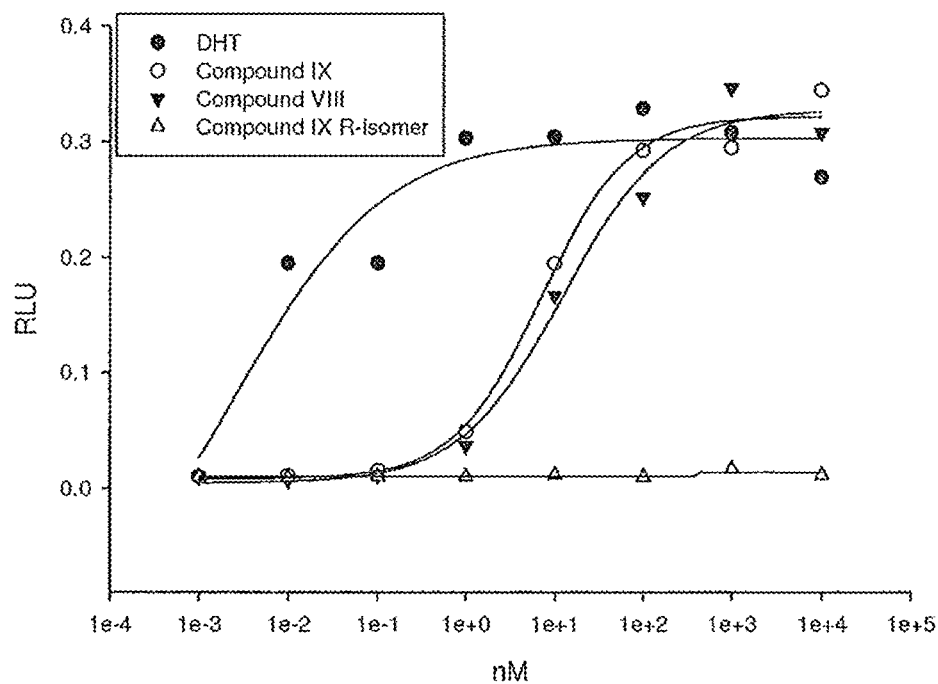
Figure 13C:
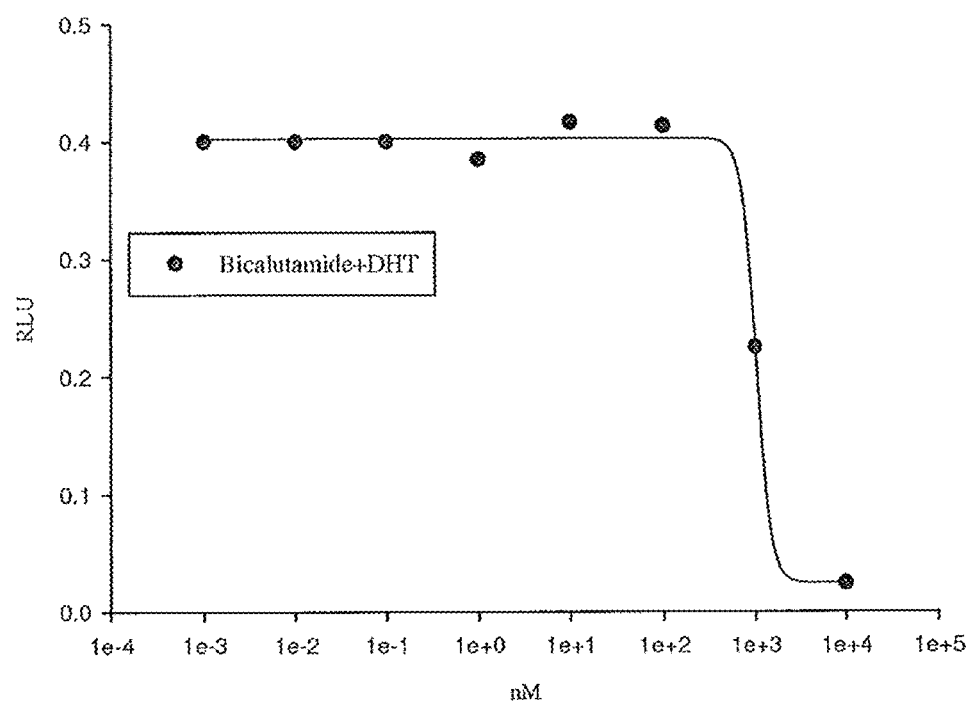
Figure 14:
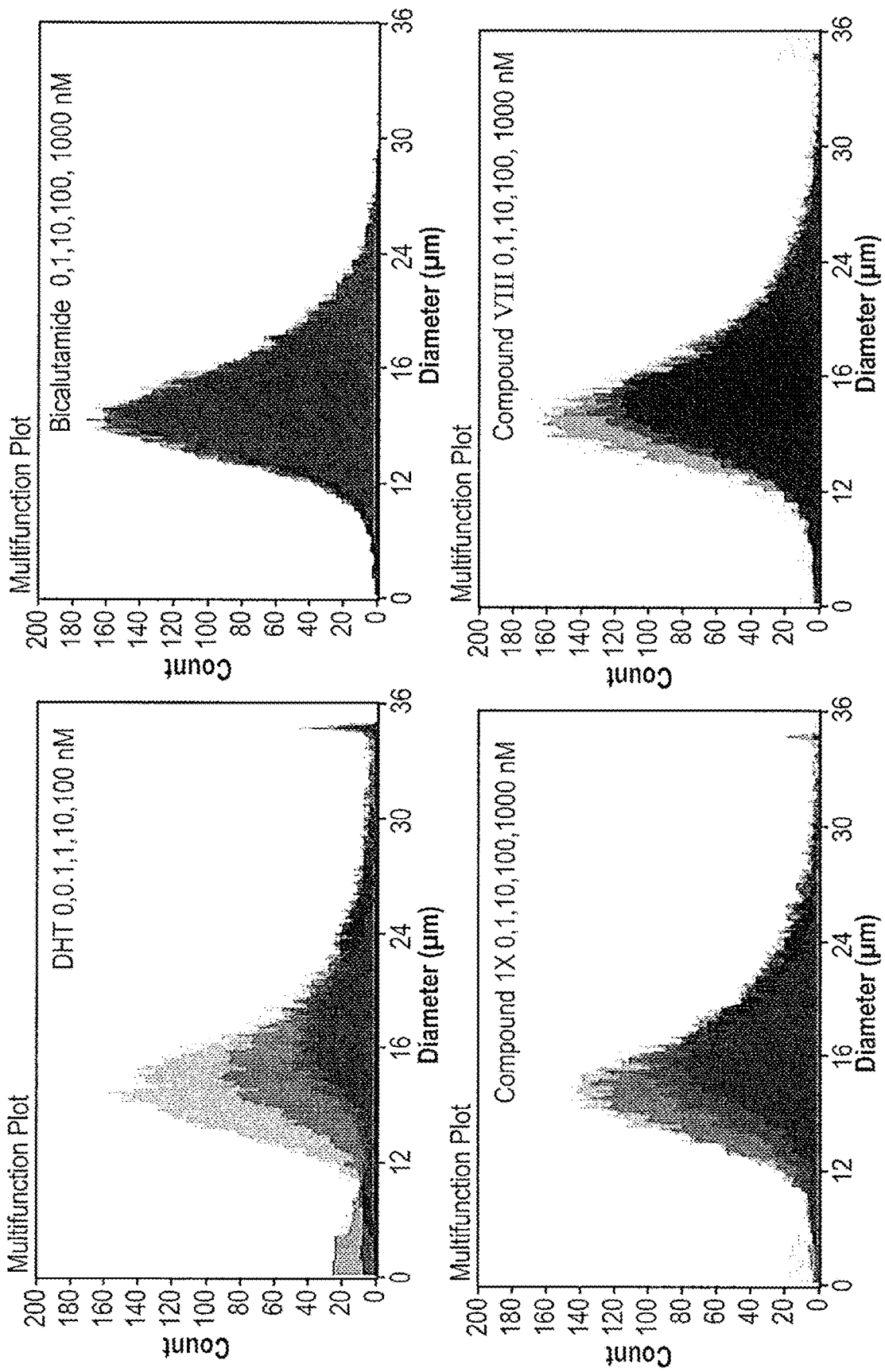
FIG. 14 demonstrates anti-proliferative activity of DHT and SARMs in MDA-MB-231 breast cancer cells stably transfected with AR. MDA-MB-231 cells stably transfected with AR using lentivirus were treated with the indicated ligands for 6 days and the number of cells counted using Coulter counter. DHT and SARMs (VIII and IX), but not the AR antagonist, bicalutamide, inhibited the proliferation of MDA-MB-231 triple negative breast cancer cells stably transfected with AR.

DHT, compound of Formula VIII and Formula IX are agonists of AR in breast cancer cells as presented in FIG. 13A-13C (HEK-293 cells in FIG. 13A and MDA-MB-231 cells in FIGS. 13B-13C). The relative binding affinities (RBAs) for AR of DHT, Formula IX, Formula VIII, and bicalutamide were 1.0, 0.330, 0.314, and 0.016, respectively, demonstrating high affinity AR binding for the SARM compounds of this invention (data not shown).

Example 17

Inhibition of Intratumoral Gene Expression

AR agonists differentially regulate genes in ER-positive and ER-negative breast cancer cells. MDA-MB-231 and MCF-7 cells infected with AR or GFP containing adenovirus were maintained in charcoal stripped serum containing medium for 3 days and were treated with DHT or Formula VIII. After overnight treatment, the cells were harvested, RNA isolated and real-time PCR for the indicated genes were performed. The expression of various genes in response to either DHT or Formula VIII were measured and normalized to GAPDH, and are presented as composite data (same effects for DHT and Formula VIII) in Table 6.

TABLE 6

Differential Regulation of Gene Expression by AR Ligands in ER-Positive (MCF7) and ER-Negative (MDA-MB-231) Breast Cancers

| | AR | PSA | Muc1 | SLUG | VCAM1 | SPARC | MMP2 |
|---|---|---|---|---|---|---|---|
| MDA-MB 231/GFP | — | — | — | — | — | — | — |
| MDA-MB-231/AR | | | ↑ | — | ↓ | ↓ | ↓ |
| MDA-MB-231/AR cs FBS | | | ↑ | — | ↓ | ↓ | ↓ |
| MCF7/GFP | | — | — | no | — | no | |
| MCF7/AR | | — | ↑ | no | — | no | |
| MCF7/AR cs FBS | | — | ↑ | no | — | no | |

VCAM1—Vascular cell adhesion protein-1—Important for anchorage—dependent growth of cells and also is a chemoattractant.
SPARC—Secreted protein acidic and rich in cysteine (aka Osteonectin)—extracellular glycoprotein important for angiogenesis.
MUC1—Mucin1—Extracellular glycoprotein associated with cancers—Its promoter has a strong ARE.
SLUG—Zinc finger transcription factor—Its promoter has a strong ARE.
MMP2—matrix metalloproteinase-2—gene that is activated by cell-cell clustering.

Example 18

Gene Expression Array of MDA-MB-231-AR Xenograft

RNA was extracted from MDA-MB-231-AR tumors (n=5/group) treated with vehicle or compound of Formula VIII. RNA was pooled and Affymetrix microarray was performed to determine the change in expression of gene signature.

Results

Figure 15:
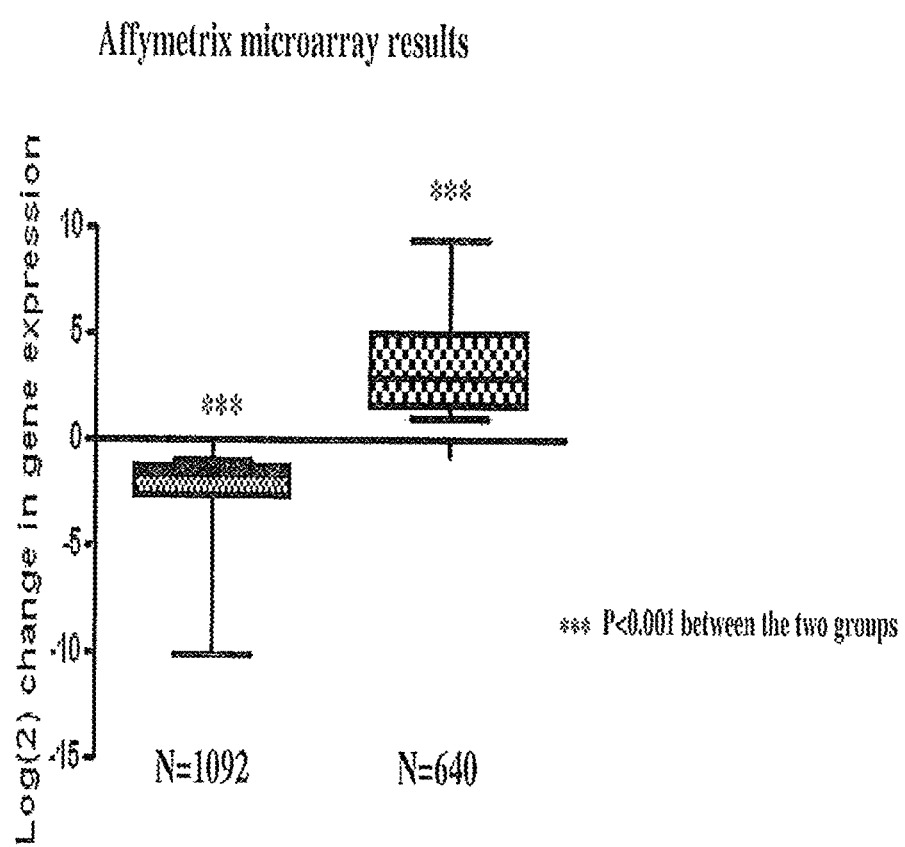
FIG. 15 presents microarray results showing that activated AR (AR activated by compound of Formula VIII) suppressed the expression of more genes than it induced in MDA-MB-231-AR xenograft breast cancer cells.

The results presented in FIG. 15 show that activation of AR in MDA-MB-231-AR xenografts suppressed the expression of more genes than it induced in these tumors. This pattern is unique in breast cancer cells and is different from gene expression results observed in prostate cancer cells, where more genes are induced than repressed (data not shown).

Figure 16:
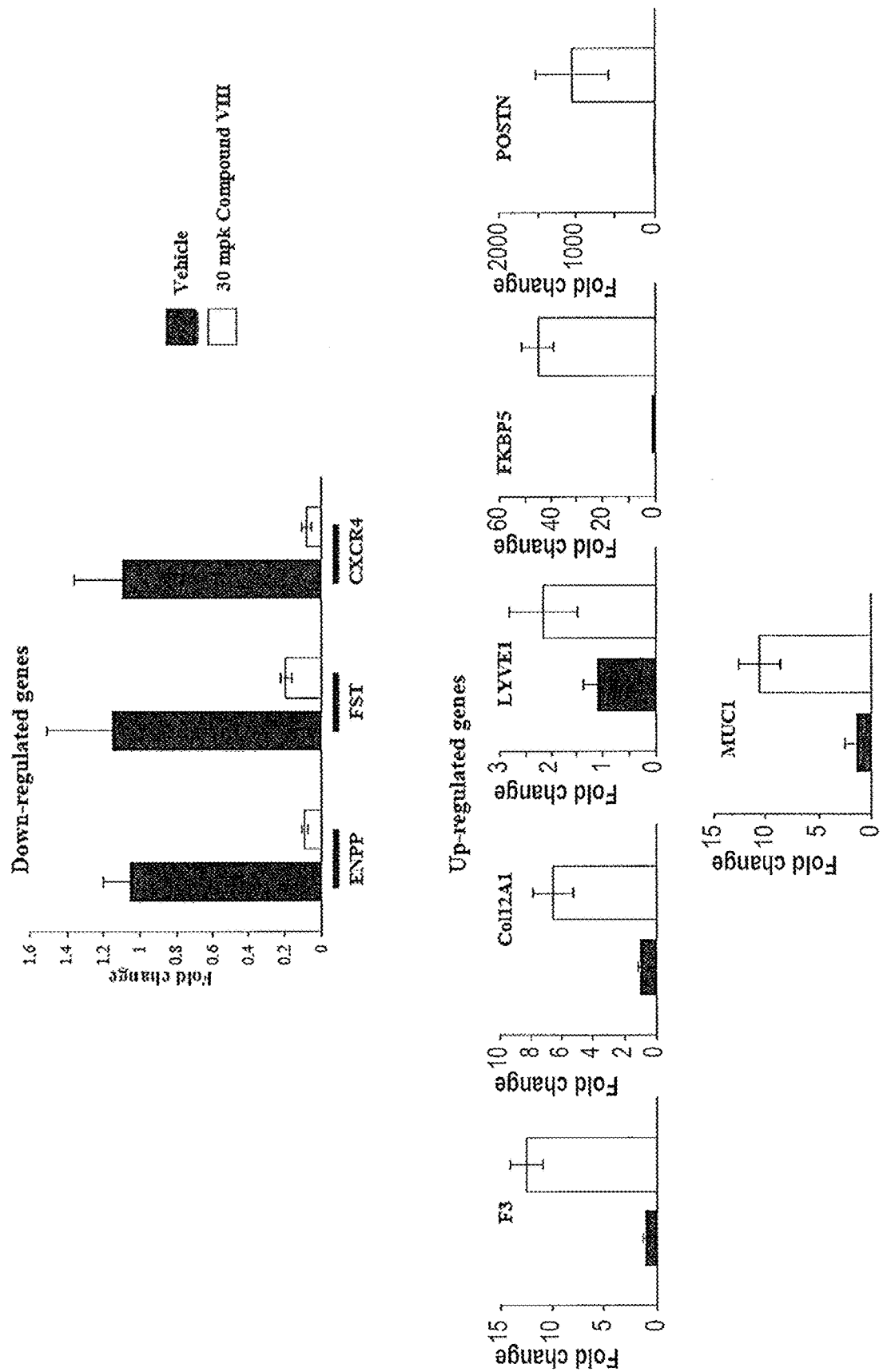
FIG. 16 depicts validation of microarray results.

The results presented in FIG. 16 validate the microarray results presented in FIG. 15 by analyzing selected genes using realtime PCR TaqMan primers and probe in ABI 7900.

Example 19

Formula VIII Inhibits the Growth of MCF-7-AR Xenograft

MCF-7 cells stably transfected with AR using lentivirus were implanted (2 million cells/mouse; n=5) in nude mice that were ovariectomized and supplemented with 17β-estradiol (50 μg/day). Once tumors reached 100-200 mm$^3$, the animals were randomized and treated with vehicle or 30 mg/kg per day of Formula VIII. Tumor volumes and body weights were measured thrice weekly. At the end of 5 weeks of treatment, the animals were sacrificed, tumors weighed and stored for RNA and protein isolation and histology. * significance at P<0.05.

In addition, uterus weights were measured in these xenograft studies, and Western blot from MCF-7 tumor xenografts were probed for AR.

Results

Figure 17:
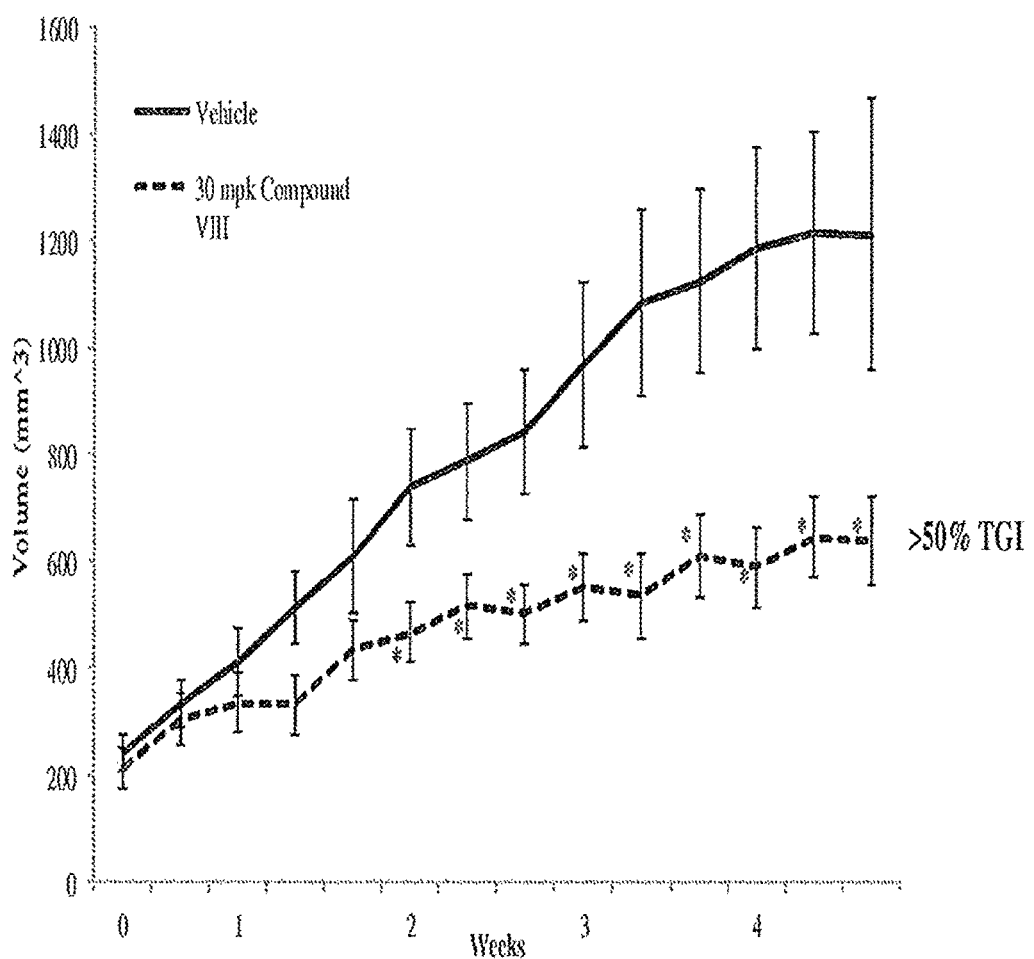
FIG. 17 illustrates that Formula VIII inhibited the growth of MCF-7-AR triple positive xenograft.

The graph presented in FIG. 17 demonstrates inhibition of triple-positive breast cancer (ER, PR, and HER2) using Formula VIII. The results show that Formula VIII inhibited the growth of MCF-7 breast cancer cell xenografts by greater than 50%.

Figure 18:
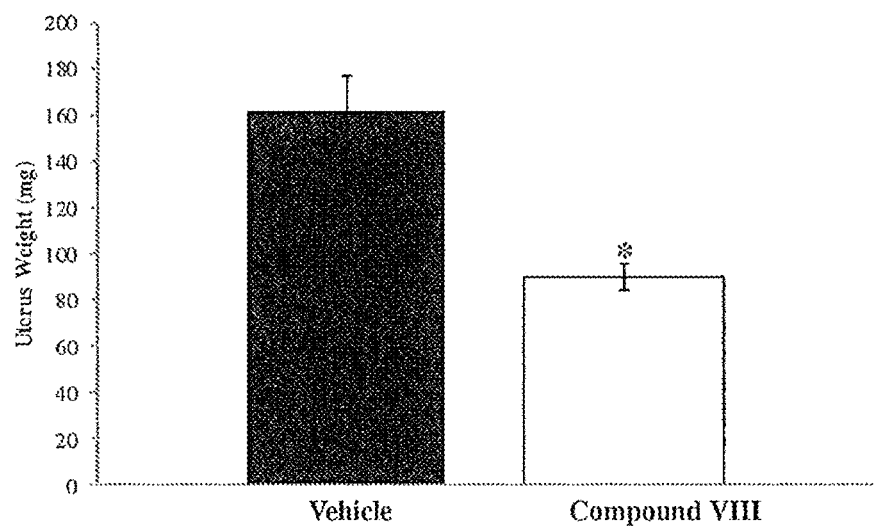
FIG. 18 presents inhibition of uterus weight gain in estrogen supplemented animals treated with Formula VIII, demonstrating the ability of a SARM to counteract estrogenic stimuli in vivo.

The results presented in FIG. 18 show Formula VIII inhibited uterus weight in these estrogen supplemented animals.

Figure 19:
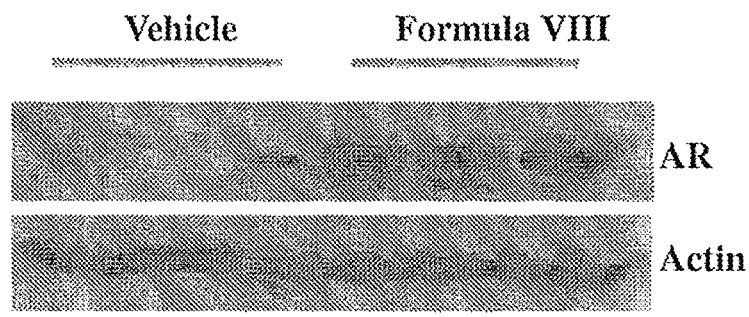
FIG. 19 shows that the AR expression pattern in response to an AR-agonist (Formula VIII) is similar to that observed in prostate cancer cells.

The results presented in FIG. 19 demonstrate that the AR expression pattern in response to agonist (Formula VIII) is similar to that observed in prostate cancer cells (data not shown).

Example 20

Formula VIII Up-Regulates JNK Phosphorylation in MCF7-AR Tumors

Protein from MCF-7-AR tumors that were treated with vehicle or compound of Formula VIII were extracted and incubated with phospho MAPK array to determine the effect of compound of Formula VIII on phosphorylation of various kinases.

Results

Figure 21:
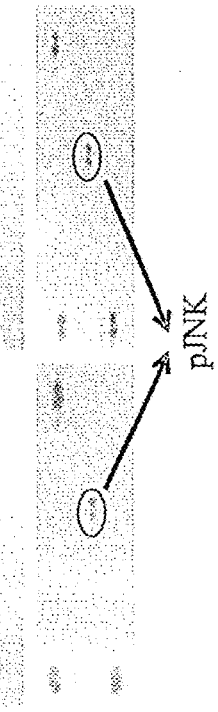
FIG. 21 demonstrates up-regulation of JNK phosphorylation in MCF7-AR tumors using Formula VIII.

The results presented in FIG. 21 show that JNK phosphorylation is upregulated in MCF-7-AR tumors by treatment with compound of Formula VIII. JNK plays a critical role in death receptor-mediated intrinsic and extrinsic apoptotic pathways. JNK activates apoptotic signaling by up-regulating pro-apoptotic genes. The observed phosphorylation of the pro-apoptotic kinase, JNK, may be suggestive of a possible mechanistic explanation of the anti-proliferation.

Example 21

Gene Expression Analysis of MDA-MB-231-AR and MCF-7-AR Xenografts Following Treatment with Formula VIII and Formula IX Microarray Analysis was performed on RNA from MDA-MB-231-AR and MCF-7-AR tumors in order to identify and compare changes in gene expression in ER-negative (MDA-MB-231-AR; triple negative) an ER-positive (MCF-7-AR; triple positive) breast cancer tumors treated with a compound of Formula VIII (30 mg/kg/day p.o. for 4 weeks). Affymetrix analysis of the xenografts was done on pooled samples of the xenografts. The analysis included ~70,000 sequences with ~30,000 genes and variations thereof represented, as well as microRNA's. RNA was isolated and expression of genes was evaluated using microarray (Affymetrix Human Gene ST 2.0 array). Expression of genes in compound of Formula VIII-treated samples was compared with the expression in vehicle-treated samples. Genes that were up- or down-regulated by more than 2 fold were considered differentially regulated by compound of Formula VIII.

Results

Table 7 below presents the sum totals of up-regulated and down-regulated genes in MDA-MB-231-AR and MCF-7-AR tumors.

TABLE 7

| Type | Up | Down | Total |
| --- | --- | --- | --- |
| MCF-7-AR | 566 | 981 | 1547 |
| MDA-MB-231-AR | 720 | 816 | 1536 |

Of particular interest was that of the 1547 regulated genes identified in MCF-7-AR tumors and the 1536 regulated genes identified in MDA-MB-231-AR tumors, the subset of overlapping genes was only 245 genes. This result indicated that Formula VIII regulated distinct sets of genes in MCF-7-AR (ER-positive; triple positive) and MDA-MB-231-AR (ER-negative; triple negative) breast cancer cells.

Tables 8 and 9 below present genes involved in mammary tumorigenesis that were differentially regulated (by at least 2 fold) by Formula VIII in MDA-MB-231-AR tumors (Table 8) and MCF-7-AR tumors (Table 9). Indications of up-regulation or down-regulation are presented in the right-most column.

TABLE 8

Breast cancer relevant genes modulated in MDA-MB-231-AR tumors

| Gene | Function | Formula VIII |
| --- | --- | --- |
| NQO1 | Anti-proliferative, reduces oxidative stress of cells, regulates p53-dependent apoptosis | Increased |
| β-Adrenoceptor2 | Increases proliferation and metastasis of breast cancer, increases inflammation | Decreased |
| Aurora kinase | Increase proliferation of breast cancer and aurora kinase inhibitors are effective preclinically | Decreased |
| BUB1 S/T kinase | expression correlates with tumor status, node- and distant-metastasis, and histological grade in BC | Decreased |
| CENPE | Promotes breast cancer growth, small molecule inhibitors of CENPE inhibit BC cell growth | Decreased |
| EHMT2 | Up-regulated in variety of cancers, including breast | Decreased |
| ERCC1 | Expressed in 70% TNBCs and its expression leads to resistance to chemotherapy | Decreased |
| IGFBP3 | Increases proliferative disease, higher IGFBP3 in serum correlates with higher grade disease | Decreased |
| ITGA2 | Cancer development and metastasis | Decreased |
| PARP1 | PARP inhibitors are currently under development for breast cancer | Decreased |
| POLD1 | Associated with multiple cancers, including breast cancer | Decreased |
| PTPRJ | Tumor suppressor | Increased |

TABLE 9

Breast cancer relevant genes modulated in MCF-7-AR tumors

| Gene | Function | Formula VIII |
| --- | --- | --- |
| MTR | Increases breast cancer risk | Decreased |
| FACGD2 | Inhibition increases the sensitivity to cancer therapeutics | Decreased |
| TIMP3 | Silenced in several aggressive cancers due to promoter methylation | Increased |
| XRCC1 | High XRCC1 leads to poor survival of cancer patients | Decreased |
| AHR | Increases sensitivity to anti-cancer agents, good prognostic marker, agonists are used for cancers | Increased |
| Catalase | Inversely correlates with breast cancer risk, good marker, prevents DNA damage | Increased |
| CDT1 | Promotes replication, increases cancer incidence | Decreased |
| ER-α | Promotes breast cancer proliferation | Decreased |
| EHMT1 | Tumor suppressor complex protein | Increased |
| ERCC2 | Promotes breast cancer and other cancers through | Decreased |

TABLE 9-continued

Breast cancer relevant genes modulated in MCF-7-AR tumors

| Gene | Function | Formula VIII |
|------|----------|--------------|
| IRS1 | DNA damage Highly expressed in breast cancer, over-expression in mice increases breast cancer incidence | Decreased |
| KLK3 | KLK3 (PSA) increase is highly correlative of positive breast cancer outcome; good prognostic marker | Increased |
| PR | Increases proliferation of breast cancer | Decreased |
| PON2 | Anti-oxidative properties; cells over-expressing PON2 have reduced oxidative stress; anti-cancer | Increased |
| NPAS2 | Tumor suppressor gene | Increased |

The results presented in Tables 7 and 8 show that SARM treatment (Formula VIII) caused net down-regulation of genes in MDA-MB-231-AR tumors (N=1042 suppressed; N=640 induced; threshold of 2-2.5-fold increase or decrease (note: plot is log of fold change; follow-up RT-PCR demonstrated 10-20-fold changes). Well known androgen-dependent genes (e.g. FKP5 and MUC1; See Table 10 below) were elevated, showing SARM penetration into the tumor. Also 29/36 known breast cancer-related genes were shown to be decreased, supporting a rational basis for the anti-proliferation activity of Formula VIII in ER-negative breast cancer.

Further analysis of the results in MDA-MB-231-AR tumors showed that Formula VIII induced known androgen-responsive genes (Table 10 below). Thus, breast cancer relevant genes such as beta2-adrenergic receptor and PARP1 were suppressed by Formula VIII; whereas ARE-dependent genes were induced by treatment of Formula VIII.

TABLE 10

| Gene | Fold | Function |
|------|------|----------|
| TFPi2 | 4.76 | Tumor suppressor, protease inhibitor family |
| F3 | 6.94 | Coagulation factor |
| Carboxipeptidase | 3.25 | Androgen responsive gene |
| SNAI2/SLUG | 2.10 | Androgen responsive gene |
| ASAM | 3.27 | |
| DUSP1 | 4.14 | Inactivates MAPK, androgen responsive gene |
| Col12a1 | 5.93 | |
| Amphiregulin | 4.47 | Regulated by androgens and estrogens |
| Protein S | 3.69 | Regulated by estrogen (down) and progestin (up) |
| PDLIM1 | 2.06 | PR regulated gene |
| FBXO32 | 6.62 | Very interesting gene. Androgens inhibit in muscle, Promotes muscle atrophy, ubiquitin, Mixed functions in cancer |
| RASD1 | 18.62 | GC-stimulated gene, Down-regulated in GC-resistant melanoma |
| IRS2 | 4.40 | |
| FKBP51 | ∞ | Androgen and GC stimulated gene |
| MUC1 | 9 | Androgen and estrogen stimulated gene |
| DUSP23 | 7.35 | Androgen stimulated |
| PTGS2 | 14 | Androgen stimulated |
| RHOB | 7.92 | Androgen regulated |

The results presented in Tables 7 and 9 show that Formula VIII did not have as strong of a gene suppressive tone in MCF-7-AR triple positive (ER-positive) tumors as in triple negative (ER-negative) tumors. Interestingly though, the MCF-7-AR analysis showed that androgen-dependent genes were up regulated and estrogen-dependent genes were suppressed (Table 11 below), as validated by RT-PCR.

TABLE 11

| Androgen Target | Estrogen Target |
|-----------------|-----------------|
| KLK3 (PSA) | PR |
| SNAI2 | ER |
| MUC1 | IGFBP4 |
| IRS2 | pS2 |
| FKBP5 | |
| DUSP23 | |
| miR21 | |

Figure 20:
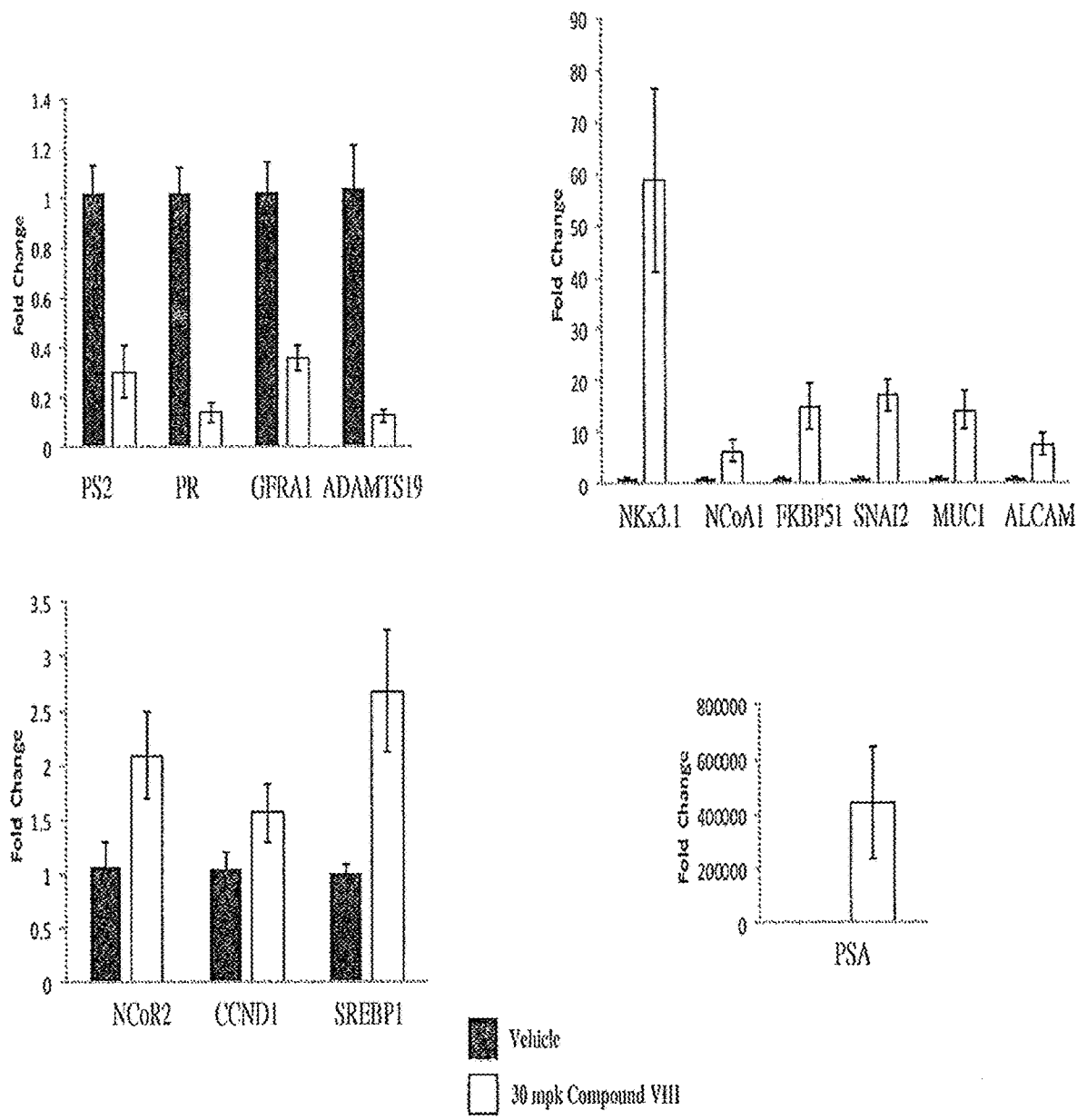
FIG. 20 depicts validation of microarray results.

The results presented in FIG. 20 validate the microarray results presented in the above analyses, by analyzing selected genes using realtime PCR TaqMan primers and probe in ABI 7900.

Figure 22:
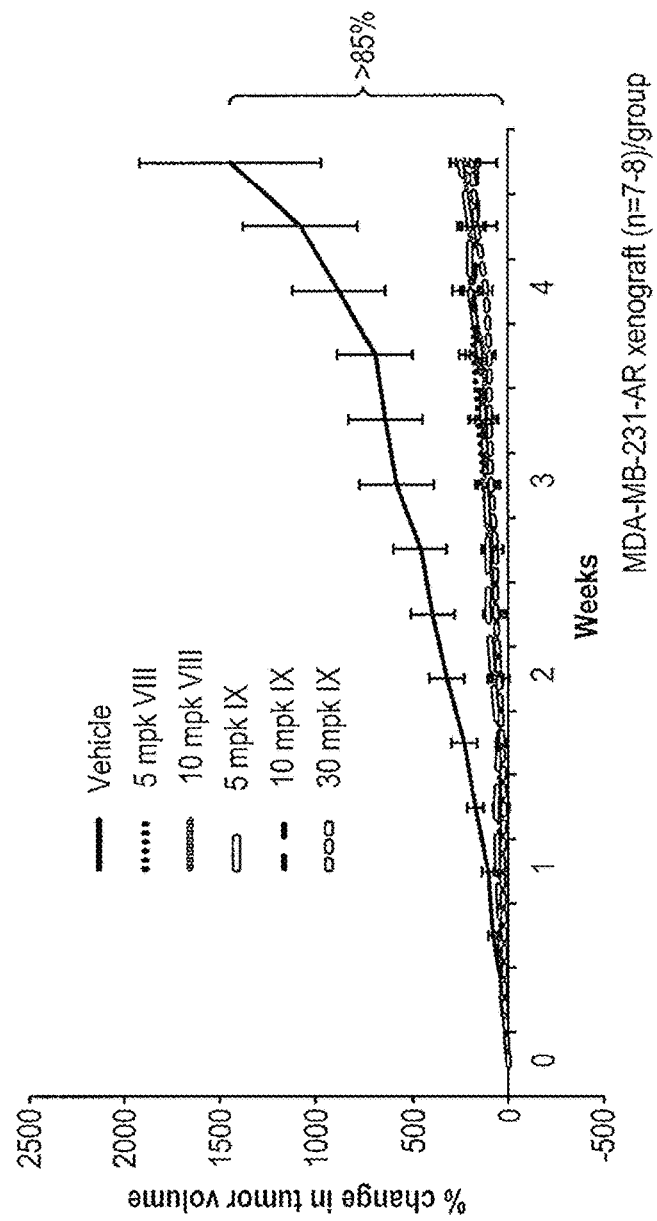
FIG. 22 shows inhibition of triple negative breast cancer (TNBC) growth using Formulae VIII and IX. Formula VIII and Formula IX demonstrated ~85% TGI at all doses tried (5, 10 mg per kg for Formula VIII; 5, 10, 30 mg per kg for Formula IX) in the TNBC model using MDA-MB-231-AR cells in nude mice.

The results presented in FIG. 22 show inhibition of triple negative breast cancer growth using Formulae VIII and IX. Formula VIII and Formula IX demonstrated ~85% TGI at all doses tried (5, 10 mg per kg for Formula VIII; 5, 10, 30 mg per kg for Formula IX) in the triple negative breast cancer model using MDA-MB-231-AR cells in nude mice.

Figure 23:
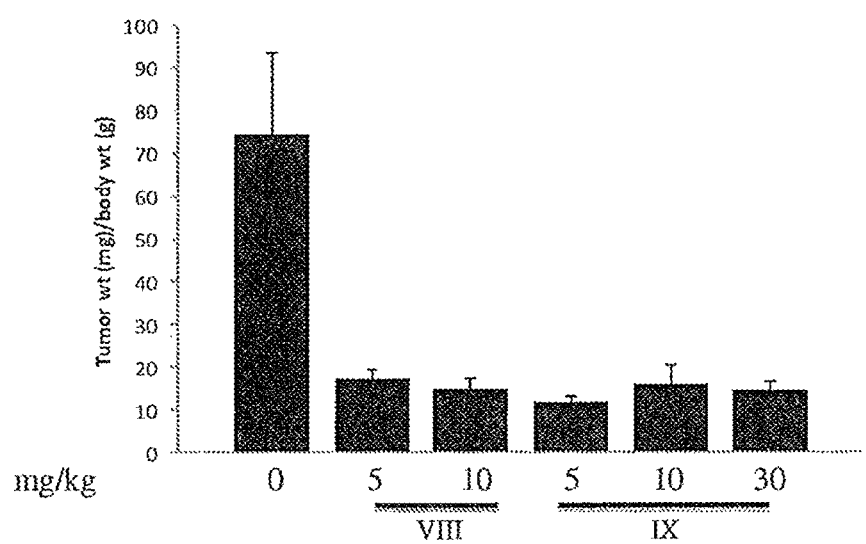
FIG. 23 demonstrates inhibition of triple negative breast cancer using Formulae VIII and IX. The tumor weights were likewise reduced for all doses of Formula VIII and Formula IX. Spleen enlargement (680 mg vs. 200-300 mg for normal mice) was seen only in vehicle treated mice, possibly indicative of prevention by the SARMs of tumor metastasis to the spleen.

The results presented in FIG. 23 demonstrate inhibition of triple negative breast cancer using Formulae VIII and IX. Tumor weights were likewise reduced for all doses of Formula VIII and Formula IX. Spleen enlargement (680 mg vs. 200-300 mg for normal mice) was seen only in vehicle treated mice, possibly indicative of prevention by the SARMs of tumor metastasis to the spleen.

Figure 25B:
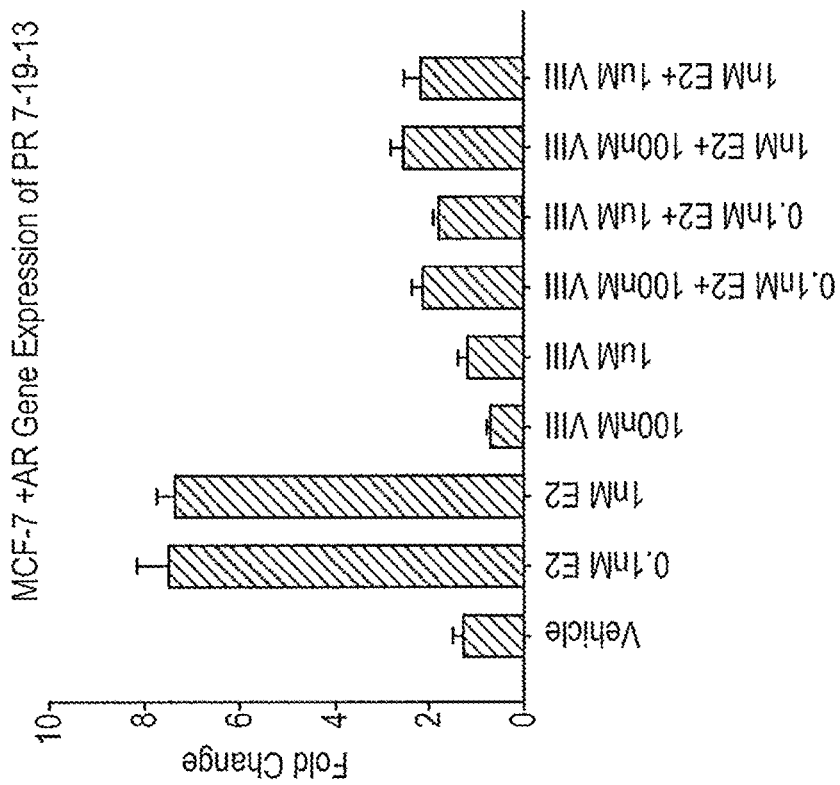
FIG. 25A-FIG. 25E depict antagonism by SARM regarding the ability of estradiol to activate ER target genes in MCF-7-AR cells.
Figure 25A:
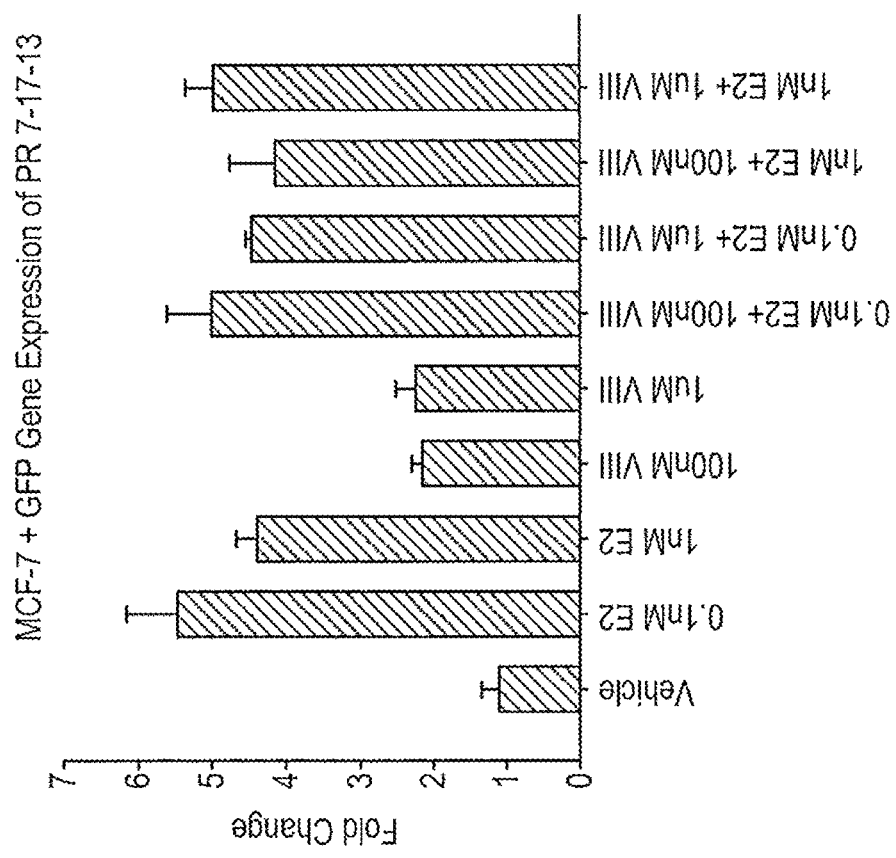
Figure 25D:
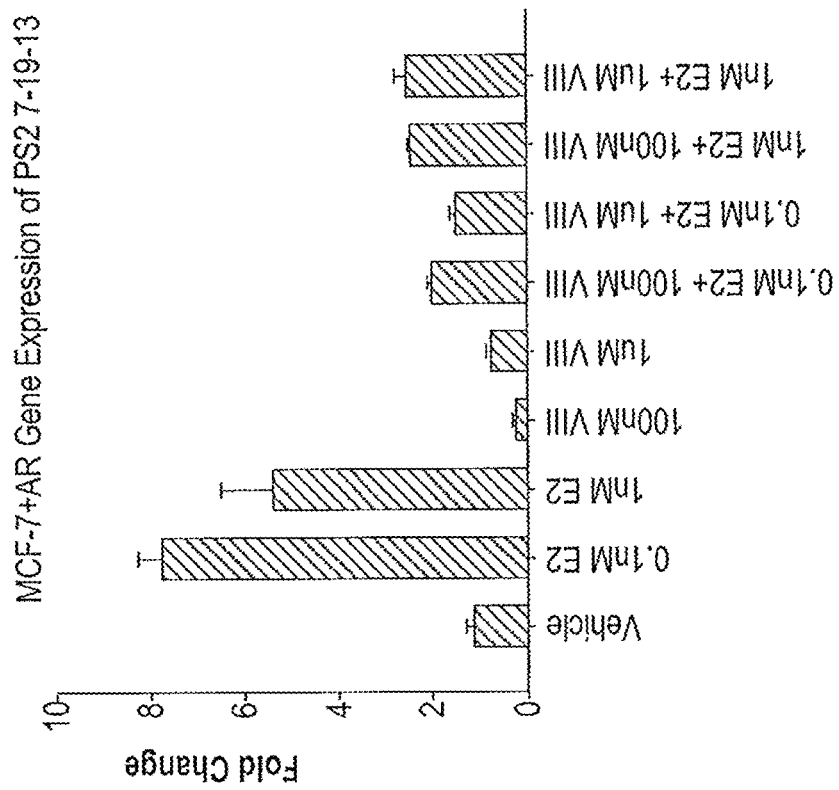
Figure 25C:
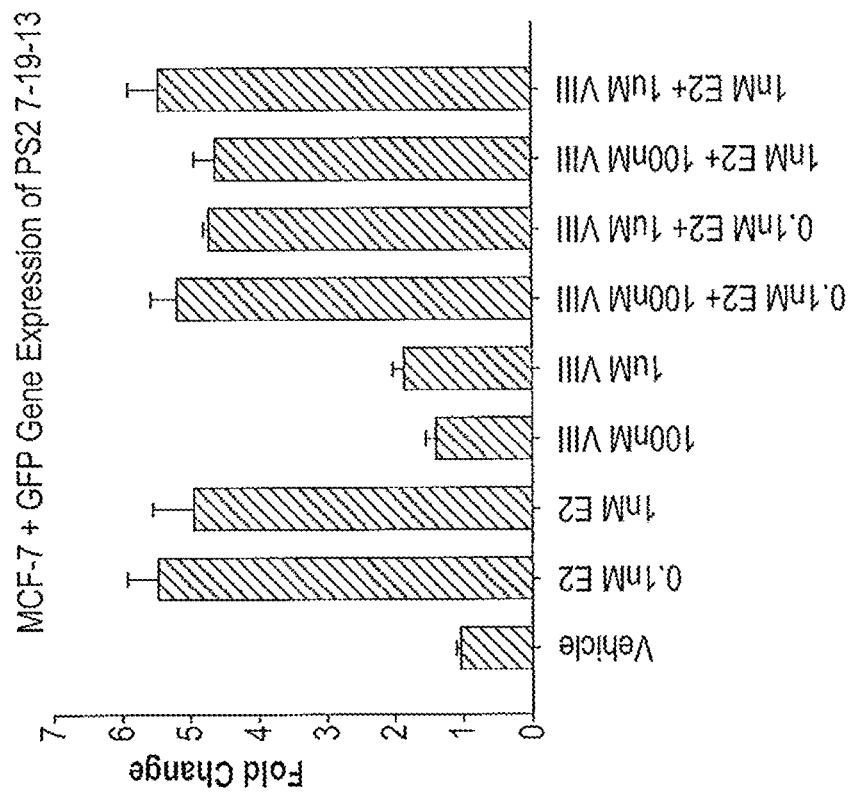
Figure 25E:
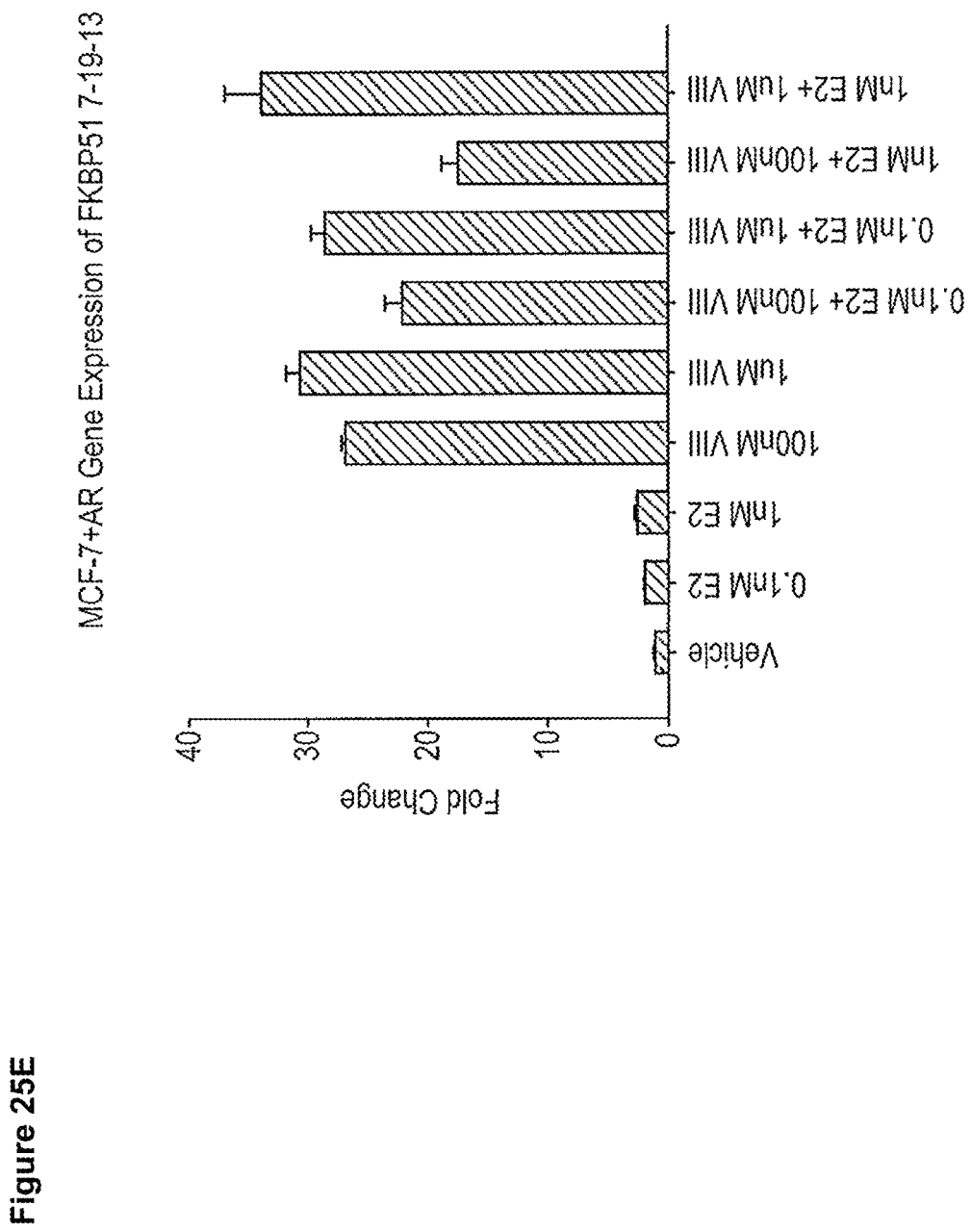

The in vitro data shown in MCF-7 cells with and without AR (FIGS. 25A-25E) support that SARM-activated AR may sequester the co-factors that are used by ER. Adding AR to the MCF-7 cells increased the effect of 17β-estradiol (when unopposed) on the ER target genes PR and pS2, but the antagonism caused by SARM alone or SARM+17β-estradiol (E2) was enhanced in this setting (FIGS. 25B and 25D) as compared to GFP (i.e. no AR; FIGS. 25A and 25C). FIG. 25E shows that AR target genes are enhanced by SARM even in the presence of 17β-estradiol.

Example 22

Xenograft Experiment with Formula IX

Xenograft Experiment.

Figure 26A:
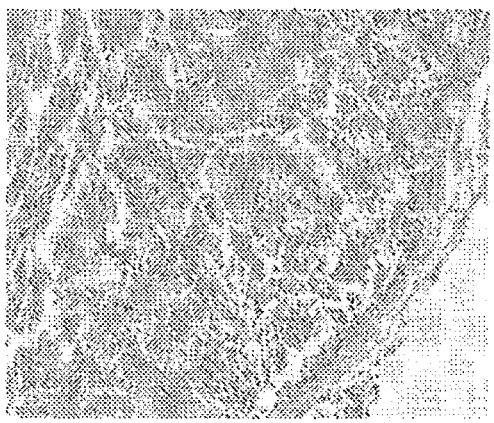
FIG. 26A and FIG. 26B depict immunohistochemistry of two regions of the same BR-0001 tumor, a triple negative breast cancer (TNBC). They show that AR expression is consistent throughout this formalin-fixed, paraffin-embedded (FFPE) tissue stained with AR antibody (AR N20 from SCBT).
Figure 26B:
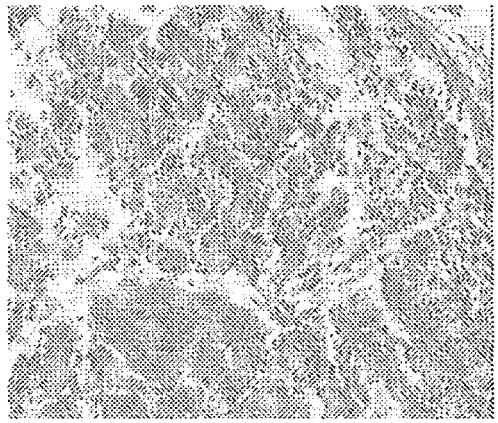
Figure 26C:
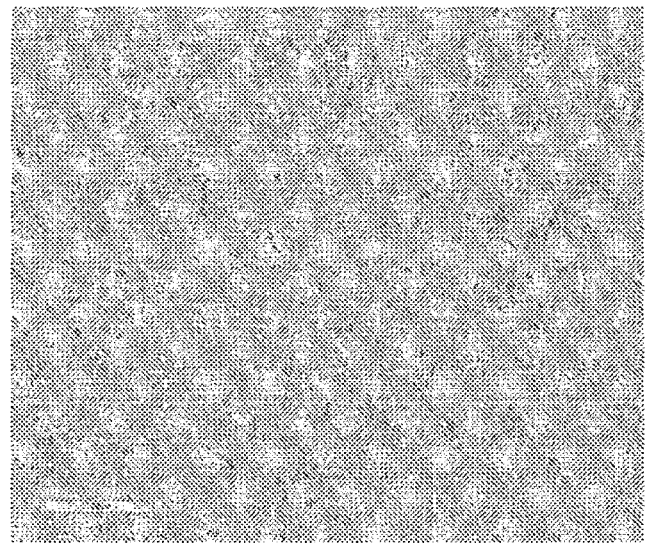
FIG. 26C depicts immunohistochemistry staining of an AR-negative TNBC FFPE tumor as a negative control.
Figure 27A:
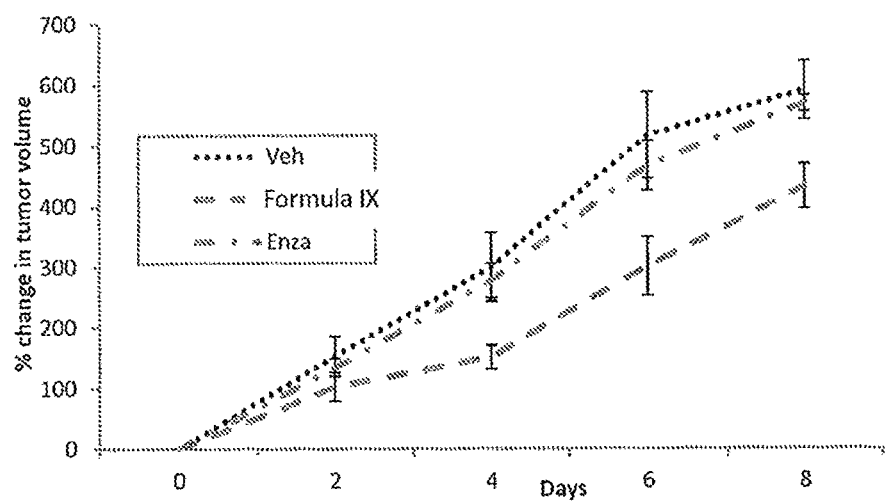
FIG. 27A-FIG. 27C depict BR-0001 tumor xenograft growth inhibition by Formula IX compared to enzalutamide (Enza) or vehicle in terms of breast cancer tumor volume (FIG. 27A and FIG. 27B) and weight (FIG. 27C) with time. Experiments 1 and 2 were duplicate experiments run at different times with n=5 and n=10 animals, respectively.
Figure 27B:
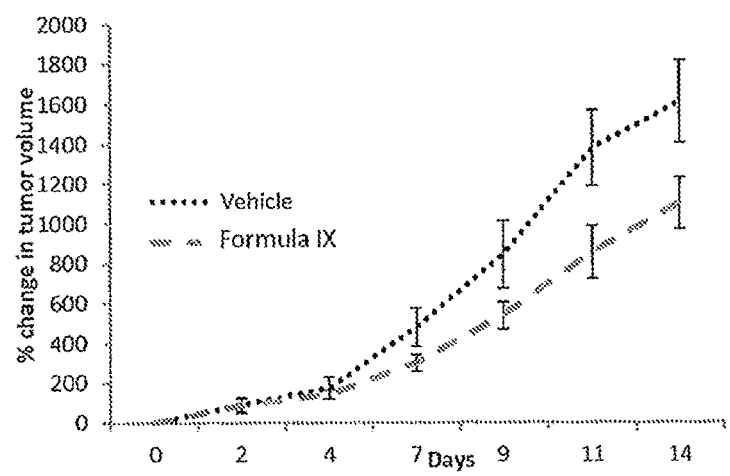
Figure 27C:
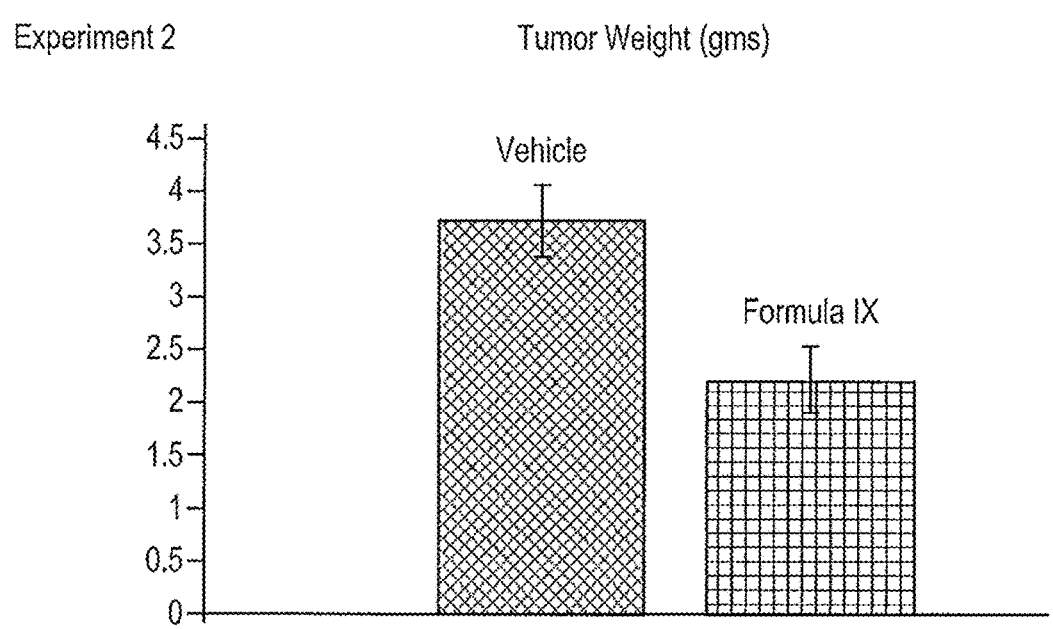

NSG mice obtained from JAX labs were housed with five animals per cage and were allowed free access to tap water and commercial rat chow (Harlan Teklad 22/5 rodent diet—8640). During the course of the study, the animals were maintained on a 12 hr light:dark cycle. Animals were anesthetized and BR-0001 TNBC fragments of 1 mm$^3$ (approximately) were implanted subcutaneously in NSG mice. Once the tumor size reached 100-200 mm$^3$, the animals were randomized and treated with vehicle control (polyethylene glycol:DMSO 9:1 ratio) or 10 mg/kg/day Formula IX (n=12) or enzalutamide orally. Tumor volume was measured thrice weekly. Tumor volume was calculated using the formula length×width×width×0.5236. Once tumors reached greater than 1500-2000 mm$^3$, animals were sacrificed and tumors weighted and stored for various analysis. Two regions of the same BR-0001 tumor, an AR-positive TNBC xenograft, were immunohistochemically stained with AR antibody (AR N20 from SCBT) (FIGS. 26A and 26B) and compared to an AR-negative (FIG. 26C) TNBC as a negative control. FIGS. 26A and 26B show that AR expression is consistent throughout this formalin-fixed, paraffin-embedded (FFPE) tissue, whereas similar FFPE in AR-negative TNBC demonstrated no staining (no AR expression). The tumor xenograft efficacy experimental results are provided in 27A-27C, with FIGS. 27A and 27B being replicate experiments. Formula IX (lower trace) produced some tumor growth inhibition of this AR-positive TNBC tumor in each experiment whereas enzalutamide was indistinguishable from vehicle treatment (FIGS. 26A and 26B). Formula IX reduced tumor weight in experiment 2 by ~40%.

Example 23

Figure 28A:
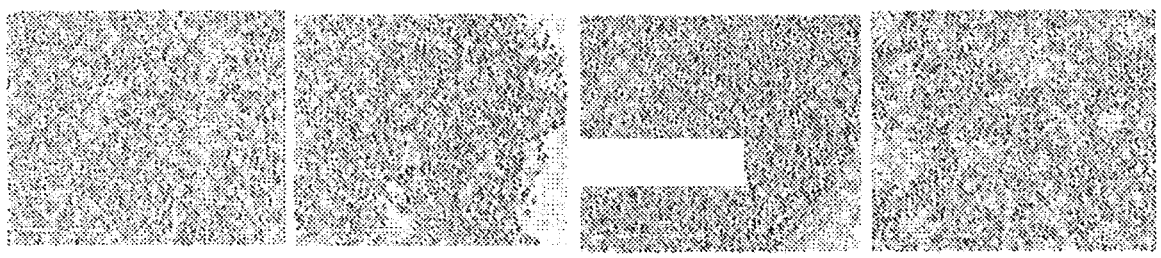
FIG. 28A-FIG. 28B depict immunohistochemistry of BR-0001 tumors from animals treated with vehicle or Formula IX and stained for Ki-67. Ki-67 was reduced in tumors of animals treated with Formula IX. Quantification of Ki-67 indicated an approximately 50% reduction in Ki-67 staining in 2 weeks of treatment. Tumors from experiment 2 were fixed in formalin and paraffin embedded. Slides were cut and stained with Ki-67 antibody (FIG. 28A), Ki-67 staining was reduced in tumors of animals treated with Formula IX. Ki-67 positive cells in each slide (total of 200 cells per view) were counted and represented as % stained cells (FIG. 28B). As a reference, inset into the graphics are bars which are 200 microns (μm) in length.
Figure 28A:
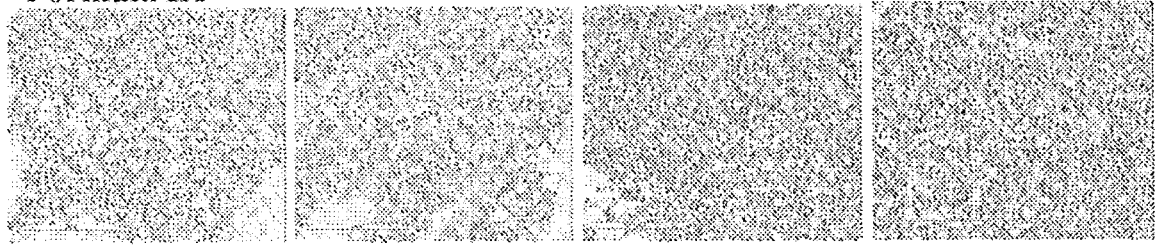
Figure 28A:
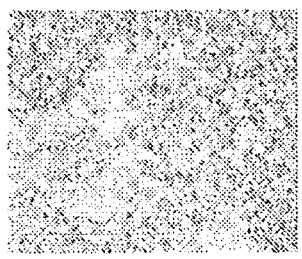
Figure 28B:
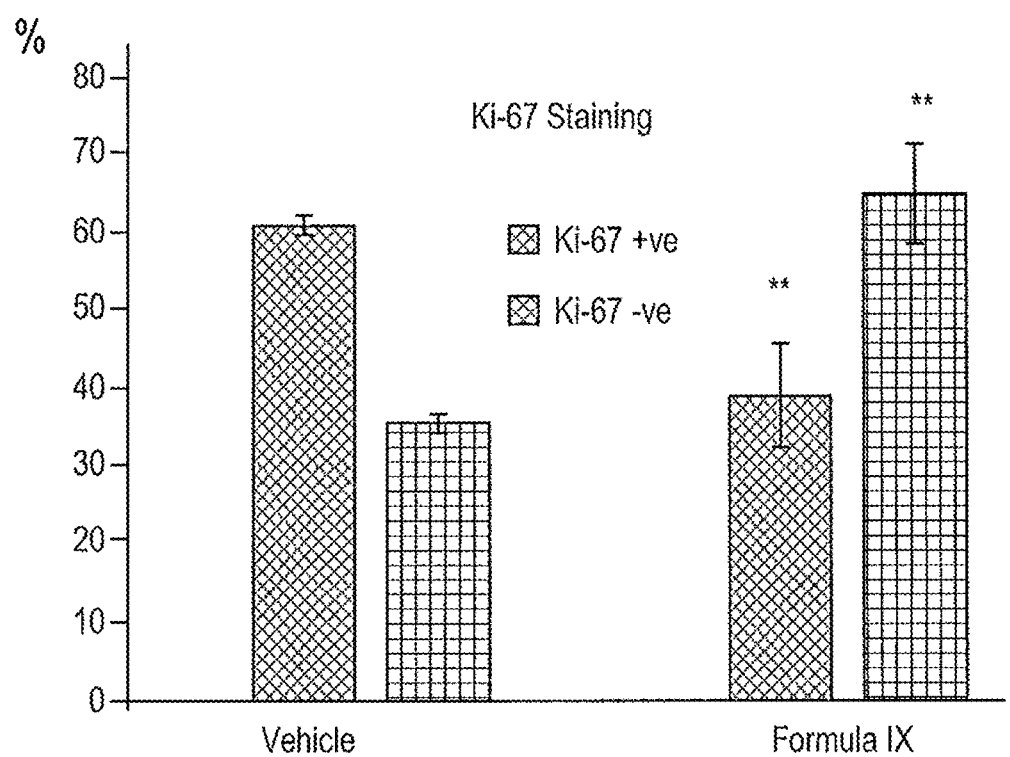

Ki-67 Staining was Reduced in AR-Positive TNBC Tumors of Animals Treated with Formula IX FIGS. 28A-28B demonstrated an approximately 50% reduction in Ki-67 staining in 2 weeks of treatment. Tumors from replicate experiment 2 (FIG. 27B) were fixed in formalin and paraffin embedded. Slides were cut and stained with Ki-67 antibody. Ki-67 positive cells (total 200 cells were counted in each slide) in each slide were counted and represented as % stained cells, as shown in FIG. 28B. Ki-67 staining was reduced in tumors of the animals treated with Formula IX.

Example 24

Gene Expression Study and Chip-Seq Study in AR-Positive TNBC Tumor Xenografts

Methods

Chromatin Immunoprecipitation Assay (ChIP).

Proteins were cross-linked by incubation with 1% formaldehyde (final concentration) at 37° C. for 10 min. Tumors were homogenized using a probe hand-held homogenizer. The cells were washed with 1×PBS twice, scraped in 1 mL of PBS containing protease inhibitors ([1 mg each of aprotinin, leupeptin, antipain, benzamidine HCl, and pepstatin/ml], 0.2 mM phenylmethylsulfonyl fluoride, and 1 mM sodium vanadate), pelleted, and resuspended in SDS lysis buffer (1% SDS, 10 mM EDTA, 50 mM Tris-HCl [pH 8.1]).

After lysis on ice for 10 min, the cell extract was sonicated (Branson sonifier 250) in a cold room eight times for 10 s each at constant duty cycle, with an output of 3 and with incubation on ice after every sonication. The debris was pelleted at 13,000 rpm for 10 min at 4° C., and the supernatant was diluted 10-fold with ChIP dilution buffer (0.01% SDS, 1.1% Triton X-100, 1.2 mM EDTA, 16.7 mM Tris HCl [pH 8.1], 167 mM NaCl). The proteins were precleared with 50 μL of 1:1 protein A-Sepharose beads in TE. An aliquot (300 μL) was reserved as input, while the remaining solution was incubated with 5 μg of AR antibody (AR N20 SCBT) and 2 μg of sheared salmon sperm DNA (Stratagene, La Jolla, Calif.) rotating overnight at 4° C.

The protein-DNA-antibody complex was precipitated by incubating with 100 μL of 1:1 protein A-Sepharose beads and 2 μg of salmon sperm DNA at 4° C. for 2 h. The beads were pelleted and washed three times with low-salt wash buffer (0.1% sodium dodecyl sulfate [SDS], 1% Triton X-100, 2 mM EDTA, 20 mM Tris HCl [pH 8.1], 0.15 M NaCl), and twice with 1×TE (10 mM Tris HCl, 1 mM EDTA; pH 8.0). DNA-protein complexes were obtained by extracting the beads with 50 μL of freshly prepared extraction buffer (1% SDS, 0.1 M NaHCO$_3$) three times. Cross-linking of the DNA protein complexes was reversed by incubating at 65° C. for 6 h. The DNA was extracted with a QIAquick PCR purification kit (QIAGEN, Valencia, Calif.) in 25 μL final volume of TE. The purified DNA was given to University of Tennessee Health Science Center Molecular Resource Center (UTHSC MRC) for next generation sequencing using ion proton sequencer.

RNA Analysis and Microarray.

Tumors were homogenized, RNA isolated, purified and submitted to the UTHSC MRC core facility for microarray analysis (ST2.0 array from Affymetrix).

Results

Figures 30A, 30B:
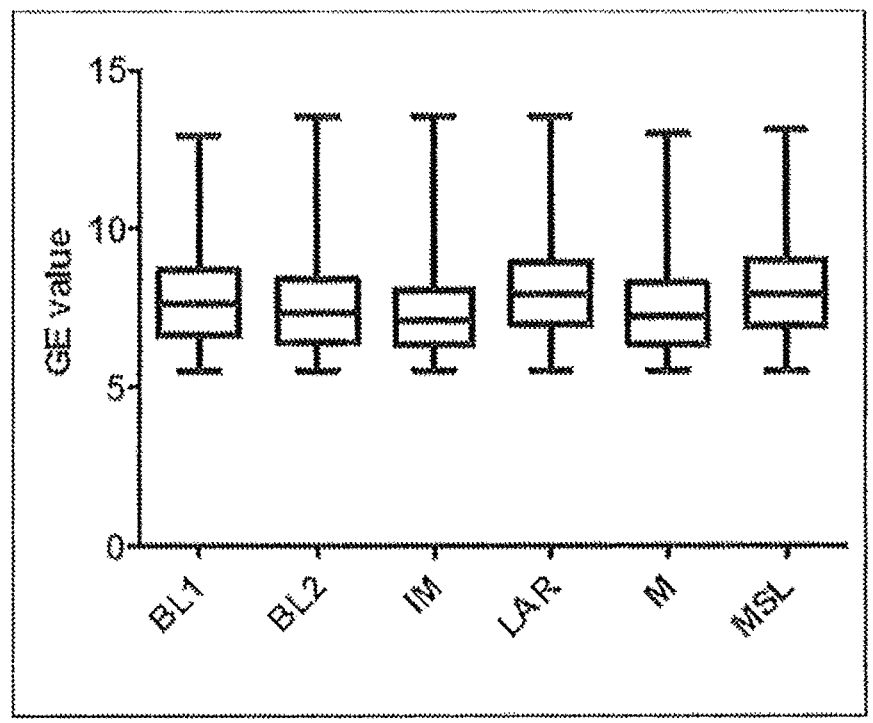
FIG. 30A and FIG. 30B depict gene expression data which is compared to the genes published (Pietenpol group) as useful to classify the Basal-Like Breast Cancer (BLBC) into subclassification. Sub-classification indicated that BR-0001 belonged to luminal androgen receptor (LAR) and mesenchymal stem-like (MSL) subtypes. The six TNBC subtypes according to the Pietenpol group include two basal-like (BL1 and BL2), an immunomodulatory (IM), a mesenchymal (M), a mesenchymal stem-like (MSL), and a luminal androgen receptor (LAR) subtype. GE—gene expression.
Figure 31:
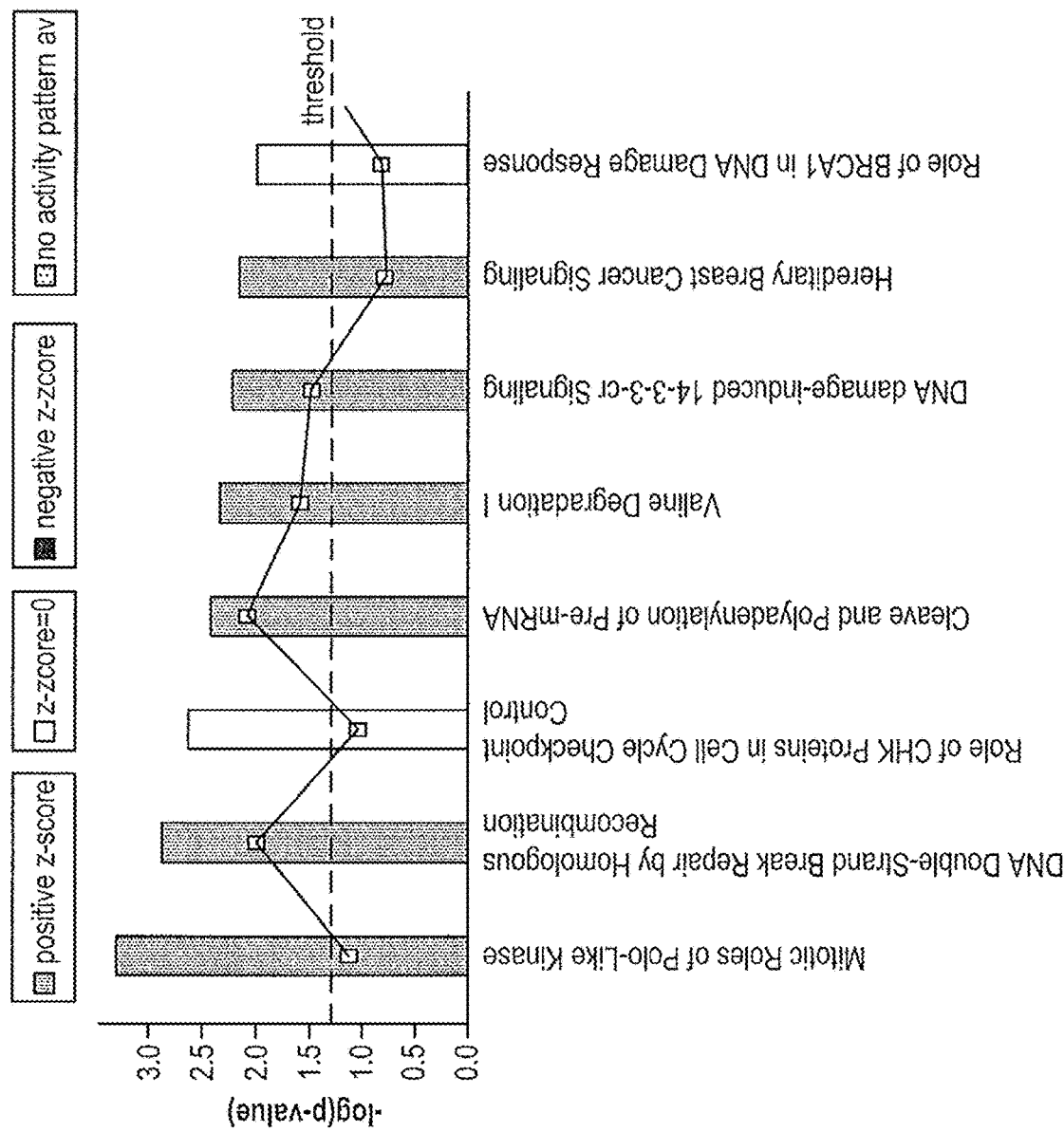
FIG. 31 depicts gene expression changes in BR-0001 tumors treated with Formula IX.

In the gene expression study described above, RNA was isolated from the BR-0001 TNBC tumors and the expression of genes in the entire genome was measured by microarray (Affymetrix, ST2.0 array). In the ChIP-Seq study, chromatin immunoprecipitation was performed in untreated BR-0001 specimen and the DNA immunoprecipitated with AR antibody was sequenced using ion torrent next-generation sequencer. It was shown that ~20% of AR-occupied promoters (−5 kb to +1 kb) were activated by androgen (mRNA increased by >1.5 fold) (data not shown). Androgen treatment primarily affected cell cycle and metabolic process according to gene set enrichment analysis (GSEA) (FIG. 31). Expression of TNBC subtype markers in FIGS. 30A and 30B show that in the SARM-treated tumors, gene markers for LAR and MSL subtypes are highly expressed.

Gene expression data was compared to PAM50 to determine the tumor type that BR-0001 belonged to. The expression (Z-score) of 50 genes required to classify the breast cancer is given in FIG. 29, in which PAM50 indicated that the tumor belonged to basal-like breast cancer (BLBC) TNBC.

Triple-negative breast cancer (TNBC) is a heterogeneous breast cancer group, and identification of its subtypes is essential for understanding the biological characteristics and clinical behaviors of TNBC as well as for developing personalized treatments. Based on 3,247 gene expression profiles from 21 breast cancer data sets, six TNBC subtypes, including 2 basal-like (BL1 and BL2), an immunomodulatory (IM), a mesenchymal (M), a mesenchymal stem-like (MSL), and a luminal androgen receptor (LAR) subtype from 587 TNBC samples with unique gene expression patterns and ontologies, were discovered (Brian D. Lehman et al., J. Clin. Invest. 2011, 121(7), 2750-2767). Cell line models representing each of the TNBC subtypes also displayed different sensitivities to targeted therapeutic agents. Gene expression data was compared to the genes published (Pietenpol group) to classify the BLBC into sub-classification. FIGS. 30A-30B depict that Pietenpol classification of TNBC suggests that the BR-0001 tumor is LAR and MSL subtypes.

Example 25

Gene Expression Changes in AR-Positive TNBC Xenograft Tumors

FIG. 31 demonstrates that in BR-0001 tumors Formula IX up-regulated gene expression. Approximately 4200 genes were up-regulated by Formula IX compared to vehicle, while approximately 1170 genes were down-regulated by Formula IX compared to vehicle. Formula IX recruited AR to 176 promoters (−5 kb to +1 kb). 20% of the promoters occupied by the AR in response to Formula IX also had the gene up-regulated by Formula IX. This showed that these genes were direct targets of the AR rather than an indirect effect. The Ingenuity Pathway Analysis (http://www.ingenuity.com/; QIAGEN, Redwood City, Calif.) suggests that genes involved in cell cycle were altered by Formula IX.

Example 26

The Efficacy and Safety of Formula IX on Metastatic or Locally Advanced ER+/AR+ Breast Cancer (BC) in Postmenopausal Women Study Design:

This is an open label, multicenter, multinational, randomized, parallel design Phase 2 study, and is to assess the efficacy and safety of Formula IX in postmenopausal subjects with ER+/AR+BC. Subjects will be randomized to receive either Formula IX 9 mg or 18 mg given PO daily for up to 24 months. Each dose arm will be treated independently and each assessed for efficacy using Simon's two-stage (optimal) design (Simon R. Optimal two-stage designs for Phase 2 clinical trials. *Controlled Clinical Trials* 1989; 10: 1-10). Subjects will be randomized in a 1:1 fashion to one of the two dose arms.

Randomization will be stratified by subjects presenting with bone only metastases and all other subjects, and further by setting of immediately preceding therapy (adjuvant setting or metastatic setting) in order to balance the proportion of subjects with these presenting features in each dose arm. There is no intent to statistically compare the two dose arms, but to determine whether either or both doses result in an acceptable clinical benefit response (CBR), defined as the proportion of evaluable subjects (i.e., subjects with centrally confirmed AR+ and who receive at least one dose of study drug) with either CR, PR, or SD by RECIST 1.1 at week 24, consistent with 30% while maintaining an acceptable safety profile. Given such a result, future exploration of Formula IX in ER+/AR+BC would be warranted at that dose level.

Thirty-six to eighty-eight (36-88) subjects with centrally confirmed AR+ who receive at least one dose of study drug (evaluable subjects) will be needed for primary efficacy analysis purposes and will be a subset of the full analysis set (FAS). Thirty-six to one hundred and eighteen (36-118) subjects, including replacement subjects, will be randomized in a 1:1 fashion to receive a daily PO dose of either Formula IX 9 mg or 18 mg. Thirty of the aforementioned subjects may be considered replacement subjects to account for lack of centrally confirmed AR+ status or for the rare subject who is randomized but does not receive study drug (assumes 25% of enrolled subjects are not evaluable for the primary efficacy analysis). Other statistical parameters that are part of the sample size calculation are $\alpha=0.025$ (one-sided) and power=90%. The first stage in each study arm will be assessed among the first 18 evaluable subjects. If at least 3/18 subjects achieve CB (defined as CR, PR, or SD) at week 24, the arm will proceed to the second stage of recruitment up to a total of 44 evaluable subjects per arm. Otherwise, the arm will be discontinued for lack of efficacy. Statistical significance, i.e., rejection of the null hypothesis of an unacceptably low CBR of $\leq 10\%$ in favor of the alternative hypothesis that indicates the higher rate, $\geq 30\%$, is more likely, will be declared if at least 9/44 subjects achieve CB at week 24 in that arm.

Subjects who are not centrally confirmed AR+ may remain on the trial, but will not be part of the primary efficacy analysis—these subjects will contribute to secondary and tertiary analyses.

Subjects on the 18 mg treatment arm who experience an adverse event (AE) with Grade $\geq 3$ intensity (National Cancer Institute—Common Terminology Criteria for Adverse Events [NCI-CTCAE], Version 4.0) and/or intolerance may have a dose reduction from 18 mg to 9 mg per day or a drug interruption based on the medical judgment of the Investigator and after confirmation by the study Medical Monitor. The drug interruption may last for a period of up to 5 days after which the subject must be rechallenged with study drug (18 mg or 9 mg) or discontinued from the study. In the case of a dose reduction, once the AE has resolved or reduced in intensity to Grade 1, the subject may be rechallenged with 18 mg or maintained at 9 mg at the discretion of the Investigator.

Subjects on the 9 mg treatment arm who experience an AE with Grade$\geq 3$ intensity (NCI-CTCAE 4.0) and/or intolerance may have a drug interruption based on the medical judgment of the Investigator and after confirmation by the study Medical Monitor. The drug interruption may last for a period of up to 5 days after which the subject must be rechallenged with study drug (9 mg) or discontinued from the study.

For safety analysis, subjects will be analyzed in the treatment arm in which they are initially dosed. For efficacy analysis, subjects will be analyzed according to the treatment arm to which they were randomized.

The subjects who demonstrate CB will be treated for up to 24 months from the date of randomization (as long as they continue to demonstrate CB from the treatment during these 24 months). Subjects who continue to demonstrate a CB from the study treatment at 24 months will be offered to continue in a safety extension study under a separate protocol. For safety purposes, all subjects will be followed-up for one month after the last dose of Formula IX is received.

For safety purposes, all subjects will be followed-up for one month after the last dose of Formula IX is received.

Target Population:

Adult postmenopausal women with metastatic or recurrent locally advanced ER+/AR+BC.

Study Duration:

The study duration is estimated at 3 years.

Description of Agent or Intervention:

Three (3) Formula IX 3.0 mg softgels for a 9 mg daily dose or six (6) Formula IX 3.0 mg softgels for an 18 mg daily dose will be taken PO with water at approximately the same time each day, with or without food.

Potential Benefits:

Based on the trial of Example 9, Formula IX 9 mg once daily has been studied in 22 postmenopausal women with metastatic ER+BC who have previously responded to hormonal therapy. The primary endpoint was assessed in 17 AR-positive subjects. Six of these 17 subjects demonstrated CB (SD) at six months. In one subject with SD (RECIST 1.1), tumor regression of 27% in a single target lesion was demonstrated. Seven subjects in total (one subject with indeterminate AR status) achieved CB at six months. Among the seven subjects who achieved CB at six months, time to progression (TTP) was estimated as 10.2 months. The results also demonstrated that, after a median duration on study of 81 days, 41 percent of all subjects (9/22) achieved CB as best response and also had increased PSA, which appears to be an indicator of AR activity. As of the finalization of this protocol, the study is still ongoing with one subject whose disease remains stable beyond 336 days.

Preclinical data with Formula IX suggests that it is also anabolic in bone and decreases bone turn over markers. Treatment with Formula IX may decrease bone turn over as compared with other hormonal therapies for the treatment of hormone receptor positive BC. Stronger bone microenvironment may decrease metastases to bone or delay time to skeletal related events.

Efficacy Objectives

The primary efficacy objective of this trial is to estimate the CBR at 24 weeks (defined as complete response [CR], partial response [PR], or SD) (by RECIST 1.1) of Formula IX 9 mg and of Formula IX 18 mg given PO daily in subjects with estrogen receptor positive and androgen receptor positive (ER+/AR+) BC who have centrally confirmed AR+ status.

The secondary efficacy objectives are to estimate the CBR at 24 weeks (by RECIST 1.1) of Formula IX 9 mg and 18 mg in all subjects randomized who receive at least one dose of study medication (the full analysis set [FAS]) regardless of AR status as determined by the central laboratory.

The additional secondary efficacy objectives apply to both centrally confirmed AR+ subjects (the evaluable subset of the FAS) as well as to all subjects in the FAS: (a) Estimate the objective response rate (ORR; defined as CR or PR) (by RECIST 1.1) of Formula IX 9 mg and 18 mg at 24 weeks; (b) Estimate the best overall response rate (BOR) of Formula IX 9 mg and 18 mg; (c) Estimate the progression free survival (PFS) of subjects receiving Formula IX 9 mg and 18 mg; (d) Estimate the TTP of subjects receiving Formula IX 9 mg and 18 mg; and (e) Estimate duration of response (time from documentation of tumor response to disease progression or death) of subjects receiving Formula IX 9 mg and 18 mg.

The tertiary objectives apply to both centrally confirmed AR+ subjects (the evaluable subset of the FAS) as well as to all subjects in the FAS (a) Assess the effect of Formula IX 9 mg and 18 mg on serum PSA; (b) Assess the effect of Formula IX 9 mg and 18 mg on Quality of Life (QoL) as measured by EQ-5D-5L; (c) Assess the effect of Formula IX 9 mg and 18 mg on circulating tumor cells (CTCs); (d) Assess the impact of duration of prior CB on outcome; (e) Assess the impact of time from diagnosis of metastases to randomization on outcome; (f) Describe the effect of Formula IX 9 mg and 18 mg on tumor volumetrics; (g) Assess the effect of plasma concentrations of Formula IX and Formula IX glucuronide on CBR at 24 weeks.

The safety objective is to describe the safety profile of Formula IX 9 mg and 18 mg PO daily in subjects with ER+/AR+BC with centrally confirmed AR+ as well as in all subjects randomized and treated.

The pharmacokinetic objective: To describe the plasma concentrations of Formula IX and Formula IX glucuronide at each of the assessed time points.

Formulation, Packaging, and Labelling:

Formula IX 3.0 mg Softgels will be supplied as opaque, white to off-white, size 5, oval Softgel capsules containing 3.0 mg of Formula IX. The liquid Softgel fill is composed of Formula IX dissolved in polyethylene glycol 400. Formula IX 3.0 mg Softgels will be packaged in blister packs. Each blister pack will contain sufficient study drug for one (1) week of dosing. At randomization (Visit 2) and at Visits 3, 4, and 5), subjects will be provided with a carton of study drug containing 7 blister packs, equivalent to 7 weeks of dosing. At Visits 6, 8, 9, 10, 11, 12, and 13, in order to accommodate the visit schedule of every 12 weeks (±7 days), the subjects will receive two carton boxes of study drug (each containing 7 blisters) to cover study treatment for 14 weeks. Subjects will be requested to bring with them the carton box with all blister packs at every visit.

Each blister pack will be comprised of an appropriate number of blister strips (1 blister for the 9 mg treatment arm and 2 blisters for the 18 mg treatment arm) encased in a child-resistant heat-sealed card. The blister strips are composed of a PVC/ACLAR base and an aluminum foil/PVC/ PVAC copolymer and polymethacrylate (product contact) lidding. Perforations on the back of the heat-seal card overlay the foil lidding. To remove the study drug, subjects will release the appropriate perforation by depressing a release button on the inside of the card. Once released, the perforation can be removed and the study drug pushed through the foil.

Pharmacokinetic Assessment:

Blood samples for pharmacokinetic assessment will be collected at baseline (pre-dose), Visit 3 (week 6), Visit 5 (week 18), and Visit 6 (week 24). One blood sample will be collected in a 6 mL $K_2$-ethylenediaminetetraacetic acid (EDTA) blood collection tube on each of these days. The exact time (hh:mm) and date that each blood sample is collected will be recorded on the electronic Case Repot Form. At the baseline visit, the blood sample should be collected before the subject is given their first dose of Formula IX. At Visits 3 (week 6), 5 (week 18), and 6 (week 24), the date and approximate time of the last dose of Formula IX prior to the blood sample should be recorded; i.e., it should be documented whether the subject took the previous dose that morning or the evening before. Immediately after collection, the tubes will be gently inverted several times to mix the anticoagulant with the blood sample.

Blood samples will be kept on wet ice (ice packs in a water bath is also acceptable) for up to 20 minutes until processed. The plasma fraction will be separated by placing the collection tube into a centrifuge for 10 minutes at 1,500×g. The plasma fraction will be withdrawn by pipette and divided into two 2 mL polypropylene transfer vials (with each tube receiving approximately equal aliquots).

All sample collection and freezing tubes will be clearly labeled in a fashion which identifies the subject, the study number, the visit number, and freezing tube aliquot letter. Labels will be fixed to freezing tubes in a manner that will prevent the label from becoming detached after freezing. Samples will be stored in a freezer at −20° C. or lower. Samples will be shipped in a thermal insulated container with sufficient dry ice to assure they remain frozen.

Any remaining plasma samples after completion of the protocol outlined pharmacokinetic analysis may be used to identify and quantify the metabolites of Formula IX.

Example 27

The Efficacy and Safety of Formula IX on Advanced, Androgen Receptor-Positive Triple Negative Breast Cancer (AR+ TNBC)

Ongoing and Completed Clinical Trials with Formula IX:

Twenty-one Phase 1, 2, and 3 clinical trials have been completed or are ongoing with Formula IX. These include: 1. Protocol G100401, a Phase 1 single ascending dose study in 96 healthy, young, male volunteers; 2. Protocol G100402, a Phase 1 multiple ascending dose study in 50 healthy, young, male volunteers, and 23 elderly male volunteers with truncal obesity; 3. Protocol G100503, a Phase 1 single dose pharmacokinetic study to assess the effect of a dosage regimen that simulates a sustained release formulation to an immediate release formulation in 18 healthy, young male volunteers and 18 postmenopausal women; 4. Protocol G100506, a Phase 1 single dose pharmacokinetic study to assess the relative bioavailability of a 3 mg hard shell capsule formulation to be used during continued clinical development and to assess the effect of food on the pharmacokinetics of the 3 mg softgel formulation in 27 healthy, young, male volunteers; 5. Protocol 006, a Phase 1 single dose and multiple dose pharmacokinetic study in 24 postmenopausal, Japanese women; 6. Protocol G200501, a Phase 2 study in 60 postmenopausal women and 60 elderly men to assess lean body mass and physical function; 7. Protocol 003, a Phase 1b study in 44 postmenopausal women; 8. Protocol G200502, a Phase 2b study in 159 men and postmenopausal women with cancer to assess lean body mass and physical function; 9. Protocol G100511, a Phase 1 study to assess the effect of severe renal impairment on the pharmacokinetics of Formula IX; 10. Protocol G100508, a Phase 1 study to assess the effect of mild and moderate hepatic impairment on the pharmacokinetics of Formula IX; 11. Protocol G100509, a Phase 1 mass balance study of Formula IX in healthy volunteers; 12. Protocol G100507, a Phase 1 study to assess the pharmacokinetics and absolute oral bioavailability of Formula IX in Caucasian and African American men and women; 13. Protocol G100510, a single-dose, randomized, double-blind, comparative, positive and placebo-controlled, four-period crossover Phase 1 study to define the electrocardiogram (ECG) effects of Formula IX, at therapeutic and supratherapeutic doses, in healthy male and female subjects: a thorough ECG trial; 14. Protocol G100512, a Phase 1 study to assess the effect of ketoconazole (Cytochrome P450, Family 3, Subfamily A [CYP3A4] inhibitor) on the pharmacokinetics of Formula IX; 15. Protocol G100513, a Phase 1 study to assess the effect of rifampin (CYP3A4 inducer) on the pharmacokinetics of Formula IX; 16. Protocol G100514, a Phase 1 study to assess the pharmacokinetic drug:drug interaction of Formula IX and celecoxib (CYP2C$_9$); 17. Protocol G100515, a Phase 1 study to assess the pharmacokinetic drug:drug interaction of Formula IX and probenecid (UGT2B7); 18. Protocol G100516, a Phase 1 study to assess the pharmacokinetic drug:drug interaction of Formula IX and rosuvastatin (breast cancer resistance protein [BCRP]); 19. Protocol G300504, a Phase 3 randomized, double-blind, placebo-controlled study of the effect of Formula IX on muscle wasting in 321 subjects with non-small cell lung cancer receiving first line platinum plus a taxane chemotherapy; 20. Protocol G300505, a Phase 3 randomized, double-blind, placebo-controlled study of the effect of Formula IX on muscle wasting in 320 subjects with non-small cell lung cancer receiving first line platinum plus a non-taxane chemotherapy; 21. Protocol G200801, an ongoing, Phase 2, open label study to examine AR status and the activity of Formula IX hormonal therapy in 22 women with ER-positive metastatic breast cancer who have previously responded to hormone therapy.

The 18 mg Dose:

Formula IX has been evaluated in 21 completed and ongoing clinical studies enrolling over 1,500 total subjects. Formula IX has been generally well-tolerated, including single doses up to 100 mg and multiple doses up to 30 mg once daily for up to 14 days. In longer studies, Formula IX has also been generally well tolerated, including 1, 3, and 9 mg daily doses for up to 184 days.

Previous clinical studies demonstrated that daily doses up to 30 mg of Formula IX were well tolerated in healthy male volunteers. Both 10 mg and 30 mg daily doses were evaluated in Protocol G100402 for up to 14 days. Elevated alanine transaminase (ALT) (any elevation outside upper limit of normal [ULN]) was the most common adverse event (AE) experienced. None of the subjects in the 10 mg dose group were discontinued from the study due to ALT elevations. In the 30 mg dose group, six subjects experienced ALT increases above two times the ULN.

Formula IX 3 mg given daily was evaluated in two completed Phase 3 trials, in over 600 subjects, for the prevention and treatment of muscle wasting (cachexia) in subjects with advanced non-small cell lung cancer receiving chemotherapy. Formula IX 3 mg increased lean body mass in both studies and was safe and well tolerated when dosed for up to 168 days. Subjects in the Formula IX and placebo groups experienced similar AEs and these AEs were consistent with the background chemotherapy regimen.

Although Formula IX 3 mg was chosen for its anabolic activity in muscle for the completed Phase 3 program, a dose of 9 mg once daily was selected for hormonal therapy in the ongoing Phase 2 trial in ER+ and AR+ metastatic breast cancer in order to achieve a higher exposure that is both safe and more likely to be efficacious in women with advanced breast cancer. Seven out of twenty-two subjects with advanced, heavily pretreated (hormonal therapy, radiation, and chemotherapy) breast cancer demonstrated clinical benefit (CB) (stable disease [SD]) at 6 months. In one subject with SD (by Response Evaluation Criteria in Solid Tumors [RECIST], Version 1.12), tumor regression of 27% was demonstrated. Consistent with the previous studies, Formula IX remained safe and well tolerated (see Example 9).

Reductions in sex hormone binding globulin (SHBG) have been identified as one of the most sensitive serum biomarkers for AR signaling in healthy volunteers and patients. SHBG was reduced by 15.1%, 15.6%, 18.2%, and 18.4% in young, healthy volunteers who received PO Formula IX 1 mg, 3 mg, 10 mg, and 30 mg daily for 14 days, respectively, in Protocol G100402 (listed as trial #2 above), suggesting that doses of 10 mg and above maximally stimulate AR activity.

Dosing Formula IX at 15-20 mg per day may provide therapeutic benefit in hormone receptor positive breast cancer by two separate mechanisms: activating AR and inhibiting progesterone receptor, thereby increasing potential efficacy. Progesterone receptor expression in cancer stem cells has been shown to be involved in proliferation of cancer epithelial cells, and inhibiting progesterone receptor's activity is now considered a novel approach to treating breast cancer. Hence, Formula IX at higher doses might provide dual anti-proliferative effects in breast cancer. In TNBC, doses of 15-20 mg per day should provide saturation of the AR potentially providing better efficacy as opposed to a lower dose with partial occupancy of the AR and absence of any progesterone receptor inhibitory effect.

Based on the safety data collected to date in both preclinical and clinical settings, the 18 mg dose is expected to be safe and generally well tolerated. However, in the event that a subject has a Grade 3 or greater toxicity, the 18 mg dose may be reduced to 9 mg until the AE resolves or for the remainder of treatment based on the Investigator's discretion. The 9 mg dose has been previously studied in postmenopausal women with metastatic breast cancer and was safe and well tolerated.

In TNBC patients, the 18 mg dose is preferred over a lower dose due to the aggressive phenotype of the disease and poor prognosis. Based on preclinical data, the 18 mg dose is more likely to saturate the AR and may lead to better clinical outcomes than a lower dose without receptor saturation or progesterone receptor inhibition.

The 18 mg dose may provide greater efficacy in TNBC without compromising subject safety. However, in the event that a subject has a Grade 3 or greater toxicity, the 18 mg dose may be reduced to 9 mg until the AE resolves or for the remainder of treatment based on the Investigator's discretion. The 9 mg dose has been previously studied in postmenopausal women with metastatic breast cancer and was safe and well tolerated.

In TNBC patients, the 18 mg dose is preferred over a lower dose due to the aggressive phenotype of the disease and poor prognosis. Based on preclinical data, the 18 mg dose is more likely to saturate the AR and may lead to better clinical outcomes than a lower dose without receptor saturation or progesterone receptor inhibition. 18 mg dose may provide greater efficacy in TNBC without compromising subject safety.

Study Design:

This is an open label, multicenter, multinational, Phase 2 study to assess the efficacy and safety of Formula IX in female subjects with androgen receptor-positive, triple negative breast cancer (AR+ TNBC). Subjects will be administered Formula IX, 18 mg orally (PO) daily for up to 12 months. Simon's two-stage (optimal) design will be used to assess primary efficacy and will require up to 41 evaluable subjects; i.e., subjects with centrally confirmed AR+ who receive at least one dose of study drug. In order to obtain these numbers of evaluable subjects, 21 to 55 subjects, including over-enrollees (see below), will be enrolled to receive a daily PO dose of GTx-024 18 mg. Fourteen of the aforementioned subjects may be over-enrollees to allow for replacement of subjects to account for lack of centrally confirmed AR+ status, or for the rare subject who is enrolled but does not receive study drug. The trial will test for an unacceptably low clinical benefit rate (CBR) of ≤5% versus a CBR more consistent with ≥20%. The first stage will be assessed among the first 21 evaluable subjects. If at least 2/21 subjects achieve clinical benefit (CB) (defined as complete response [CR], partial response [PR], or stable disease [SD], per Response Evaluation Criteria in Solid Tumors [RECIST], Version 1.12) at week 16, then the trial will proceed to the second stage of recruitment of up to a total of 41 subjects in the evaluable subset of the Full Analysis Set (FAS). Otherwise, the trial will be discontinued for lack of efficacy.

Subjects who are not confirmed AR+ may remain on the trial, but will not be part of the primary efficacy analysis—these subjects will contribute to secondary and tertiary analyses. Subjects who experience an adverse event (AE) with Grade≥3 intensity (National Cancer Institute Common Terminology Criteria for Adverse Events [NCI-CTCAE], Version 4.0) and/or intolerance may have a dose reduction from 18 mg to 9 mg per day or a drug interruption based on the medical judgment of the Investigator and after confirmation by the study Medical Monitor. The subjects who demonstrate clinical benefit (CB) will be treated for up to 12 months from the date of the first dose of study treatment (as long as they continue to demonstrate CB from the treatment during these 12 months). Subjects who continue to demonstrate a beneficial response from the study treatment at 12 months will be offered to continue in a safety extension study under a separate protocol. All subjects will be followed-up for one month after the last dose of Formula IX is received, for safety purposes.

Primary efficacy objective of this trial is to estimate the clinical beneficial rate (CBR) at 16 weeks (defined as complete response (CR), partial response (PR), or stable disease (SD)) (by RECIST 1.1) of Formula IX 18 mg given orally (PO) daily in subjects with TNBC and centrally confirmed AR+ status.

Secondary Efficacy Objectives:

Estimate the CBR at 16 weeks of Formula IX 18 mg in all subjects enrolled who receive at least one dose of study medication (i.e., the full analysis set (FAS)) regardless of AR status as determined by the central laboratory.

The following secondary efficacy objectives apply to both centrally confirmed AR+ subjects (the evaluable subset of the FAS) as well as to all subjects in the FAS:

Estimate the objective response rate (ORR; defined as CR or PR) (by RECIST 1.1) of Formula IX 18 mg at 16 weeks.

Estimate the CBR of Formula IX 18 mg at 24 weeks.

Estimate the ORR (defined as CR or PR) of Formula IX 18 mg at 24 weeks.

Estimate the best overall response rate (BOR) of Formula IX 18 mg.

Estimate the progression free survival (PFS) of subjects receiving Formula IX 18 mg.

Estimate the time-to-progression (TTP) of subjects receiving Formula IX 18 mg.

Estimate duration of response (time from documentation of tumor response to disease progression or death) of subjects receiving Formula IX 18 mg.

Tertiary Objectives:

The following tertiary efficacy objectives apply to both centrally confirmed AR+ subjects (the evaluable subset of the FAS) as well as to all subjects in the FAS:

Assess the effect of Formula IX 18 mg on serum prostate specific antigen (PSA).

Assess the effect of Formula IX 18 mg on Quality of Life (QoL) as measured by EQ-5D-5L.

Assess the effect of Formula IX 18 mg on circulating tumor cells (CTCs).

Assess the impact of duration of prior CB on outcome.

Assess the impact of time from diagnosis of metastases to study enrollment on outcome.

Describe the effect of Formula IX 18 mg on tumor volumetrics.

Assess the effect of plasma concentrations of Formula IX and Formula IX glucuronide on CBR at 16 and 24 weeks.

Safety Objective:

To describe the safety profile of Formula IX 18 mg PO daily in subjects with TNBC and centrally confirmed AR+ as well as in all subjects enrolled and treated.

Pharmacokinetic Objective:

To describe the plasma concentrations of Formula IX and Formula IX glucuronide at each of the assessed time points.

Target Population:

Adult women with advanced TNBC with centrally confirmed AR+.

Subject Inclusion Criteria:

Subjects eligible for inclusion in this study must meet all of the following criteria:

Able and willing to give voluntary, written and signed, informed consent;

Women ≥18 years of age;

Women with TNBC who have received at least one but no more than two prior chemotherapy regimens for the treatment of advanced or metastatic TNBC;

Confirmation of AR+(defined as ≥10% nuclear AR staining by immunohistochemistry [IHC]) TNBC in either the primary or metastatic lesion, assessed during the screening period by a local laboratory or by medical history;

TNBC confirmed by medical history as: human epidermal growth factor receptor 2 [HER2]-negative (confirmed by IHC 0, 1+ regardless of fluorescence in situ hybridization [FISH] ratio; IHC 2+ with FISH ratio lower than 2.0 or HER2 gene copy less than 6.0; FISH ratio of 0, indicating gene deletion, when positive and negative in situ hybridization [ISH] controls are present); estrogen receptor (ER) negative (confirmed as ER expression less than or equal to 1% positive tumor nuclei); progesterone receptor-negative (confirmed as progesterone receptor expression less than or equal to 1% positive tumor nuclei);

Availability of paraffin embedded or formalin fixed tumor tissue; OR, a minimum of 10 and up to 20 slides of archived tumor tissue for central laboratory confirmation of AR status and molecular subtyping. Metastatic tumor tissue is preferred when possible;

Subjects must have either measurable disease or bone-only non-measurable disease, evaluable according to RECIST 1.1;

Eastern Cooperative Oncology Group (ECOG) performance status of 0 or 1 at the time of screening and enrollment;

Negative pregnancy test in women of childbearing potential (premenopausal or less than 12 months of amenorrhea post-menopause, and who have not undergone surgical sterilization), no more than 7 days before the first dose of study treatment;

For women of childbearing potential who are sexually active, agreement to use a highly effective, non-hormonal form of contraception during and for at least 6 months after completion of study treatment; OR, a fertile male partner willing and able to use effective non-hormonal means of contraception (barrier method of contraception in conjunction with spermicidal jelly, or surgical sterilization) during and for at least 6 months after completion of study treatment;

Adequate organ function as shown by: Absolute neutrophil count ≥1,500 cells/mm³; Platelet count≥100,000 cells/mm3; Hemoglobin ≥9 g/dL; Serum aspartate aminotransferase (AST) and alanine aminotransferase (ALT) ≤2.5 Upper Limit of the Normal range (ULN) (or ≤5 if hepatic metastases are present); Total serum bilirubin ≤2.0×ULN (unless the subject has documented Gilbert Syndrome); Alkaline phosphatase levels ≤2.5×ULN (≤5×ULN in subjects with liver metastasis); Serum creatinine <2.0 mg/dL or 177 μmol/L; International normalized ratio (INR) or activated partial thromboplastin time (aPTT)<1.5×ULN (unless on anticoagulant treatment at screening);

Able to swallow capsules;

Any toxicity from prior chemotherapy has resolved or Grade 1 (NCI-CTCAE, Version 4.0).

Formulation, Packaging, and Labelling

Formula IX 3.0 mg Softgels will be supplied as opaque, white to off-white, size 5, oval Softgels. The liquid Softgel fill is composed of Formula IX dissolved in polyethylene glycol 400. Dosing instructions will be provided on the study drug label and in the subject information sheet.

Example 28

Formula IX Reduced the Growth of HER2-Positive Tumors

Methods

Figure 32:
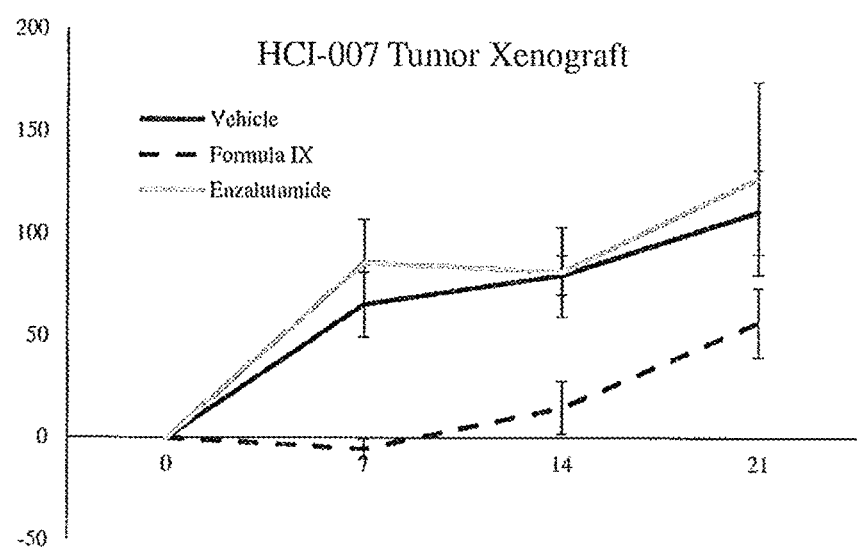
FIG. 32 depicts reduced tumor growth of ER-positive, PR-positive, HER2-positive and AR-positive tumors composed of HCI-007 cells using Formula IX.

HCI-007 tumor pieces (1 mm³) were implanted surgically (one per mouse) under the skin on the flanks of NSG mice. Simultaneously, 17β-estradiol pellet (Innovative Research of America) was implanted surgically under the skin of each mouse. Tumors were allowed to grow and reach approximately 100 mm³ volume (1*W*W*0.526). Mice were randomized and treated orally with vehicle (15% DMSO+85% PEG-300), Formula IX (10 mg/kg), or enzalutamide (20 mg/kg). Tumor volume was measured weekly and represented as % change in tumor volume (FIG. 32). Mice were sacrificed and tumors stored for further analysis.

Results

As described in FIG. 32, ER-positive, PR-positive, HER2-positive and AR-positive tumors of animals treated with vehicle and enzalutamide grew comparably, while the tumors of mice treated with Formula IX grew slowly. Tumors of animals treated with Formula IX regressed during the first 7 days, before started to slowly increase. (See also Example 30, and FIGS. 35A-35C.)

Conclusion

These results support the previous results observed in MCF-7 cells xenograft demonstrating that Formula IX reduced the growth of HER2-positive tumors. (See Example 30.)

Example 29

Formula IX Inhibits Growth in HCI-013 Patient Derived Xenografts that are Triple Positive (ER, PR, HER2), and Also Express AR Methods HCI-013 tumor pieces (1 mm³) were implanted surgically (one per mouse) under the skin on the flanks of NSG mice. Tumors were allowed to grow and reach approximately 100 mm³ volume (1*W*W*0.526). Mice were randomized and treated orally with vehicle (15% DMSO+85% PEG-300) or Formula IX (10 mg/kg). Tumor volume was measured weekly and represented as % change in tumor volume. Mice were sacrificed, tumors weighed, and stored for further analysis.

Results

Figure 33A:
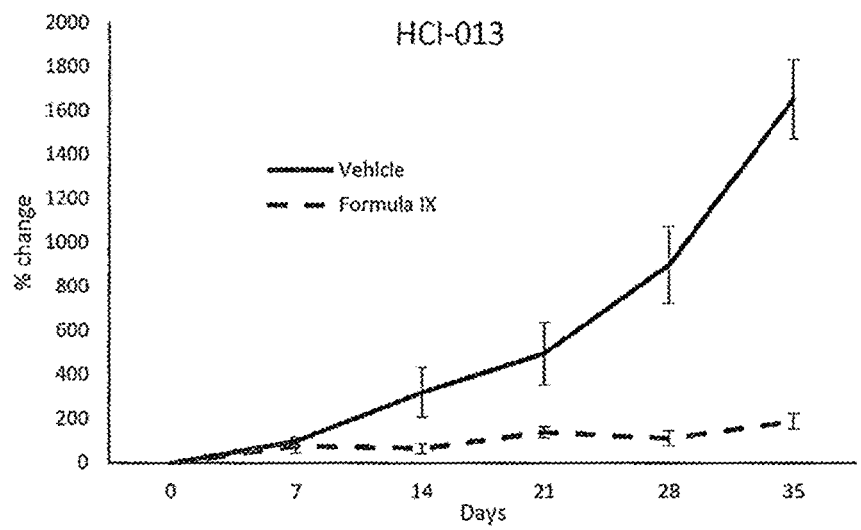
FIG. 33A and FIG. 33B depict potent tumor growth reduction using Formula IX in xenografts composed of HCI-013 cells. HCI-013 phenotype is a triple positive and also expresses AR.
Figure 33B:
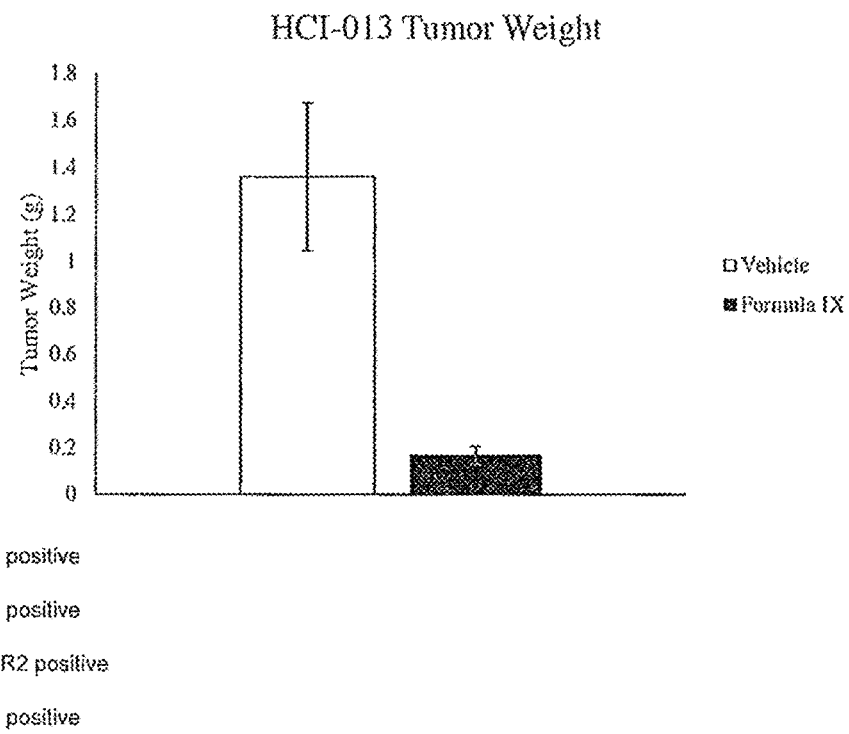

As described in FIGS. 33A and 33B, triple positive HER2 tumors of animals treated with vehicle grew robustly, while the tumors of mice treated with Formula IX grew very slowly. Tumors of Formula IX treated animals did not grow appreciably through the duration of the experiment suggesting that there is almost a 100% tumor growth inhibition (TGI) (FIG. 33A). The tumor volume results are reflected in tumor weights observed at the end of the experiment (FIG. 33B).

Conclusion

These results indicate that Formula IX is extremely potent in tumors that are triple positive (express ER, PR, and HER2) and also express AR. See also Example 30, where HCI-13 was further characterized to include genotyping of the ER in the tumor which revealed the Y537S mutant ER was present in the HCI-13 tumor.

Example 30

Inhibition of Proliferation and Growth of Patient-Derived Xenografts (PDX) and Tissues that Express Wildtype and Mutant Refractory ER In the study, it was found that proliferation and growth of patient-derived xenografts (PDX) and tissues that express wildtype and mutant refractory ER were inhibited by AR agonists and tissue-selective AR modulators (SARMs), but not by antagonists. The AR agonists inhibited the growth of these tumors by reprogramming the ER cistrome and subsequently inhibiting ER function and by altering the phosphokinome signature.

Materials and Methods
Reagents

TaqMan PCR primers and fluorescent probes, master mixes, and Cells-to-Ct reagents were obtained from Life Technologies (Carlsbad, Calif.). Cell culture medium and charcoal-stripped fetal bovine serum (csFBS) were purchased from Fisher Scientific (Waltham, Mass.). FBS was purchased from Hyclone (San Angelo, Tex.). AR-N20 antibody was procured from Santa Cruz Biotechnology (Santa Cruz, Calif.). Enzalutamide was purchased from MedKoo Biosciences (Chapel Hill, N.C.). ER-α (D8H$_8$) antibody was procured from Cell Signaling (Danvers, Mass.). Actin antibody, DHT, tamoxifen, and fulvestrant were purchased from Sigma (St. Louis, Mo.). Vetspon dental cubes/sponges (Patterson Veterinary Supplies Inc., NC0654350) were obtained from Fisher Scientific (Waltham, Mass.). Epidermal growth factor (EGF) was purchased from R&D systems (Minneapolis, Minn.), phorbol 12-myristate 13-acetate (PMA) was obtained from Acros organics, and 17β-estradiol was obtained from Tocris (Bristol, UK). All other reagents used were analytical grade.

Cell Culture

MCF-7 and ZR-75-1 cells were obtained from American Type Culture Collection (ATCC, Manassas, Va.). The cells were cultured in accordance with the ATCC recommendations.

Growth Assay

Cells were plated at varying densities in growth medium in 96 well plates. Cells were treated as indicated in the figures and viability measured using sulforhodamine B (SRB) or the number of cells counted using Coulter counter.

Transfection

MCF-7 stable cells were generated by lentiviral infection of green-fluorescent protein (GFP) or the AR cloned into pLenti U6 Pgk-puro vector as described earlier (Narayanan et al. (2014) PLoS One 9, e103202; Yang et al. (2010) Canc Res 70, 8108-8116; Yepuru et al. (2013) Clin Cancer Res 19(20), 5613-5625).

Tumor Xenograft Experiments

All animal protocols were approved by The University of Tennessee Health Science Center (UTHSC) Institutional Animal Care and Use Research Committee. Xenograft experiments were performed as previously published (Narayanan et al. (2014) PLoS One 9, e103202). Briefly, 3 million MCF-7 cells were suspended in 0.05 ml MEM+10% FBS and 0.05 ml Matrigel/nude mouse and were injected subcutaneously. Once the tumor size reached 100-200 mm$^3$, the animals were randomized and treated orally with the indicated drugs formulated in DMSO:PEG-300 (15:85). HCI-7, HCI-9, and HCI-13 PDXs were gifts kindly donated by Dr. Alana Welm (Huntsman Cancer Institute, Salt Lake City, Utah). HCI PDX tumor fragments (1 mm$^3$) were surgically implanted under the mammary fat pad in female NOD SCID Gamma (NSG) mice. Tumor volume was measured twice weekly for MCF-7 xenograft and once or twice weekly for HCI PDXs. At the end of the study, animals were sacrificed and tumors were excised, weighed, and stored for various analyses.

Patient Specimen Collection

Specimens from breast cancer patients were collected with patient consent under a protocol approved by the UTHSC Institutional Review Board (IRB). Specimens were collected immediately after surgery in RPMI medium containing penicillin:streptomycin and Fungizone and transported to the laboratory on ice. The tissues were finely minced and treated with collagenase for 2 hours. The digested tissues were washed with serum-free medium and frozen in liquid nitrogen in freezing medium (5% DMSO+ 95% FBS) or implanted under the mammary fat pad in female NSG mice.

Sponge Culture

HCI-13 tumors grown in female mice were allowed to reach 500-1000 mm$^3$ before the animals were sacrificed and the tumors were excised to be used for sponge culture. Patient specimens frozen in liquid nitrogen in freezing medium were used for sponge culture. Sponge cultures were performed in accordance to the protocol published earlier (Dean et al. (2012) Cell Cycle 11, 2756-2761; Hu et al. (2016) Cancer Res 76, 5881-5893; Ochnik et al. (2014) Menopause 21, 79-88). Tumors were sliced into small pieces (~1 mm$^3$) and incubated on pre-soaked gelatin sponges (5 fragments/sponge) in 12 well plates containing 1.5 mL medium (MEM+10% FBS+2 mM L-glutamine+10 µg/mL insulin+10 µg/mL hydrocortisone+penicillin:streptomycin). The cultures were performed in triplicates for HCI-13 and singly for patient specimens. Pooled samples (n=5/sponge) from each sponge constituted one sample. Medium was replaced the next day and treated as indicated in the figures. Tissues were harvested after 3 days of treatment, RNA extracted, and expression of various genes measured. Although the same procedure was adopted for specimens obtained from breast cancer patients, the specimens were cultured singly (n=5/sponge=one sample) and not in triplicates as performed for HCI-13. Characteristics of the patient specimens used in PDX and in sponge cultures are provided in Table 12.

TABLE 12

| Patient ID | ER (%) | PR (%) | HER2 (of 3) | Ki-67 (%) | Type | Treatments prior to sample collection |
|---|---|---|---|---|---|---|
| 1005 | 90 | 90 | 1+ | 12 | Adenocarcinoma | No previous treatment |
| 1075 | 30 | 10 | N.D. | 70 | Invasive ductal carcinoma | Neoadjuvant (taxol) |
| 1074 | 90 | N.D. | 0-1+ | 19 | Invasive lobular carcinoma | Radiation, tamoxifen |
| 1073 | 95 | 95 | 1+/3+ | 8 | Infiltrating ductal carcinoma | No previous treatment |
| 1053 | 100 | 0 | 3+ | N.D. | Infiltrating lobular carcinoma | Taxol, Herceptin |
| 1050 | 100 | 84 | 0 | N.D. | Infiltrating ductal carcinoma | No previous treatment |
| 1045 | 100 | 90 | N.D. | ND. | Infiltrating lobular carcinoma | No previous treatment |

TABLE 12-continued

| Patient ID | ER (%) | PR (%) | HER2 (of 3) | Ki-67 (%) | Type | Treatments prior to sample collection |
|---|---|---|---|---|---|---|
| HCI-13 | + | + | + | | Infiltrating lobular carcinoma. Bone, brain, lung, pericardium, liver mets | Leuprolide, letrozole, exemestane, tamoxifen, zoledronic acid, cyclophosphamide, methotrexate, 5-fluorouracil, paclitaxel, doxorubicin, carboplatin, gemcitabine |
| HCl-7 | + | + | + | N.D. | Luminal B | Paclitaxel, doxorubicin gemcitabine, carboplatin |
| HCl-9 | − | − | − | N.D. | Poorly differentiated adenocarcinoma | Cyclophosphamide,paclitaxel, 5-fluorouracil, anastrazole, fulvestrant, zolendronic acid |

Microarray

RNA from tumors was extracted and verified qualitatively and quantitatively. Total RNA (200 ng/sample; n=4/group) from each sample was amplified and labeled using the WT Plus Kit from Affymetrix and processed according to Affymetrix protocol. The arrays (Human ST2.0, Affymetrix, Santa Clara, Calif.) were washed and stained on Affymetrix Fluidics station 450 and scanned on an Affymetrix GCS 3000 scanner.

Data from microarrays were normalized using Affymetrix Expression Console. Mean, Standard Deviation, and Variance were calculated across the groups. Fold Change from vehicle-treated samples was calculated, and a fold change of 1.5 was used as cutoff. Student's t-test was used to determine the significance and a cutoff of p value<0.05 was used for significance discovery. False discovery rate was calculated using Benjamini & Hochberg method, and a cutoff for FDR<0.05 was used to create a significant differential expression list. The gene candidate list was loaded to Ingenuity Pathway Analysis and gene set enrichment analysis (GSEA) performed for further discovery. Microarray experiments were performed at the UTHSC Molecular Resources Center (MRC), and data analysis was performed by the UTHSC Molecular Bioinformatics (mBio) core facility.

Phospho-Proteomics

Frozen samples from HCI-13 PDX treated with vehicle or Formula IX were cut into 8 μm cryosections and mounted on uncharged glass slides. Whole tissue lysates were directly prepared from the tissue sections using a 1:1 mixture of T-PER (Tissue Protein Extraction Reagent; Pierce, Rockford, Ill.) and 2× Tris-Glycine SDS Sample Buffer (Invitrogen, Carlsbad, Calif.) supplemented with 5% 2-mercaptoethanol. Samples were boiled for 8 minutes and stored at −80° C. until arrayed.

Samples and standard curves for internal quality assurance were printed onto nitrocellulose-coated slides (Grace Bio-labs, Bend, Oreg.) using an Aushon 2470 arrayer (Aushon BioSystems, Billerica, Mass.). Selected arrays were used to estimate the amount of protein in each sample using a Sypro Ruby Protein Blot Stain (Molecular Probes, Eugene, Oreg.) protocol following manufacturer's instructions (Pin et al. (2014) Curr Protoc Prtein Sci 75, Unit 27 27). Remaining arrays were tested with a single primary antibody using an automated system (Dako Cytomation, Carpinteria, Calif.) as previously described (Baldelli et al. (2015) Oncotarget 6, 32368-32379). Arrays were first incubated with Reblot Antibody stripping solution (Chemicon, Temecula, Calif.), followed by two washes in PBS, and I-block solution (Tropix, Bedford, Mass.) for 4 hours. Arrays were probed with a total of 174 antibodies targeting a wide range of protein kinases and their activation via phosphorylation. Antibodies specificity was tested using standard immunoblotting on a panel of cell lysates. Selected arrays were stained with an anti-rabbit or anti-mouse biotinylated secondary antibody alone (Vector Laboratories Inc., Burlingame, Calif. and Dako Cytomation, Carpinteria, Calif., respectively) and used as negative controls for nonspecific binding/background subtraction.

The commercially available Signal Amplification System (CSA; Dako Cytomation) and a streptavidin-conjugated IRDye 680 secondary antibody (LI-COR Biosciences, Lincoln, Nebr.) were used as signal detection methods. Images were acquired on the laser-based PowerScanner (TECAN, Monnedorf, Switzerland), and data were analyzed using the MicroVigene software Version 5.1 (Vigene Tech, Carlisle, Mass.) as previously described (Baldelli et al. (2015) Oncotarget 6, 32368-32379). Intra and inter-assay reproducibilities have been previously reported (Pierobon et al. (2014) J Proteome Res 13, 2846-2855; Rapkiewicz et al. (2007) Cancer 111, 173-184).

Chromatin Immunoprecipitation Assay (ChIP)-Sequencing (ChIP-Seq)

HCI-13 xenograft specimens were snap frozen and stored for ChIP-sequencing analysis. ChIP-Seq study was performed in vehicle or Formula IX-treated HCI-13 PDX grown in NSG mice. ChIP was performed with ER (n=4/group) or AR (n=/group) antibodies and genome-wide sequencing was performed on a NextSeq 500 sequencer. For ChIP, a standard SDS-based protocol was used, as has been described (Carroll et al. (2005) Cell 122, 33-43). Briefly, a whole cell lysate was made from tissues. The lysate was sonicated using a Covaris E210 machine (Covaris Inc., Woburn, Mass.), for 30 min per sample (settings: duty cycle 20%, intensity 8 at 200 cycles per burst). ER or AR was immunoprecipitated, washed, and the complex eluted. The DNA-protein complex was reverse cross-linked by incubating at 65° C. for 6 hours to overnight. After reverse cross-linking, precipitated and input DNA was purified using QIAquick PCR purification columns (Qiagen).

For library preparation the ThruPLEX-FD Prep Kit (Rubicon Genomics, Ann Arbor, Mich.) was used. For each library 2-10 ng DNA was used. After amplification, fragments of 200-600 bp were selected using a Pippin Prep machine using 2% agarose ethidium bromide-containing cassettes (Sage Science, Beverly, Mass.). After size selection, the DNA was cleaned using Ampure beads and analyzed on a Fragment Analyzer (Advanced Analytical, Ames, Iowa). For sequencing, NextSeq 500 sequencing platform (Illumina, San Diego, Calif.) was used. Human genome build 19 (hg19) was used as the reference genome. Sequencing data from ChIP experiments were aligned to the human genome using Bowtie. For peak calling MACS2 was used.
Immunohistochemistry Fourteen cases of invasive breast cancer, luminal B subtype, were chosen randomly from the formalin fixed paraffin embedded samples available from the tissue bank of the pathological department of Tohoku University Hospital. The luminal B classification of these samples was on the basis of having ERα expression greater than 1% and a Ki-67 labelling index of greater than 20 percent. The samples had variable levels of PR expression (Labelling Index, Average 48.9, Range 0-100) and other clinicopathological characteristics (Ki67, Average 38%, Range 20-48%; Nottingham Grade, 1 n=1, 2 n=10, 3 n=3). The use of these samples was approved by the Tohoku University School of Graduate Medicine Ethic review board (2014-1-107). Blocks of tissue were retrieved and sectioned at a thickness of 3 NM and mounted on glass slides. In order to assess co-localisation mirror image sectioning was used. The slides were then stained for ERα and AR (ERα, 1:50 dilution, Clone 6F11, Leica; AR, 1:50 dilution, Clone AR441, Dako) using immunohistochemistry as previously described (McNamara et al. (2013) Cancer Sci 104, 639-646; Niikawa et al. (2008) Clin Cancer Res 14, 4417-4426).
Statistics Statistical analysis was performed using GraphPad prism software (La Jolla, Calif.). Experiments containing two groups were analyzed by simple t-test, while those containing more than two groups were analyzed by one way analysis of variance (ANOVA) followed by Tukey post-hoc test. Microarray, phospho-proteomics, and ChIP-Seq statistical analyses are described under the respective methods.

Figure 34A:
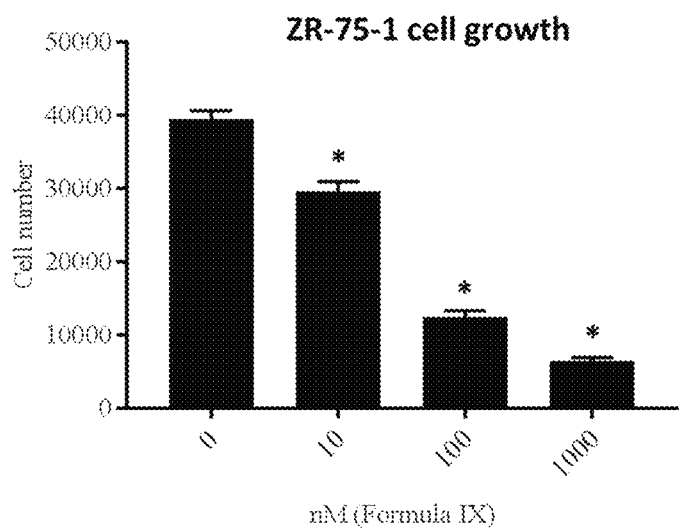
FIG. 34A-FIG. 34E depict that AR agonists inhibited proliferation of ER- and AR-positive breast cancer cells.
Figure 34B:
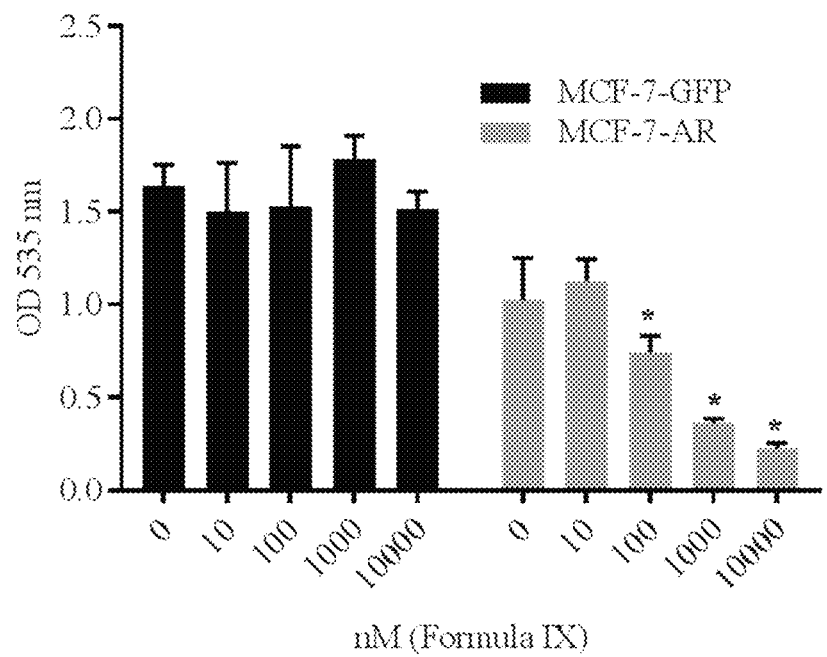

All in vitro experiments were performed at least in triplicate. Data are represented as mean±S.E.
Results The SARM Formula IX, is an AR agonist that binds to and activates the AR at less than 10 nM (Narayanan et al. (2014) PLoS One 9, e103202; Ponnusamy et al. (2017) Hum Mol Genet. 26(13), 2526-2540). Clinically, Formula IX has been evaluated in over 1000 patients in multiple clinical trials (see Example 27 for a partial list) and was shown to increase lean mass and physical function without having significant virilizing side effects (Dobs et al. (2013) Lancet Oncol 14, 335-345). One of the motivating factors to explore SARMs in preclinical studies for breast cancer was that SARMs are non-metabolizable SARMs to weaker androgen or estrogen metabolites which confound results in breast cancer, which is in contrast with steroidal androgens such as DHT.
Formula IX Inhibited (ER, PR, and AR Positive) Breast Cancer Cell Proliferation To determine the effect of AR agonists on the proliferation of ER-positive breast cancer cells, ZR-75-1 breast cancer cells that endogenously express AR, ER, and PR were treated with vehicle or a dose response regimen of Formula IX and the number of cells were counted after 6 days of treatment. Proliferation of ZR-75-1 cells was significantly reduced dose dependently by Formula IX (FIG. 34A). The results were reproduced in MCF-7 cells stably transfected with AR, but not with GFP (FIG. 34B). Although a few previous reports have shown that MCF-7 cells express AR and respond to AR ligands (Buchanan et al. (2005) Cancer Res 65, 8487-8496), the MCF-7 cell line clone in the study lacks or minimally expresses AR, which is in concordance with other reports (De Amicis et al. (2010) Breast Cancer Res Treat 121, 1-11).

Figure 34C:
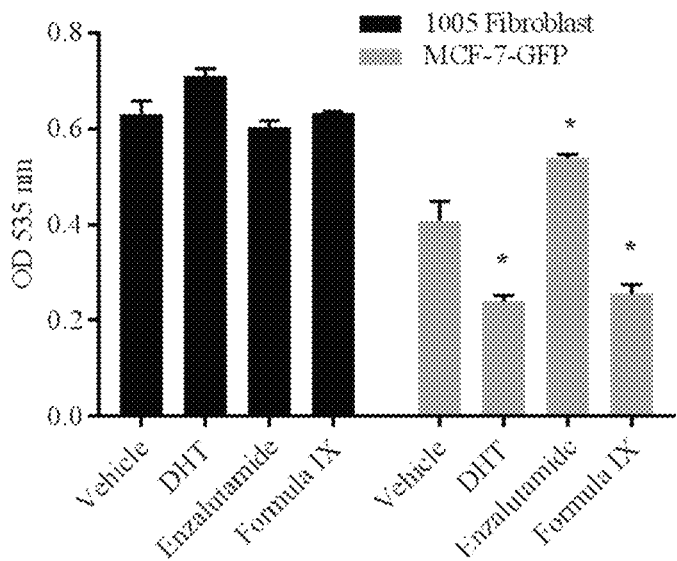

Tumor microenvironment contains tumor epithelial cells, stromal cells, cancer-associated fibroblasts (CAFs), and endothelial cells. The collective function of these cells promotes the aggressive growth of tumors due to secretion of paracrine factors. The CAFs are important for the sustained growth of cancers, and they differ from normal fibroblasts in their capacity to secrete factors that promote proliferation of cancer cells. To determine how an AR agonist affects the paracrine factors secreted by CAFs and subsequently the proliferation of epithelial cells, CAFs were isolated from an ER, PR, and AR-positive breast cancer tissue obtained from a 59-year-old African American patient (Sample ID 1005). The CAFs were treated with vehicle, 10 nM DHT, or 1 µM Formula IX or 1 µM of an AR antagonist, enzalutamide. Medium was collected over a period of 10 days and pooled. CAFs were stained with SRB to evaluate the effect of AR ligands on proliferation. Of the tested materials, neither AR agonist, DHT and Formula IX, nor AR antagonist enzalutamide, affected the proliferation of breast cancer CAFs (FIG. 34C, left side).

Figure 35A:
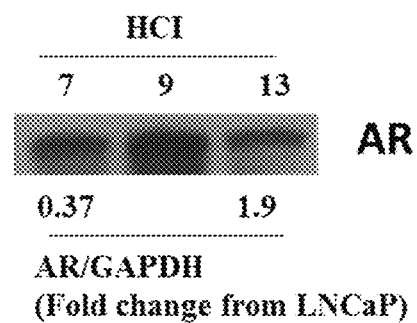
FIG. 35A-FIG. 35D depict that AR agonists inhibited proliferation and growth of wildtype and mutant ER and AR-positive xenografts.
Figure 35B:
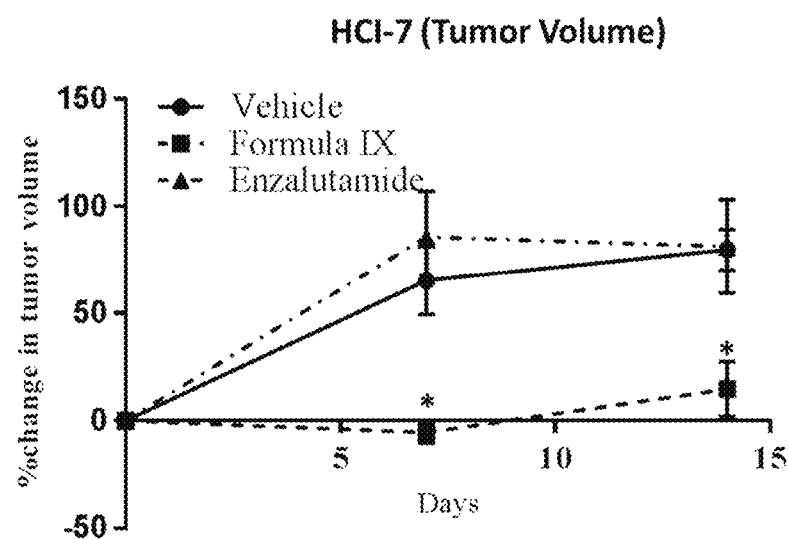
Figure 35C:
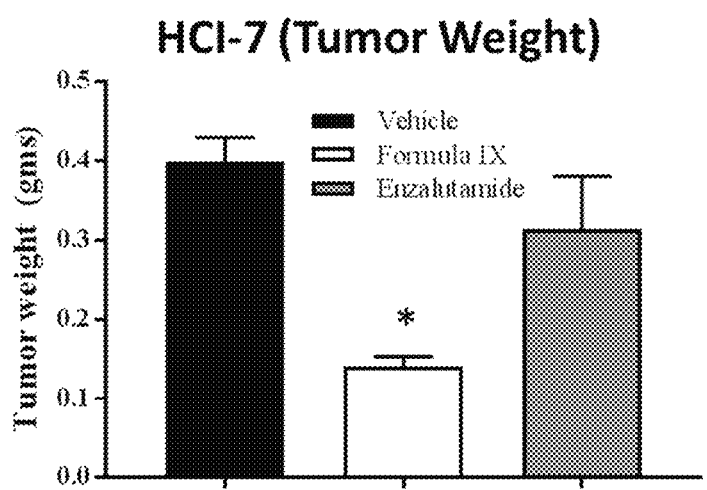

MCF-7 cells stably transfected with GFP (MCF-7-GFP) that lack AR were plated in 96 well plates and fed with conditioned medium obtained from CAFs treated with vehicle, DHT, Formula IX, or enzalutamide. Conditioned medium was replaced on days 4 and 7 and the cells were stained with SRB to measure viability. Both DHT and Formula IX-treated conditioned medium, but not enzalutamide-treated medium, inhibited the proliferation of MCF-7-GFP cells (FIG. 34C, right side). The anti-proliferative effects rendered by DHT and Formula IX would have evolved from inhibiting any paracrine secretion that occurred in CAFs, and could not be direct effects on the AR-negative MCF-7 clone.
Formula IX Inhibited Wild-Type ER-Positive Breast Cancer PDX (HCI-7) Growth To determine if the growth inhibitory properties of Formula IX in vitro could be observed in vivo, Formula IX was tested in a PDX expressing wildtype AR. From the several PDXs available, three AR-positive PDXs were identified, based on gene expression profile. These PDXs, HCI-7, HCI-9, and HCI-13 (Table 12) express high levels of AR that are comparable to the expression found in LNCaP cells (FIG. 35A). To determine the effect of Formula IX on the growth of wildtype ER-positive breast cancer PDX, HCI-7 (wtER-positive, PR-positive, AR-positive) luminal A tumor fragments were implanted under the mammary fat pad of female NSG mice. Once the tumors reached 100-200 mm³, the mice were randomized and treated orally with vehicle, 10 mg/kg Formula IX, or 30 mg/kg enzalutamide. The enzalutamide dose was selected based on previous published experiments (Park et al. (2016) Cancer Invest 34, 517-520; Pollock et al. (2016) Nat Chem Biol 12, 795-801) as well as from internal experiments conducted in prostate cancer xenografts and in Hershberger studies. The growth of HCI-7, which is a slow growing tumor, was inhibited significantly by Formula IX, but not by enzalutamide (FIG. 35B (see also FIG. 32)). Tumor weights measured at the end of the study were also significantly smaller in the Formula IX-treated group (FIG. 35C).

Figure 35D:
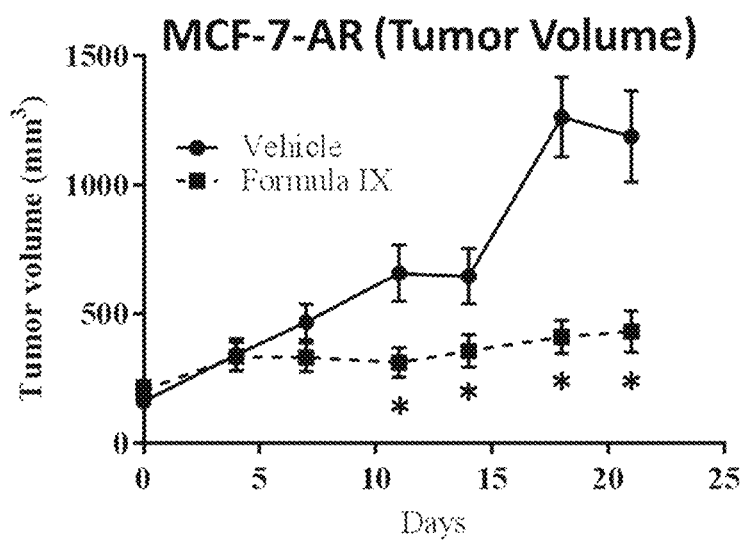

To confirm the results obtained in HCI-7, a xenograft was developed with MCF-7 cells (wtER, PR and HER2 positive) stably transfected with AR (MCF-7-AR) that express wild-type ER. Tumor volumes, measured three times per week, were significantly reduced by Formula IX with a calculated tumor growth inhibition of greater than 60% (FIG. 35D), supporting the use of SARMs in ER-positive and AR-positive breast cancers.

Figure 34D:
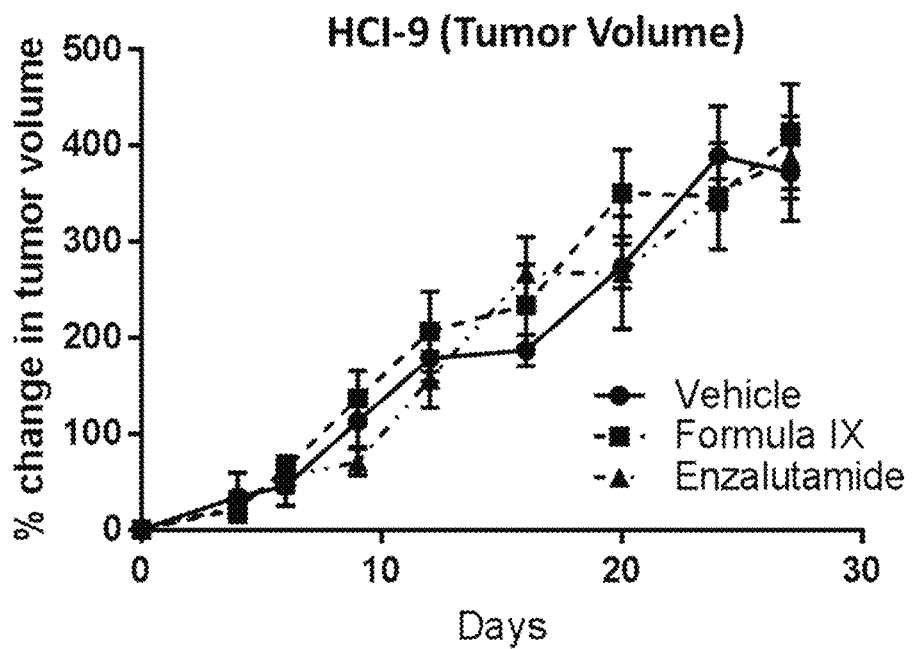

To determine if the same effect is observed in an AR-positive, but ER-negative breast cancer, HCI-9 tumor fragments were implanted under the mammary fat pad of NSG mice. Once the tumors grew to 100-200 mm$^3$, the animals were randomized and treated orally with vehicle, Formula IX, or enzalutamide. Neither Formula IX nor enzalutamide altered the growth trajectory of the tumors, indicating that the AR agonist was not effective in HCI-9 PDX that does not express ER (FIG. 34D). Collectively, these results indicate that the AR might require ER to inhibit cell proliferation and tumor growth.

AR Agonist Inhibited Growth of Estrogen-Independent Mutant ER-Positive PDX (HCI-13)

It was discovered by internal sequencing as well as from literature that HCI-13 PDX expresses an ER that is mutated in the LBD at Y537 (Sikora et al. (2014) Cancer Res 74, 1463-1474). This mutation frequently occurs in refractory ER-positive breast cancers that have been treated with ER antagonists (e.g., tamoxifen or fulvestrant) or aromatase inhibitors (e.g., letrozole, anastrozole, exemestane) (Jeselsohn et al. (2018) Cancer Cell 33, 173-186; Toy et al. (2017) Cancer Disc 7, 277-287). Genome-wide ChIP-seq studies with cells expressing this mutant indicated that the DNA binding signature of this mutant ER is distinct from that of the wildtype ER and that this mutation reprogrammed the ER cistrome. HCI-13 was obtained from a patient who was treated with and relapsed from drugs ranging from ER-targeted therapeutics to chemotherapy (Table 12). To determine whether this ER mutant expressing PDX is dependent on estrogen for growth, HCI-13 tumors were implanted under the mammary fat pad in sham-operated and ovariectomized mice. Tumor growth was monitored over a period of 4 weeks. The growth rate in both sham-operated and in ovariectomized mice was comparable, indicating that the ER in HCI-13 is constitutively active and does not require estrogen to grow (FIG. 36A).

To determine if Formula IX will have the ability to inhibit the growth of a constitutively active mutant ER-driven breast cancer, HCI-13 tumor fragments were implanted under the mammary fat pad in NSG mice. Once the tumors attained 100-200 mm$^3$, the animals were randomized and treated with vehicle or Formula IX. Formula IX inhibited the growth of HCI-13 by almost 95% (FIG. 36B and FIG. 36C). The tumors that were weighed at the time of sacrifice also reflected an almost complete inhibition of tumor (FIG. 36C).

Since the Y537S mutation in the ER-LBD results in resistance of ER antagonists, degraders, and aromatase inhibitors, it was hypothesized that the mutant ER in HCI-13 might be refractory to the inhibitory effects of ER antagonists. To prove this hypothesis, ex vivo sponge culture was used to grow HCI-13. HCI-13 tumor fragments were cultured on gelatin sponges as described in the methods and were treated with vehicle, DHT, Formula IX, enzalutamide, and fulvestrant. At the end of 3 days of incubation, the tumors were harvested, RNA isolated, and the expression of ER- and AR-target genes was measured by real time PCR (FIG. 36D-FIG. 36G).

Figure 34E:
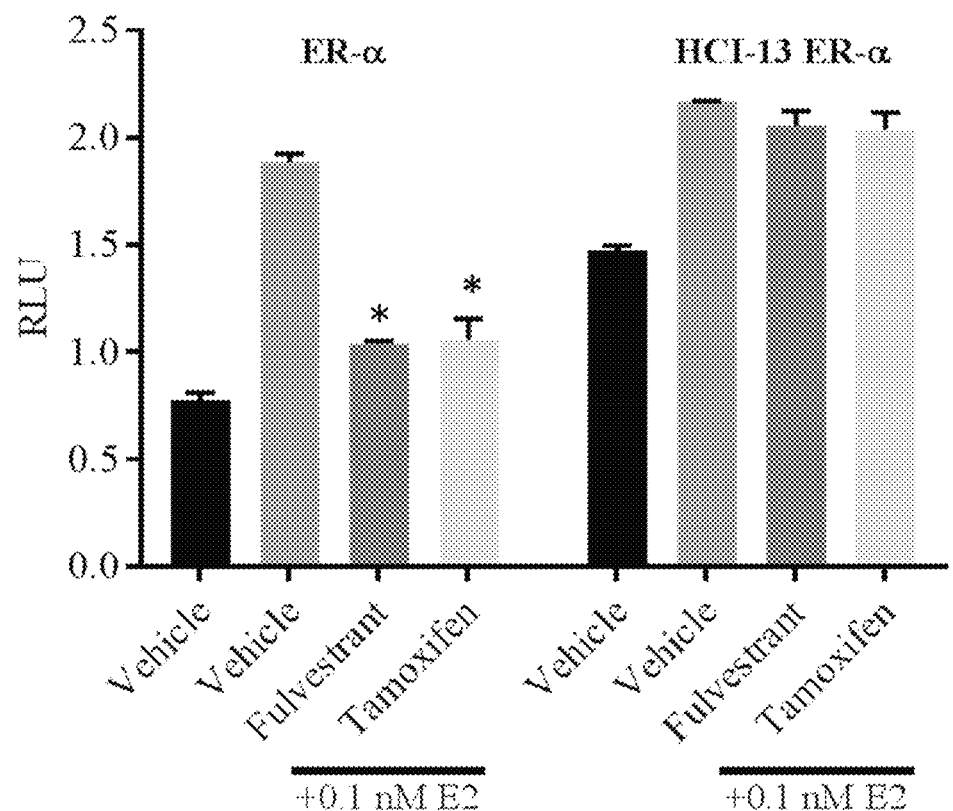

The results clearly show that while fulvestrant, a clinically used effective ER degrader, was ineffective, DHT and Formula IX were effective in inhibiting the expression of constitutively active ER-induced pS2 and PR gene (FIG. 36D-FIG. 36E). Both DHT and Formula IX induced the AR-target gene, FKBP5 (FIG. 36F), indicating that the AR is functional. Measurement of the proliferation marker MKI67 (i.e., Ki67) indicated that similar to the expression of pS2 and PR, MK167 expression was inhibited by Formula IX and DHT, but not by fulvestrant or enzalutamide (FIG. 36G). These results were reproduced in an ER transactivation assay with an ER cDNA cloned from HCI-13 (FIG. 34E). While fulvestrant and tamoxifen inhibited the activity of wildtype ER (FIG. 34E, left side), HCI-13 ER was not inhibited by either of the compounds (FIG. 34E, right side). These results confirm that when ER inhibitors and degraders develop resistance, AR agonists might offer a mechanistically distinct approach to inhibit the resistant ER function.

Ex Vivo Culture with ER-Positive (Except 2005 and HCI-9) Tumor Specimens Indicated the Heterogeneity of Response to ER and AR Ligands Like other cancers, breast cancer is also heterogeneous in its genomic profile as well as in its response to treatments. To determine the effect of Formula IX and fulvestrant on growth inhibition, breast cancer specimens obtained from patients were cultured, on dental sponges, as indicated above. The specimens were treated with vehicle, 1 µM Formula IX, or 100 nM fulvestrant. Three days after treatment, RNA was isolated from the tissues and expression of ER- and AR-target genes was measured. Expression of the AR and ER plotted as relative to HCI-13 expression indicates that the two targets were expressed only at a fraction of the levels observed in HCI-13 (FIG. 36K). HCI-13 expresses AR at levels comparable to that of LNCaP prostate cancer cells and the other specimens ranged from 0.2-20%, with the triple-negative specimen, 2005, having the least expression. Fulvestrant inhibited the ER function in 4 of 8 specimens, while Formula IX inhibited the ER function in 3 of 8 specimens (FIG. 36H-FIG. 36I). Interestingly, Formula IX inhibited the ER function in specimen 1005, where fulvestrant functioned as an agonist. Specimen 1005 could be comparable to that of HCI-13 in its response to ER antagonists. These results are in concordance with the HCI-13 observation that AR agonists might inhibit ER function even in cases where ER antagonists will fail to inhibit. The ability of Formula IX to be an AR agonist was observed in 4 of 8 specimens (FIG. 36J) which included all 3 specimens for which Formula IX was able to suppress ER function. Moreover, as most of these patients have not received many treatments prior to the procurement of the tissues (Table 12), no mutation in the ER was expected.

Formula IX Inhibited HCI-13 Breast Cancer Growth by Inhibiting the Function of Constitutively Active ER The gene expression studies in sponge culture demonstrate that the AR agonists inhibit ER-target genes. To determine the mechanism for the anti-proliferative effects of Formula IX in HCI-13, RNA from HCI-13 tumors obtained from animals shown in FIG. 36B-FIG. 36C were subjected to Affymetrix microarray. In total, 3029 genes were differentially regulated by Formula IX in HCI-13 tumors compared to vehicle-treated tumors. Formula IX up-regulated 1792 genes and down-regulated 1237 genes. Heatmap of the differentially regulated genes clearly indicates a shift in the expression pattern of genes due to Formula IX treatment (FIG. 37A). Some of the most up-regulated genes include Cyp4F8, MYBPC1, RAB3B, LRRC26, AQP4, and CST4 (FIG. 37B). Although the role of upregulated genes like Cyp4F8 and Mybpc1 in breast cancer is unclear and needs to be determined, downregulated genes such as MUC-2 and IL10RA) have been shown to play important role in cancers.

Ingenuity pathway analysis (IPA) showed that the ER-target genes were highly enriched even more than the AR-target genes in Formula IX-treated specimens (p values of $6.66^{-11}$ vs $2.83^{-7}$; FIG. 37C). A subset of the ER-target genes was down-regulated by Formula IX, while all the AR-target genes were up-regulated by Formula IX (FIG. 37D-FIG. 37G). While ER-target genes such as TFF1, PGR, NRIP1 were down-regulated by Formula IX (not shown), other ER-target genes such as CTSD and CCND1 were not inhibited by Formula IX. These results provide evidence that Formula IX functions in breast cancer by at least partially inhibiting the ER-signaling pathway to reduce the growth of cancer.

Some direct and indirect regulation of ER-targets were observed in Formula IX-treated samples. ER increases PDZK1 expression, which in-turn inhibits the expression of SLC26A3, a tumor suppressor gene. Interestingly, Formula IX significantly inhibited the expression of PDZK1, which restored the expression of the tumor-suppressor gene, SLC26A3. Similarly, anti-apoptotic gene BCL-2 and genes present in its network such as PARP and WT1 were significantly down-regulated by Formula IX. Although these genes do not belong to the list of ER-direct target genes, cross-talk between ER and the BCL-2 pathway has been reported previously. Expression of another class of oncogenic proteins, histone class, was inhibited by Formula IX. About 17 members of histone group were inhibited significantly by Formula IX. The histone class has been implicated in aggressive cancers and endocrine-resistance (Nayak et al. (2015) Horm Cancer 6, 214-224).

Although IPA analysis did not provide any evidence for regulation of ERBB2 (human epidermal growth factor receptor 2 or HER2/neu) pathway by Formula IX, GSEA enrichment analysis revealed that Formula IX affected the genes regulated by ERBB2 (FIG. 37H). It is not clear at this point whether the regulation of ERBB2 is a result of growth inhibition or inhibition of the ER pathway. Irrespective of the mechanism, a downregulation of ERBB2 pathway, which is an oncogenic and tumor-promoting pathway, may be an added advantage of using Formula IX or an AR agonist in ER-positive breast cancers.

ChIP-Seq Analysis Demonstrates that Formula IX Reprogrammed ER and AR Cistromes

Previous studies have demonstrated that the interaction of Y537S mutant ER with DNA has been reprogrammed and might share limited similarity to the wildtype ER genome interaction. To determine if the effect of Formula IX on ER function is due to direct effect on ER binding to DNA, ChIP-sequencing was performed in the tumor samples obtained from animals shown in FIG. 36B-FIG. 36C. ER binding to 1248 regions (q<0.05) on the DNA was reprogrammed by Formula IX, with 792 regions enriched with ER and 456 regions depleted of ER (FIG. 38A and FIG. 38H). AR showed a similar pattern of DNA binding i.e. regions enriched with ER were also enriched for AR, and the regions that were depleted of ER were also depleted of AR (FIG. 38A and FIG. 38H). This indicates that the ER and AR are potentially shuttling as a complex. The motifs that were enriched by the ER represent androgen response element (ARE; SEQ ID NO: 1), glucocorticoid response element (GRE; SEQ ID NO: 2), and Forkhead box protein A1 or FOXA1 response elements (FOXA1RE; SEQ ID NO: 3), while the regions that were depleted of ER represent estrogen response element (ERE; SEQ ID NO: 4) and FOXA1RE (SEQ ID NO: 5) (FIG. 38A and FIG. 38H). Although the regions depleted by ER favor the gene expression pattern, the enrichment of ER at AREs and GREs is surprising and has not been previously reported. The principal component analysis (PCA) plot suggests the clear demarcation in the clustering of vehicle- and Formula IX-treated samples (FIG. 38C). FIG. 38B and FIG. 40 show representative regions enriched and depleted of ER and AR. AR and ER binding to pS2 ERE, PSA (KLK3) promoter ARE, and PSA enhancer ARE was validated by ChIP real-time PCR (FIG. 38D). It is important to recognize that as Formula IX neither binds to ER nor alters ER activity (Kearbey et al. (2007) Pharmaceutical Res 24, 328-335; Narayanan et al. (2008) Molecular Endocrinology 22, 2448-2465) its effect on ER cistrome is mediated by activating the AR.

As this is the first study to evaluate the effect of AR agonists such as DHT and Formula IX on ER cistrome in ER-positive breast cancers, the regions bound by ER were mapped in response to Formula IX. Between 50 and 60% of the ER enriched and depleted sites were mapped to distal regulatory regions, while only around 2-3% of the sites mapped to promoter regions (FIG. 38E). Interestingly, while the intron and exon binding percentage match with previous reports, the proportion of the ER bound to promoters and distal regulatory elements are distinct from that observed in response to estrogens or with a constitutively active ER. Other studies have indicated that the ER cistrome comprises of about 30-40% at distal regulatory regions and 7-22% in proximal promoter regions, and AR-regulated ER cistrome comprises of 50-60% and 2-3% of these regions, respectively.

Formula IX Reprogrammed the FOXA1RE Sites

It is interesting to observe that FOXA1RE motifs are represented in both the enriched and depleted ER cistrome. The enriched cistrome motifs represent ARE, GRE, and FOXA1RE, while the depleted cistrome motifs represent ERE and FOXA1RE. As FOXA1 pioneering transcription factor is important for the function of both AR and ER and has overlapping binding sites with ARE and ERE, it is highly possible that the activated AR might sequester FOXA1 from the FOXA1REs adjacent to the EREs to open up the nucleosome and facilitate its binding to ARE and GRE. Since ER is functioning as a complex with AR, it is also sequestered from EREs and FOXA1REs towards AREs, GREs, and FOXA1REs. To determine the validity of this hypothesis the motifs shared by ERE and FOXA1REs were mapped in the downregulated cistrome. The majority of the EREs and FOXA1REs overlap in the downregulated motifs (FIG. 38F). On the other hand, majority of the GREs and AREs in the upregulated motifs overlap with FOXA1REs. The results of this analysis confirm the hypothesis that the ER:AR:FOXA1 complex shuttles from the ER binding sites to AR binding sites to facilitate the conversion of nucleosomes to open chromatin and AR binding.

To confirm that the AR and ER are localized as a complex and that they migrate together between cistromes, an immunoprecipitation was conducted with ER and AR antibodies and Western blot for SRC-1. It was hypothesized that if the AR and ER exist as distinct, separate complexes, Formula IX treatment will increase the interaction of SRC-1 with AR and reduce the interaction with ER. If AR and ER exist as a complex together, then Formula IX treatment will increase the interaction of both AR and ER with SRC-1. Treatment of HCI-13 PDX with Formula IX resulted in an increase in the interaction between AR and SRC-1 and also between ER and SRC-1 (FIG. 38G). Although this is not a direct evidence for the AR:ER complex, this evidence combined with ChIP-Seq data suggest that the two proteins exist as a complex and the main difference is the cistrome binding that results in activation or inactivation of genes.

AR and ER Colocalized in Luminal B Breast Cancers

To determine the nuclear reactivity of AR and ER and potential colocalization in breast cancer specimens, immunohistochemistry was performed in several luminal B breast cancer specimens. Nuclear immunoreactivity of both AR and ER and expression at high levels was observed in all the breast cancer specimens examined (FIG. 39). Additionally, several samples had moderate levels of cytoplasmic immunoreactivity for both markers. As levels of expression of both markers exceeded 60% in all samples, a high percentage of cells were positive for both ER and AR. The patterns of staining were also similar between the markers. Overall, the number of cells immunoreactive for AR in any one sample exceeded those which were immunoreactive for ER. However, the semi-quantitative nature of immunohistochemistry precludes us from being able to state conclusively that AR was expressed at greater levels than ERα. It was also possible to observe samples in which immunoreactivity for AR was weaker or absent while ER immunoreactivity was present; however, these were less frequent.

Phospho-Proteomic Analysis Showed the Inhibition of Oncogenic and Induction of Tumor-Suppressor Protein Phosphorylation by AR Agonist To determine the effect of Formula IX on the functions of various proteins, phospho-proteomics was performed in HCI-13 tumors treated with vehicle or Formula IX. Formula IX inhibited the phosphorylation of various oncogenic proteins such as pERK, PKC $z_c$, RSK3, Ezrin, BCL2, ELF4G, and ER (FIG. 41A-FIG. 41C). Formula IX also inhibited the expression of proliferation marker Ki67. Alternatively, Formula IX increased the phosphorylation of tumor suppressor proteins such as p53, p27, ACC, and the AR. Formula IX also increased the phosphorylation of STATS, which could be a tumor suppressor or an oncogene depending on the context (FIG. 41A-FIG. 41C). These results demonstrate that activating the AR with an agonist promotes the alteration of appropriate pathways that facilitate tumor growth inhibition.

To understand the consequences of these protein alterations, cell signaling activators and inhibitors in HCI-13 sponge cultures were used to determine their effects on AR and ER target gene expression, FKBP5 and pS2, respectively. Because ERK and PKC phosphorylation were down-regulated by Formula IX, HCI-13 sponge cultures were treated with activators of the two pathways, EGF and PMA (FIG. 41D-FIG. 41E). Treatment of HCI-13 tumor fragments with PMA completely reversed the pS2 gene expression that was inhibited by Formula IX, while EGF only marginally reversed the inhibition observed with Formula IX. PMA reversed the effects of Formula IX on pS2 gene expression without affecting the ability of Formula IX to increase the expression of AR target gene, FKBP5 (FIG. 41E). This suggests that PMA is potentially working downstream of the AR to regulate the ER.

Discussion

Almost all oncology therapeutics are inhibitors or antagonists of their therapeutic targets. Prolonged use of these agents will result in selective pressure and eventually resistant mutations. These resistant mutations can either attenuate or prevent the anti-tumor activity of the drug or in the worst case scenario convert the drug into an agonist and cause aggressive tumor growth. In the presence of an agonist, the AR will exist in an agonistic conformation as observed in nature and not in an unstable antagonistic conformation. This conformational property might be less prone to the formation of AR mutations that could prevent AR binding or cause agonist effects on the cistrome.

The results obtained in HCI-13 are extremely encouraging. A tumor that relapsed and continued to grow in the presence of a range of therapeutics was inhibited by Formula IX (an AR agonist and nonsteroidal SARM) with a tumor growth inhibition of over 90%. This result and the result from ex vivo studies support the use of SARMs even after the tumors relapse from other treatment options. Although the HCI-13 is only one example of mutant ER, this mutation Y537S is one of the common mutants found in the clinic and could serve as a representative (Katzenellenbogen et al. (2018) Nat Rev Cancer 18(6), 377-388).

The unique property of inhibiting the ER function by activating the AR demonstrates the complex interaction between various nuclear receptors and their associated proteins. The microarray results indicate that the inhibition of ER and HER2 (human epidermal growth factor receptor 2) pathways by Formula IX could provide greater benefit to patients in whom both oncogenic pathways are activated. This beneficial effect is further enhanced by the increase in the phosphorylation of various tumor suppressors and inhibition of the phosphorylation of oncogenes.

The ChIP-Seq results suggest that the AR and ER exist as a complex in the presence of Formula IX and shift from an ER cistrome to an AR cistrome along with the pioneering transcription factor FOXA1. Based on these results, a model was proposed (FIG. 42). In the absence of an activated AR, the constitutively active ER binds to EREs by utilizing FOXA1REs to create an open chromatin and promote the growth of the tumor. In the presence of an AR agonist, AR interacts with ER and the complex shifts from ERE and adjacent FOXA1REs to ARE and adjacent FOXA1REs. In this case, the FOXA1 is sequestered away from EREs towards AREs to open the nucleosomes and facilitate the binding of the complex.

Overall, these mechanism-based preclinical and translational studies support the use of an SARMs such as Formula IX to treat refractory hormone receptor-positive breast cancer. Further, heterogeneity is seen the response of ER-positive clinical specimens and hence it might be optimal to pharmacogenomically screen for Y537S ER mutant expressing breast cancers in order to enriched the clinical benefit rate of Formula IX. Tissue-selective AR agonism might offer an alternative hormonal approach for hormone receptor-positive breast cancers.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating a subject suffering from ER mutant expressing breast cancer, comprising a step of administering to said subject a selective androgen receptor modulator (SARM) compound represented by a structure of formula II:

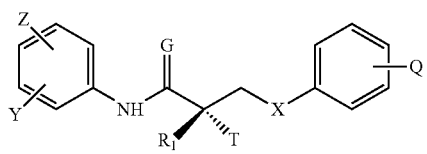

wherein
X is O;
G is O;
T is OH;
R is alkyl, haloalkyl, dihaloalkyl, trihaloalkyl, $CH_2F$, $CHF_2$, $CF_3$, $CF_2CF_3$, aryl, phenyl, halogen, alkenyl or OH;
$R_1$ is $CH_3$;
Z is $NO_2$ or CN;
Y is $CF_3$, F, Br, Cl, I, or CN;
Q is CN, alkyl, halogen, NHCOR, NHCOOR, CONHR, $NHCSCH_3$, $NHCSCF_3$, or NHCSR;
wherein said ER mutant expressing breast cancer is Y537S mutation expressing breast cancer, and wherein said treating does not include preventing.

2. The method of claim 1, comprising administering an optical isomer, a racemic mixture, a metabolite, a pharmaceutically acceptable salt, a pharmaceutical product, a hydrate, an N-oxide, or a crystal of said selective androgen receptor modulator, or any combination thereof.

3. The method of claim 1, wherein said administering comprises intravenously, intraarterially, or intramuscularly injecting to said subject said pharmaceutical product in liquid form; subcutaneously implanting in said subject a pellet containing said pharmaceutical product; orally administering to said subject said pharmaceutical product in a liquid or solid form; or topically applying to the skin surface of said subject said pharmaceutical product.

4. The method of claim 2, wherein said pharmaceutical product is a pellet, a tablet, a capsule, a solution, a suspension, an emulsion, an elixir, a gel, a cream, a suppository or a parenteral formulation.

5. The method of claim 1, wherein said SARM compound is represented by a structure of Formula:

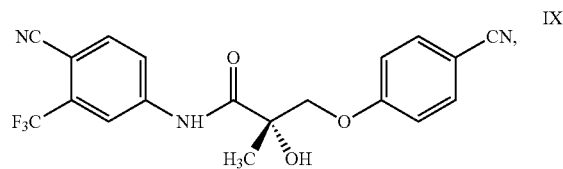

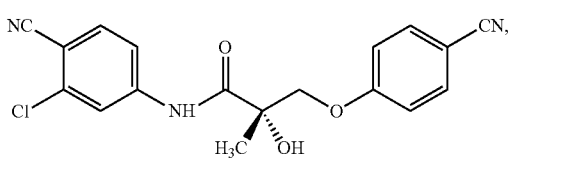

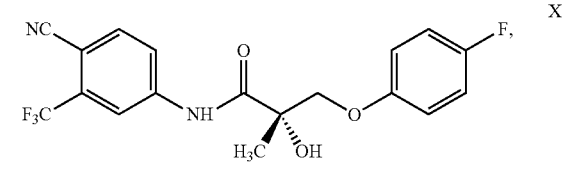

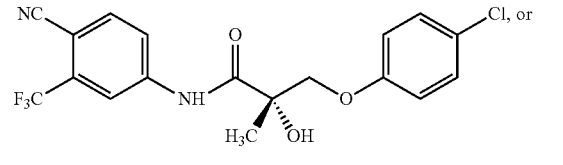

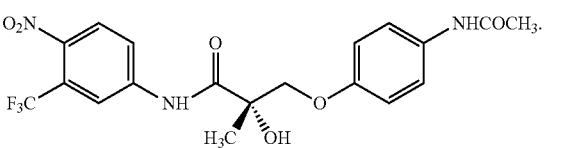

* * * * *